(12) United States Patent
Kasai et al.

(10) Patent No.: US 8,586,571 B2
(45) Date of Patent: Nov. 19, 2013

(54) HETEROCYCLIC COMPOUND

(75) Inventors: Shizuo Kasai, Osaka (JP); Tomohiro Kaku, Osaka (JP); Masahiro Kamaura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/738,486

(22) PCT Filed: Oct. 17, 2008

(86) PCT No.: PCT/JP2008/068901
§ 371 (c)(1),
(2), (4) Date: Apr. 16, 2010

(87) PCT Pub. No.: WO2009/051244
PCT Pub. Date: Apr. 23, 2009

(65) Prior Publication Data
US 2010/0292206 A1    Nov. 18, 2010

Related U.S. Application Data

(60) Provisional application No. 60/960,897, filed on Oct. 18, 2007.

(51) Int. Cl.
| | | |
|---|---|---|
| C07D 205/04 | (2006.01) |
| C07D 205/08 | (2006.01) |
| C07D 205/00 | (2006.01) |
| C07D 211/22 | (2006.01) |
| C07D 211/44 | (2006.01) |
| C07D 211/46 | (2006.01) |
| C07D 211/78 | (2006.01) |
| C07D 211/88 | (2006.01) |
| C07D 413/10 | (2006.01) |
| C07D 413/12 | (2006.01) |
| C07D 413/06 | (2006.01) |
| C07D 417/06 | (2006.01) |
| C07D 417/08 | (2006.01) |
| C07D 417/10 | (2006.01) |
| C07D 471/04 | (2006.01) |
| C07D 495/04 | (2006.01) |
| C07D 513/04 | (2006.01) |
| C07D 401/06 | (2006.01) |
| A61K 31/4427 | (2006.01) |
| A61K 31/397 | (2006.01) |
| A61K 31/445 | (2006.01) |
| A61K 31/40 | (2006.01) |
| A61P 3/10 | (2006.01) |

(52) U.S. Cl.
USPC ............ 514/210.01; 514/210.17; 514/201.18; 514/327; 514/423; 544/335; 544/350; 546/221; 546/268.1; 548/155; 548/180; 548/200; 548/236; 548/248; 548/540; 548/952

(58) Field of Classification Search
None
See application file for complete search history.

(56) References Cited

U.S. PATENT DOCUMENTS

| 4,505,907 A | * | 3/1985 | Wright et al. ............ 514/210.17 |
|---|---|---|---|
| 5,130,309 A | | 7/1992 | Shanklin, Jr. et al. |
| 7,358,370 B2 | * | 4/2008 | Huang et al. ................ 548/360.1 |
| 7,790,763 B2 | * | 9/2010 | Jolidon et al. ................. 514/423 |
| 2007/0219198 A1 | | 9/2007 | Xiang et al. |

FOREIGN PATENT DOCUMENTS

| JP | 53-31669 | 3/1978 |
|---|---|---|
| WO | 02/05501 A1 | 1/2002 |
| WO | 02/055501 A2 | 7/2002 |
| WO | 02/066470 A1 | 8/2002 |
| WO | 02/068406 A2 | 9/2002 |
| WO | 02/068406 A3 | 9/2002 |
| WO | 2004/005279 A2 | 1/2004 |
| WO | 2004/005279 A3 | 1/2004 |
| WO | 2004/007457 A2 | 1/2004 |
| WO | 2004/007457 A3 | 1/2004 |
| WO | 2004/007458 A1 | 1/2004 |
| WO | 2004/007481 A2 | 1/2004 |
| WO | 2004/007481 A3 | 1/2004 |
| WO | 2006/012374 A1 | 2/2006 |
| WO | 2006/023778 A2 | 3/2006 |
| WO | 2006/023778 A3 | 3/2006 |
| WO | 2007/092435 A2 | 8/2007 |
| WO | 2007/092435 A3 | 8/2007 |
| WO | 2007/106705 A1 | 9/2007 |
| WO | 2009/042444 A2 | 4/2009 |
| WO | 2009/117676 A2 | 9/2009 |

OTHER PUBLICATIONS

Type1diabetes, 2011, http://www.ncbi.nlm.nih.gov/pubmedhealth/PMH0001350.*
Type2diabetes, 2011, http://www.mayoclinic.com/health/type-2-diabetes/DS00585.*
LeGrand et al., caplus an 2003;757517.*
Yuan et al., caplus an 2006:104503.*
Supplementary European Search Report dated May 12, 2011 in corresponding European Application No. 08 83 8911.

* cited by examiner

*Primary Examiner* — Sun Jae Loewe
(74) *Attorney, Agent, or Firm* — Wenderoth, Lind & Ponack, L.L.P.

(57) ABSTRACT

The present invention relates to

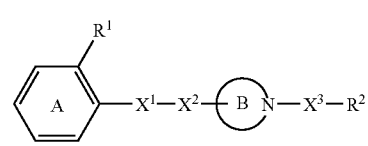

wherein each symbol is as defined in the specification. The compound of the present invention has a superior RBP4-lowering action, and is useful as a medicament for the prophylaxis or treatment of disease and condition mediated by increased RBP4.

21 Claims, No Drawings

HETEROCYCLIC COMPOUND

This application is a U.S. national stage of International Application No. PCT/JP2008/068901 filed Oct. 17, 2008, and claims the benefit of U.S. provisional application Ser. No. 60/960,897 filed Oct. 18, 2007.

TECHNICAL FIELD

The present invention relates to a novel heterocyclic compound, which is useful as an agent for the prophylaxis or treatment of diabetes and the like; and the like.

BACKGROUND OF THE INVENTION

Retinol binding protein 4 (hereinafter sometimes to be abbreviated as "RBP4") is known to be a sole blood retinol transport protein mainly produced in the liver. In recent years, moreover, RBP4 is suggested to be an insulin resistance-inducing factor from the following literatures and the like.
(1) Since RBP4 expression increases in the adipocytes of GLUT4 knockout mouse showing insulin resistance, RBP4 is suggested to be a potential adipocytokine inducing insulin resistance (see Nature 436, 356-362 (2005)).
(2) It has been reported that RBP4 overexpression mouse shows hyperglycemia and hyperinsulinemia, and RBP4 knockout mouse shows promotion of glucose tolerance and insulin sensitivity as phenotype (see Nature 436, 356-362 (2005)).
(3) It has been reported that mouse bred on a high-fat diet shows high blood. RBP4 value, which is correlated with induction of insulin resistance (see Nature 436, 356-362 (2005)).
(4) It has been reported that disease model mouse showing diabetes•obesity pathology such as ob/ob mouse, 11β-HSD1 overexpression (adipose tissue specific) mouse, MC4R knockout mouse, GLUT4 knockout (adipose tissue•skeletal muscle specific) mouse and the like also shows high blood RBP4 value (see Nature 436, 356-362 (2005)).
(5) It has been reported that blood RBP4 concentration and insulin sensitivity•sugar disposal rate are inversely correlated in human. It has also been reported that the glucose infusion rate decreases as the blood RBP4 concentration increases in euglycemic hyperinsulinemic glucose clamp test (see Cell Metab., 6, 79-87 (2007)).
(6) While exercise is known to improve insulin sensitivity, an extremely high correlation between such an improving effect and lowering of blood RBP4 concentration has been reported recently (see N. Engl. J. Med., 354, 2552-2563 (2006)).
(7) WO2005-059564 describes that a compound that controls RBP4% activity is useful for the treatment of insulin resistance.

All these suggest that a compound capable of lowering blood RBP4 concentration can be a therapeutic drug for diabetes.

RBP4 is stably present in blood in the form of a complex resulting from the binding of retinol and TTR (transthyretin). When RBP4 is dissociated from TTR and becomes free, it is decomposed in and excreted from the kidney comparatively rapidly. It is unknown whether the binding of RBP4 and retinol is indeed essential for the formation of a complex with TTR. However, fenretinide, a retinol derivative, inhibits the binding of RBP4 and retinol, and consequently inhibits formation of a complex with TTR. It is known that administration of fenretinide to animal induces lowering of blood RBP4 (see Biochim. Biophys. Acta, 1294, 48-54 (1996)).

From the foregoing findings, a compound that inhibits formation of a complex of RBP4 and TTR by inhibiting the binding of RBP4 and retinol is expected to lower blood RBP4 concentration and consequently induce correction of hyperglycemia and improvement of insulin resistance.

In recent years, moreover, a report has documented that blood RBP4 value and blood TG (triglyceride) or LDL cholesterol value positively correlate in human, and blood RBP4 value negatively correlates with HDL cholesterol value (see J. Atheroscler. Thromb., 13, 209-215 (2006), N. Engl. J. Med., 355, 1392-1395 (2006), Diabetes, 56 (Supplement 1), A378 (1477-P) (2007)), thus suggesting relationship with lipid metabolism.

In view of the above, a medicament having an action to lower blood RBP4 value (concentration) (also referred to as "RBP4 lowering action" in the present specification) (also referred to as "RBP4 lowering agent" in the present specification) is expected to be widely applicable to lifestyle-related diseases.

WO 2006/023778 describes a compound represented by the formula:

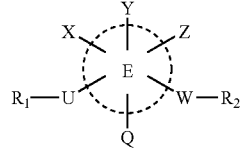

wherein E is phenyl, heteroaryl; X, Y and Z show H, OH, alkyl, alkoxy and the like; U and W show CO, SO, $SO_2$, S, NH and the like; n is 1 or 2; Q is H, alkyl and the like; and $R_1$ and $R_2$ show H, alkyl, alkenyl, heterocycle and the like.

JP-A-53-31669 describes a compound represented by the formula:

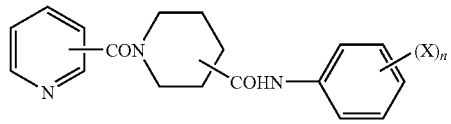

wherein X is lower alkyl, lower alkoxy, halogen; n is 1 or 2 (when n is 2, X may be the same or different), which is useful as a therapeutic agent for ulcer.

WO 02/055501 describes a compound represented by the formula:

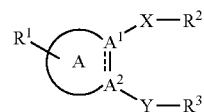

wherein $A^1$ and $A^2$ are C, N; A is a 5- or 6-membered aromatic heterocyclic group;
X is

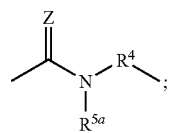

Y is

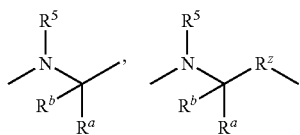

and the like; Z is O, S; $R^a$ and $R^b$ show H, halogen and the like; $R^1$ is H, halogen and the like; $R^2$ is an optionally substituted 6- to 10-membered aryl group; $R^3$ is an optionally substituted aryl group; $R^4$ is a bond, a $C_{2-4}$ alkenyl group and the like; $R^{5a}$ is H, lower alkyl and the like; $R^7$ is H, lower alkyl, an optionally substituted heterocycle-$C_{1-6}$ alkyl group, which is useful for the treatment of cancer.

patent document 1: WO2005/059564
patent document 2: WO2006/023778
patent document 3: JP-A-53-31669
patent document 4: WO02/055501
non-patent document 1: Nature 436, 356-362 (2005)
non-patent document 2: Cell Metab., 6, 79-87 (2007)
non-patent document 3: N. Engl. J. Med., 354, 2552-2563 (2006)
non-patent document 4: Biochim. Biophys. Acta, 1294, 48-54 (1996)
non-patent document 5: J. Atheroscler. Thromb., 13, 209-215 (2006)
non-patent document 6: N. Engl. J. Med., 355, 1392-1395 (2006)
non-patent document 7: Diabetes, 56(Supplement 1), A378 (1477-P) (2007)

DISCLOSURE OF THE INVENTION

Problems to be Solved by the Invention

As a result of the intensive studies of the compounds having a RBP4 decreasing action, the present inventors have surprisingly found compounds represented by the following formula (I), a salt thereof or a prodrug thereof has a superior RBP4 decreasing action, which resulted in the completion of the present invention.

Accordingly, the present invention relates to the following:
[1] a compound represented by the formula

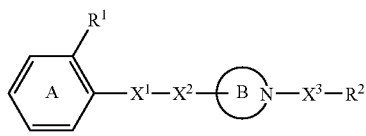

(I)

wherein
ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine, pyrrolidine or piperidine;
$X^3$ is CO or $SO_2$;
$R^2$ is a substituent, provided that
(1) when —$X^1$—$X^2$— is —NH— and ring B is piperidine, then $X^3$ is CO;
(2) when $X^3$ is CO, then $R^2$ is not a tert-butoxy group, or a salt thereof (hereinafter sometimes to be referred to as compound (I)),
[2] the compound of the aforementioned [1], wherein ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine, pyrrolidine or piperidine;
$X^3$ is CO; and
$R^2$ is an acyl group or an optionally substituted hydrocarbon group,
[3] the compound of the aforementioned [1], wherein ring A is benzene optionally further substituted by 1 to 3 substituents selected from (1) a halogen atom, (2) an optionally halogenated $C_{1-6}$ alkyl group and (3) an optionally halogenated $C_{1-6}$ alkoxy group,
[4] the compound of the aforementioned [1], wherein $R^1$ is an isopropyl group or a tert-butyl group,
[5] the compound of the aforementioned [1], wherein X' is O,
[6] the compound of the aforementioned [1], wherein $X^2$ is a bond or methylene,
[7] the compound of the aforementioned [1], wherein ring B is or

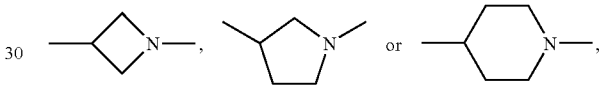

[8] the compound of the aforementioned [1], wherein $X^3$ is CO,
[9] the compound of the aforementioned [1], wherein $R^2$ is an acyl group or an optionally substituted hydrocarbon group,
[10] the compound of the aforementioned [1], wherein ring A is benzene optionally further substituted by 1 to 3 substituents selected from (1) a halogen atom, (2) an optionally halogenated $C_{1-6}$ alkyl group and (3) an optionally halogenated $C_{1-6}$ alkoxy group;
$R^1$ is an isopropyl group or a tert-butyl group;
$X^1$ is O;
$X^2$ is a bond or methylene;
ring B is

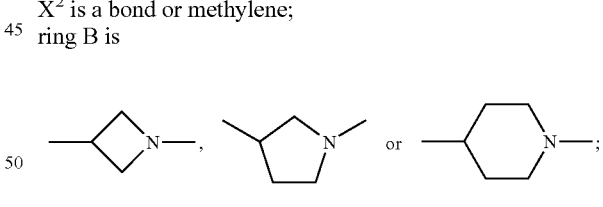

$X^3$ is CO;
$R^2$ is an acyl group or an optionally substituted hydrocarbon group,
[11] 4-(3-(2-tert-butylphenoxy)azetidin-1-yl)-4-oxobutanoic acid or a salt thereof,
[12] 3-{3-[(2-tert-butyl-4-fluorophenoxy)methyl]azetidin-1-yl}-3-oxopropanoic acid or a salt thereof,
[13] 2-{[3-(2-tert-butyl-4-chlorophenoxy)azetidin-1-yl]carbonyl}pyridine or a salt thereof,
[14] 4-[3-(2-tert-butyl-4-chlorophenoxy)azetidin-1-yl]-4-oxobutanoic acid or a salt thereof,
[15] 3-{3-[(2-tert-butylphenoxy)methyl]pyrrolidin-1-yl}-3-oxopropanoic acid or a salt thereof,
[16] {3-[(2-tert-butyl-4-chlorophenoxy)methyl]azetidin-1-yl}(oxo)acetic acid or a salt thereof,

[17] 3-{3-[(2-tert-butyl-4-fluorophenoxy)methyl]pyrrolidin-1-yl}-3-oxopropanoic acid or a salt thereof,
[18] a prodrug of the compound of the aforementioned [1],
[19] a medicament comprising the compound of the aforementioned [1] or a prodrug thereof,
[20] the medicament of the aforementioned [19] which is a RBP4-lowering agent,
[21] the medicament of the aforementioned [19] which is a prophylactic or therapeutic agent for diabetes,
[22] a method for the prophylaxis or treatment of a retinol-binding protein 4-associated disease in a mammal, comprising administering an effective amount of the compound of the aforementioned [1] or a prodrug thereof to the mammal,
[23] a method for the prophylaxis or treatment of diabetes in a mammal, comprising administering the compound of the aforementioned [1] or a prodrug thereof to the mammal,
[24] use of the compound of the aforementioned [1] or a prodrug thereof, for the production of a prophylactic or therapeutic agent for a retinol-binding protein 4-associated disease,
[25] use of the compound of the aforementioned [1] or a prodrug thereof, for the production of a prophylactic or therapeutic agent for diabetes,
[26] a retinol-binding protein 4-lowering agent comprising a compound represented by the formula

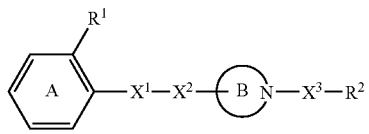

(I)

wherein
ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine, pyrrolidine or piperidine;
$X^3$ is CO or $SO_2$; and
$R^2$ is a substituent, or a salt thereof or a prodrug thereof,
and the like.

Effect of the Invention

The present invention provides a prophylactic or therapeutic agent for a disease or condition mediated by an increase in RBP4 such as diabetes, obesity and the like.

DETAILED DESCRIPTION OF THE INVENTION

The definition of each symbol in the formula (I) is described in detail in the following.
The "halogen atom" in the present specification means, unless otherwise specified, a fluorine atom, a chlorine atom, a bromine atom or an iodine atom.
The "$C_{1-3}$ alkylenedioxy group" in the present specification means, unless otherwise specified, methylenedioxy, ethylenedioxy or the like.
The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.
The "$C_{1-6}$ alkoxy-carbonyl group" in the present specification means, unless otherwise specified, methoxycarbonyl, ethoxycarbonyl, propoxycarbonyl, tert-butoxycarbonyl or the like.
The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.
The "$C_{6-14}$ aryl-carbonyl group" in the present specification means, unless otherwise specified, benzoyl, naphthylcarbonyl, biphenylcarbonyl or the like.
Ring A is benzene optionally further substituted. The benzene optionally has 1 to 4 substituents besides $R^1$ group and $X^1$ group at substitutable positions.
Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom,
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{6-14}$ aryl-carbonyl group optionally substituted by 1 to 3 halogen atoms,
   (d) a $C_{1-6}$ alkoxy-carbonyl group optionally substituted by 1 to 3 halogen atoms,
   (e) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
   (f) a carbamoyl group optionally mono- or di-substituted by alkyl group(s) optionally substituted by 1 to 3 halogen atoms, and (g) an aromatic heterocyclic group (e.g., thienyl, furyl, pyridyl, pyrazolyl, imidazolyl, tetrazolyl, oxazolyl, thiazolyl, oxadiazolyl, thiadiazolyl);

(6) a $C_{1-6}$ alkyl-carbonyl group optionally substituted by 1 to 3 halogen atoms;

(7) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);

(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by substituent(s) selected from
  (a) a $C_{1-6}$ alkyl group optionally substituted by 1 to 3 halogen atoms,
  (b) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
  (c) a $C_{6-14}$ arylsulfonyl group (e.g., phenylsulfonyl) optionally substituted by an aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (d) an aromatic heterocyclic group (e.g., thienyl, furyl, pyridyl, pyrazolyl, imidazolyl, tetrazolyl, oxazolyl, thiazolyl, oxadiazolyl, thiadiazolyl);

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{1-6}$ alkoxy group optionally substituted by 1 to 3 substituents selected from
  (a) halogen atom,
  (b) carboxy group,
  (c) hydroxy group,
  (d) a $C_{1-6}$ alkoxy-carbonyl group optionally substituted by 1 to 3 $C_{6-14}$ aryl group (e.g., phenyl),
  (d) a $C_{1-6}$ alkoxy group, and
  (f) an amino group optionally mono- or di-substituted by substituent(s) selected from a $C_{1-6}$ alkyl group and $C_{1-6}$ alkoxy-carbonyl group;

(15) a $C_{2-6}$ alkenyloxy group (e.g., ethenyloxy) optionally substituted by 1 to 3 halogen atoms;

(16) a $C_{7-13}$ aralkyloxy group (e.g., benzyloxy);

(17) a $C_{6-14}$ aryloxy group (e.g., phenyloxy, naphthyloxy);

(18) a $C_{1-6}$ alkyl-carbonyloxy group (e.g., acetyloxy, tert-butylcarbonyloxy);

(19) a $C_{6-14}$ aryl-carbonyl group optionally substituted by 1 to 3 substituents selected from
  (a) a halogen atom, and
  (b) a $C_{1-6}$ alkyl group optionally substituted by 1 to 3 halogen atoms;

(20) a non-aromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;

(21) a mercapto group;

(22) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;

(23) a $C_{7-13}$ aralkylthio group (e.g., benzylthio);

(24) a $C_{6-14}$ arylthio group (e.g., phenylthio, naphthylthio);

(25) a cyano group;

(26) a nitro group;

(27) a halogen atom;

(28) a $C_{1-3}$ alkylenedioxy group;

(29) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms;

(30) a formyl group;

(31) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);

(32) a $C_{2-10}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a non-aromatic heterocyclic group (e.g., tetrahydrofuryl, morpholinyl, thiomorpholinyl, piperidinyl, pyrrolidinyl, piperazinyl, thiazolidinyl) optionally substituted by 1 to 3 substituents selected from
    (i) a $C_{1-6}$ alkyl group optionally substituted by 1 to 3 halogen atoms,
    (ii) a hydroxy group,
    (iii) a $C_{1-6}$ alkoxy group optionally substituted by 1 to 3 halogen atoms,
    (iv) a halogen atom, and
    (v) an oxo group;

(33) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom,
and the like.

When the number of the substituents is not less than 2, the respective substituents may be the same or different.

Preferable examples of the substituent of the "benzene optionally further substituted" for ring A include (1) a halogen atom;

(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);

(3) a $C_{1-6}$ alkoxy group optionally substituted by 1 to 3 substituents selected from
  (a) a halogen atom,
  (b) a carboxy group,
  (c) a hydroxy group, (d) a $C_{1-6}$ alkoxy-carbonyl group,
(e) a $C_{1-6}$ alkoxy group, and
(f) an amino group optionally mono- or di-substituted by $C_{1-6}$ alkyl group(s); and the like. Of these, halogen atom, optionally halogenated $C_{1-6}$ alkyl group, optionally halogenated $C_{1-6}$ alkoxy group and the like are preferable.

Examples of the aforementioned "optionally halogenated $C_{1-6}$ alkyl group" include $C_{1-6}$ alkyl group optionally having 1 to 3 halogen atoms, and the like. Specific examples include methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the aforementioned "optionally halogenated $C_{1-6}$ alkoxy group" include $C_{1-6}$ alkoxy group optionally having 1 to 3 halogen atoms, and the like. Specific examples include, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, isopentyloxy, hexyloxy and the like.

Ring A is, preferably, benzene optionally further substituted by 1 to 3 substituents selected from
(1) a halogen atom;
(2) a $C_{1-6}$ alkyl group optionally substituted by 1 to 3 substituents selected from
 (a) a halogen atom,
 (b) a carboxy group,
 (c) a hydroxy group,
 (d) a $C_{1-6}$ alkoxy-carbonyl group,
 (e) a $C_{1-6}$ alkoxy group, and
 (f) an amino group optionally mono- or di-substituted by $C_{1-6}$ alkyl group(s) (preferably, optionally halogenated $C_{1-6}$ alkyl group);
(3) a $C_{1-6}$ alkoxy group optionally substituted by 1 to 3 substituents selected from
 (a) a halogen atom,
 (b) a carboxy group,
 (c) a hydroxy group,
 (d) a $C_{1-6}$ alkoxy-carbonyl group,
 (e) a $C_{1-6}$ alkoxy group, and
 (f) an amino group optionally mono- or di-substituted by $C_{1-6}$ alkoxy group(s) (preferably, optionally halogenated $C_{1-6}$ alkoxy group); and the like.

Ring A is, more preferably, benzene optionally further substituted by 1 to 3 substituents selected from
(1) a halogen atom,
(2) an optionally halogenated $C_{1-6}$ alkyl group, and
(3) an optionally halogenated $C_{1-6}$ alkoxy group.

Ring A is, further preferably, benzene optionally further substituted by 1 to 3 substituents selected from
(1) a halogen atom, and
(2) a $C_{1-6}$ alkyl group.

$R^1$ is an optionally substituted branched $C_{3-6}$ alkyl group.

Examples of the "branched $C_{3-6}$ alkyl group" of the "optionally substituted branched $C_{3-6}$ alkyl group" for $R^1$ include isopropyl, isobutyl, sec-butyl, tert-butyl, isopentyl, neopentyl, 1-ethylpropyl, isohexyl, 1,1-dimethylbutyl, 2,2-dimethylbutyl, 3,3-dimethylbutyl, 2-ethylbutyl and the like. Of these, preferred are isopropyl and tert-butyl.

The "branched $C_{3-6}$ alkyl group" for $R^1$ optionally has 1 to 3 substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms,
 (d) a halogen atom, and
 (e) an oxo group;
(5) an amino group optionally mono- or di-substituted by substituent(s) selected from
 (a) a $C_{1-6}$ alkyl group optionally substituted by 1 to 3 halogen atoms,
 (b) a $C_{1-6}$ alkyl-carbonyl group optionally substituted by 1 to 3 halogen atoms,
 (c) a $C_{6-14}$ aryl-carbonyl group optionally substituted by 1 to 3 halogen atoms,
 (d) a $C_{1-6}$ alkoxy-carbonyl group optionally substituted by 1 to 3 halogen atoms,
 (e) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
 (f) a carbamoyl group optionally mono- or di-substituted by $C_{1-6}$ alkyl group(s) optionally substituted by 1 to 3 halogen atoms, and
 (g) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
 (a) a halogen atom,
 (b) a $C_{1-6}$ alkoxy group, and
 (c) a $C_{6-14}$ aryl group (e.g., phenyl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by substituent(s) selected from
 (a) a $C_{1-6}$ alkyl group optionally substituted by 1 to 3 halogen atoms,
 (b) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms, (c) a $C_{6-14}$ arylsulfonyl group (e.g., phenylsulfonyl) optionally substituted by an aromatic heterocyclic group (e.g., thienyl, furyl, pyridyl, pyrazolyl, imidazolyl, tetrazolyl, oxazolyl, thiazolyl, oxadiazolyl, thiadiazolyl), and (d) an aromatic heterocyclic group (e.g., thienyl, furyl, pyridyl, pyrazolyl, imidazolyl, tetrazolyl, oxazolyl, thiazolyl, oxadiazolyl, thiadiazolyl);

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{1-6}$ alkoxy group optionally substituted by 1 to 3 substituents selected from
- (a) a halogen atom,
- (b) a carboxy group,
- (c) a $C_{1-6}$ alkoxy group,
- (d) a $C_{1-6}$ alkoxy-carbonyl group optionally substituted by 1 to 3 $C_{6-14}$ aryl groups (e.g., phenyl), and
- (e) an amino group optionally mono- or di-substituted by substituent(s) selected from a $C_{1-6}$ alkyl group and a $C_{1-6}$-alkoxy-carbonyl group;

(15) a $C_{2-6}$ alkenyloxy group (e.g., ethenyloxy) optionally substituted by 1 to 3 halogen atoms;

(16) a $C_{7-13}$ aralkyloxy group (e.g., benzyloxy);

(17) a $C_{6-14}$ aryloxy group (e.g., phenyloxy, naphthyloxy);

(18) a $C_{1-6}$ alkyl-carbonyloxy group (e.g., acetyloxy, tert-butylcarbonyloxy);

(19) a $C_{6-14}$ aryl-carbonyl group optionally substituted by 1 to 3 substituents selected from
- (a) a halogen atom, and
- (b) $C_{1-6}$ alkyl groups optionally substituted by 1 to 3 halogen atoms;

(20) a non-aromatic heterocyclylcarbonyl group (e.g., pyrrolidinylcarbonyl, morpholinylcarbonyl) optionally substituted by 1 to 3 substituents selected from $C_{1-6}$ alkyl groups optionally substituted by 1 to 3 halogen atoms;

(21) a mercapto group;

(22) a $C_{1-6}$ alkylthio group (e.g., methylthio, ethylthio) optionally substituted by 1 to 3 substituents selected from
- (a) a halogen atom, and
- (b) a $C_{1-6}$ alkoxy-carbonyl group;

(23) a $C_{7-13}$ aralkylthio group (e.g., benzylthio);

(24) a $C_{6-14}$ arylthio group (e.g., phenylthio, naphthylthio) optionally substituted by a hydroxy group;

(25) a cyano group;

(26) a nitro group;

(27) a halogen atom;

(28) a $C_{1-3}$ alkylenedioxy group;

(29) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from $C_{1-6}$ alkyl groups optionally substituted by 1 to 3 halogen atoms;

(30) a $C_{7-13}$ aralkyloxy-carbonyl group (e.g., benzyloxycarbonyl);

(31) a $C_{6-14}$ arylthio group (e.g., phenylthio) optionally substituted by a hydroxy group;

(32) a $C_{6-14}$ arylsulfinyl group (e.g., phenylsulfinyl) optionally substituted by a hydroxy group;

(33) a $C_{6-14}$ arylsulfonyl group (e.g., phenylsulfonyl) optionally substituted by a hydroxy group;

(34) an aromatic heterocyclylthio group (e.g., triazolylthio);

(35) an aromatic heterocyclylsulfinyl group (e.g., triazolylsulfinyl);

(36) an aromatic heterocyclylsulfonyl group (e.g., triazolylsulfonyl);

(37) a sulfoxy group; and the like.

When the number of the substituents is not less than 2, the respective substituents may be the same or different.

The substituent of the "branched $C_{3-6}$ alkyl group" for $R^1$ is preferably (1) a hydroxy group;

(2) an amino group optionally mono- or di-substituted by substituent(s) selected from
- (a) a $C_{1-6}$ alkyl group optionally substituted by 1 to 3 halogen atoms,
- (b) a $C_{1-6}$ alkyl-carbonyl group optionally substituted by 1 to 3 halogen atoms, and
- (c) a $C_{1-6}$ alkylsulfonyl group optionally substituted by 1 to 3 halogen atoms;

(3) cyano group and the like.

$R^1$ is, preferably, a branched $C_{3-6}$ alkyl group (preferably, isopropyl, tert-butyl) optionally substituted by 1 to 3 substituents selected from (1) a hydroxy group;

(2) an amino group optionally mono- or di-substituted by substituent(s) selected from
- (a) a $C_{1-6}$ alkyl group optionally substituted by 1 to 3 halogen atoms,
- (b) a $C_{1-6}$ alkyl-carbonyl group optionally substituted by 1 to 3 halogen atoms, and
- (c) a $C_{1-6}$ alkylsulfonyl group optionally substituted by 1 to 3 halogen atoms; and (3) a cyano group.

$R^1$ is, more preferably, isopropyl or tert-butyl.

$X^1$ is O, S, SO, $SO_2$ or NH.

Preferably $X^1$ is O.

$X^2$ is a bond or a $C_{1-3}$ alkylene group.

Examples of the "$C_{1-3}$ alkylene group" for $X^2$ include —$CH_2$—, —$(CH_2)_2$—, —$(CH_2)_3$—, —$CH(CH_3)$—, —CH($C_2H_5$)—, —$CH(CH_3)CH_2$—, —$CH_2CH(CH_3)$—, —$C(CH_3)_2$—, —$CH_2$—$CH(CH_3)$— and the like. Of these, preferably is —$CH_2$—, —$CH(CH_3)$—, —$(CH_2)_2$— and —$(CH_2)_3$—. More preferred is —$CH_2$-(methylene).

$X^2$ is preferably a bond, —$CH_2$—, —$CH(CH_3)$—, —$(CH_2)_2$— or —$(CH_2)_3$—. $X^2$ is more preferably a bond or —$CH_2$—.

Ring B is azetidine, pyrrolidine or piperidine.

Preferably, ring B is

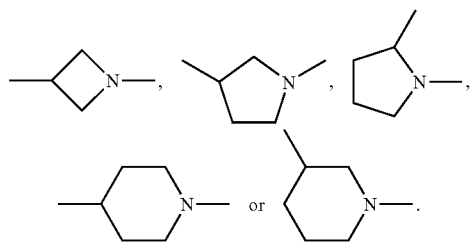

Ring B is more preferably

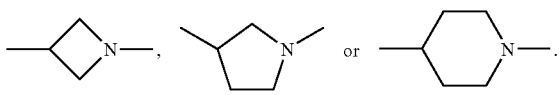

$X^3$ is CO or $SO_2$.

In compound (I), when —$X^1$—$X^2$— is —NH— and ring B is piperidine, then $X^3$ is CO.

$X^3$ is preferably CO.

$R^2$ is a substituent.

In compound (I), when $X^3$ is CO, then $R^2$ is not a tert-butoxy group.

Examples of the "substituent" for $R^2$ include an "optionally substituted hydrocarbon group", an "optionally substituted heterocyclic group", an "optionally substituted hydroxy group", an "optionally substituted mercapto group", an "optionally substituted amino group", a "cyano group", a "nitro group", an "acyl group", a "halogen atom" and the like.

Examples of the "hydrocarbon group" of the "optionally substituted hydrocarbon group" for $R^2$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

Examples of the $C_{3-10}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Examples of the $C_{3-10}$ cycloalkenyl group include 2-cyclopenten-1-yl, 3-cyclopenten-1-yl, 2-cyclohexen-1-yl, 3-cyclohexen-1-yl and the like.

Examples of the $C_{4-10}$ cycloalkadienyl group include 2,4-cyclopentadien-1-yl, 2,4-cyclohexadien-1-yl, 2,5-cyclohexadien-1-yl and the like.

The above-mentioned $C_{3-10}$ cycloalkyl group, $C_{3-10}$ cycloalkenyl group and $C_{4-10}$ cycloalkadienyl group each may form a fused ring group with a benzene ring. Examples of the fused ring group include indanyl, dihydronaphthyl, tetrahydronaphthyl, fluorenyl and the like.

Examples of the $C_{6-14}$ aryl group include phenyl, naphthyl, anthryl, phenanthryl, acenaphthyl, biphenylyl and the like.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable positions.

Examples of the substituent include those similar to the substituent of the aforementioned "optionally substituted branched $C_{3-6}$ alkyl group" for $R^1$. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group exemplified as the aforementioned "hydrocarbon group" optionally have 1 to 3 substituents at substitutable position(s).

Examples of the substituent include those similar to the substituent of the aforementioned "benzene optionally further substituted" for ring A. When the number of the substituents is not less than 2, the respective substituents may be the same or different.

Examples of the "heterocyclic group" of the "optionally substituted heterocyclic group" for $R^2$ include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms elected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include a monocyclic aromatic heterocyclic group such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

a fused aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2- a]pyridin-3-yl), imidazothiazolyl (e.g., imidazo[2,1-b]thiazol-6-yl), thienopyridinyl (e.g., thieno[2,3-b]pyridin-3-yl), thienopyrazinyl (e.g., thieno[2,3-b]pyrazin-6-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms elected from an oxygen atom, a sulfur atom and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, a group wherein the above-mentioned group is partially saturated, and the like.

Preferable examples of the non-aromatic heterocyclic group include
a monocyclic non-aromatic heterocyclic group such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimine-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;
a fused non-aromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like.

The "heterocyclic group" of the above-mentioned "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the above-mentioned "optionally substituted hydrocarbon group" optionally has. When the heterocyclic group is a "non-aromatic heterocyclic group", the substituent further includes an oxo group. When the number of the substituents is not less than 2, the respective substituents may be the same or different.

Examples of the "optionally substituted hydroxy group" for $R^2$ include a hydroxyl group optionally substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Here, examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the aforementioned "optionally substituted hydrocarbon group".

Examples of the heterocyclic group include those similar to the "heterocyclic group" of the aforementioned "optionally substituted heterocyclic group".

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group each optionally have 1 to 3 substituents at substitutable positions. When the number of the substituents is not less than 2, the respective substituents may be the same or different.

Here, examples of the substituent of the $C_{1-10}$ alkyl group, $C_{2-10}$ alkenyl group and $C_{1-6}$ alkyl-carbonyl group include those similar to the substituents that the $C_{1-10}$ alkyl group and the like exemplified as the "hydrocarbon group" in the aforementioned "optionally substituted hydrocarbon group" optionally have.

In addition, examples of the substituent of the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituents that the $C_{3-10}$ cycloalkyl group and the like exemplified as the "hydrocarbon group" in the aforementioned "optionally substituted hydrocarbon group" optionally have. Examples of the substituent of the heterocyclic group include those similar to the substituents of the aforementioned "optionally substituted heterocyclic group".

Examples of the "optionally substituted mercapto group" for $R^2$ include a mercapto group optionally substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the substituent include those similar to the substituents of the aforementioned "optionally substituted hydroxy group".

Examples of the "optionally substituted amino group" for $R^2$ include a mono- or di-substituted amino group optionally substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, and an acyl group and the like, each of which is optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "heterocyclic group" of the above-mentioned "optionally substituted heterocyclic group". Of these, a 5- to 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituents that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituents that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituents of the above-mentioned "optionally substituted heterocyclic group".

Examples of the "acyl group" exemplified as the substituent of the "optionally substituted amino group" for $R^2$ include a group represented by the formula: $-COR^A$, $-CO-OR^A$, $-SO_3R^A$, $-SO_2R^A$, $-SOR^A$, $-CO-NR^{A'}R^{B'}$, $R^{B'}$ or $-SO_2NR^{A'}R^{B'}$, wherein $R^A$ is a hydrogen atom, an optionally substituted hydrocarbon group or an optionally substituted heterocyclic group, $R^{A'}$ and $R^{B'}$ are each independently a hydrogen atom, a sulfamoyl group optionally mono- or di-substituted by a $C_{1-6}$ alkyl group(s), a sulfonyl group optionally mono- or di-substituted by a $C_{1-6}$ alkyl group, an optionally substituted hydrocarbon group or an optionally substituted heterocyclic group, or $R^{A'}$ and $R^{B'}$ form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A'}$ or $R^{B'}$ include those similar to the "optionally substituted hydrocarbon group" and "optionally substituted heterocyclic group", which are exemplified as the "substituent" for $R^2$.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 3 substituents at substitutable positions. Examples of the substituent include those similar to the substituents of the above-mentioned "optionally substituted heterocyclic group". When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group optionally substituted by 1 to 3 substituents selected from
   (i) a halogen atom,
   (ii) a $C_{1-6}$ alkoxy-carbonyl group,
   (iii) a $C_{6-14}$ aryl group (e.g., phenyl), and
   (iv) a $C_{1-6}$ alkoxy group;
(4) a $C_{1-6}$ alkoxy-carbonyl group optionally substituted by 1 to 3 substituents selected from
   (i) a halogen atom,
   (ii) a $C_{6-14}$ aryl group (e.g., phenyl), and
   (iii) a $C_{1-6}$ alkoxy group;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group optionally substituted by 1 to 3 halogen atoms;
(7) a carbamoyl group optionally mono- or di-substituted by substituent(s) selected from
   (i) a $C_{1-6}$ alkyl group optionally substituted by 1 to 3 substituents selected from
      (a) a halogen atom,
      (b) a $C_{1-6}$ alkoxy-carbonyl group,
      (c) a $C_{6-14}$ aryl group (e.g., phenyl),
      (d) a $C_{1-6}$ alkoxy group,
      (e) a hydroxy group, and
      (f) an aromatic heterocyclic group (e.g., thienyl, furyl, pyridyl, pyrazolyl, imidazolyl, tetrazolyl, oxazolyl, thiazolyl, oxadiazolyl, thiadiazolyl),
   (ii) a $C_{3-10}$ cycloalkyl group (e.g., cyclohexyl),
   (iii) a $C_{6-14}$ aryl group (e.g., phenyl) optionally substituted by 1 to 3 substituents selected from
      (a) a halogen atom,
      (b) a $C_{1-6}$ alkyl group optionally substituted by 1 to 3 halogen atoms, and
      (c) a $C_{1-6}$ alkoxy group,
   (iv) an aromatic heterocyclic group (e.g., thienyl, furyl, pyridyl, pyrazolyl, imidazolyl, tetrazolyl, oxazolyl, triazolyl, thiazolyl, oxadiazolyl, thiadiazolyl),
   (v) a sulfamoyl group optionally mono- or di-substituted by $C_{1-6}$ alkyl group,
   (vi) a sulfonyl group mono- or di-optionally substituted by $C_{1-6}$ alkyl group,
   (vii) a $C_{1-6}$ alkoxy group;
(8) a $C_{1-6}$ alkylsulfonyl group (e.g., methylsulfonyl, ethylsulfonyl, isopropylsulfonyl) optionally substituted by 1 to 3 substituents selected from
   (i) a halogen atom, and
   (ii) a $C_{6-14}$ aryl group (e.g., phenyl);
(9) a $C_{6-14}$ arylsulfonyl group (e.g., benzenesulfonyl) optionally substituted by 1 to 3 halogen atoms;
(10) a sulfamoyl group optionally mono- or di-substituted by substituent(s) selected from
   (i) a $C_{1-6}$ alkyl group optionally substituted by 1 to 3 substituents selected from
      (a) a halogen atom, and
      (b) a non-aromatic heterocyclic group (e.g., pyrrolidinyl) optionally substituted by oxo group(s);
(11) a thiocarbamoyl group optionally mono- or di-substituted by substituent(s) selected from a $C_{1-6}$ alkyl group optionally substituted by 1 to 3 halogen atoms;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl) optionally substituted by 1 to 3 substituents selected from a $C_{1-6}$ alkyl group optionally substituted by 1 to 3 halogen atoms; and the like.

Examples of the "acyl group" for $R^2$ include those similar to the "acyl group" exemplified as the substituent of the above-mentioned "optionally substituted amino group" for $R^2$.

$R^2$ is, preferably,
(1) an optionally substituted hydrocarbon group,
(2) an optionally substituted heterocyclic group,
(3) an acyl group,
(4) an optionally substituted amino group,
(5) an optionally substituted hydroxy group, and the like.

$R^2$ is, more preferably,
(1) a $C_{1-10}$ alkyl group optionally substituted by 1 to 3 substituents selected from
    (i) a $C_{6-14}$ aryl group (e.g., phenyl) optionally substituted by 1 to 3 halogen atoms,
    (ii) a $C_{6-14}$ aryl-carbonyl group,
    (iii) a carboxy group,
    (iv) a $C_{1-6}$ alkoxy-carbonyl group,
    (v) a cyano group,
    (vi) a carbamoyl group monosubstituted by a $C_{6-14}$ arylsulfonyl group (e.g., phenylsulfonyl) optionally substituted by an aromatic heterocyclic group (e.g., oxazolyl),
    (vii) a carbamoyl group monosubstituted by a $C_{1-6}$ alkylsulfonyl group (e.g., methylsulfonyl, pentylsulfonyl),
    (viii) a carbamoyl group monosubstituted by an aromatic heterocyclic group (e.g., tetrazolyl),
    (ix) a $C_{7-13}$ aralkyloxy-carbonyl group (e.g., benzyloxycarbonyl),
    (x) a hydroxy group,
    (xi) an aromatic heterocyclic group (e.g., tetrazolyl),
    (xii) a non-aromatic heterocyclic group (e.g., dihydrooxadiazolyl) optionally substituted by an oxo group,
    (xiii) a $C_{6-14}$ arylthio group (e.g., phenylthio) optionally substituted by a hydroxy group,
    (xiv) a $C_{6-14}$ arylsulfinyl group (e.g., phenylsulfinyl) optionally substituted by a hydroxy group,
    (xv) a $C_{6-14}$ arylsulfonyl group (e.g., phenylsulfonyl) optionally substituted by a hydroxy group,
    (xvi) an aromatic heterocyclylthio group (e.g., triazolylthio),
    (xvii) an aromatic heterocyclylsulfinyl group (e.g., triazolylsulfinyl),
    (xviii) an aromatic heterocyclylsulfonyl group (e.g., triazolylsulfonyl), and
    (xix) a sulfoxy group;
(2) a $C_{2-10}$ alkenyl group optionally substituted by 1 to 3 substituents selected from
    (i) a carboxy group, and
    (ii) a $C_{1-6}$ alkoxy-carbonyl group;
(3) a $C_{3-10}$ cycloalkyl group (e.g., cyclopropyl) optionally substituted by 1 to 3 substituents selected from
    (i) a carboxy group,
    (ii) a $C_{1-6}$ alkoxy-carbonyl group,
    (iii) a cyano group,
    (iv) a formyl group, and
    (v) a $C_{2-10}$ alkenyl group substituted by non-aromatic heterocyclic group (e.g., thiazolidinyl) optionally substituted by oxo group;
(4) a $C_{6-14}$ aryl group optionally substituted by 1 to 3 substituents selected from
    (i) a carboxy group,
    (ii) a $C_{1-6}$ alkoxy-carbonyl group,
    (iii) a cyano group,
    (iv) a $C_{1-6}$ alkyl-carbonyl group,
    (v) a formyl group,
    (vi) a $C_{1-6}$ alkyl group optionally substituted by 1 to 3 substituents selected from
        (a) a hydroxy group,
        (b) a carboxy group, and
        (c) a $C_{1-6}$ alkoxy-carbonyl group,
    (vii) a $C_{2-10}$ alkenyl group optionally substituted by 1 to 3 substituents selected from
        (a) a non-aromatic heterocyclic group (e.g., thiazolidinyl) optionally substituted by oxo group,
        (b) a carboxy group, and
        (c) a $C_{1-6}$ alkoxy-carbonyl group,
    (viii) a non-aromatic heterocyclic group (e.g., dihydrooxadiazolyl) substituted by oxo group,
    (ix) a hydroxy group, and
    (x) a $C_{1-6}$ alkoxy group optionally substituted by 1 to 3 substituents selected from
        (a) a halogen atom,
        (b) a carboxy group, and
        (c) a $C_{1-6}$ alkoxy-carbonyl group;
(5) a heterocyclic group (e.g., monocyclic aromatic heterocyclic group (e.g., pyridyl, oxazolyl, isoxazolyl, thiazolyl, pyrazinyl, pyrimidinyl), fused aromatic heterocyclic group (e.g., benzothiazolyl, imidazothiazolyl, pyrazolopyridinyl, imidazopyridinyl, thienopyrazinyl)), monocyclic non-aromatic heterocyclic group (e.g., piperidinyl, dihydropyridyl, isothiazolidinyl) optionally substituted by 1 to 3 substituents selected from
    (i) a $C_{1-6}$ alkyl group,
    (ii) an oxo group,
    (iii) a hydroxy group, and
    (iv) a sulfonyl group optionally substituted by a $C_{1-6}$ alkyl group (e.g., methyl);
(6) a carbamoyl group optionally mono- or di-substituted by substituent(s) selected from
    (i) a $C_{1-6}$ alkyl group optionally substituted by 1 to 3 substituents selected from
        (a) a $C_{6-14}$ aryl group (e.g., phenyl),
        (b) a hydroxy group, and
        (c) a $C_{1-6}$ alkoxy group,
    (ii) a $C_{3-10}$ cycloalkyl group (e.g., cyclohexyl),
    (iii) a $C_{6-14}$ aryl group (e.g., phenyl),
    (iv) a sulfamoyl group optionally substituted by a $C_{1-6}$ alkyl group (e.g., pentyl),
    (v) a sulfonyl group optionally substituted by a $C_{1-6}$ alkyl group (e.g., pentyl),
    (vi) a $C_{1-6}$ alkoxy group,
    (vii) an aromatic heterocyclic group (e.g., triazolyl), and
    (viii) an amino group optionally substituted by a $C_{1-6}$ alkoxy-carbonyl group (e.g. tert-butoxycarbonyl)
(7) an amino group optionally mono- or di-substituted by substituent(s) selected from a $C_{1-6}$ alkyl group;
(8) a hydroxy group;
(9) a $C_{1-6}$ alkoxy group;
(10) a carboxy group;
(11) a $C_{1-6}$ alkoxy-carbonyl group; and the like.

In addition, $R^2$ is, preferably,
(1) an optionally substituted hydrocarbon group,
(2) an acyl group, and the like.

$R^2$ is, further preferably,
(1) a $C_{1-10}$ alkyl group optionally substituted by 1 to 3 substituents selected from
    (i) a $C_{6-14}$ aryl group (e.g., phenyl) optionally substituted by 1 to 3 halogen atoms,
    (ii) a $C_{6-14}$ aryl-carbonyl group,
    (iii) a carboxy group,
    (iv) a $C_{1-6}$ alkoxy-carbonyl group,
    (v) a cyano group, (vi) a carbamoyl group monosubstituted by a $C_{6-14}$ arylsulfonyl group (e.g., phenylsulfonyl) optionally substituted by an aromatic heterocyclic group (e.g., oxazolyl),
(vii) a carbamoyl group monosubstituted by a $C_{1-6}$ alkylsulfonyl group (e.g., methylsulfonyl, pentylsulfonyl),
(viii) a carbamoyl group monosubstituted by an aromatic heterocyclic group (e.g., tetrazolyl), and
(xi) an aromatic heterocycle (e.g., tetrazolyl);
(2) a carbamoyl group optionally mono- or di-substituted by substituent(s) selected from
(i) a $C_{1-6}$ alkyl group optionally substituted by 1 to 3 substituents selected from
(a) a $C_{6-14}$ aryl group (e.g., phenyl), and
(b) a hydroxy group,
(ii) a $C_{3-10}$ cycloalkyl group (e.g., cyclohexyl),
(iii) a $C_{6-14}$ aryl group (e.g., phenyl),
(iv) a sulfamoyl group optionally substituted by a $C_{1-6}$ alkyl group (e.g., pentyl),
(v) a sulfonyl group optionally substituted by a $C_{1-6}$ alkyl group (e.g., pentyl),
(vi) a $C_{1-6}$ alkoxy group, and
(vii) an aromatic heterocyclic group (e.g., triazolyl);
(3) a carboxy group;
(4) a $C_{1-6}$ alkoxy-carbonyl group; and the like.

Preferable examples of compound (I) include the following compounds.
[Compound A1]
A compound (I) wherein ring A is benzene optionally substituted by 1 to 4 substituents in addition to $R^1$, which are selected from
(1) a halogen atom;
(2) a $C_{1-6}$ alkyl group optionally substituted by 1 to 3 substituents selected from
(a) to (a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s)
(preferably, optionally halogenated $C_{1-6}$ alkyl group); and
(3) a $C_{1-6}$ alkoxy group optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s)
(preferably, optionally halogenated $C_{1-6}$ alkoxy group);
$R^1$ is a branched $C_{3-6}$ alkyl group (preferably, isopropyl, tert-butyl) optionally substituted by 1 to 3 substituents selected from
(1) a hydroxy group;
(2) an amino group optionally mono- or di-substituted by substituent(s) selected from
(a) a $C_{1-6}$ alkyl group optionally substituted by 1 to 3 halogen atoms,
(b) a $C_{1-6}$ alkyl-carbonyl group optionally substituted by 1 to 3 halogen atoms, and
(c) a $C_{1-6}$ alkylsulfonyl group optionally substituted by 1 to 3 halogen atoms; and
(3) a cyano group;
$X^1$ is O, S, SO, $SO_2$ or NH (preferably, O);
$X^2$ is a bond, —$CH_2$—, —$CH(CH_3)$—, —$(CH_2)_2$—, or —$(CH_2)_3$— (preferably, a bond or —$CH_2$—);

ring B is azetidine, pyrrolidine or piperidine (preferably, (preferably, 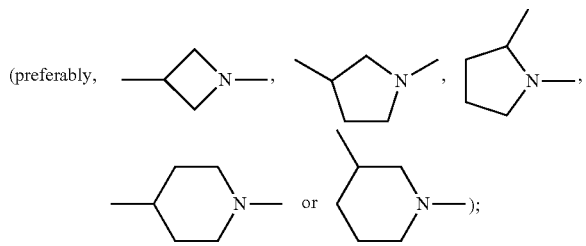

$X^3$ is CO or $SO_2$ (preferably, CO); and
$R^2$ is
(1) a $C_{1-10}$ alkyl group optionally substituted by 1 to 3 substituents selected from
(i) a $C_{6-14}$ aryl group (e.g., phenyl) optionally substituted by 1 to 3 halogen atoms,
(ii) a $C_{6-14}$ aryl-carbonyl group,
(iii) a carboxy group,
(iv) a $C_{1-6}$ alkoxy-carbonyl group,
(v) a cyano group,
(vi) a carbamoyl group monosubstituted by a $C_{6-14}$ arylsulfonyl group (e.g., phenylsulfonyl) optionally substituted by aromatic heterocyclic group (e.g., oxazolyl),
(vii) a carbamoyl group monosubstituted by a $C_{1-6}$ alkylsulfonyl group (e.g., methylsulfonyl, pentylsulfonyl),
(viii) a carbamoyl group monosubstituted by an aromatic heterocyclic group (e.g., tetrazolyl),
(ix) a $C_{7-13}$ aralkyloxy-carbonyl group (e.g., benzyloxycarbonyl),
(x) a hydroxy group,
(xi) an aromatic heterocycle (e.g., tetrazolyl),
(xii) a non-aromatic heterocyclic group (e.g., dihydrooxadiazolyl) optionally substituted by an oxo group,
(xiii) a $C_{6-14}$ arylthio group (e.g., phenylthio) optionally substituted by a hydroxy group,
(xiv) a $C_{6-14}$ arylsulfinyl group (e.g., phenylsulfinyl) optionally substituted by a hydroxy group,
(xv) a $C_{6-14}$ arylsulfonyl group (e.g., phenylsulfonyl) optionally substituted by hydroxy group,
(xvi) an aromatic heterocyclylthio group (e.g., triazolylthio),
(xvii) an aromatic heterocyclylsulfinyl group (e.g., triazolylsulfinyl),
(xviii) an aromatic heterocyclylsulfonyl group (e.g., triazolylsulfonyl), and
(xix) a sulfoxy group;
(2) a $C_{2-10}$ alkenyl group optionally substituted by 1 to 3 substituents selected from
(i) a carboxy group, and
(ii) a $C_{1-6}$ alkoxy-carbonyl group;
(3) a $C_{3-10}$ cycloalkyl group (e.g., cyclopropyl) optionally substituted by 1 to 3 substituents selected from
(i) a carboxy group,
(ii) a $C_{1-6}$ alkoxy-carbonyl group,
(iii) a cyano group,
(iv) a formyl group, and
(v) a $C_{2-10}$ alkenyl group substituted by a non-aromatic heterocyclic group (e.g., thiazolidinyl) optionally substituted by an oxo group;
(4) a $C_{6-14}$ aryl group optionally substituted by 1 to 3 substituents selected from
(i) a carboxy group,
(ii) a $C_{1-6}$ alkoxy-carbonyl group, (iii) a cyano group,
(iv) a $C_{1-6}$ alkyl-carbonyl group,
(v) a formyl group,
(vi) a $C_{1-6}$ alkyl group optionally substituted by 1 to 3 substituents selected from
  (a) a hydroxy group,
  (b) a carboxy group, and
  (c) a $C_{1-6}$ alkoxy-carbonyl group,
(vii) a $C_{2-10}$ alkenyl group optionally substituted by 1 to 3 substituents selected from
  (a) a non-aromatic heterocyclic group (e.g., thiazolidinyl) optionally substituted by an oxo group,
  (b) a carboxy group, and
  (c) a $C_{1-6}$ alkoxy-carbonyl group,
(viii) a non-aromatic heterocyclic group (e.g., dihydrooxadiazolyl) substituted by oxo group,
(ix) a hydroxy group, and
(x) a $C_{1-6}$ alkoxy group optionally substituted by 1 to 3 substituents selected from
  (a) a halogen atom,
  (b) a carboxy group, and
  (c) a $C_{1-6}$ alkoxy-carbonyl group;
(5) a heterocyclic group (e.g., monocyclic aromatic heterocyclic group (e.g., pyridyl, oxazolyl, isoxazolyl, thiazolyl, pyrazinyl, pyrimidinyl), fused aromatic heterocyclic group (e.g., benzothiazolyl, imidazothiazolyl, pyrazolopyridinyl, imidazopyridinyl, thienopyrazinyl), monocyclic non-aromatic heterocyclic group (e.g., piperidinyl, dihydropyridyl, isothiazolidinyl)) optionally substituted by 1 to 3 substituents selected from
  (i) a $C_{1-6}$ alkyl group,
  (ii) an oxo group,
  (iii) a hydroxy group, and
  (iv) a sulfonyl group optionally substituted by $C_{1-6}$ alkyl group (e.g., methyl);
(6) a carbamoyl group optionally mono- or di-substituted by substituent(s) selected from
  (i) a $C_{1-6}$ alkyl group optionally substituted by 1 to 3 substituents selected from
    (a) a $C_{6-14}$ aryl group (e.g., phenyl),
    (b) a hydroxy group, and
    (c) a $C_{1-6}$ alkoxy group,
  (ii) a $C_{3-10}$ cycloalkyl group (e.g., cyclohexyl),
  (iii) a $C_{6-14}$ aryl group (e.g., phenyl),
  (iv) a sulfamoyl group optionally substituted by a $C_{1-6}$ alkyl group (e.g., pentyl),
  (v) a sulfonyl group optionally substituted by a $C_{1-6}$ alkyl group (e.g., pentyl),
  (vi) a $C_{1-6}$ alkoxy group,
  (vii) an aromatic heterocyclic group (e.g., triazolyl), and
  (viii) an amino group optionally substituted by a $C_{1-6}$ alkoxy-carbonyl group (e.g., tert-butoxycarbonyl);
(7) an amino group optionally mono- or di-substituted by substituent(s) selected from a $C_{1-6}$ alkyl group;
(8) a hydroxy group;
(9) a $C_{1-6}$ alkoxy group;
(10) a carboxy group; or
(11) a $C_{1-6}$ alkoxy-carbonyl group.
[Compound A2]
A compound (I) wherein
ring A is benzene optionally substituted by 1 to 4 substituents in addition to $R^1$, which are selected from
(1) a halogen atom; and
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s)
(preferably, unsubstituted $C_{1-6}$ alkyl group);
$R^1$ is a branched $C_{3-6}$ alkyl group (preferably, isopropyl, tert-butyl) optionally substituted by 1 to 3 substituents selected from
  (1) a hydroxy group;
  (2) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms, and
    (c) a $C_{1-6}$ alkylsulfonyl group optionally substituted by 1 to 3 halogen atoms; and
  (3) a cyano group;
$X^1$ is O, S, SO, $SO_2$ or NH (preferably, O);
$X^2$ is a bond, —$CH_2$—, —$CH(CH_3)$—, —$(CH_2)_2$—, or —$(CH_2)_3$— (preferably, a bond or —$CH_2$—);
ring B is azetidine, pyrrolidine or piperidine;
$X^3$ is CO or $SO_2$ (preferably, CO); and
$R^2$ is
(1) a $C_{1-10}$ alkyl group optionally substituted by 1 to 3 substituents selected from
  (i) a $C_{6-14}$ aryl group (e.g., phenyl) optionally substituted by 1 to 3 halogen atoms,
  (ii) a $C_{6-14}$ aryl-carbonyl group,
  (iii) a carboxy group,
  (iv) a $C_{1-6}$ alkoxy-carbonyl group,
  (v) a cyano group,
  (vi) a carbamoyl group monosubstituted by a $C_{6-14}$ arylsulfonyl group (e.g., phenylsulfonyl) optionally substituted by aromatic heterocyclic group (e.g., oxazolyl),
  (vii) a carbamoyl group monosubstituted by a $C_{1-6}$ alkylsulfonyl group (e.g., methylsulfonyl, pentylsulfonyl),
  (viii) a carbamoyl group monosubstituted by an aromatic heterocyclic group (e.g., tetrazolyl);
(2) a $C_{2-10}$ alkenyl group optionally substituted by 1 to 3 substituents selected from
  (i) a carboxy group, and
  (ii) a $C_{1-6}$ alkoxy-carbonyl group;
(3) a $C_{3-10}$ cycloalkyl group (e.g., cyclopropyl) optionally substituted by 1 to 3 substituents selected from
  (i) a carboxy group,
  (ii) a $C_{1-6}$ alkoxy-carbonyl group,
  (iii) a cyano group,
  (iv) a $C_{2-10}$ alkenyl group substituted by a non-aromatic heterocyclic group (e.g., thiazolidinyl) optionally substituted by an oxo group;
(4) a $C_{6-14}$ aryl group optionally substituted by 1 to 3 substituents selected from
  (i) a carboxy group,
  (ii) a $C_{1-6}$ alkoxy-carbonyl group,
  (iii) a cyano group,
  (iv) a $C_{1-6}$ alkyl-carbonyl group,
  (v) a formyl group,
  (vi) a $C_{1-6}$ alkyl group optionally substituted by 1 to 3 substituents selected from
    (a) a hydroxy group, and
    (b) a $C_{1-6}$ alkoxy-carbonyl group,
  (vii) a $C_{2-10}$ alkenyl group optionally substituted by 1 to 3 substituents selected from
    (a) a non-aromatic heterocyclic group (e.g., thiazolidinyl) optionally substituted by an oxo group, (b) a carboxy group, and
(c) a $C_{1-6}$ alkoxy-carbonyl group,
(viii) a non-aromatic heterocyclic group (e.g., dihydrooxadiazolyl) substituted by oxo group;
(5) a heterocyclic group (e.g., monocyclic aromatic heterocyclic group (e.g., pyridyl, oxazolyl, isoxazolyl, thiazolyl, pyrazinyl, pyrimidinyl), fused aromatic heterocyclic group (e.g., benzothiazolyl, imidazothiazolyl, pyrazolopyridinyl, imidazopyridinyl, thienopyrazinyl)) optionally substituted by 1 to 3 substituents selected from a $C_{1-6}$ alkyl group;
(6) a carbamoyl group optionally mono- or di-substituted by substituent(s) selected from
(i) a $C_{1-6}$ alkyl group optionally substituted by a $C_{6-14}$ aryl group (e.g., phenyl),
(ii) a $C_{3-10}$ cycloalkyl group (e.g., cyclohexyl),
(iii) a $C_{6-14}$ aryl group (e.g., phenyl),
(iv) a sulfamoyl group optionally substituted by a $C_{1-6}$ alkyl group (e.g., pentyl), and
(v) a sulfonyl group optionally substituted by a $C_{1-6}$ alkyl group (e.g., pentyl);
(7) an amino group optionally mono- or di-substituted by substituent(s) selected from a $C_{1-6}$ alkyl group;
(8) a hydroxy group;
(9) a $C_{1-6}$ alkoxy group;
(10) a carboxy group; or
(11) a $C_{1-6}$ alkoxy-carbonyl group.
[Compound B1]
A compound (I) wherein ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group; ring B is azetidine, pyrrolidine or piperidine;
$X^3$ is CO; and
$R^2$ is an acyl group or an optionally substituted hydrocarbon group.
[Compound B2]
A compound (I) wherein
ring A is benzene optionally further substituted by 1 to 3 substituents in addition to $R^1$, which are selected from
(1) a halogen atom,
(2) an optionally halogenated $C_{1-6}$ alkyl group, and
(3) an optionally halogenated $C_{1-6}$ alkoxy group;
$R^1$ is an optionally substituted branched $C_{3-6}$ alkyl group;
$X^1$ is O, S, SO, $SO_2$ or NH;
$X^2$ is a bond or $C_{1-3}$ alkylene group;
ring B is azetidine, pyrrolidine or piperidine;
$X^3$ is CO; and
$R^2$ is an acyl group or an optionally substituted hydrocarbon group.
[Compound B3]
A compound (I) wherein
ring A is benzene optionally further substituted by 1 to 3 substituents in addition to $R^1$, which are selected from
(1) a halogen atom,
(2) an optionally halogenated $C_{1-6}$ alkyl group, and
(3) an optionally halogenated $C_{1-6}$ alkoxy group;
$R^1$ is an optionally substituted branched $C_{3-6}$ alkyl group;
$X^1$ is O;
$X^2$ is a bond or methylene group;
ring B is azetidine, pyrrolidine or piperidine;
$X^3$ is CO; and
$R^2$ is an acyl group or an optionally substituted hydrocarbon group.

[Compound 34]
A compound (I) wherein
ring A is benzene optionally further substituted by 1 to 3 substituents in addition to $R^1$, which are selected from
(1) a halogen atom,
(2) an optionally halogenated $C_{1-6}$ alkyl group, and
(3) an optionally halogenated $C_{1-6}$ alkoxy group;
$R^1$ is an optionally substituted branched $C_{3-6}$ alkyl group;
$X^1$ is O, S, SO, $SO_2$ or NH;
$X^2$ is a bond or $C_{1-3}$ alkylene group;
ring B is

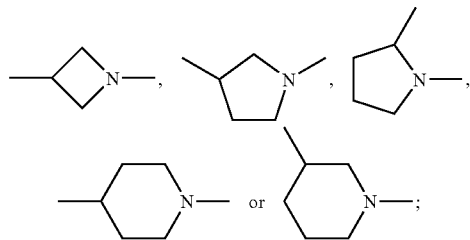

$X^3$ is CO; and
$R^2$ is an acyl group or an optionally substituted hydrocarbon group.
[Compound B5]
A compound (I) wherein
ring A is benzene optionally further substituted by 1 to 3 substituents in addition to $R^1$, which are selected from
(1) a halogen atom,
(2) an optionally halogenated $C_{1-6}$ alkyl group, and
(3) an optionally halogenated $C_{1-6}$ alkoxy group;
$R^1$ is an optionally substituted branched $C_{3-6}$ alkyl group (preferably, isopropyl group or tert-butyl group);
$X^1$ is O;
$X^2$ is a bond or methylene;
ring B is

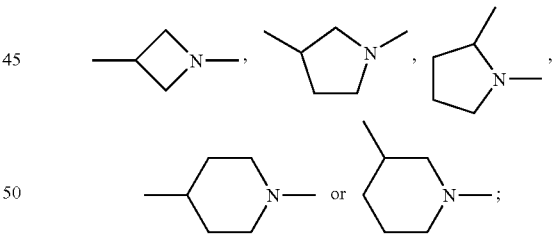

$X^3$ is CO; and
$R^2$ is an acyl group or an optionally substituted hydrocarbon group.
[Compound C1]
A compound (I) wherein
ring A is benzene optionally further substituted by 1 to 3 substituents in addition to $R^1$, which are selected from
(1) a halogen atom,
(2) an optionally halogenated $C_{1-6}$ alkyl group, and
(3) an optionally halogenated $C_{1-6}$ alkoxy group;
$R^1$ is isopropyl group or tert-butyl group;
$X^1$ is O;
$X^2$ is a bond or methylene;

ring B is

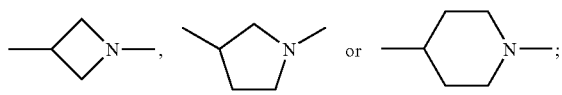

X³ is CO; and
R² is an acyl group or an optionally substituted hydrocarbon group.
[Compound C2]
A compound (I) wherein
ring A is benzene optionally further substituted by 1 to 3 substituents in addition to R¹, which are selected from
(1) a halogen atom,
(2) an optionally halogenated $C_{1-6}$ alkyl group, and
(3) an optionally halogenated $C_{1-6}$ alkoxy group;
R¹ is isopropyl group or tert-butyl group;
X¹ is O;
X² is a bond or methylene;
ring B is

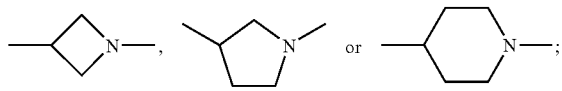

X³ is CO; and
R² is
(1) a $C_{1-10}$ alkyl group optionally substituted by 1 to 3 substituents selected from
  (i) a $C_{6-14}$ aryl group (e.g., phenyl) optionally substituted by 1 to 3 halogen atoms,
  (ii) a $C_{6-14}$ aryl-carbonyl group,
  (iii) a carboxy group,
  (iv) a $C_{1-6}$ alkoxy-carbonyl group,
  (v) a cyano group,
  (vi) a carbamoyl group monosubstituted by a $C_{6-14}$ arylsulfonyl group (e.g., phenylsulfonyl) optionally substituted by aromatic heterocyclic group (e.g., oxazolyl),
  (vii) a carbamoyl group monosubstituted by a $C_{1-6}$ alkylsulfonyl group (e.g., methylsulfonyl, pentylsulfonyl),
  (viii) a carbamoyl group monosubstituted by an aromatic heterocyclic group (e.g., tetrazolyl),
  (ix) a $C_{7-13}$ aralkyloxy-carbonyl group (e.g., benzyloxycarbonyl),
  (x) a hydroxy group,
  (xi) an aromatic heterocycle (e.g., tetrazolyl),
  (xii) a non-aromatic heterocyclic group (e.g., dihydrooxadiazolyl) optionally substituted by an oxo group,
  (xiii) a $C_{6-14}$ arylthio group (e.g., phenylthio) optionally substituted by a hydroxy group,
  (xiv) a $C_{6-14}$ arylsulfinyl group (e.g., phenylsulfinyl) optionally substituted by a hydroxy group,
  (xv) a $C_{6-14}$ arylsulfonyl group (e.g., phenylsulfonyl) optionally substituted by hydroxy group,
  (xvi) an aromatic heterocyclylthio group (e.g., triazolylthio),
  (xvii) an aromatic heterocyclylsulfinyl group (e.g., triazolylsulfinyl),
  (xviii) an aromatic heterocyclylsulfonyl group (e.g., triazolylsulfonyl), and
  (xix) a sulfoxy group;
(2) a $C_{2-10}$ alkenyl group optionally substituted by 1 to 3 substituents selected from
  (i) a carboxy group, and
  (ii) a $C_{1-6}$ alkoxy-carbonyl group;
(3) a $C_{3-10}$ cycloalkyl group (e.g., cyclopropyl) optionally substituted by 1 to 3 substituents selected from
  (i) a carboxy group,
  (ii) a $C_{1-6}$ alkoxy-carbonyl group,
  (iii) a cyano group,
  (iv) a formyl group, and
  (v) a $C_{2-10}$ alkenyl group substituted by a non-aromatic heterocyclic group (e.g., thiazolidinyl) optionally substituted by an oxo group;
(4) a $C_{6-14}$ aryl group optionally substituted by 1 to 3 substituents selected from
  (i) a carboxy group,
  (ii) a $C_{1-6}$ alkoxy-carbonyl group,
  (iii) a cyano group,
  (iv) a $C_{1-6}$ alkyl-carbonyl group,
  (v) a formyl group,
  (vi) a $C_{1-6}$ alkyl group optionally substituted by 1 to 3 substituents selected from
    (a) a hydroxy group,
    (b) a carboxy group, and
    (c) a $C_{1-6}$ alkoxy-carbonyl group,
  (vii) a $C_{2-10}$ alkenyl group optionally substituted by 1 to 3 substituents selected from
    (a) a non-aromatic heterocyclic group (e.g., thiazolidinyl) optionally substituted by an oxo group,
    (b) a carboxy group, and
    (c) a $C_{1-6}$ alkoxy-carbonyl group,
  (viii) a non-aromatic heterocyclic group (e.g., dihydrooxadiazolyl) substituted by oxo group,
  (ix) a hydroxy group, and
  (x) a $C_{1-6}$ alkoxy group optionally substituted by 1 to 3 substituents selected from
    (a) a halogen atom,
    (b) a carboxy group, and
    (c) a $C_{1-6}$ alkoxy-carbonyl group;
(5) a heterocyclic group (e.g., monocyclic aromatic heterocyclic group (e.g., pyridyl, oxazolyl, isoxazolyl, thiazolyl, pyrazinyl, pyrimidinyl), fused aromatic heterocyclic group (e.g., benzothiazolyl, imidazothiazolyl, pyrazolopyridinyl, imidazopyridinyl, thienopyrazinyl), monocyclic non-aromatic heterocyclic group (e.g., piperidinyl, dihydropyridyl, isothiazolidinyl)) optionally substituted by 1 to 3 substituents selected from
  (i) a $C_{1-6}$ alkyl group,
  (ii) an oxo group,
  (iii) a hydroxy group, and
  (iv) a sulfonyl group optionally substituted by $C_{1-6}$ alkyl group (e.g., methyl);
(6) a carbamoyl group optionally mono- or di-substituted by substituent(s) selected from
  (i) a $C_{1-6}$ alkyl group optionally substituted by 1 to 3 substituents selected from
    (a) a $C_{6-14}$ aryl group (e.g., phenyl),
    (b) a hydroxy group, and
    (c) a $C_{1-6}$ alkoxy group,
  (ii) a $C_{3-10}$ cycloalkyl group (e.g., cyclohexyl),
  (iii) a $C_{6-14}$ aryl group (e.g., phenyl),
  (iv) a sulfamoyl group optionally substituted by a $C_{1-6}$ alkyl group (e.g., pentyl),
  (v) a sulfonyl group optionally substituted by a $C_{1-6}$ alkyl group (e.g., pentyl),
  (vi) a $C_{1-6}$ alkoxy group,
  (vii) an aromatic heterocyclic group (e.g., triazolyl), and
  (viii) an amino group optionally substituted by a $C_{1-6}$ alkoxy-carbonyl group (e.g., tert-butoxycarbonyl);
(7) an amino group optionally mono- or di-substituted by substituent(s) selected from a $C_{1-6}$ alkyl group;

(8) a hydroxy group;
(9) a $C_{1-6}$ alkoxy group;
(10) a carboxy group; or
(11) a $C_{1-6}$ alkoxy-carbonyl group.
[Compound C3]
A compound (I) wherein
ring A is benzene optionally further substituted by 1 to 3 substituents in addition to $R^1$, which are selected from (1) a halogen atom,
(2) an optionally halogenated $C_{1-6}$ alkyl group, and
(3) an optionally halogenated $C_{1-6}$ alkoxy group;
$R^1$ is isopropyl group or tert-butyl group;
$X^1$ is O;
$X^2$ is a bond or methylene;
ring B is

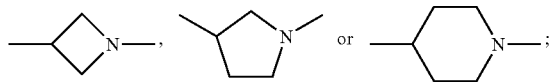

$X^3$ is CO; and
$R^2$ is
(1) a $C_{1-10}$ alkyl group optionally substituted by 1 to 3 substituents selected from
    (i) a $C_{6-14}$ aryl group (e.g., phenyl) optionally substituted by 1 to 3 halogen atoms,
    (ii) a $C_{6-14}$ aryl-carbonyl group,
    (iii) a carboxy group,
    (iv) a $C_{1-6}$ alkoxy-carbonyl group,
    (v) a cyano group,
    (vi) a carbamoyl group monosubstituted by a $C_{6-14}$ arylsulfonyl group (e.g., phenylsulfonyl) optionally substituted by aromatic heterocyclic group (e.g., oxazolyl),
    (vii) a carbamoyl group monosubstituted by a $C_{1-6}$ alkylsulfonyl group (e.g., methylsulfonyl, pentylsulfonyl),
    (viii) a carbamoyl group monosubstituted by an aromatic heterocyclic group (e.g., tetrazolyl);
(2) a carbamoyl group optionally mono- or di-substituted by substituent(s) selected from
    (i) a $C_{1-6}$ alkyl group optionally substituted by 1 to 3 substituents selected from
        (a) a $C_{6-14}$ aryl group (e.g., phenyl),
        (b) a hydroxy group, and
        (c) a $C_{1-6}$ alkoxy group,
    (ii) a $C_{3-10}$ cycloalkyl group (e.g., cyclohexyl),
    (iii) a $C_{6-14}$ aryl group (e.g., phenyl),
    (iv) a sulfamoyl group optionally substituted by a $C_{1-6}$ alkyl group (e.g., pentyl),
    (v) a sulfonyl group optionally substituted by a $C_{1-6}$ alkyl group (e.g., pentyl),
    (vi) a $C_{1-6}$ alkoxy group,
    (vii) an aromatic heterocyclic group (e.g., triazolyl), and
    (viii) an amino group optionally substituted by a $C_{1-6}$ alkoxy-carbonyl group (e.g., tert-butoxycarbonyl);
(3) a carboxy group; or
(4) a $C_{1-6}$ alkoxy-carbonyl group.
[Compound D]
4-(3-(2-tert-butylphenoxy)azetidin-1-yl)-4-oxobutanoic acid or a salt thereof;
3-{3-[(2-tert-butyl-4-fluorophenoxy)methyl]azetidin-1-yl}-3-oxopropanoic acid or a salt thereof;
2-{[3-(2-tert-butyl-4-fluorophenoxy)azetidin-1-yl]carbonyl}pyridine or a salt thereof;
4-[3-(2-tert-butyl-4-chlorophenoxy)azetidin-1-yl]-4-oxobutanoic acid or a salt thereof;
3-{3-[(2-tert-butylphenoxy)methyl]pyrrolidin-1-yl}-3-oxopropanoic acid or a salt thereof;
{3-[(2-tert-butyl-4-chlorophenoxy)methyl]azetidin-1-yl}(oxo)acetic acid or a salt thereof; or
3-{3-[(2-tert-butyl-4-fluorophenoxy)methyl]pyrrolidin-1-yl}-3-oxopropanoic acid or a salt thereof.

As a salt of the compound represented by the formula (I), a pharmacologically acceptable salt is preferable. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt: ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

Examples of the prodrug of compound (I) include a compound wherein an amino group of compound (I) is acylated, alkylated or phosphorylated (e.g., a compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated);
a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated, dimethylaminomethylcarbonylated and the like);
a compound wherein a carboxyl group of compound (I) is esterified or amidated (e.g., a compound wherein a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated and the like) and the like. These compounds can be produced from compound (I) by a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In addition, compound (I) may be labeled with an isotope (e.g., $^3H$, $^{14}C$, $^{35}S$, $^{125}I$) and the like.

Moreover, compound (I) may be a non-solvate (e.g., anhydride) or a solvate (e.g., hydrate).

Furthermore, a deuterium converter wherein $^1H$ is converted to $^2H(D)$ is also encompassed in compound (I).

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid dosage forms; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the dosage form of the above-mentioned pharmaceutical composition include oral preparations such as tablets (inclusive of sugar-coated tablets, film-coated tablets, sublingual tablets, orally disintegrating tablets), capsules (inclusive of soft capsules, microcapsules), granules, powders, troches, syrups, emulsions, suspensions, films (e.g., orally disintegrable films) and the like; and parenteral agents such as injections (e.g., subcutaneous injections, intravenous injections, intramuscular injections, intraperitoneal injections, drip infusions), external preparations (e.g., dermal preparations, ointments), suppository (e.g., rectal suppositories, vaginal suppositories), pellets, nasal preparations, pulmonary preparations (inhalants), eye drops and the like. These may be safely administered orally or parenterally (e.g., topically, rectally, intravenously administered).

These preparations may be release control preparations (e.g., sustained-release microcapsule) such as immediate-release preparation, sustained-release preparation and the like.

A pharmaceutical composition can be produced by a method conventionally used in the technical field of pharmaceutical preparation, for example, the method described in the Japanese Pharmacopoeia and the like.

The content of the compound of the present invention in a pharmaceutical composition is about 0.01 to 100 wt %, preferably about 2 to 85 wt %, of the total composition.

While the dose of the compound of the present invention varies depending on the subject of administration, administration route, disease and the like, it is, for example, about 1 to 1000 mg, preferably about 3 to 300 mg, more preferably about 10 to 200 mg, in an amount of the compound of the present invention as an active ingredient of an oral preparation for administration to an adult (body weight about 60 kg) as a prophylactic or therapeutic drug for diabetes, and the dose can be administered in one to several portions a day.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior RBP4 (retinol-binding protein 4)-lowering action.

The compound of the present invention can be used as a prophylactic or therapeutic agent for retinol-binding protein 4-associated diseases. In addition, the compound of the present invention can be used as a prophylactic or therapeutic agent for a disease or condition mediated by an increase in retinol-binding protein 4.

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, tumor (e.g., leukemia, breast cancer, prostate cancer, skin cancer), irritable bowel syndrome, acute or chronic diarrhea, inflammatory disease (e.g., rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory intestine disease (including inflammatory colitis), ulcerative colitis, stomach mucous membrane injury (including stomach mucous membrane injury caused by aspirin)), small intestine mucous membrane injury, malabsorption, testis dysfunction, visceral obesity syndrome, sarcopenia or age-related macular degeneration.

The compound of the present invention can also be used for secondary prevention or suppression of progression of the above-mentioned various diseases (e.g., cardiovascular events such as myocardial infarction and the like).

With the aim of enhancing the action of the compound of the present invention or decreasing the dose of the compound and the like, the compound can be used in combination with other medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Vildagliptin, Sitagliptin, Saxagliptin, T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agent for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agents (e.g., 4-(4-chlorophenyl)-2-(2-methyl-1-imidazolyl)-5-[3-(2-methylphenoxy)propyl]oxazole) described in WO01/14372), nerve regeneration promoters (e.g., Y-128), PKC inhibitors (e.g., ruboxistaurin mesylate), AGE inhibitors (e.g., ALT946, pimagedine, pyratoxanthine, N-phenacylthiazolium bromide (ALT766), ALT-711, EXO-226, pyridorin, pyridoxamine), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitor and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agent include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agent include central nervous system antiobesity drugs (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO01/82925 and WO01/87834); neuropeptide Y antagonists (e.g., CP-422935); cannabinoid receptor antagonists (e.g., SR-141716, SR-147778); ghrelin antagonist; 11β-hydroxysteroid dehydrogenase inhibitors (e.g., BVT-3498)), pancreatic lipase inhibitors (e.g., orlistat, cetilistat), β3 agonists (e.g., AJ-9677, AZ40140), anorectic peptides (e.g., leptin, CNTF (ciliary neurotrophic factor)), cholecystokinin agonists (e.g., lintitript, FPL-15849), feeding deterrents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparin (e.g., heparin sodium, heparin calcium, dalteparin sodium), warfarin (e.g., warfarin potassium), anti-thrombin drug (e.g., aragatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like can be mentioned.

In the following, the production methods of the compound of the present invention are explained.

Compound (I) can be produced according to a method known per se, for example, a method described in detail below, or a method analogous thereto.

Each symbol in the following reaction schemes is as defined above unless otherwise specified. In addition, $Y^1$, $Y^2$, $Y^3$ and $Z^1$ mean the following.

$Y^1$ and $Y^3$ are each a leaving group. Specific examples of $Y^1$ and $Y^3$ include a halogen atom (preferably, chlorine, bromine, iodine), a hydroxy group, an optionally halogenated $C_{1-6}$ alkylsulfonyloxy group (e.g., methanesulfonyloxy, ethanesulfonyloxy, trifluoromethanesulfonyloxy), an arylsulfonyloxy group optionally having substituent(s) (e.g., benzenesulfonyloxy, p-toluenesulfonyloxy) and the like.

$Y^2$ is a leaving group. Specific examples of $Y^2$ include a phenyloxy group optionally having 1 to 5 substituents selected from a halogen atom (preferably, chlorine, bromine), a hydroxy group and an electron-withdrawing group (e.g., halogen, nitro group) (e.g., phenyloxy, 2,3,4,5,6-pentachlorophenyloxy, 4-nitrophenyloxy), a (succinimid-1-yl)oxy group, a group forming an active ester group such as (benzothiazol-2-yl)thio group and the like, and the like.

$Z^1$ is an amino-protecting group.

In the following production methods, when a specific production method of a starting material compound is not described, commercially available products are easily available, or it can be produced according to a method known per se or a method analogous thereto.

In compound (I) of the present invention, a compound (VII) wherein $X^1$ is O, S or NH can be produced, for example, according to reaction scheme 1 shown below.

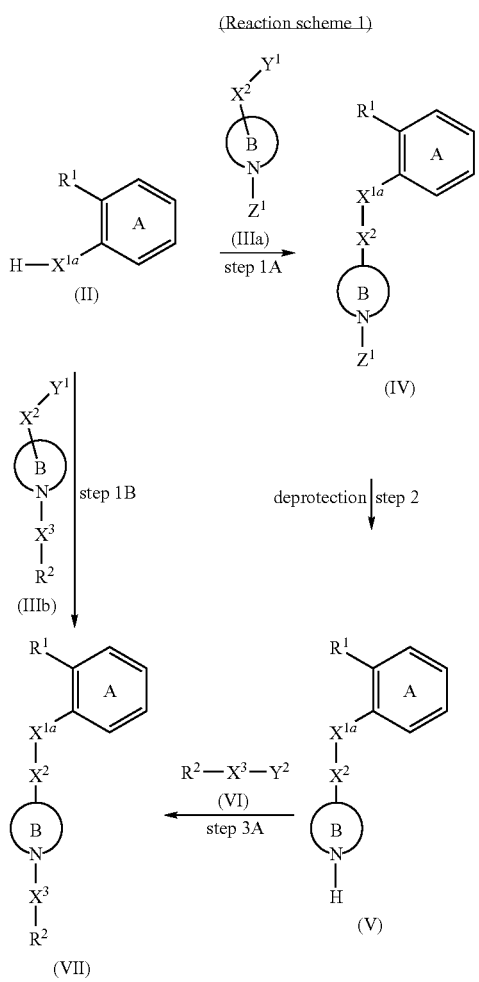

(Reaction scheme 1)

In the above, $X^{1a}$ is O, S or NH.

In this production method, compound (II) is reacted with compound (IIIc) to give compound (IV), $Z^1$ which is an amino-protecting group of compound (IV) is removed to give compound (V), and compound (V) is reacted with a compound represented by $R^2—X^3—Y^2$ to give compound (VII). In addition, compound (VII) can also be produced by reacting compound (II) with compound (IIIb).

(Step 1A)

Compound (IV) can be produced by reacting compound (II) with compound (IIIa).

The amount of compound (IIIa) to be used is generally 1 to 100 equivalents, preferably 1 to 10 equivalents, per 1 equivalent of compound (II).

In the production method of compound (IV), when $Y^1$ of compound (IIIa) is a halogen atom, the reaction can be performed in the presence of a base.

Examples of the base include amine (e.g., triethylamine, N,N-diisopropylethylamine, pyridine, 4-dimethylaminopyridine), alkali metal carbonate (e.g., potassium carbonate, sodium carbonate, cesium carbonate), alkali metal phosphate (e.g., tripotassium phosphate, trisodium phosphate), alkali metal hydride (e.g., sodium hydride, potassium hydride), alkali metal hydroxide (e.g., sodium hydroxide, potassium hydroxide) and the like. Of these, potassium carbonate, tripotassium phosphate, sodium hydride and the like are preferable.

The amount of the base to be used is generally 0.1 to 100 equivalents, preferably 1 to 10 equivalents, per 1 equivalent of compound (II).

This reaction is performed, for example, in a solvent such as ether solvents, halogenated hydrocarbon solvents, nitrile solvents, aromatic solvents, ester solvents, amide solvents, water and the like. Two or more kinds of these solvents may be used in a mixture at an appropriate ratio. Among these, N,N-dimethylformamide, toluene-water, tetrahydrofuran and the like are preferable.

This reaction can be performed, for example, in the presence of a phase-transfer catalyst (e.g., tetrabutylammonium bromide, tetrabutylammonium chloride, tetrapropylammonium hydroxide).

The amount of the phase-transfer catalyst to be used is generally 0.001 to 10 equivalents, preferably 0.01 to 1 equivalent, per 1 equivalent of compound (II).

The reaction temperature of this reaction is generally 0° C. to 150° C., preferably about 0° C. to 100° C.

The reaction time of this reaction is, for example, 0.5 hr to 7 days, preferably 0.5 hr to 1 day.

In the production of compound (IV), when $Y^1$ of compound (IIIa) is a hydroxy group, compound (IV) can also be produced by converting the hydroxy group to a halogen atom by using a halogenating reagent and thereafter following the aforementioned method.

Examples of the halogenated reagent include thionyl chloride, thionyl bromide, phosphorus trichloride, phosphorus pentachloride, phosphorus oxychloride, carbon tetrabromide and the like.

The amount of the halogenated reagent to be used is generally 1 to 100 equivalents, preferably 1 to 10 equivalents, per 1 equivalent of compound (IIIa).

This reaction is generally performed in an inert solvent (e.g., ether solvents, halogenated hydrocarbon solvents, aromatic solvents etc.) or without solvent. Two or more kinds of these solvents may be used in a mixture at an appropriate ratio. Among these, tetrahydrofuran, toluene, carbon tetrachloride and the like are preferable.

The reaction temperature of this reaction is generally −20° C. to 200° C., preferably 0° C. to 100° C.

The reaction time of this reaction is, for example, 0.5 hr to 16 hr.

In the production of compound (IV), when $Y^1$ of compound (IIIa) is a hydroxy group, compound (IV) can also be produced by converting the hydroxy group to an optionally halogenated $C_{1-6}$ alkylsulfonyloxy group, an arylsulfonyloxy group and the like by using optionally halogenated $C_{1-6}$ alkylsulfonyl chloride (e.g., methanesulfonyl chloride, ethanesulfonyl chloride, trifluoromethanesulfonyl chloride), arylsulfonyl chloride optionally having substituents (e.g., benzenesulfonyl chloride, p-toluenesulfonyl chloride) and the like and thereafter following the aforementioned method.

The amount of the optionally halogenated $C_{1-6}$ alkylsulfonyl chloride or arylsulfonyl chloride optionally having substituents to be used is generally 1 to 100 equivalents, preferably 1 to 10 equivalents, per 1 equivalent of compound (IIIa).

This reaction is generally performed in an inert solvent (e.g., ether solvents, halogenated hydrocarbon solvents, aromatic solvents etc.) or without solvent. Two or more kinds of these solvents may be used in a mixture at an appropriate ratio. Among these, tetrahydrofuran, toluene, carbon tetrachloride and the like are preferable.

In the reaction of compound (IIIa) with the optionally halogenated $C_{1-6}$ alkylsulfonylchloride or arylsulfonylchloride optionally having substituent(s), a base may be used as necessary.

Examples of the base include amine (e.g., triethylamine, N,N-diisopropylethylamine, pyridine, 4-dimethylaminopyridine), alkali metal carbonate (e.g., potassium carbonate, sodium carbonate, cesium carbonate), alkali metal phosphate (e.g., tripotassium phosphate, trisodium phosphate), alkali metal hydride (e.g., sodium hydride, potassium hydride), alkali metal hydroxide (e.g., sodium hydroxide, potassium hydroxide) and the like. Of these, potassium carbonate, tripotassium phosphate, sodium hydride and the like are preferable.

The reaction temperature of this reaction is generally −20° C. to 200° C., preferably 0° C. to 100° C.

The reaction time of this reaction is, for example, 0.5 hr to 48 hr.

In the production of compound (IV), when $X^{1a}$—H and $Y^1$ are a hydroxy group, compound (IV) can be produced according to the Mitsunobu reaction (e.g., the method described in Tetrahedron Letters, 34, 1639 (1993); Tetrahedron Letters, 35, 5081 (1994); Tetrahedron Letters, 36, 2531 (1995); Tetrahedron Letters, 37, 2549 (1996); The Journal of Medicinal Chemistry, 44, 2933 (2001); and the like).

(Step 1B)

Compound (VII) can be produced by reacting compound (II) with compound (IIIb) in the same manner as in step 1A.

(Step 2)

In the production of compound (V), protecting group $Z^1$ of compound (IV) can be removed according to a method known per se, for example, the method described in Protective Groups in Organic Synthesis, John Wiley and Sons (1980) and the like. Examples thereof include methods using acid, base, ultraviolet rays, hydrazine, phenylhydrazine, sodium N-methyldithiocarbamate, tetrabutylammonium fluoride, palladium acetate, trialkylsilylhalide (e.g., trimethylsilyliodide, trimethylsilylbromide etc.) and the like, a reduction method and the like.

(Step 3A)

Compound (VII) can be produced by reacting compound (V) with compound (VI).

As Compound (VI), for example, a commercially available product such as carboxylic acid, carboxylic acid halide, sulfonic acid halide and the like can be used. In addition, compound (VI) can also be produced by a method known per se such as activation of carboxylic acid and the like (the method described in Experimental Chemical Course (Jikken Kagaku Koza), 5th Edition, vol. 16, page 1, page 117 (2005) Maruzen; and the like).

The amount of compound (VI) to be used in the following reactions is generally 1 to 100 equivalents, preferably 1 to equivalents, per 1 equivalent of compound (V).

When $Y^2$ of compound (VI) is a halogen atom, the reaction can be performed in the presence of a base. Examples of the base include amines (e.g., triethylamine, N,N-diisopropylethylamine, pyridine, 4-dimethylaminopyridine), alkali metal carbonates (e.g., potassium carbonate, sodium carbonate, cesium carbonate), hydroxide alkali metals (e.g., lithium hydroxide, sodium hydroxide, potassium hydroxide) and the like. Among these, triethylamine, N,N-diisopropylethylamine, pyridine, 4-dimethylaminopyridine, potassium carbonate, sodium carbonate and the like are preferable.

The amount of the base to be used is generally 0.1 to 100 equivalents, preferably 1 to 10 equivalents, per 1 equivalent of compound (VI).

This reaction is performed, for example, in a solvent such as ether solvents, halogenated hydrocarbon solvents, nitrile solvents, aromatic solvents, ester solvents, amide solvents, water and the like. Two or more kinds of these solvents may be used in a mixture at an appropriate ratio. Among these, tetrahydrofuran, dichloromethane, pyridine, ethyl acetate-water and the like are preferable.

The reaction temperature of this reaction is generally about 0° C. to 100° C., preferably 0 to 80° C.

The reaction time of this reaction is, for example, 0.5 hr to 1 day.

When $Y^2$ of compound (VI) is a hydroxy group, the reaction can be performed using a condensing agent (e.g., 1-ethyl-3-(3'-dimethylaminopropyl)carbodiimide (EDCI), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), 1,3-dicyclohexylcarbodiimide (DCC), bis(2-oxo-3-oxazolidinyl)phosphine chloride (BOP—Cl) and (benzotriazol-1-yloxy)tripyrrolidinophosphonium hexafluorophosphate (PyBOP)). Among these, EDCI, HBTU and the like are preferable.

The amount of the condensing agent to be used is generally 1 to 10 equivalents, preferably 1 to 3 equivalents, per 1 equivalent of compound (VI).

To promote this reaction, an additive such as N-hydroxysuccinimide (HOSu), N-hydroxybenzotriazole (HOBt), amines (e.g., triethylamine, N,N-diisopropylethylamine, pyridine, 4-dimethylaminopyridine) and the like may be used in combination with a condensing agent.

The amount of the additive to be used is generally 0.1 to 100 equivalents, preferably 0.1 to 10 equivalents, per 1 equivalent of compound (VI).

This reaction is generally performed in an inert solvent (e.g., ether solvents, halogenated hydrocarbon solvents, nitrile solvents, amide solvents). Two or more kinds of these solvents may be used in a mixture at an appropriate ratio. Among these, tetrahydrofuran, dichloromethane, acetonitrile and the like are preferable.

The reaction temperature of this reaction is generally about 0° C. to 100° C., preferably 0° C. to 80° C.

The reaction time of this reaction is, for example, 0.5 hr to 3 days.

When $Y^2$ of compound (VI) is a hydroxy group, the reaction can be performed according to a method known per se (e.g., the method described in Experimental Chemistry Course (Jikken Kagaku Koza), 5th Edition, vol. 16, 99 page (2005) Maruzen Co., Ltd.; and the like) and using a halogenating reagent (e.g., thionyl chloride, oxalyl chloride, dichlorotriphenylphosphorane, diethylaminosulfur trifluoride (DAST), cyanuryl fluoride), wherein the hydroxy group is converted to a halogen atom (preferably, chlorine, bromine, fluorine), and compound (VII) can also be produced according to the aforementioned method.

The amount of the halogenating reagent to be used is generally 1 to 100 equivalents, preferably 1 to 10 equivalents, per 1 equivalent of compound (VI).

To promote the reaction, an additive such as N,N-dimethylformamide, amines (e.g., triethylamine, N,N-diisopropylethylamine, pyridine, 4-dimethylaminopyridine) and the like may be used in this reaction.

The amount of the additive to be used is generally 0.1 to 100 equivalents, preferably 0.1 to 10 equivalents, per 1 equivalent of compound (VI).

This reaction is generally performed in an inert solvent (e.g., ether solvents, halogenated hydrocarbon solvents, nitrile solvents, amide solvents) or without solvent. Two or more kinds of these solvents may be used in a mixture at an appropriate ratio. Among these, tetrahydrofuran, dichloromethane, acetonitrile, N,N-dimethylformamide and the like are preferable.

The reaction temperature of this reaction is generally about −20° C. to 150° C., preferably 0° C. to 90° C.

The reaction time of this reaction is, for example, 0.5 hr to 3 days.

When $Y^2$ of compound (VI) is a group that forms an active ester group such as phenyloxy group, (succiniimide-1-yl)oxy group, (benzothiazol-2-yl)thio group and the like, the reaction can be performed in the presence of a base. Examples of the base include amines (e.g., triethylamine, N,N-diisopropylethylamine, pyridine, 4-dimethylaminopyridine), alkali metal carbonate (e.g., potassium carbonate, sodium carbonate, cesium carbonate) and the like. Among these, triethylamine, N,N-diisopropylethylamine, pyridine, 4-dimethylaminopyridine and the like are preferable.

The amount of the base to be used is generally 0.1 to 100 equivalents, preferably 1 to 10 equivalents, per 1 equivalent of compound (VI).

This reaction is performed in a solvent such as ether solvents, halogenated hydrocarbon solvents, nitrile solvents, aromatic solvents, ester solvents, amide solvents and the like. Two or more kinds of these solvents may be used in a mixture at an appropriate ratio. Among these, tetrahydrofuran, dichloromethane, pyridine and the like are preferable.

The reaction temperature of this reaction is generally about 0° C. to 100° C., preferably 0 to 80° C.

The reaction time of this reaction is, for example, 0.5 hr to 1 day.

Compound (II) to be used in reaction scheme 1 can be produced by the method shown in reaction scheme 9 or a method analogous thereto, or a method known per se.

As compounds (IIIa) and (IIIb) to be used in reaction scheme 1, for example, commercially available products can be used. In addition, the compounds can be produced according to the method shown in reaction scheme 2, or a method analogous thereto.

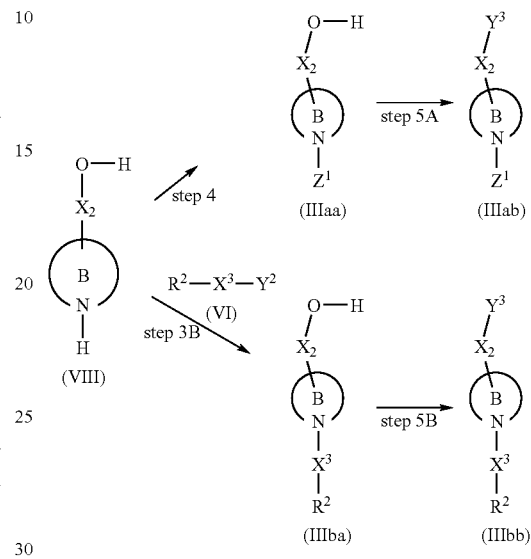

(Reaction scheme 2)

(Step 4)

In the production of compound (IIIaa), protecting group $Z^1$ may be introduced according to a method known per se, for example, the method described in Protective Groups in Organic Synthesis, John Wiley and Sons (1980) and the like. Specific examples of the protecting group include a $C_{1-6}$ alkyl-carbonyl group (e.g., acetyl, trifluoroacetyl), a $C_{1-6}$ alkoxycarbonyl group (e.g., methoxycarbonyl, tert-butoxycarbonyl), a $C_{7-10}$ aralkyloxy-carbonyl group (e.g., benzyloxycarbonyl), a $C_{7-13}$ aralkyl group (e.g., benzyl, benzhydryl) and the like.

Compound (VIII) can be produced according to a method known per se.

(Step 5A)

Compound (IIIab) can be produced by using compound (IIIaa) and, for example, according to a reaction similar to step 1A of reaction scheme 1.

(Step 3B)

Compound (IIIba) can be produced by reacting compound (VIII) with compound (VI) in the same manner as in step 3A.

(Step 5B)

Compound (IIIbb) can be produced by using compound (IIIba) and, for example, according to a reaction similar to step 1A of reaction scheme 1.

Compound (VIIb) which is compound (I) wherein $X^1$ is SO and compound (VIIc) which is compound (I) wherein $X^1$ is $SO_2$ can be produced, for example, according to the method shown in reaction scheme 3 or a method analogous thereto.

(Reaction scheme 3)

[Structure (VIIa)] →step 6A→ [Structure (VIIb)] →step 6B→ [Structure (VIIc)]

(Step 6A)

Compound (VIIa) is compound (I) wherein $X^1$ is S, and can be produced by the method shown in the above-mentioned reaction scheme 1.

Compound (VIIb) can be produced by subjecting compound (VIIa) to an oxidation reaction.

The oxidation reaction can be generally performed by using an oxidant and according to a method known per se (e.g., the method described in Experimental Chemical Course (Jikken Kagaku Koza), 5th Edition, vol. 17, page 205 (2005) Maruzen; and the like, or a method analogous thereto).

Examples of the oxidant include m-chloroperbenzoic acid, benzoyl peroxide, bis(trimethylsilyl)peroxide, dimethyldioxirane, hydrogen peroxide and the like.

The amount of the oxidant to be used is about 1-about equivalents, preferably about 1-1.2 equivalents, per 1 equivalent of compound (VIIa).

This reaction can be performed, for example, in the presence of a catalytic amount of titanium tetraisopropoxide, sodium tartrate, sodium phosphotungstate, phenylphosphonic acid, quaternary ammonium salt and the like.

The amount of the catalyst to be used is generally 0.001-0.1 equivalent per 1 equivalent of compound (VIIa).

This reaction is generally performed in an inert solvent (e.g., halogenated hydrocarbon solvents, ester solvent, nitrile solvents, ether solvents etc.) or without solvent. Two or more kinds of these solvents may be used in a mixture at an appropriate ratio. Of these, dichloromethane, ethyl acetate, acetonitrile and the like are preferable.

The reaction temperature of this reaction is generally 0° C. to 100° C., preferably about 0° C. to 80° C.

The reaction time of this reaction is, for example, 0.5 hr to 1 day.

(Step 6B)

Compound (VIIc) can be produced by an oxidation reaction of compound (VIIb) in the same manner as in step 6A.

Compound (IIa) which is compound (II) wherein $X^{1a}$ is O can be produced, for example, according to the method shown in reaction scheme 9, or a method analogous thereto.

(Reaction scheme 9)

[Structure (IXa)] →(L) step 13, $R^1$—$L^1$→ [Structure (IIa)]

(Step 13)

Compound (IIa) can be produced from compound (IXa) and a compound (L) represented by the formula: $R^1$-$L^1$ according to a method known per se, for example, the method described in The Chemistry of Phenols, part 1, page 605 (2003) Wiley; Experimental Chemical Course (Jikken Kagaku Koza), 5th Edition, vol. 14, page 221 (2005) Maruzen; and the like.

Compound (IXa) can be produced according to a method known per se.

In the compounds obtained by each reaction mentioned above, a functional group in the molecule can also be converted to an object functional group by combining chemical reactions known per se. Here, examples of the chemical reaction include oxidation reaction, reduction reaction, alkylation reaction, acylation reaction, urea forming reaction, hydrolysis, amination reaction, esterification reaction, aryl coupling reaction, deprotection reaction and the like.

In the above-mentioned production methods, the "ether solvents", "halogenated hydrocarbon solvents", "aromatic solvents", "nitrile solvents", "ester solvent", "amide solvents", "ketone solvents", "sulfoxide solvents" and "alcohol solvent" mean the following.

Examples of the aforementioned "ether solvents" include diethyl ether, tetrahydrofuran (THF), 1,4-dioxane, 1,2-dimethoxyethane and the like.

Examples of the aforementioned "halogenated hydrocarbon solvents" include dichloromethane, chloroform, 1,2-dichloroethane, carbon tetrachloride and the like.

Examples of the aforementioned "aromatic solvents" include benzene, toluene, xylene, pyridine and the like.

Examples of the aforementioned "nitrile solvents" include acetonitrile, propionitrile and the like.

Examples of the aforementioned "ester solvent" include ethyl acetate, methyl acetate and the like.

Examples of the aforementioned "amide solvents" include N,N-dimethylformamide(DMF), N,N-dimethylacetamide, N-methylpyrrolidone and the like.

Examples of the aforementioned "ketone solvents" include acetone, methylethyl ketone and the like.

Examples of the aforementioned "sulfoxide solvents" include dimethyl sulfoxide (DMSO) and the like.

Examples of the aforementioned "alcohol solvent" include methanol, ethanol, isopropanol, tert-butanol and the like.

In the above-mentioned production methods, when the starting compound has an amino group, a carboxyl group, a hydroxy group or a carbonyl group as a substituent, a protecting group generally used in peptide chemistry and the like may be introduced into these groups. By removing the protecting group as necessary after the reaction, the object compound can be obtained.

Examples of the amino-protecting group include formyl group, $C_{1-6}$ alkyl-carbonyl group (e.g., acetyl, propanoyl), $C_{1-6}$ alkoxy-carbonyl group (e.g., methoxycarbonyl, ethoxycarbonyl), benzoyl group, $C_{7-13}$ aralkyl-carbonyl group (e.g., benzylcarbonyl), $C_{7-13}$ aralkyloxy-carbonyl group (e.g., benzyloxycarbonyl, 9-fluorenylmethoxycarbonyl), $C_{7-13}$ aralkyl group (e.g., benzyl, benzhydryl), trityl group, phthaloyl group, N,N-dimethylaminomethylene group, trisubstituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from halogen atom, $C_{1-6}$ alkoxy group, nitro group and the like.

Examples of the carboxyl-protecting group include $C_{1-6}$ alkyl group, $C_{7-20}$ aralkyl group (e.g., benzyl, trityl), phenyl group, trisubstituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from halogen atom, $C_{1-6}$ alkoxy group, nitro group and the like.

Examples of the hydroxyl-protecting group include $C_{1-6}$ alkyl group, phenyl group, trityl group, $C_{7-13}$ aralkyl group (e.g., benzyl), formyl group, $C_{1-6}$ alkyl-carbonyl group (e.g., acetyl, propanoyl), benzoyl group, $C_{7-13}$ aralkyl-carbonyl group (e.g., benzylcarbonyl), 2-tetrahydropyranyl group, 2-tetrahydrofuranyl group, trisubstituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These group are optionally substituted by 1 to 3 substituents selected from halogen atom, $C_{1-6}$ alkyl group, $C_{1-6}$ alkoxy group, nitro group and the like.

Examples of the carbonyl-protecting group include cyclic acetal (e.g., 1,3-dioxane), noncyclic acetal (e.g., di-$C_{1-6}$ alkyl acetal) and the like.

In addition, these protecting groups may be introduced or removed according to a method known per se, for example, the method described in Protective Groups in Organic Synthesis, John Wiley and Sons (1980) and the like. Examples of the method include methods to be used acid, base, ultraviolet rays, hydrazine, phenylhydrazine, sodium N-methyldithiocarbamate, tetrabutylammonium fluoride, palladium acetate, trialkylsilylhalide (e.g., trimethylsilyliodide, trimethylsilylbromide etc.) and the like, reduction method and the like.

The compound of the present invention obtained by each of the above-mentioned production methods can be subjected to a means known per se, such as solvent extraction, liquid conversion, solvent transfer, crystallization, recrystallization, chromatography and the like can be isolated and purified. On the other hand, the starting compound may be directly used as a starting material of the next step in the form of a reaction mixture without isolation. In addition, when the starting compound used for each of the above-mentioned production method is commercially available, the commercially available product can be directly used.

When the starting compound can form a salt during production of compound of the present invention, the compound may be used as a salt. Examples of the salt include those exemplified as the salt usable for compound (I).

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se.

Compound (I) may be a crystal.

Crystals of compound (I) (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

The present invention is explained in more detail in the following by referring to Experimental Examples, Reference Examples, Examples and Formulation Examples, which are not to be construed as limitative.

EXAMPLES

In the following Reference Examples and Examples, room temperature means 1-30° C. unless otherwise indicated.

In the following Reference Examples and Examples, melting point, mass spectrum (MS) and nuclear magnetic resonance spectrum (NMR) were measured under the following conditions. melting point measurement tools: Yanagimoto micromelting point measuring apparatus, or Büchi melting point measuring apparatus type B-545 was used.
MS measurement tools: Waters Corporation ZMD, Waters Corporation ZQ2000 or Micromass Ltd., platform II, ionization method: Electron Spray Ionization (ESI) or Atmospheric Pressure Chemical Ionization (APCI). Unless specifically indicated, ESI was used.
NMR measurement tools: Varian Inc. Varian Gemini 200 (200 MHz), Varian Mercury-300 (300 MHz), Varian INOVA-400 (400 MHz) or Bruker BioSpin Corp. AVANCE 300. Chemical shifts are given in ppm with tetramethylsilane as the internal standard, and coupling constants (J) are given in hertz (Hz).
In Reference Examples and Examples, purification by preparative HPLC was performed under the following conditions.
Preparative HPLC tools: Waters Corporation, UV purification system
column: Develosil ODS-UG-10
solvent: Solution A; 0.1% trifluoroacetic acid-containing water
Solution B; 0.1% trifluoroacetic acid-containing acetonitrile
gradient: 10 min gradient, 5-100% gradient
Gradient cycle: 0.00 min (A/B=95/5), 1.00 min (A/B=95/5), 2.00 min (A/B=80/20), 5.00 min (A/B=5/95), 5.10 min (A/B=0/100), 7.00 min (A/B=100/0)
flow rate: 150 mL/min, detection method: UV 220 nm The abbreviations in Reference Examples and Examples follow those generally used in the pertinent technical field and, for example, mean the following.
s: singlet
d: doublet
t: triplet q: quartet
quin: quintet
dd: double doublet
dt: double triplet
dq: double quartet
ddd: double double doublet
td: triple doublet
tt: triple triplet
m: multiplet
br: broad
brs: broad singlet
J: coupling constant
THF: tetrahydrofuran
DMF: dimethylformamide
DMSO: dimethyl sulfoxide
$CDCl_3$: deuterated chloroform
EDCI: 1-ethyl-3-(3-dimethylaminopropyl)carbodiimide
HOBt: 1-hydroxybenzotriazole
m-CPBA: m-chlorobenzoic acid
DIPEA: N,N-diisopropylethylamine
p-TsCl: p-toluenesulfonyl chloride
MeOH: methanol
EtOH: ethanol
HBTU: O-(Benzotriazol-1-yl)-N,N,N',N'-tetramethyluronium hexafluorophosphate
quant: quantitative Reference Example 1

1-benzhydryl-3-(2-tert-butylphenoxy)azetidine

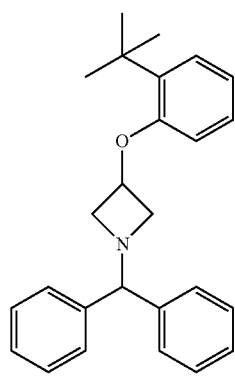 [SMILES: CC(C)(C)c1ccccc1OC1CN(C(c2ccccc2)c2ccccc2)C1]

A stirred solution of 1-(diphenylmethyl)-3-azetidinylmethane sulfonate (12.68 g, 39.9 mmol), 2-tert-butylphenol (6.0 g, 39.9 mmol), tetrabutylammonium bromide (1.29 g, 3.99 g) and sodium hydroxide (15.0 mL of 8.0 M solution in water, 120 mmol) in toluene (40 mL) was heated at 100° C. for 5 h. Then, the reaction mixture was cooled to room temperature, diluted with ethyl acetate and separated. The organic layer was washed with water, saturated sodium chloride, dried ($Na_2SO_4$), filtered and concentrated under reduced pressure. Purification by flash column chromatography (silica gel, 100:0 to 98:2 heptane/ethyl acetate) provided impure 1-benzhydryl-3-(2-tert-butylphenoxy)azetidine (9.10 g, 66%) as a yellow oil, which was used without further purification or characterization.

Reference Example 2

3-(2-tert-butylphenoxy)azetidine

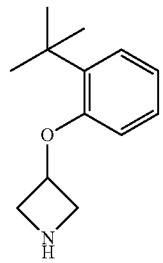

To a solution of 1-benzhydryl-3-(2-tert-butylphenoxy)azetidine (9.10 g, 24.5 mmol) and 10% Pd/C (10% on carbon, 1.90 g) in methanol (300.0 mL) was stirred under hydrogen atmosphere (1 atm) at room temperature. After 24 h the reaction mixture was filtered through a pad of Celite, the Celite pad was washed with methanol and the filtrate was concentrated under reduced pressure. Purification by flash column chromatography (silica gel; 70:30 to 0:100 heptane/ethyl acetate, 98:2 ethyl acetate/methanol, 90:9:1 ethyl acetate/methanol/7.0 N ammonia-methanol) provided 3-(2-tert-butylphenoxy)azetidine (2.00 g, 40%) as a yellow oil.

$^1$H NMR (500 MHz, $CDCl_3$) δ 7.30-7.28 (m, 1H), 7.14-7.11 (m, 1H), 6.92-6.89 (m, 1H), 6.52-6.50 (m, 1H), 5.04-5.03 (m, 1H), 3.99-3.96 (m, 2H), 3.89-3.85 (m, 2H), 2.42 (s, 1H), 1.40 (s, 9H).

Reference Example 3

2-tert-butyl-4-fluorophenol

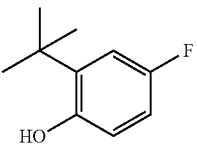

To a stirred solution of 4-fluorophenol (5.00 g, 45.0 mmol) and tert-butanol (4.67 g, 63.0 mmol) in dichloromethane (80 mL) was added conc. sulfuric acid (3.0 mL) at room temperature. After 16 h the reaction mixture was concentrated under reduced pressure and the resulting residue was diluted with ethyl acetate. The organic layer was washed with water, neutralized with saturated sodium hydrogen carbonate, dried ($Na_2SO_4$), filtered and concentrated under reduced pressure. Purification by flash column chromatography (silica gel, 100:0 to 90:10 heptane/ethyl acetate) provided 2-tert-butyl-4-fluorophenol (2.54 g, 34%) as a pale green oil.

¹H NMR (500 MHz, CDCl₃) δ 6.99-6.98 (m, 1H), 6.76-6.73 (m, 1H), 6.60-6.58 (m, 1H), 4.68 (br s, 1H), 1.39 (s, 9H).

Reference Example 4

1-benzhydryl-3-(2-tert-butyl-4-fluorophenoxy)azetidine

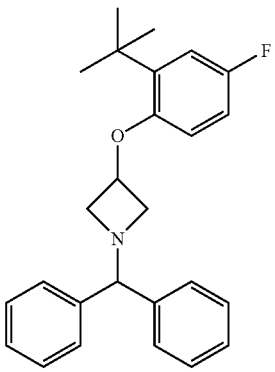 [SMILES: CC(C)(C)c1cc(F)ccc1OC1CN(C(c2ccccc2)c2ccccc2)C1]

The title compound was prepared by a procedure similar to the one described for 1-benzhydryl-3-(2-tert-butylphenoxy)azetidine to provide 1-benzhydryl-3-(2-tert-butyl-4-fluorophenoxy)azetidine (4.11 g, 72%) as a yellow oil.

¹H NMR (500 MHz, CDCl₃) δ 7.43-7.16 (m, 10H), 6.99-6.96 (m, 1H), 6.75-6.71 (m, 1H), 6.45-6.42 (m, 1H), 4.77-4.72 (m, 1H), 4.42 (s, 1H), 3.76-3.67 (m, 2H), 3.21-3.09 (m, 2H), 1.36 (s, 9H).

Reference Example 5

3-(2-tert-butyl-4-fluorophenoxy)azetidine

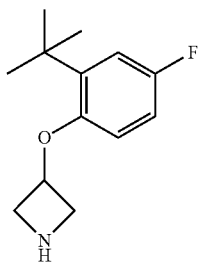 [SMILES: CC(C)(C)c1cc(F)ccc1OC1CNC1]

The title compound was prepared by a procedure similar to the one described for 3-(2-tert-butylphenoxy)azetidine to provide 3-(2-tert-butyl-4-fluorophenoxy)azetidine (1.49 g, 64%) as a colorless oil.

¹H NMR (500 MHz, CDCl₃) δ 7.02-6.99 (m, 1H), 6.81-6.77 (m, 1H), 6.44-6.41 (m, 1H), 4.98-4.93 (m, 1H), 3.95-3.92 (m, 2H), 3.85-3.82 (m, 2H), 2.04 (br s, 1H), 1.38 (s, 9H).

Reference Example 6 tert-butyl 3-(2-tert-butylphenylthio)azetidine-1-carboxylate

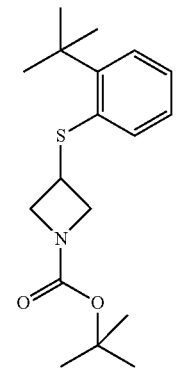 [SMILES: CC(C)(C)OC(=O)N1CC(Sc2ccccc2C(C)(C)C)C1]

To an ice-cold stirred solution of tert-butyl 3-hydroxyazetidine-1-carboxylate (2.20 g, 12.7 mmol) and triethylamine (1.54 g, 15.2 mmol) in THF (60.0 mL) was added methanesulfonyl chloride (1.60 g, 14.0 mmol) and the resulting reaction mixture was warmed to room temperature. After 2 h the reaction mixture was filtered and filtrate concentrated under reduced pressure. The residue was dissolved in toluene (30.0 mL), added to a stirred solution of 80% 2-tert-butylthiophenol (2.12 g, 10.2 mmol), tetrabutylammonium bromide (0.41 g, 1.27 mmol) and sodium hydroxide (4.80 ml of 8.0 M solution in water, 38.4 mmol) in toluene (30.0 mL) and the resulting reaction mixture was heated at 100° C. for 3 h. Then, the reaction mixture was cooled to room temperature, diluted with ethyl acetate and separated. The organic layer was washed with water, saturated sodium chloride, dried (Na₂SO₄), filtered and concentrated under reduced pressure. The residue was purified by flash column chromatography (silica gel, 95:5 to 80:20 heptane/ethyl acetate) provided tert-butyl 3-(2-tert-butylphenylthio)azetidine-1-carboxylate (1.80 g, 55%) as a pale yellow oil.

¹H NMR (500 MHz, CDCl₃) δ 7.40-7.38 (m, 1H), 7.16-7.11 (m, 2H), 7.03-7.01 (m, 1H), 4.37-4.34 (m, 2H), 4.04-4.00 (m, 1H), 3.94-3.91 (m, 2H), 1.49 (s, 9H), 1.44 (s, 9H).

Reference Example 7

3-(2-tert-butylphenylthio)azetidine Hydrochloride

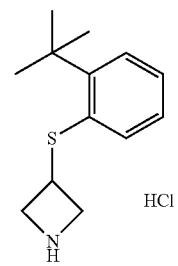

To a stirred solution of tert-butyl 3-(2-tert-butylphenylthio) azetidine-1-carboxylate (1.70 g, 5.29 mmol) in dioxane (5.0 mL) was added hydrogen chloride (5.3 mL of 4.0 M solution in dioxane, 21.2 mmol) at room temperature. After 24 h the reaction mixture was concentrated under reduced pressure and the resulting residue was triturated with diethyl ether to provide 3-(2-tert-butylphenylthio)azetidine hydrochloride (1.18 g, 87%) as a white solid.

$^1$H NMR (500 MHz, DMSO-d$_6$) δ 9.14 (br s, 1H), 7.41-7.39 (m, 1H), 7.22-7.20 (m, 2H), 7.13-7.11 (m, 1H), 4.45-4.35 (m, 3H), 3.93-3.89 (m, 2H), 1.45 (s, 9H).

Reference Example 8

1-benzhydryl-N-(2-tert-butylphenyl)azetidin-3-amine

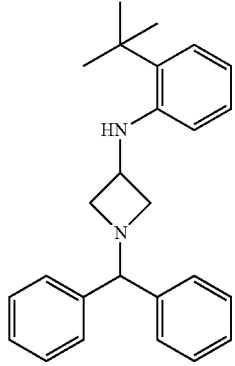 [SMILES: CC(C)(C)c1ccccc1NC1CN(C(c2ccccc2)c2ccccc2)C1]

A mixture of 2-tert-butylaniline (0.50 g, 3.35 mmol) and 1-(diphenylmethyl)-3-azetidinylmethanesulfonate (1.60 g, 5.03 mmol) was heated at 100° C. for 15 min. After this toluene (5.0 ml) was added to the resulting yellow solid, the reaction mixture was cooled to room temperature, partitioned between THF and water and separated. The organic layer was washed with saturated sodium chloride, dried (Na$_2$SO$_4$), filtered and concentrated under reduced pressure. The residue was purified by flash column chromatography (silica gel, 90:10 to 80:20 heptane/ethyl acetate) to provide 1-benzhydryl-N-(2-tert-butylphenyl)azetidin-3-amine (0.73 g, 59%) as a yellow gum-like substance.

$^1$H NMR (500 MHz, CDCl$_3$) δ 7.43-7.41 (m, 4H), 7.34-7.17 (m, 6H), 7.06-7.03 (m, 2H), 6.70-6.67 (m, 1H), 6.43 (d, J=7.9 Hz, 1H), 4.38 (s, 1H), 4.17-4.15 (m, 2H), 3.72-3.71 (m, 2H), 2.86 (br s, 2H), 1.43 (s, 9H).

Reference Example 9

N-(2-tert-butylphenyl)azetidin-3-amine

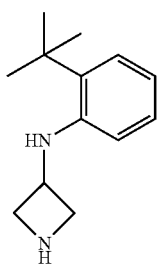

The title compound was prepared by a procedure similar to the one described for 3-(2-tert-butylphenoxy)azetidine to provide N-(2-tert-butylphenyl)azetidin-3-amine (0.40 g, 99%) as a yellow gum-like substance, which was used without further purification or characterization.

Reference Example 10 tert-butyl 3-(tosyloxy)pyrrolidine-1-carboxylate

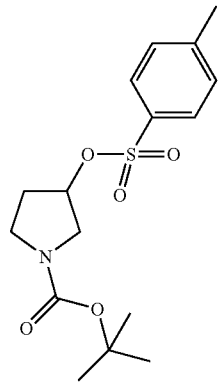 [SMILES: Cc1ccc(S(=O)(=O)OC2CCN(C(=O)OC(C)(C)C)C2)cc1]

To a stirred solution of R-(−)-N-Boc-3-pyrrolidinol (5.03 g, 26.9 mmol) in pyridine (30.0 mL) was added p-TsCl (5.63 g, 30.0 mmol) at room temperature. After 16 h the reaction mixture was concentrated under reduced pressure and the resulting residue was partitioned between ethyl acetate (200.0 mL) and 1.0 N hydrochloric acid (200.0 mL) and separated. The organic layer was washed with water (2×100 ml), saturated sodium chloride (100 mL), dried (MgSO$_4$), filtered, and concentrated under reduced pressure. Purification by flash column chromatography (silica gel, 80:20 to 50:50 heptane/ethyl acetate) to provide tert-butyl 3-(tosyloxy)pyrrolidine-1-carboxylate (6.79 g, 74%) as colorless oil.

$^1$H NMR (500 MHz, CDCl$_3$) δ 7.79 (d, J=8.0 Hz, 2H), 7.36 (d, J=8.0 Hz, 2H), 5.05 (br s, 1H), 3.48-3.38 (m, 4H), 2.46 (s, 3H), 2.17-1.91 (m, 1H), 1.91-1.71 (m, 1H), 1.46 (s, 9H).

Reference Example 11 tert-butyl 3-(2-tert-butylphenoxy)pyrrolidine-1-carboxylate

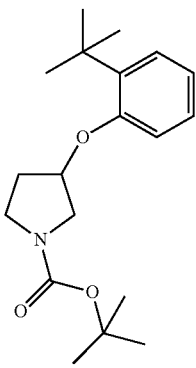 [SMILES: CC(C)(C)OC(=O)N1CCC(Oc2ccccc2C(C)(C)C)C1]

A stirred solution of tert-butyl 3-(tosyloxy)pyrrolidine-1-carboxylate (6.79 g, 19.9 mmol), 2-(tert-butyl)phenol (1.49 g, 9.95 mmol) and $K_3PO_4$ (6.33 g, 29.9 mmol) in DMF (20.0 mL) was heated at 80° C. for 16 h. Then, the reaction mixture was cooled to room temperature, poured into water (80.0 mL) and extracted with ethyl acetate (2×40.0 ml). The combined organics were washed with water (2×80 mL), saturated sodium chloride (100 ml), dried ($MgSO_4$), filtered, and concentrated under reduced pressure. Purification by flash column chromatography (silica gel, 80:20 heptane/ethyl acetate) to provide a pale orange solid (2.47 g, 78%). This solid (2.47 g) was triturated with a heptane/ethyl acetate solution to provide tert-butyl 3-(2-tert-butylphenoxy)pyrrolidine-1-carboxylate (0.81 g, 33%) as a colorless powder: mp 81-82° C.

$^1$H NMR (500 MHz, $CDCl_3$) δ 7.32-7.29 (m, 1H), 7.17-7.13 (m, 1H), 6.92-6.89 (m, 1H), 6.78 (d, J=8.0 Hz, 1H), 4.98 (s, 1H), 3.76-3.52 (m, 4H), 2.29-2.26 (m, 1H), 2.16-2.15 (m, 1H), 1.45% (s, 9H), 1.35 (s, 9H).

Reference Example 12

3-(2-tert-butylphenoxy)pyrrolidine Hydrochloride

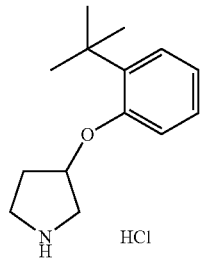 [SMILES: CC(C)(C)c1ccccc1OC1CCNC1 ; Cl]

A stirred solution of tert-butyl 3-(2-tert-butylphenoxy)pyrrolidine-1-carboxylate (0.78 g, 2.44 mmol) and hydrochloric acid (7.0 mL of a 4.0 N solution in dioxane, 28.0 mmol) was reacted at room temperature for 16 h. Then, the reaction mixture was concentrated under reduced pressure. The residue was triturated with ethyl acetate to provide 3-(2-tert-butylphenoxy)pyrrolidine hydrochloride as a colorless solid (0.52 g, 83%).

$^1$H NMR (500 MHz, DMSO-$d_6$) δ 9.43 (s, 1H), 7.27 (dd, J=1.5, 7.5 Hz, 1H), 7.21-7.18 (m, 1H), 6.95-6.90 (m, 2H), 5.18-5.16 (m, 1H), 3.67-3.63 (m, 1H), 3.44-3.39 (m, 1H), 3.32-3.29 (m, 1H), 3.26-3.21 (m, 1H), 2.26-2.20 (m, 2H), 1.34 (s, 9H).

Reference Example 13 tert-butyl 4-(tosyloxy)piperidine-1-carboxylate

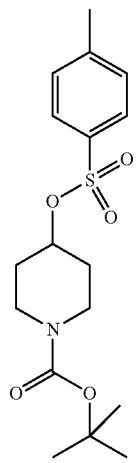 [SMILES: Cc1ccc(S(=O)(=O)OC2CCN(C(=O)OC(C)(C)C)CC2)cc1]

The title compound was prepared by a procedure similar to the one described for tert-butyl 3-(tosyloxy)pyrrolidine-1-carboxylate to provide tert-butyl 4-(tosyloxy)piperidine-1-carboxylate (5.01 g, 52%) as a colorless solid.

$^1$H NMR (500 MHz, $CDCl_3$) δ 7.80 (d, J=8.0 Hz, 2H), 7.34 (d, J=8.0 Hz, 2H), 4.69-4.66 (m, 1H), 3.62-3.57 (m, 2H), 3.28-3.22 (m, 2H), 2.45 (s, 3H), 1.79-1.74 (m, 2H), 1.72-1.66 (m, 2H), 1.44 (s, 9H).

Reference Example 14 tert-butyl 4-(2-tert-butylphenoxy)piperidine-1-carboxylate

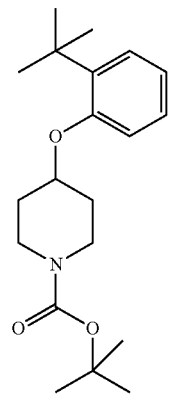 [SMILES: CC(C)(C)OC(=O)N1CCC(Oc2ccccc2C(C)(C)C)CC1]

The title compound was prepared by a procedure similar to the one described for tert-butyl 3-(2-tert-butylphenoxy)pyrrolidine-1-carboxylate to provide tert-butyl 4-(2-tert-butylphenoxy)piperidine-1-carboxylate (2.30 g, 98%) as a pale yellow solid. This solid (2.30 g) was triturated with a heptane/ethyl acetate solution to provide tert-butyl 4-(2-tert-butylphenoxy)piperidine-1-carboxylate (0.68 g, 30%) as a colorless powder: mp 102-103° C.

$^1$H NMR (500 MHz, $CDCl_3$) δ 7.31-7.30 (m, 1H), 7.17-7.13 (m, 1H), 6.88-6.82 (m, 2H), 4.61-4.57 (m, 1H), 3.73-3.68 (m, 2H), 3.45-3.40 (m, 2H), 2.00-1.96 (m, 2H), 1.87-1.81 (m, 2H), 1.60 (s, 9H), 1.44 (s, 9H).

Reference Example 15

4-(2-tert-butylphenoxy)piperidine Hydrochloride

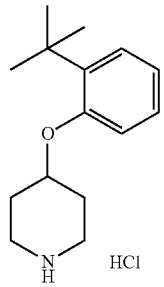 [SMILES: CC(C)(C)c1ccccc1OC1CCNCC1 ; Cl]

The title compound was prepared by a procedure similar to the one described for 3-(2-tert-butylphenoxy)pyrrolidine hydrochloride to provide 4-(2-tert-butylphenoxy)piperidine hydrochloride (0.51 g, 98%) as a colorless solid.

¹H NMR (500 MHz, DMSO-d₆) δ 9.00-8.92 (br s, 1H), 7.25 (dd, J=7.5, 1.5 Hz, 1H), 7.19-7.15 (m, 1H), 7.02 (d, J=8.0 Hz, 1H), 6.89-6.85 (m, 1H), 4.78-4.73 (m, 1H), 3.25-3.21 (m, 2H), 3.15-3.10 (m, 2H), 2.21-2.18 (m, 2H), 1.94-1.87 (m, 2H), 1.36 (s, 9H).

Reference Example 16 tert-butyl 4-({[(4-methylphenyl)sulfonyl]oxy}methyl)piperidine-1-carboxylate

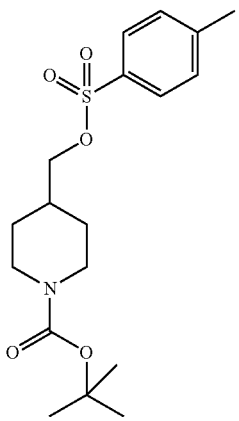 [SMILES: Cc1ccc(S(=O)(=O)OCC2CCN(C(=O)OC(C)(C)C)CC2)cc1]

The title compound was prepared by a procedure similar to the one described for tert-butyl 3-(tosyloxy)pyrrolidine-1-carboxylate to provide tert-butyl 4-({[(4-methylphenyl)sulfonyl]oxy}methyl)piperidine-1-carboxylate (27.79 g, 82%) as a white powder.

¹H NMR (300 MHz, CDCl₃) δ 7.81-7.75 (m, 2H), 7.39-7.32 (m, 2H), 4.18-3.99 (m, 2H), 3.84 (d, J=6.3 Hz, 2H), 2.74-2.56 (m, 2H), 2.46 (s, 3H), 1.89-1.75 (m, 1H), 1.69-1.59 (m, 2H), 1.44 (s, 9H), 1.18-1.02 (m, 2H).

Reference Example 17 tert-butyl 4-[(2-tert-butyl-4-fluorophenoxy)methyl]piperidine-1-carboxylate

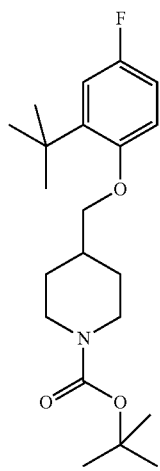 [SMILES: CC(C)(C)OC(=O)N1CCC(COc2ccc(F)cc2C(C)(C)C)CC1]

The title compound was prepared by a procedure similar to the one described for tert-butyl 3-(2-tert-butylphenoxy)pyrrolidine-1-carboxylate to provide tert-butyl 4-[(2-tert-butyl-4-fluorophenoxy)methyl]piperidine-1-carboxylate (7.47 g, 76%) as a white powder.

¹H NMR (300 MHz, CDCl₃) δ 7.03-6.96 (m, 1H), 6.86-6.78 (m, 1H), 6.78-6.71 (m, 1H), 4.27-4.07 (m, 2H), 3.80 (d, J=6.4 Hz, 2H), 2.85-2.70 (m, 2H), 2.10-1.92 (m, 1H), 1.91-1.80 (m, 2H), 1.47 (s, 9H), 1.40-1.25 (m, 11H).

Reference Example 18

4-[(2-tert-butyl-4-fluorophenoxy)methyl]piperidine hydrochloride

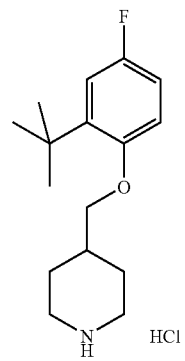 [SMILES: CC(C)(C)c1cc(F)ccc1OCC1CCNCC1 ; Cl]

The title compound was prepared by a procedure similar to the one described for 3-(2-tert-butylphenylthio)azetidine hydrochloride to provide 4-[(2-tert-butyl-4-fluorophenoxy)methyl]piperidine hydrochloride (5.87 g, 95%) as a white powder.

¹H NMR (300 MHz, DMSO-d₆) δ 8.95-8.90 (br s, 1H), 8.70-8.50 (br s, 1H), 6.96-6.71 (m, 3H), 3.87 (d, J=6.0 Hz, 2H), 3.38-3.27 (m, 2H), 3.02-2.85 (m, 2H), 2.20-2.05 (m, 1H), 2.00-1.90 (m, 2H), 1.84-1.45 (m, 2H), 1.34 (s, 9H).

Reference Example 19

2-(1-hydroxy-1-methylethyl)phenol

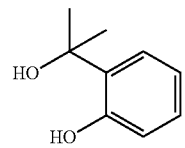

To an ice-cold stirred solution of methyl lithium (100 mL of 1.0M solution in diethyl ether, 100 mmol) was added 2-hydroxyacetophenone (6.50 g, 47.7 mmol) and the resulting mixture was warmed to room temperature. After 3 h the reaction mixture was poured into 1N hydrochloric acid (100 ml) and extracted with ethyl acetate (2×100 mL). The combined organic layer was washed with water (2×60 mL), saturated sodium chloride (100 mL), dried (MgSO₄), and filtered. The filtrate was concentrated under reduced pressure. The residue was purified by flash column chromatography (silica gel, 85:15 hexane/ethyl acetate) to provide 2-(1-hydroxy-1-methylethyl)phenol (1.84 g, 25%) as a yellow oil.

$^1$H NMR (300 MHz, CDCl$_3$) δ 8.95 (s, 1H), 7.19-7.13 (m, 1H), 7.10-7.05 (m, 1H), 6.89-6.78 (m, 2H), 2.54 (br s, 1H), 1.67 (s, 6H).

Reference Example 20

2-(2-{[1-(diphenylmethyl)azetidin-3-yl]oxy}phenyl)propan-2-ol

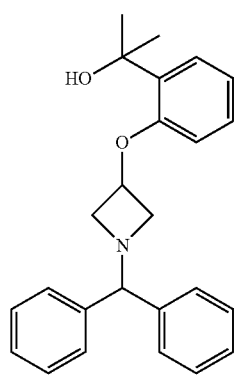 [SMILES: CC(C)(O)c1ccccc1OC1CN(C(c2ccccc2)c2ccccc2)C1]

The title compound was prepared by a procedure similar to the one described for 1-benzhydryl-3-(2-tert-butylphenoxy)azetidine to provide impure 2-(2-{[1-(diphenylmethyl)azetidin-3-yl]oxy}phenyl)propan-2-ol (3.54 g, 78%) as a orange oil, which was used without further purification or characterization.

$^1$H NMR (300 MHz, CDCl$_3$) δ 7.43-7.05 (m, 11H), 6.96-6.77 (m, 2H), 6.61-6.57 (m, 1H), 4.95-4.85 (m, 1H), 4.41 (s, 1H), 4.03 (br s, 1H), 3.78-3.71 (m, 2H), 3.18-3.11 (m, 2H), 1.63 (s, 6H).

Reference Example 21

2-[2-(azetidin-3-yloxy)phenyl]propan-2-ol

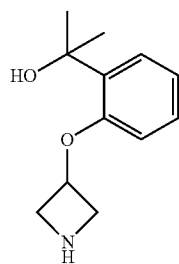

The title compound was prepared by a procedure similar to the one described for 3-(2-tert-butylphenoxy)azetidine to provide impure 2-[2-(azetidin-3-yloxy)phenyl]propan-2-ol (1.69 g, 86%) as a orange solid, which was used without further purification or characterization.

$^1$H NMR (300 MHz, CDCl$_3$) δ 7.47-7.42 (m, 1H), 7.24-7.15 (m, 1H), 7.05-6.97 (m, 1H), 6.54-6.50 (m, 1H), 5.08-5.00 (m, 1H), 4.58-4.51 (m, 1H), 4.47-4.41 (m, 1H), 4.25-4.19 (m, 1H), 3.91-3.81 (m, 1H), 3.05-2.85 (br s, 1H), 1.64 (s, 6H).

Reference Example 22 tert-butyl 4-({[(4-methylphenyl)sulfonyl]oxy}methyl)piperidine-1-carboxylate

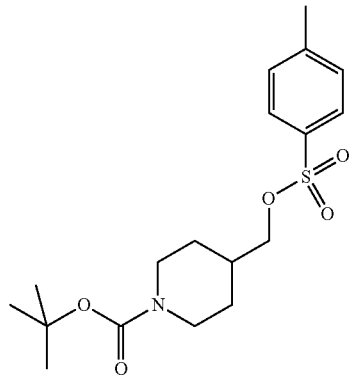 [SMILES: Cc1ccc(S(=O)(=O)OCC2CCN(C(=O)OC(C)(C)C)CC2)cc1]

The title compound was prepared by a procedure similar to the one described for tert-butyl 3-(tosyloxy)pyrrolidine-1-carboxylate to provide tert-butyl 4-({[(4-methylphenyl)sulfonyl]oxy}methyl)piperidine-1-carboxylate (16.94 g, 85%) as a yellow oil.

$^1$H NMR (300 MHz, CDCl$_3$) δ 7.79-7.75 (m, 2H), 7.36-7.33 (m, 2H), 4.15-4.08 (m, 2H), 3.84 (d, J=6.3 Hz, 2H), 2.69-2.61 (m, 2H), 2.46 (s, 3H), 2.04-1.77 (m, 1H), 1.67-1.63 (m, 2H), 1.46 (s, 9H), 1.16-1.07 (m, 2H).

Reference Example 23 tert-butyl 4-[(2-tert-butylphenoxy)methyl]piperidine-1-carboxylate

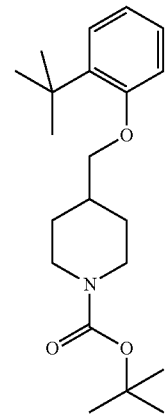 [SMILES: CC(C)(C)OC(=O)N1CCC(COc2ccccc2C(C)(C)C)CC1]

The title compound was prepared by a procedure similar to the one described for tert-butyl 3-(2-tert-butylphenoxy)pyrrolidine-1-carboxylate to provide tert-butyl 4-[(2-tert-butylphenoxy)methyl]piperidine-1-carboxylate (12.69 g, 80%) as a yellow oil.

$^1$H NMR (300 MHz, CDCl$_3$) δ 7.29-7.27 (m, 1H), 7.24-7.12 (m, 1H), 6.91-6.82 (m, 2H), 4.20-4.10 (m, 2H), 3.83 (d,

J=6.0 Hz, 2H), 2.81-2.73 (m, 2H), 2.07-1.99 (m, 1H), 1.89-1.81 (m, 2H), 1.47 (s, 9H), 1.39 (s, 9H), 1.37-1.27 (m, 2H).

Reference Example 24

4-[(2-tert-butylphenoxy)methyl]piperidine Hydrochloride

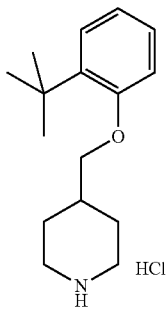

The title compound was prepared by a procedure similar to the one described for 3-(2-tert-butylphenoxy)pyrrolidine hydrochloride to provide 4-[(2-tert-butylphenoxy)methyl]piperidine hydrochloride (9.2 g, 90%) as a colorless solid.

$^1$H NMR (300 MHz, DMSO-$d_6$) δ 9.17 (br s, 1H), 8.94 (br s, 1H), 7.23-7.20 (m, 1H), 7.18-7.12 (m, 1H), 6.98-6.95 (m, 1H), 6.88-6.83 (m, 1H), 3.87 (d, J=6.0 Hz, 2H), 3.33-3.28 (m, 2H), 2.98-2.82 (m, 2H), 2.15-2.10 (m, 1H), 1.97-1.93 (m, 2H), 1.66-1.52 (m, 2H), 1.35 (s, 9H).

Reference Example 25 tert-butyl 4-(2-hydroxyethyl)piperidine-1-carboxylate

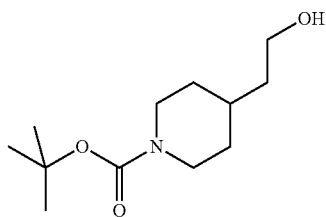 [SMILES: CC(C)(C)OC(=O)N1CCC(CCO)CC1]

To a stirred solution of 2-piperidin-4-ylethanol (25.5 g, 197 mmol) in tetrahydrofuran (250 mL) was added di-tert-butyl dicarbonate (43.0 g, 197 mmol) at room temperature. After 16 h the reaction mixture was concentrated under reduced pressure to provide tert-butyl 4-(2-hydroxyethyl)piperidine-1-carboxylate (44.3 g, 98%) as colorless oil.

$^1$H NMR (300 MHz, CDCl$_3$) δ 4.11-4.05 (m, 2H), 3.72-3.66 (m, 2H), 2.73-2.65 (m, 2H), 1.74-1.59 (m, 4H), 1.55-1.43 (m, 2H), 1.38 (s, 9H), 1.19-1.09 (m, 2H).

Reference Example 26 tert-butyl 4-[2-(2-tert-butylphenoxy)ethyl]piperidine-1-carboxylate

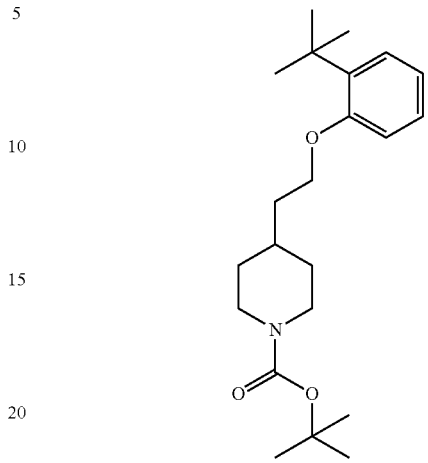

To an ice-cold stirred solution of tert-butyl 4-(2-hydroxyethyl)piperidine-1-carboxylate (44.3 g, 193 mmol) in pyridine (30.0 mL) was added p-TsCl (5.63 g, 30.0 mmol). After stirring for 16 h at room temperature, the reaction mixture was concentrated under reduced pressure and the resulting residue was partitioned between ethyl acetate (300.0 ml) and 1.0 N hydrochloric acid (200.0 mL) and separated. The organic layer was washed with water (2×100 mL), saturated sodium chloride (100 mL), dried (MgSO$_4$), filtered and filtrate concentrated under reduced pressure. The residue was dissolved in DMF (100.0 mL), added to a stirred solution of 2-(tert-butyl)phenol (10.8 g, 72.0 mmol) and K$_3$PO$_4$ (45.8 g, 216 mmol) in DMF (60.0 mL) and the resulting reaction mixture was heated at 80° C. for 16 h. Then, the reaction mixture was cooled to room temperature, poured into water (150.0 mL) and extracted with ethyl acetate (2×100.0 mL). The combined organics were washed with water (2×150 ml), saturated sodium chloride (100 mL), dried (MgSO$_4$), filtered, and concentrated under reduced pressure. The residue was purified by flash column chromatography (silica gel, 95:5 to 90:10 hexane/ethyl acetate) to provide tert-butyl 4-[2-(2-tert-butylphenoxy)ethyl]piperidine-1-carboxylate (31.7 g, 44%) as a yellow oil.

$^1$H NMR (300 MHz, CDCl$_3$) δ 7.29-7.25 (m, 1H), 7.18-7.12 (m, 1H), 6.90-6.84 (m, 2H), 4.13-4.08 (m, 1H), 4.03 (t, J=6.3 Hz, 2H), 2.74-2.66 (m, 2H), 1.81-1.65 (m, 6H), 1.46 (s, 9H), 1.38 (s, 9H), 1.32-1.13 (m, 2H).

Reference Example 27

4-[2-(2-tert-butylphenoxy)ethyl]piperidine Hydrochloride

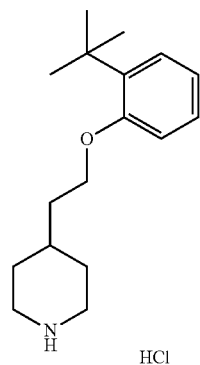 [SMILES: CC(C)(C)c1ccccc1OCCC1CCNCC1 ; Cl]

The title compound was prepared by a procedure similar to the one described for 3-(2-tert-butylphenoxy)pyrrolidine hydrochloride to provide 4-[2-(2-tert-butylphenoxy)ethyl]piperidine hydrochloride (12.0 g, 92%) as a colorless solid.

$^1$H NMR (300 MHz, DMSO-$d_6$) δ 9.25 (br s, 1H), 9.05 (br s, 1H), 7.22-7.20 (m, 1H), 7.19-7.12 (m, 1H), 6.97-6.94 (m, 1H), 6.87-6.82 (m, 1H), 4.02 (t, J=6.3 Hz, 2H), 3.25-3.21 (m, 2H), 2.83-2.78 (m, 2H), 1.88-1.64 (m, 5H), 1.55-1.39 (m, 2H), 1.34 (s, 9H).

Reference Example 28 tert-butyl 3-({[(4-methylphenyl)sulfonyl]oxy}methyl)pyrrolidine-1-carboxylate

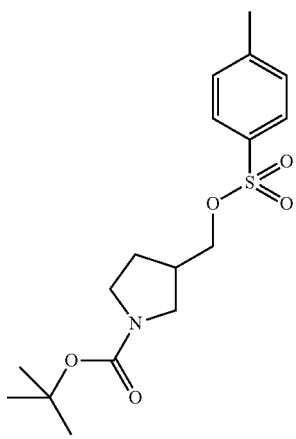 [SMILES: Cc1ccc(S(=O)(=O)OCC2CCN(C(=O)OC(C)(C)C)C2)cc1]

The title compound was prepared by a procedure similar to the one described for tert-butyl 3-(tosyloxy)pyrrolidine-1-carboxylate to provide tert-butyl 3-({[(4-methylphenyl)sulfonyl]oxy}methyl)pyrrolidine-1-carboxylate (8.37 g, 95%) as a yellow oil.

$^1$H NMR (300 MHz, CDCl$_3$) δ 7.78 (d, J=8.4 Hz, 2H), 7.35 (d, J=8.4 Hz, 2H), 4.01-3.93 (m, 2H), 3.48-3.42 (m, 1H), 3.34-3.31 (m, 2H), 3.03-2.97 (m, 1H), 2.56-2.53 (m, 1H), 2.46 (s, 3H), 1.97-1.93 (m, 1H), 1.67-1.63 (m, 1H), 1.44 (s, 9H).

Reference Example 29 tert-butyl 3-[(2-tert-butylphenoxy)methyl]pyrrolidine-1-carboxylate

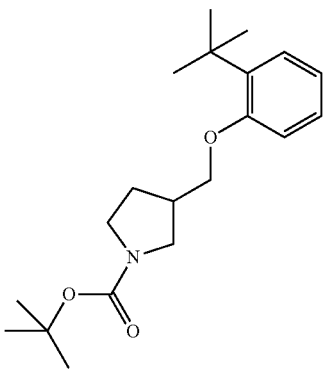 [SMILES: CC(C)(C)OC(=O)N1CCC(COc2ccccc2C(C)(C)C)C1]

The title compound was prepared by a procedure similar to the one described for tert-butyl 3-(2-tert-butylphenoxy)pyrrolidine-1-carboxylate to provide tert-butyl 3-[(2-tert-butylphenoxy)methyl]pyrrolidine-1-carboxylate (6.74 g, 100%) as a yellow oil.

$^1$H NMR (300 MHz, CDCl$_3$) δ 7.29-7.25 (m, 1H), 7.19-7.13 (m, 1H), 6.91-6.81 (m, 2H), 4.00-3.89 (m, 2H), 3.72-3.37 (m, 3H), 3.24-3.18 (m, 1H), 2.78-2.74 (m, 1H), 2.10-2.08 (m, 1H), 1.83-1.76 (m, 1H), 1.47 (s, 9H), 1.38 (s, 9H).

Reference Example 30

3-[(2-tert-butylphenoxy)methyl]pyrrolidine Hydrochloride

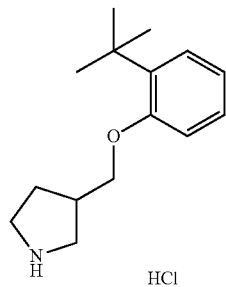 [SMILES: CC(C)(C)c1ccccc1OCC1CCNC1 ; Cl]

The title compound was prepared by a procedure similar to the one described for 3-(2-tert-butylphenoxy)pyrrolidine hydrochloride to provide 3-[(2-tert-butylphenoxy)methyl]pyrrolidine hydrochloride (4.9 g, 91%) as a colorless solid.

$^1$H NMR (300 MHz, DMSO-$d_6$) δ 9.35 (br s, 2H), 7.24-7.14 (m, 2H), 6.96-6.84 (m, 2H), 4.02 (d, J=7.2 Hz, 2H), 3.42-3.13 (m, 3H), 3.03-2.97 (m, 1H), 2.81-2.76 (m, 1H), 2.19-2.13 (m, 1H), 1.80-1.73 (m, 1H), 1.34 (s, 9H).

Reference Example 31

3-[(2-tert-butylphenoxy)methyl]-1-(diphenylmethyl)azetidine

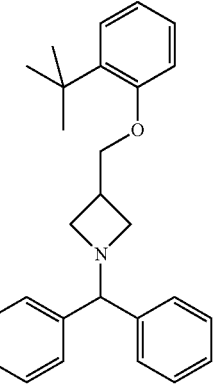

The title compound was prepared by a procedure similar to the one described for tert-butyl 4-[2-(2-tert-butylphenoxy)ethyl]piperidine-1-carboxylate to provide 3-[(2-tert-butylphenoxy)methyl]-1-(diphenylmethyl)azetidine (10.5 g, 46%) as a yellow solid.

$^1$H NMR (300 MHz, CDCl$_3$) δ 7.43-7.40 (m, 3H), 7.28-7.23 (m, 5H), 7.19-7.13 (m, 4H), 6.90-6.83 (m, 2H), 4.39 (s, 1H), 4.13-4.10 (m, 2H), 3.38 (t, J=7.8 Hz, 2H), 3.08 (d, J=7.8 Hz, 2H), 3.03-2.94 (m, 1H), 1.36 (s, 9H).

Reference Example 32

3-[(2-tert-butylphenoxy)methyl]azetidine Hydrochloride

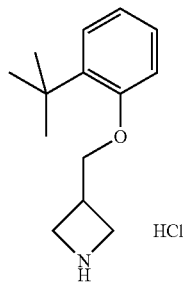 [SMILES: CC(C)(C)c1ccccc1OCC1CNC1 ; Cl]

The title compound was prepared by a procedure similar to the one described for 3-(2-tert-butylphenoxy)pyrrolidine hydrochloride to provide 3-[(2-tert-butylphenoxy)methyl]azetidine hydrochloride (5.4 g, 78%) as a colorless solid.

$^1$H NMR (300 MHz, DMSO-$d_6$) δ 9.38 (br s, 2H), 7.24-7.15 (m, 2H), 6.97-6.94 (m, 1H), 6.91-6.86 (m, 1H), 4.22 (d, J=6.9 Hz, 2H), 4.10-4.04 (m, 2H), 3.84-3.78 (m, 2H), 3.28-3.23 (m, 1H), 1.35 (s, 9H).

Reference Example 33

4-(1,3-oxazol-5-yl)benzenesulfonamide

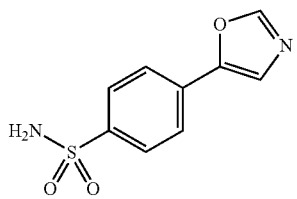 [SMILES: NS(=O)(=O)c1ccc(-c2cnco2)cc1]

To a stirred solution of 4-(1,3-oxazol-5-yl)benzenesulfonyl chloride (1.00 g, 4.10 mmol) in tetrahydrofuran (15.0 mL) was added 25% ammonia water solution (5.00 mL) at room temperature. After 1 h the reaction mixture was partitioned between ethyl acetate (100.0 mL) and 1.0 N hydrochloric acid (10.0 mL) and separated. The organic layer was washed with water (2×40 mL), saturated sodium chloride (80 mL), dried (MgSO$_4$), filtered. The filtrate was concentrated under reduced pressure to provide 4-(1,3-oxazol-5-yl)benzenesulfonamide (800 mg, 87%) as a solid.

$^1$H NMR (300 MHz, DMSO-$d_6$) δ 8.46 (s, 1H), 7.95-7.88 (m, 4H), 7.81 (s, 1H), 7.40 (s, 2H).

Reference Example 34

2-formylcyclopropanecarboxylic acid

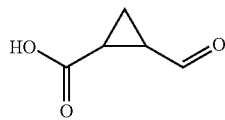

To a stirred solution of ethyl 2-formylcyclopropanecarboxylate (9.95 g, 70.0 mmol) in tetrahydrofuran (150 mL) and MeOH (50 mL) was added 8 N sodium hydroxide solution (8.8 ml, 70.4 mmol) at room temperature. After 3 h the reaction mixture was partitioned between ethyl acetate (200.0 mL) and 1.0 N hydrochloric acid (100 mL) and separated. The organic layer was washed with water (2×60 mL), saturated sodium chloride (100 mL), dried (MgSO$_4$), filtered. The filtrate was concentrated under reduced pressure to provide 2-formylcyclopropanecarboxylic acid (6.53 g, 82%) as a solid.

$^1$H NMR (300 MHz, CDCl$_3$) δ 10.91 (br s, 1H), 9.31 (s, 1H), 2.54-2.46 (m, 1H), 2.31-2.19 (m, 1H), 1.69-1.53 (m, 2H).

Reference Example 35 tert-butyl 4-(2-tert-butyl-5-methylphenoxy)piperidine-1-carboxylate

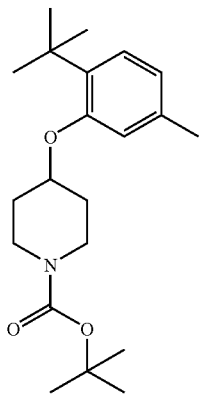 [SMILES: Cc1ccc(C(C)(C)C)c(OC2CCN(C(=O)OC(C)(C)C)CC2)c1]

The title compound was prepared by a procedure similar to the one described for tert-butyl 3-(2-tert-butylphenoxy)pyrrolidine-1-carboxylate to provide tert-butyl 4-(2-tert-butyl-5-methylphenoxy)piperidine-1-carboxylate (1.50 g, 45%) as a yellow oil.

$^1$H NMR (300 MHz, CDCl$_3$) δ 7.17 (d, J=8.1 Hz, 1H), 6.68 (d, J=8.1 Hz, 1H), 6.63 (s, 1H), 4.61-4.56 (m, 1H), 3.73-3.64 (m, 2H), 3.48-3.40 (m, 2H), 2.30 (s, 3H), 2.01-1.94 (m, 2H), 1.89-1.81 (m, 2H), 1.47 (s, 9H), 1.37 (s, 9H).

Reference Example 36

4-(2-tert-butyl-5-methylphenoxy)piperidine Hydrochloride

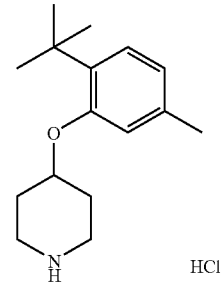 [SMILES: Cc1ccc(C(C)(C)C)c(OC2CCNCC2)c1 ; Cl]

The title compound was prepared by a procedure similar to the one described for 3-(2-tert-butylphenoxy)pyrrolidine hydrochloride to provide 4-(2-tert-butyl-5-methylphenoxy)piperidine hydrochloride (1.2 g, 98%) as a colorless solid.

¹H NMR (300 MHz, DMSO-d₆) δ 9.14 (br s, 1H), 8.99 (br s, 1H), 7.08 (d, J=8.1 Hz, 1H), 6.82 (s, 1H), 6.66-6.63 (m, 1H), 4.75-4.70 (m, 1H), 3.19-3.12 (m, 4H), 2.25 (s, 3H), 2.21-2.16 (m, 2H), 1.99-1.83 (m, 2H), 1.32 (s, 9H).

Reference Example 37

(3-hydroxyazetidin-1-yl)(phenyl)methanone

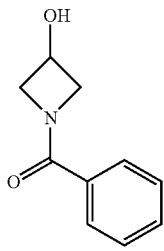

To a stirred mixture of 3-hydroxyazetidine hydrochloride (10.0 g, 91.3 mmol), benzoyl chloride (12.8 g, 91.3 mmol) in 3:2 water/ethyl acetate (500 mL) was added potassium carbonate (63.1 g, 456.5 mmol) at room temperature. After 16 h the organic layer was separated and concentrated under reduced pressure. The resulting residue was dissolved in 2:1 THF/methanol (150 mL) and stirred with 1.0 N sodium hydroxide (50.0 mL) at room temperature. After 1 h the reaction mixture was concentrated under reduced pressure, the resulting residue was partitioned between ethyl acetate and water and separated. The organic layer was washed with saturated sodium chloride, dried (Na₂SO₄), filtered and concentrated under reduced pressure to provide (3-hydroxyazetidin-1-yl)(phenyl)methanone (13.5 g, 83%) as a colorless gum-like substance.

¹H NMR (500 MHz, CDCl₃) δ 7.61-7.58 (m, 2H), 7.48-7.44 (m, 1H), 7.41-7.38 (m, 2H), 4.71-4.66 (m, 1H), 4.46-4.42 (m, 2H), 4.17-4.06 (br m, 2H), 3.27 (br s, 1H).

Reference Example 38

1-benzoylazetidin-3-yl methanesulfonate

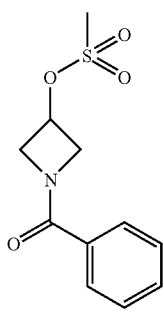 [SMILES: CS(=O)(=O)OC1CN(C(=O)c2ccccc2)C1]

A stirred solution of (3-hydroxyazetidin-1-yl)(phenyl)methanone (13.5 g, 76.2 mmol), methanesulfonyl chloride (12.6 g, 110 mmol) and triethylamine (12.3 g, 121 mmol) in THF (300 ml) was heated at 50° C. for 3 h. Then, the reaction mixture was cooled to room temperature and the resulting precipitate was collected by filtration. The filtrate was concentrated under reduced pressure, the residue was partitioned between ethyl acetate and water and separated. The organic layer was washed with saturated sodium chloride, dried (Na₂SO₄), filtered and concentrated under reduced pressure. The residue was purified by flash column chromatography (silica gel, 50:50 to 80:20, ethyl acetate/heptane) provided 1-benzoylazetidin-3-yl methanesulfonate (12.8 g, 66%) as a white solid.

¹H NMR (500 MHz, CDCl₃) δ 7.63-7.60 (m, 2H), 7.51-7.39 (m, 3H), 5.33-5.29 (m, 1H), 4.61-4.57 (m, 2H), 4.46-4.33 (m, 2H), 3.09 (s, 3H).

Reference Example 39 phenyl(3-(o-tolyloxy)azetidin-1-yl)methanone

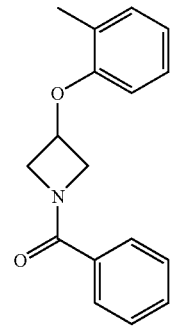 [SMILES: Cc1ccccc1OC1CN(C(=O)c2ccccc2)C1]

To a stirred solution of o-cresol (0.16 g, 1.51 mmol) in DMF (10 ml) was added 60% sodium hydride (0.063 g, 1.59 mmol) at room temperature. After 10 min 1-benzoylazetidin-3-yl methanesulfonate (0.50 g, 1.96 mmol) was added and the resulting reaction mixture was heated at 60° C. for 16 h. After this reaction mixture was cooled to room temperature, partitioned between ethyl acetate and water and separated. The organic layer was washed with saturated sodium chloride, dried (Na₂SO₄), filtered and concentrated under reduced pressure. The residue was purified by flash column chromatography (silica gel, 80:20 to 50:50, heptane/ethyl acetate) to provide a white solid. Trituration of the solid with heptane/ethyl acetate and collection of the resulting solids by filtration provided phenyl(3-(o-tolyloxy)azetidin-1-yl)methanone (0.14 g, 35%) as a white solid.

¹H NMR (500 MHz, CDCl₃) δ 7.67-7.65 (m, 2H), 7.49-7.40 (m, 3H), 7.17 (d, J=7.4 Hz, 1H), 7.13-7.09 (m, 1H), 6.92-6.89 (m, 1H), 6.44 (d, J=8.1 Hz, 1H), 5.02-4.98 (m, 1H), 4.65-4.61 (m, 2H), 4.35-4.30 (br m, 2H), 2.25 (s, 3H).

Reference Example 40

2-tert-butyl-4-chlorophenol

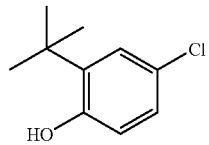

To a mixture of p-chlorophenol (19.0 g, 147.8 mmol) and tert-butanol (21.9 g, 295.6 mmol) was added concentrated sulfuric acid (15 mL), and the mixture was stirred at room temperature for 2 days. The reaction mixture was poured into ice water (300 mL), and the mixture was extracted with ethyl acetate. The extract was washed with saturated brine, dried over anhydrous magnesium sulfate, and filtered. The filtrate was concentrated under reduced pressure. The residue was purified by silica gel column chromatography (hexane:ethyl acetate 95:5) to give the title compound (14.3 g, yield 54%) as a brown oil.

$^1$H NMR (300 MHz, CDCl$_3$) δ 7.21 (d, J=2.7 Hz, 1H), 7.02 (dd, J=8.3, 2.7 Hz, 1H), 6.60 (d, J=8.7 Hz, 1H), 4.95 (br s, 1H), 1.39 (s, 9H).

Reference Example 41

2-tert-butyl-4-bromophenol

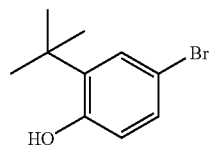

To a solution of 2-tert-butylphenol (25.0 g, 166.4 mmol) in acetonitrile (150 mL) was added N-bromosuccinimide (30.0 g, 168.5 mmol), and the mixture was stirred at room temperature for 16 hr. Petroleum ether (150 mL) was added to the reaction mixture, and the mixture was stirred at 0° C. for 1 hr. The precipitated white solid was filtered, and the filtrate was concentrated under reduced pressure. The residue was purified by silica gel column chromatography (hexane:ethyl acetate 95:5-90:10) to give the title compound as a yellow oil. This was used for the next reaction without further purification.

$^1$H NMR (300 MHz, CDCl$_3$) δ 7.35 (d, J=2.7 Hz, 1H), 7.16 (dd, J=8.3, 2.3 Hz, 1H), 6.55 (d, J=8.3 Hz, 1H), 4.99 (s, 1H), 1.38 (s, 9H).

Reference Example 42

[1-(diphenylmethyl)azetidin-3-yl]methyl methanesulfonate

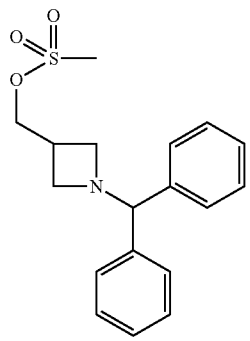 [SMILES: CS(=O)(=O)OCC1CN(C(c2ccccc2)c2ccccc2)C1]

To a solution of [1-(diphenylmethyl)azetidin-3-yl]methanol (30.0 g, 118.4 mmol) in pyridine (200 mL) was slowly added methanesulfonyl chloride (17.0 g, 148.4 mmol), and the mixture was stirred at room temperature for 16 hr. The reaction mixture was diluted with water, and concentrated under reduced pressure. The residue was partitioned between ethyl acetate and 1N sodium hydroxide, and the ethyl acetate layer was washed with saturated brine, dried over anhydrous magnesium sulfate and filtered. The filtrate was concentrated under reduced pressure, and the obtained solid was washed with hexane to give the title compound (30.3 g, yield 77%) as a pale yellow solid.

$^1$H NMR (300 MHz, CDCl$_3$) δ 7.46-7.33 (m, 4H), 7.32-7.08 (m, 6H), 4.40 (d, J=6.8 Hz, 2H), 4.34 (s, 1H), 3.27 (t, J=7.7 Hz, 2H), 3.00 (s, 3H), 2.98-2.90 (m, 2H), 2.87-2.72 (m, 1H).

Reference Example 43

3-(2-tert-butyl-4-chlorophenoxy)-1-(diphenylmethyl) azetidine

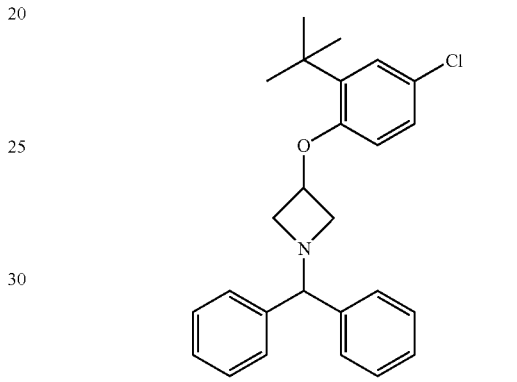

According to a method similar to that in Reference Example 1, the title compound (26.2 g, 87%) was obtained as a pale yellow amorphous form from 2-tert-butyl-4-chlorophenol (13.8 g, 74 mmol) obtained in Reference Example 40 and 1-(diphenylmethyl)azetidin-3-yl methanesulfonate (35.0 g, 110 mmol).

$^1$H NMR (300 MHz, CDCl$_3$) δ 7.47-7.35 (m, 4H), 7.33-7.22 (m, 4H), 7.22-7.14 (m, 3H), 7.01 (dd, J=8.7, 2.7 Hz, 1H), 6.44 (d, J=8.7 Hz, 1H), 4.83-4.68 (m, 1H), 4.41 (s, 1H), 3.84-3.63 (m, 2H), 3.15-3.03 (m, 2H), 1.36 (s, 9H).

Reference Example 44

3-(2-tert-butyl-4-chlorophenoxy)azetidine

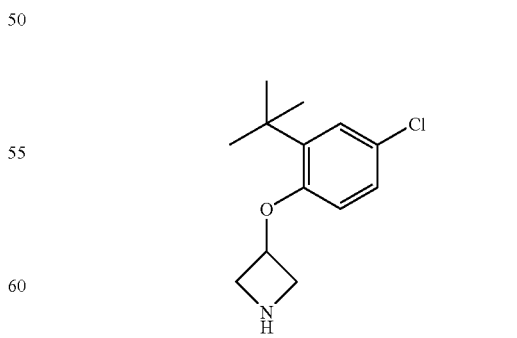

To a solution of 3-(2-tert-butyl-4-chlorophenoxy)-1-(diphenylmethyl)azetidine (25.1 g, 61.8 mmol) obtained in Reference Example 43 in dichloromethane (150 ml) was added 1-chloroethyl chlorocarbonate (10.0 g, 70.0 mmol), and the mixture was heated under reflux for 8 hr. The reaction mixture was cooled to room temperature, and the solvent was removed under reduced pressure. Methanol (100 mL) was added to the residue and the mixture was stirred for 16 hr. The reaction mixture was diluted with ethyl acetate, and extracted with 6N hydrochloric acid. The extract was neutralized with sodium hydroxide, and the mixture was extracted with ethyl acetate. The extract was washed with saturated brine, dried over anhydrous magnesium sulfate and filtered. The filtrate was concentrated under reduced pressure to give a pale yellow solid. This was recrystallized from hexane-ethyl acetate to give the title compound (32.0 g, yield 52%) as a pale red solid.

$^1$H NMR (300 MHz, CDCl$_3$) δ 7.26 (d, J=2.7 Hz, 1H), 7.10 (dd, J=8.7, 2.7 Hz, 1H), 6.32 (d, J=8.7 Hz, 1H), 5.18-5.05 (m, 1H), 4.54-4.42 (m, 2H), 4.27 (dd, J=12.1, 6.1 Hz, 2H), 1.36 (s, 9H).

Reference Example 45

3-(4-bromo-2-tert-butylphenoxy)-1-(diphenylmethyl)azetidine

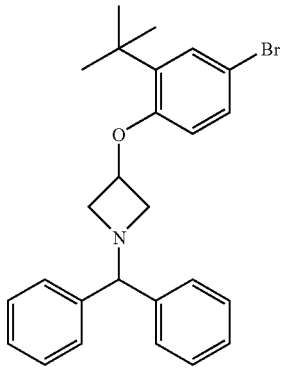 [SMILES: CC(C)(C)c1cc(Br)ccc1OC1CN(C(c2ccccc2)c2ccccc2)C1]

According to a method similar to that in Reference Example 1, the title compound (6.91 g, 88%) was obtained as a yellow oil from 2-tert-butyl-4-bromophenol (5.3 g, 16.5 mmol) obtained in Reference Example 41 and 1-(diphenylmethyl)azetidin-3-yl methanesulfonate (10.5 g, 33.1 mmol).

LC/MS ESI(+) m/z: 452 (M+H)$^+$.

Reference Example 46

3-(2-tert-butyl-4-bromophenoxy)azetidine

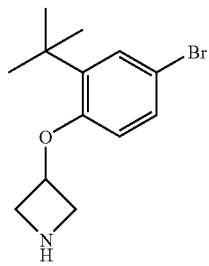 [SMILES: CC(C)(C)c1cc(Br)ccc1OC1CNC1]

To a solution of 3-(4-bromo-2-tert-butylphenoxy)-1-(diphenylmethyl)azetidine (3.70 g, 8.21 mmol) obtained in Reference Example 45 in acetonitrile (160 mL) was added 1-chloroethyl chlorocarbonate (1.29 g, 9.04 mmol), and the mixture was stirred at 60° C. for 16 hr. The reaction mixture was cooled to room temperature, and concentrated under reduced pressure. The obtained residue was dissolved in methanol (80 ml). The solution was heated under reflux for 16 hr. The reaction mixture was cooled to room temperature, and concentrated under reduced pressure. The obtained residue was partitioned between ethyl acetate and 1N sodium hydroxide solution. The ethyl acetate layer was washed with water and saturated brine, dried over anhydrous magnesium sulfate and filtered. The filtrate was concentrated under reduced pressure and the obtained residue was purified by NH-silica gel column chromatography (hexane:ethyl acetate 95:5-ethyl acetate:methanol 90:10) to give the title compound (1.23 g, 53%) as a colorless oil.

$^1$H NMR (300 MHz, CDCl$_3$) δ 7.37 (d, J=2.5 Hz, 1H), 7.22 (dd, J=8.7, 2.5 Hz, 1H), 6.38 (d, J=8.7 Hz, 1H), 4.18-4.09 (m, 1H), 3.98-3.89 (m, 2H), 3.88-3.77 (m, 2H), 1.38 (s, 9H).

Reference Example 47

3-[(2-tert-butyl-4-fluorophenoxy)methyl]-1-(diphenylmethyl)azetidine

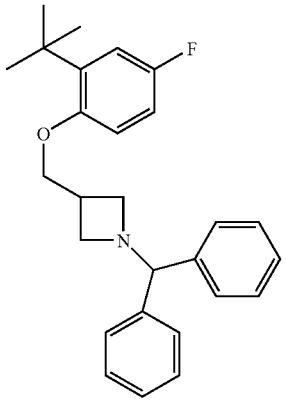 [SMILES: CC(C)(C)c1cc(F)ccc1OCC1CN(C(c2ccccc2)c2ccccc2)C1]

2-tert-Butyl-4-fluorophenol (3.35 g, 19.9 mmol) obtained in Reference Example 3, [1-(diphenylmethyl)azetidin-3-yl] methyl methanesulfonate (6.20 g, 18.1 mmol) obtained in Reference Example 42 and potassium phosphate (11.5 g, 54.3 mmol) were stirred in DMF (120 mL) at 80° C. for 16 hr. The reaction mixture was cooled to room temperature, and partitioned between ethyl acetate and water. The ethyl acetate layer was washed with water and saturated brine, dried over anhydrous magnesium sulfate and filtered. The filtrate was concentrated under reduced pressure, and the obtained residue was purified by silica gel column chromatography (hexane:ethyl acetate 90:10-80:20) to give the title compound (5.64 g, 77%) as a pale yellow solid.

LC/MS ESI(+) m/z: 404 (M+H)$^+$.

Reference Example 48

3-[(2-tert-butyl-4-fluorophenoxy)methyl]azetidine

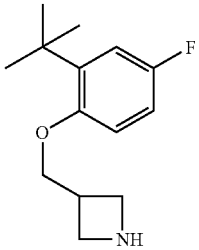 [SMILES: CC(C)(C)c1cc(F)ccc1OCC1CNC1]

A solution (80:20, 300 mL) of 3-[(2-tert-butyl-4-fluorophenoxy)methyl]-1-(diphenylmethyl)azetidine (5.60 g, 13.9 mmol) obtained in Reference Example 47 and palladium hydroxide (10%, 50% containing water, 1.80 g) in methanol-THF was stirred under a hydrogen atmosphere (0.4 MPa) at 50° C. for 8 hr. The reaction mixture was cooled to room temperature, filtered, and the filtrate was concentrated under reduced pressure. The obtained residue was partitioned between hexane-ethyl acetate (1:1) solution and 1N hydrochloric acid to separate the aqueous layer from a yellow oil part, and the mixture was adjusted to pH 10 with 8N sodium hydroxide under ice-cooling. The mixture was extracted with ethyl acetate, and the extract was washed with water and saturated brine, dried over anhydrous magnesium sulfate and filtered. The filtrate was concentrated under reduced pressure to give the title compound (2.42 g, 73%) as pale yellow amorphous crystals.

$^1$H NMR (300 MHz, CDCl$_3$) δ 7.00 (dd, J=10.6, 3.0 Hz, 1H), 6.90-6.62 (m, 2H), 4.24 (br s, 1H), 4.16 (d, J=6.8 Hz, 2H), 4.09-3.96 (m, 2H), 3.88-3.70 (m, 2H), 3.42-3.21 (m, 1H), 1.33 (s, 9H).

Reference Example 49

3-[(2-tert-butyl-4-chlorophenoxy)methyl]-1-(diphenylmethyl)azetidine

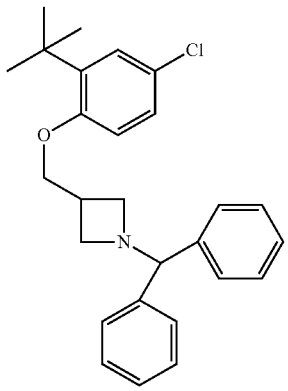 [SMILES: CC(C)(C)c1cc(Cl)ccc1OCC1CN(C(c2ccccc2)c2ccccc2)C1]

According to a method similar to that in Reference Example 47, the title compound (4.04 g, 79%) was obtained as colorless amorphous crystals from 2-tert-butyl-4-chlorophenol (2.46 g, 13.3 mmol) obtained in Reference Example 40 and [1-(diphenylmethyl)azetidin-3-yl]methyl methanesulfonate (4.0 g, 12.1 mmol) obtained in Reference Example 42.

$^1$H NMR (300 MHz, CDCl$_3$) δ 7.48-7.35 (m, 5H), 7.32-7.23 (m, 2H), 7.24-7.06 (m, 5H), 6.76 (d, J=8.9 Hz, 1H), 4.46-4.34 (m, 1H), 4.10 (d, J=6.4 Hz, 2H), 3.37 (t, J=7.2 Hz, 2H), 3.13-2.87 (m, 3H), 1.33 (s, 9H).

Reference Example 50

3-[(2-tert-butyl-4-chlorophenoxy)methyl]azetidine

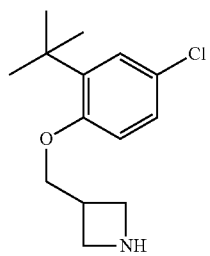 [SMILES: CC(C)(C)c1cc(Cl)ccc1OCC1CNC1]

According to a method similar to that in Reference Example 46, the title compound (1.60 g, 67%) was obtained from 3-[(2-tert-butyl-4-chlorophenoxy)methyl]-1-(diphenylmethyl)azetidine (3.93 g, 9.36 mmol) obtained in Reference Example 49.

$^1$H NMR (300 MHz, CDCl$_3$) δ 7.22 (d, J=2.7 Hz, 1H), 7.12 (dd, J=8.7, 2.7 Hz, 1H), 6.78 (d, J=8.7 Hz, 1H), 4.13 (d, J=6.8 Hz, 2H), 4.13-4.07 (m, 1H), 3.89-3.68 (m, 2H), 3.64-3.50 (m, 2H), 3.31-3.19 (m, 1H), 1.34 (s, 9H).

Reference Example 51 tert-butyl 3-{[(4-methylphenyl)sulfonyl]oxy}pyrrolidine-1-carboxylate

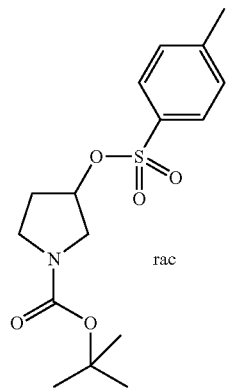 [SMILES: Cc1ccc(S(=O)(=O)OC2CCN(C(=O)OC(C)(C)C)C2)cc1]

To a solution of R,S-3-pyrrolidinol (25.0 g, 287 mmol) in THF (250 mL) was added di-tert-butyl carbonate (62.6 g, 287 mmol) under ice-cooling, and the mixture was stirred at room temperature for 16 hr. The reaction mixture was concentrated, and the obtained residue was diluted with pyridine (200 mL). Thereto was added p-toluenesulfonic acid chloride (54.7 g, 287 mmol) under ice-cooling, and the mixture was stirred at room temperature for 16 hr. The reaction mixture was partitioned between ethyl acetate and water, and the ethyl acetate layer was washed with saturated brine, dried over anhydrous magnesium sulfate and filtered. The filtrate was concentrated to give the title compound (78.4 g, 80%) as a white solid.

$^1$H NMR (300 MHz, CDCl$_3$) δ 7.79 (d, J=8.3 Hz, 2H), 7.51-7.30 (m, 2H), 5.23-4.94 (m, 1H), 3.65-3.26 (m, 4H), 2.60-2.38 (m, 3H), 2.27-1.88 (m, 2H), 1.45 (s, 9H).

Reference Example 52 tert-butyl 3-(2-tert-butylphenoxy)pyrrolidine-1-carboxylate

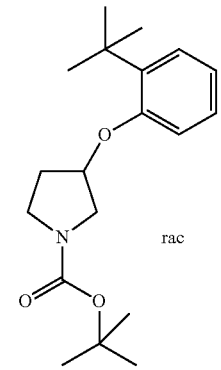 [SMILES: CC(C)(C)OC(=O)N1CCC(Oc2ccccc2C(C)(C)C)C1]

According to a method similar to that in Reference Example 11, the title compound (4.38 g, quant.) was obtained from 2-tert-butylphenol (2.0 g, 13.3 mmol) and tert-butyl 3-{([(4-methylphenyl)sulfonyl]oxy}pyrrolidine-1-carboxylate (10.0 g, 29.2 mmol) obtained in Reference Example 51.

¹H NMR (300 MHz, CDCl₃) δ 7.36-7.27 (m, 1H), 7.22-7.07 (m, 1H), 6.97-6.82 (m, 1H), 6.82-6.72 (m, 1H), 5.03-4.91 (m, 1H), 4.21-4.02 (m, 2H), 3.84-3.42 (m, 2H), 2.37-2.07 (m, 2H), 1.45 (s, 9H), 1.35 (s, 9H).

Reference Example 53

3-(2-tert-butylphenoxy)pyrrolidine hydrochloride

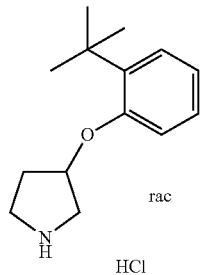 [SMILES: CC(C)(C)c1ccccc1OC1CCNC1 ; Cl]

According to a method similar to that in Reference Example 12, the title compound (3.33 g, 97%) was obtained from tert-butyl 3-(2-tert-butylphenoxy)pyrrolidine-1-carboxylate (4.30 g, 13.4 mmol) obtained in Reference Example 52.

¹H NMR (300 MHz, CDCl₃) δ 9.73 (br s, 1H), 7.30-7.21 (m, 1H), 7.23-7.12 (m, 1H), 7.00-6.82 (m, 2H), 5.89 (s, 1H), 3.73-3.54% (m, 1H), 3.48-3.07 (m, 3H), 2.32-2.11 (m, 2H), 1.33 (s, 9H).

Reference Example 54 tert-butyl 3-(2-tert-butyl-4-fluorophenoxy)pyrrolidine-1-carboxylate

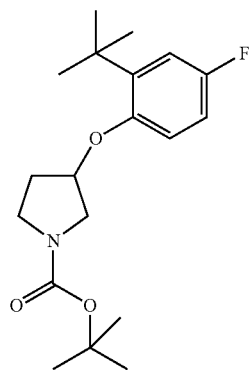 [SMILES: CC(C)(C)OC(=O)N1CCC(Oc2ccc(F)cc2C(C)(C)C)C1]

According to a method similar to that in Reference Example 11, the title compound (3.75 g, 76%) was obtained from 2-tert-butyl-4-fluorophenol (2.46 g, 14.6 mmol) obtained in Reference Example 3 and tert-butyl 3-{[(4-methylphenyl)sulfonyl]oxy}pyrrolidine-1-carboxylate (10.0 g, 29.2 mmol) obtained in Reference Example 51.

¹H NMR (300 MHz, CDCl₃) δ 7.11-6.94 (m, 1H), 6.90-6.77 (m, 1H), 6.74-6.62 (m, 1H), 5.03-4.81 (m, 1H), 3.85-3.38 (m, 4H), 2.36-2.10 (m, 2H), 1.45 (s, 9H), 1.33 (s, 9H).

Reference Example 55

3-(2-tert-butyl-4-fluorophenoxy)pyrrolidine

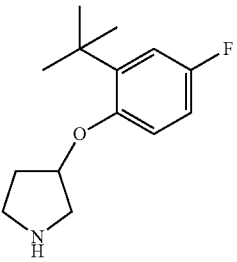 [SMILES: CC(C)(C)c1cc(F)ccc1OC1CCNC1]

According to a method similar to that in Reference Example 12, hydrochloride of the title compound was obtained from tert-butyl 3-(2-tert-butyl-4-fluorophenoxy)pyrrolidine-1-carboxylate (3.75 g, 11.1 mmol) obtained in Reference Example 54. This was partitioned between ethyl acetate and 1N sodium hydroxide, and the ethyl acetate layer was washed with water and saturated brine, dried over anhydrous magnesium sulfate, filtered, and concentrated. The obtained residue was dissolved in toluene (30 mL), and the mixture was concentrated under reduced pressure at 80° C. to give the title compound (2.44 g, 93%).

¹H NMR (300 MHz, CDCl₃) δ 7.05-6.95 (m, 1H), 6.81 (dt, J=8.9, 3.7 Hz, 1H), 6.75-6.66 (m, 1H), 4.98-4.73 (m, 1H), 3.28-3.04 (m, 3H), 3.03-2.86 (m, 1H), 2.22-1.96 (m, 2H), 1.91 (s, 1H), 1.35 (s, 9H).

Reference Example 56 tert-butyl 3-(2-tert-butyl-4-chlorophenoxy)pyrrolidine-1-carboxylate

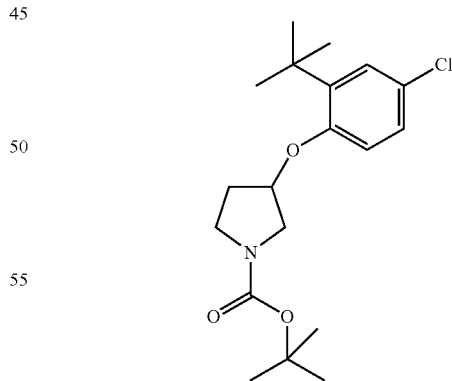

According to a method similar to that in Reference Example 11, the title compound (4.57 g, 88%) was obtained from 2-tert-butyl-4-chlorophenol (2.70 g, 14.6 mmol) obtained in Reference Example 40 and tert-butyl 3-{[(4-methylphenyl)sulfonyl]oxy}pyrrolidine-1-carboxylate (10.0 g, 29.2 mmol) obtained in Reference Example 51.

LC/MS ESI(+) m/z: 298 (M-tBu+H)⁺.

Reference Example 57

3-(2-tert-butyl-4-chlorophenoxy)pyrrolidine

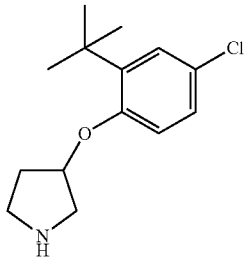 [SMILES: CC(C)(C)c1cc(Cl)ccc1OC1CCNC1]

According to a method similar to that in Reference Example 12, hydrochloride (2.80 g) of the title compound was obtained from tert-butyl 3-(2-tert-butyl-4-chlorophenoxy)pyrrolidine-1-carboxylate (4.50 g, 12.7 mmol) obtained in Reference Example 56. The hydrochloride (1.40 g, 4.82 mmol) was treated by a method similar to that in Reference Example 55 to give the title compound (0.86 g, 46%).

$^1$H NMR (300 MHz, CDCl$_3$) δ 7.23 (d, J=2.7 Hz, 1H), 7.10 (dd, J=8.7, 2.7 Hz, 1H), 6.72 (d, J=8.7 Hz, 1H), 4.91-4.79 (m, 1H), 3.31-3.05 (m, 3H), 3.04-2.85 (m, 1H), 2.26-1.88 (m, 2H), 1.35 (s, 9H).

Reference Example 58 tert-butyl 3-[(2-tert-butyl-4-fluorophenoxy)methyl]pyrrolidine-1-carboxylate

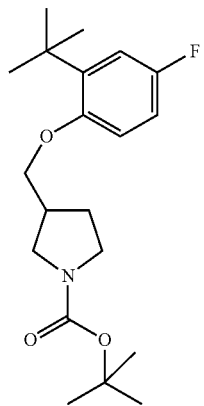 [SMILES: CC(C)(C)OC(=O)N1CCC(COc2ccc(F)cc2C(C)(C)C)C1]

2-tert-Butyl-4-fluorophenol (3.34 g, 19.9 mmol) obtained in Reference Example 3, tert-butyl 3-({[(4-methylphenyl)sulfonyl]oxy}methyl)pyrrolidine-1-carboxylate (7.77 g, 21.9 mmol) obtained in Reference Example 28 and potassium phosphate (12.7 g, 59.7 mmol) were stirred in DMF at 80° C. for 16 hr. The reaction mixture was cooled to room temperature, and partitioned between ethyl acetate and water. The ethyl acetate layer was washed with water and saturated brine, dried over anhydrous magnesium sulfate and filtered. The filtrate was concentrated under reduced pressure and the obtained residue was purified by silica gel column chromatography (hexane:ethyl acetate 90:10-80:20) to give the title compound (5.08 g, 72%) as a colorless oil.

$^1$H NMR (300 MHz, CDCl$_3$) δ 7.05-6.94 (m, 1H), 6.89-6.78 (m, 1H), 6.77-6.69 (m, 1H), 3.99-3.79 (m, 2H), 3.79-3.33 (m, 3H), 3.28-3.14 (m, 1H), 2.88-2.60 (m, 1H), 2.22-2.06 (m, 1H), 1.93-1.69 (m, 1H), 1.47 (s, 9H), 1.36 (s, 9H).

Reference Example 59

3-[(2-tert-butyl-4-fluorophenoxy)methyl]pyrrolidine hydrochloride

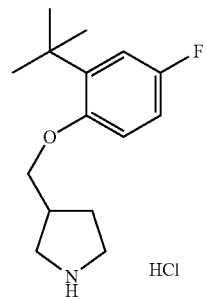 [SMILES: CC(C)(C)c1cc(F)ccc1OCC1CCNC1 ; Cl]

According to a method similar to that in Reference Example 12, the title compound (3.05 g, 75%) was obtained as a white solid from tert-butyl 3-[(2-tert-butyl-4-fluorophenoxy)methyl]pyrrolidine-1-carboxylate (5.00 g, 14.2 mmol) obtained in Reference Example 58.

$^1$H NMR (300 MHz, DMSO-d$_6$) δ 9.32 (br s, 1H), 7.13-6.87 (m, 3H), 4.01 (d, J=7.2 Hz, 2H), 3.46-3.12 (m, 3H), 3.07-2.92 (m, 1H), 2.85-2.69 (m, 1H), 2.28-2.05 (m, 1H), 1.86-1.63 (m, 1H), 1.33 (s, 9H).

Reference Example 60 tert-butyl 3-[(2-tert-butyl-4-chlorophenoxy)methyl]pyrrolidine-1-carboxylate

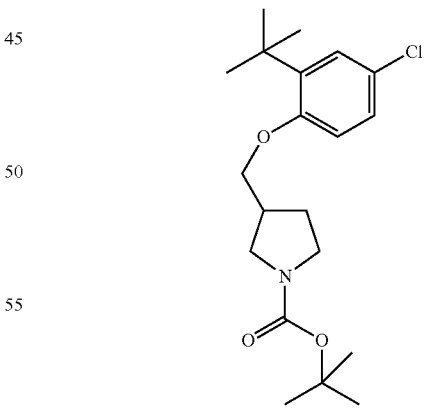

According to a method similar to that in Reference Example 58, the title compound (4.19 g, 69%) was obtained as a colorless oil from 2-tert-butyl-4-chlorophenol (3.07 g, 16.6 mmol) obtained in Reference Example 40 and tert-butyl 3-({[(4-methylphenyl)sulfonyl]oxy}methyl)pyrrolidine-1-carboxylate (6.49 g, 18.3 mmol) obtained in Reference Example 28.

$^1$H NMR (300 MHz, CDCl$_3$) δ 7.23 (d, J=2.3 Hz, 1H), 7.11 (dd, J=8.7, 2.3 Hz, 1H), 6.74 (d, J=8.7 Hz, 1H), 4.04-3.80 (m, 2H), 3.79-3.29 (m, 3H), 3.29-3.11 (m, 1H), 2.86-2.58 (m, 1H), 2.25-2.06 (m, 1H), 1.78 (br s, 1H), 1.47 (s, 9H), 1.36 (s, 9H).

Reference Example 61

3-[(2-tert-butyl-4-chlorophenoxy)methyl]pyrrolidine hydrochloride

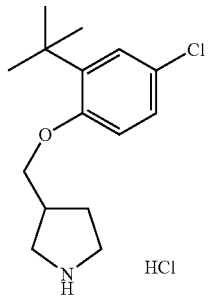 [SMILES: CC(C)(C)c1cc(Cl)ccc1OCC1CCNC1 ; Cl]

According to a method similar to that in Reference Example 12, the title compound (2.35 g, 70%) was obtained as a white solid from tert-butyl 3-[(2-tert-butyl-4-chlorophenoxy)methyl]pyrrolidine-1-carboxylate (4.10 g, 11.1 mmol) obtained in Reference Example 60.
$^1$H NMR (300 MHz, DMSO-d$_6$) δ 9.29 (br s, 1H), 7.29-7.20 (m, 1H), 7.18 (d, J=2.6 Hz, 1H), 6.99 (d, J=8.7 Hz, 1H), 4.03 (d, J=7.0 Hz, 2H), 3.47-3.08 (m, 3H), 3.06-2.92 (m, 1H), 2.87-2.70 (m, 1H), 2.25-2.03 (m, 1H), 1.84-1.63 (m, 1H), 1.33 (s, 9H).

Reference Example 62 tert-butyl 4-(2-tert-butyl-4-fluorophenoxy)piperidine-1-carboxylate

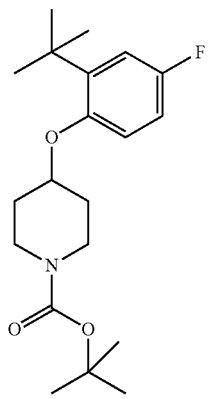 [SMILES: CC(C)(C)OC(=O)N1CCC(Oc2ccc(F)cc2C(C)(C)C)CC1]

According to a method similar to that in Reference Example 11, the title compound (6.50 g, 66%) was obtained as a pale yellow solid from 2-tert-butyl-4-fluorophenol (4.73 g, 28.1 mmol) obtained in Reference Example 3 and tert-butyl 4-(tosyloxy)piperidine-1-carboxylate (20.0 g, 56.3 mmol) obtained in Reference Example 13.
LC/MS ESI(+) m/z: 296 (M-tBu+H)$^+$ Reference Example 63

4-(2-tert-butyl-4-fluorophenoxy)piperidine

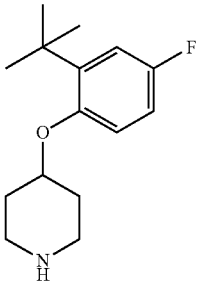 [SMILES: CC(C)(C)c1cc(F)ccc1OC1CCNCC1]

According to a method similar to that in Reference Example 55, the title compound (2.83 g, 40%) was obtained as a pale-brown oil from tert-butyl 4-(2-tert-butyl-4-fluorophenoxy)piperidine-1-carboxylate obtained in Reference Example 62.
$^1$H NMR (300 MHz, CDCl$_3$) δ 7.00 (dd, J=11.0, 3.0 Hz, 1H), 6.86-6.65 (m, 2H), 4.54-4.30 (m, 1H), 3.29-3.04 (m, 2H), 2.87-2.64 (m, 2H), 2.24-1.94 (m, 2H), 1.92-1.64 (m, 2H), 1.38 (s, 9H).

Reference Example 64 tert-butyl 4-(2-tert-butyl-4-chlorophenoxy)piperidine-1-carboxylate

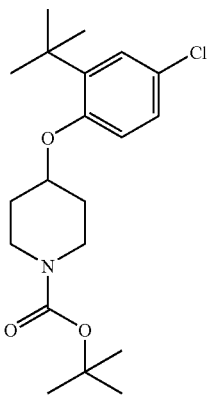 [SMILES: CC(C)(C)OC(=O)N1CCC(Oc2ccc(Cl)cc2C(C)(C)C)CC1]

According to a method similar to that in Reference Example 11, the title compound (5.89 g, quant.) was obtained as a pale yellow oil from 2-tert-butyl-4-chlorophenol (3.00 g, 16.2 mmol) obtained in Reference Example 40 and tert-butyl 4-(tosyloxy)piperidine-1-carboxylate (11.55 g, 32.5 mmol) obtained in Reference Example 13.
LC/MS ESI(+) m/z: 312 (M-tBu+H)$^+$

Reference Example 65

4-(2-tert-butyl-4-chlorophenoxy)piperidine hydrochloride

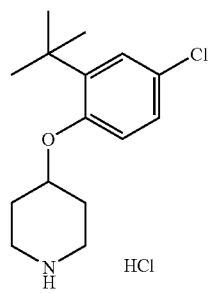 [SMILES: CC(C)(C)c1cc(Cl)ccc1OC1CCNCC1 ; Cl]

According to a method similar to that in Reference Example 12, the title compound (2.48 g, 50%) was obtained from tert-butyl 4-(2-tert-butyl-4-chlorophenoxy)piperidine-1-carboxylate (5.89 g, 16.2 mmol) obtained in Reference Example 64.

$^1$H NMR (300 MHz, DMSO-$d_6$) δ 9.10 (br s, 1H), 7.27-7.14 (m, 2H), 7.06 (d, J=8.9 Hz, 1H), 4.79-4.66 (m, 1H), 3.27-3.15 (m, 2H), 3.14-3.01 (m, 2H), 2.29-2.08 (m, 2H), 2.01-1.74 (m, 2H), 1.34 (s, 9H).

Reference Example 66 tert-butyl 4-[(2-tert-butyl-4-chlorophenoxy)methyl]piperidine-1-carboxylate

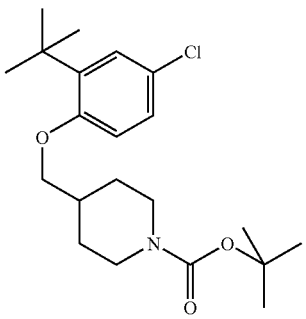 [SMILES: CC(C)(C)OC(=O)N1CCC(COc2ccc(Cl)cc2C(C)(C)C)CC1]

According to a method similar to that in Reference Example 58, the title compound (8.2 g, 79%) was obtained as a colorless solid from 2-tert-butyl-4-chlorophenol (5.6 g, 30.0 mmol) obtained in Reference Example 40 and tert-butyl 4-({[(4-methylphenyl)sulfonyl]oxy}methyl)piperidine-1-carboxylate (10.0 g, 27.1 mmol) obtained in Reference Example 22.

$^1$H NMR (300 MHz, CDCl$_3$) δ 7.22 (d, J=2.6 Hz, 1H), 7.11 (dd, J=8.7, 2.6 Hz, 1H), 6.75 (d, J=8.9 Hz, 1H), 4.34-4.02 (m, 2H), 3.80 (d, J=6.2 Hz, 2H), 2.86-2.62 (m, 2H), 2.12-1.92 (m, 1H), 1.92-1.78 (m, 2H), 1.47 (s, 9H), 1.43-1.19 (m, 11H).

Reference Example 67

4-[(2-tert-butyl-4-chlorophenoxy)methyl]piperidine hydrochloride

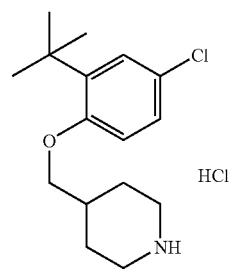 [SMILES: CC(C)(C)c1cc(Cl)ccc1OCC1CCNCC1 ; Cl]

According to a method similar to that in Reference Example 12, the title compound (7.23 g, quant.) was obtained as a pale yellow solid from tert-butyl 4-[(2-tert-butyl-4-chlorophenoxy)methyl]piperidine-1-carboxylate (8.2 g, 21.4 mmol) obtained in Reference Example 66.

$^1$H NMR (300 MHz, DMSO-$d_6$) δ 8.82 (br s, 2H), 7.22 (dd, J=8.7, 2.7 Hz, 1H), 7.17 (d, J=2.7 Hz, 1H), 7.01 (d, J=8.7 Hz, 1H), 3.89 (d, J=6.1 Hz, 2H), 3.45-3.21 (m, 2H), 2.92 (td, J=12.7, 2.7 Hz, 2H), 2.22-2.03 (m, 1H), 2.01-1.86 (m, 2H), 1.67-1.44 (m, 2H), 1.34 (s, 9H).

Reference Example 68 tert-butyl 3-{[(4-methylphenyl)sulfonyl]oxy}piperidine-1-carboxylate

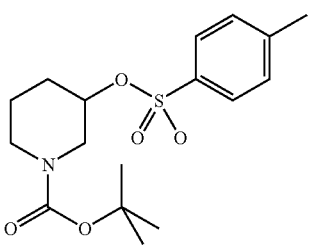

A mixture of 3-hydroxypiperidine (10.0 g, 98.9 mmol), di-tert-butyldicarbonate (22.7 g, 103.8 mmol) and potassium carbonate (68.3 g, 495 mmol) in ethyl acetate-water (200 mL-300 mL) was stirred at room temperature for 16 hr. The ethyl acetate layer was separated, washed with saturated brine, dried over anhydrous magnesium sulfate and filtered. The filtrate was concentrated under reduced pressure. The obtained residue was purified by silica gel column chromatography (hexane:ethyl acetate 80:20-50:50) to give a colorless oil (18.9 g). This was dissolved in pyridine (100 mL), p-toluenesulfonyl chloride (19.7 g, 103.3 mmol) was added, and the mixture was stirred at room temperature for 2 days. The reaction solution was concentrated under reduced pressure, and the obtained residue was partitioned between ethyl acetate and water. The ethyl acetate layer was separated, washed with 1N hydrochloric acid, water and saturated brine, dried over anhydrous magnesium sulfate, and filtered. The filtrate was concentrated under reduced pressure. The obtained residue was purified by silica gel column chromatography (hexane:ethyl acetate 90:10-80: 20-50:50) to give the title compound (32.2 g, 96%) as a colorless oil.

$^1$H NMR (300 MHz, CDCl$_3$) δ 7.81 (d, J=8.5 Hz, 2H), 7.34 (d, J=7.9 Hz, 2H), 4.45 (br s, 1H), 3.63-3.48 (m, 1H), 3.48-3.15 (m, 3H), 2.45 (s, 3H), 1.95-1.66 (m, 3H), 1.52-1.36 (m, 10H).

Reference Example 69

3-(2-tert-butylphenoxy)piperidine

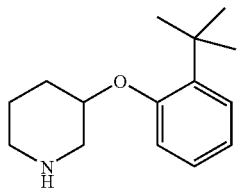 [SMILES: CC(C)(C)c1ccccc1OC1CCCNC1]

tert-Butyl 3-{[(4-methylphenyl)sulfonyl]oxy}piperidine-1-carboxylate (32.0 g, 90.0 mmol) obtained in Reference Example 68, 2-tert-butylphenol (13.5 g, 45.0 mmol) and potassium phosphate (28.7 g, 135 mmol) were stirred in DMF (400 mL) at 80° C. for 16 hr. The reaction solution was concentrated under reduced pressure, and the residue was partitioned between ethyl acetate and water. The ethyl acetate layer was washed with water and saturated brine, dried over anhydrous magnesium sulfate, and filtered. The filtrate was concentrated under reduced pressure. The obtained residue was purified by silica gel column chromatography (hexane: ethyl acetate 100:0-90:10-85:15), and the obtained brown oil (25 g) was dissolved in ethyl acetate (90 mL). 4N Hydrochloric acid-ethyl acetate solution (90 mL) was added, and the mixture was stirred at room temperature for 16 hr. The reaction solution was extracted with water, and the extract was adjusted to pH 10 with 8N sodium hydroxide. The mixture was extracted with ethyl acetate, and the extract was washed with saturated brine, and filtered. The filtrate was concentrated under reduced pressure. The residue was dissolved in toluene, and the mixture was concentrated under reduced pressure at 100° C. This concentration operation was repeated twice to give the title compound (3.19 g, 30%) as a brown oil. This was used for the next reaction without further purification.

Reference Example 70 tert-butyl 2-(hydroxymethyl)pyrrolidine-1-carboxylate

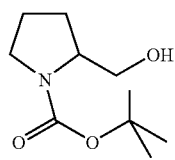

To a solution of DL-proline (10.0 g, 86.9 mmol) in THF (20 mL) were added boron trifluoride etherate complex (12.9 g, 91.2 mmol) and borane-tetrahydrofuran (1.0 mol/L THF solution, 100 mL) at 0° C., and the mixture was stirred at room temperature for 16 hr. After completion of the reaction, the mixture was further heated under reflux for 1 hr and cooled to room temperature. THF-water (1:1, 2.5 mL) and 6N sodium hydroxide were successively added to the reaction solution, and the mixture was heated under reflux for 2 hr. The reaction solution was cooled to room temperature, and concentrated under reduced pressure. The residue was washed with diethyl ether. The remaining residue, di-tert-butyl dicarbonate (19.9 g, 91.2 mmol) and potassium carbonate (36.0 g, 260 mmol) were dissolved in diethyl ether-water (100 mL-150 mL), and the mixture was stirred at room temperature for 16 hr. The diethyl ether layer was separated and washed with saturated brine, dried over anhydrous magnesium sulfate, and filtered. The filtrate was concentrated under reduced pressure. The obtained residue was purified by silica gel column chromatography (hexane-ethyl acetate 95:5-60:40-50:50) to give the title compound (13.6 g, 76%) as a colorless oil.

$^1$H NMR (300 MHz, CDCl$_3$) δ 4.74 (d like, 1H), 3.96 (br s, 1H), 3.74-3.21 (m, 4H), 2.13-1.67 (m, 4H), 1.49 (s, 9H).

Reference Example 71 tert-butyl 2-({[(4-methylphenyl)sulfonyl]oxy}methyl)pyrrolidine-1-carboxylate

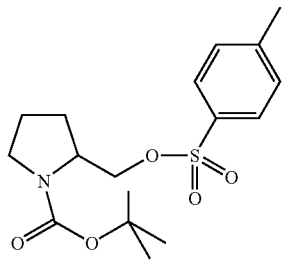 [SMILES: Cc1ccc(S(=O)(=O)OCC2CCCN2C(=O)OC(C)(C)C)cc1]

According to a method similar to that in Reference Example 10, the title compound (20.7 g, 87%) was obtained as a colorless oil from tert-butyl 2-(hydroxymethyl)pyrrolidine-1-carboxylate obtained in Reference Example 70.

$^1$H NMR (300 MHz, CDCl$_3$) δ 7.77 (d, J=8.0 Hz, 2H), 7.34 (d, J=8.0 Hz, 2H), 4.17-4.03 (m, 1H), 3.90 (br s, 2H), 3.29 (d, J=6.1 Hz, 2H), 2.44 (s, 3H), 2.02-1.74 (m, 4H), 1.38 (br s, 9H).

Reference Example 72

3-[(1E)-3-ethoxy-3-oxoprop-1-en-1-yl]benzoic acid

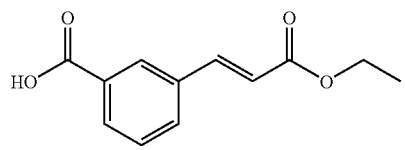 [SMILES: CCOC(=O)/C=C/c1cccc(C(=O)O)c1]

A solution of 3-iodobenzoic acid (20.2 g, 81.4 mmol), ethyl acrylate (9.0 g, 90.2 mmol), triethylamine (24 mL) and palladium acetate (92 mg, 0.41 mmol) in DMF (130 mL) was stirred at 140° C. for 3 hr. The reaction mixture was cooled to room temperature, partitioned between ethyl acetate and 1N hydrochloric acid, and the ethyl acetate layer was washed with water and saturated brine, dried over anhydrous magnesium sulfate and filtered. The filtrate was concentrated under reduced pressure and the obtained residue was purified by silica gel column chromatography (hexane:ethyl acetate 50:50-0:100) to give the title compound (18.7 g, quant.) as an orange solid.

$^1$H NMR (300 MHz, CDCl$_3$) δ 8.35-8.23 (m, 1H), 8.19-8.09 (m, 1H), 7.71 (d, J=16.0 Hz, 1H), 7.79-7.69 (m, 1H), 7.52 (t, J=7.7 Hz, 1H), 6.54 (d, J=16.0 Hz, 1H), 4.29 (q, J=7.2 Hz, 2H), 1.36 (t, J=7.2 Hz, 3H).

Reference Example 73

3-(3-ethoxy-3-oxopropyl)benzoic acid

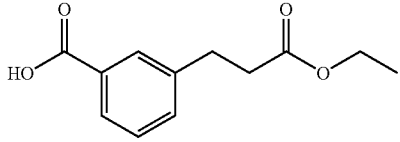 [SMILES: CCOC(=O)CCc1cccc(C(=O)O)c1]

To a solution of 3-[(1E)-3-ethoxy-3-oxoprop-1-en-1-yl]benzoic acid (8.6 g, 39.1 mmol) obtained in Reference Example 72 in ethanol (500 mL) was added palladium carbon (10%, 50% containing water, 4.1 g), and the mixture was stirred under a hydrogen atmosphere at room temperature for 3 hr. The reaction mixture was filtered, and the filtrate was concentrated under reduced pressure to give the title compound (8.7 g, quant.) as a white solid.

$^1$H NMR (300 MHz, CDCl$_3$) δ 8.02-7.84 (m, 2H), 7.54-7.30 (m, 2H), 4.14 (q, J=7.2 Hz, 2H), 3.03 (t, J=7.6 Hz, 2H), 2.66 (t, J=8.0 Hz, 2H), 1.24 (t, J=7.0 Hz, 3H).

Reference Example 74

3-[3-(2-tert-butylphenoxy)azetidin-1-yl]-3-oxopropylprop-2-enoate

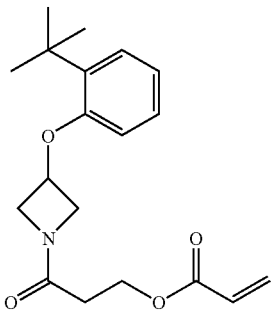 [SMILES: C=CC(=O)OCCC(=O)N1CC(Oc2ccccc2C(C)(C)C)C1]

According to a method similar to that in Example 9, a mixture (418 mg) of the title compound and a byproduct was obtained as a colorless oil from 3-(2-tert-butylphenoxy)azetidine (400 mg, 1.95 mmol) obtained in Reference Example 2 and 3-(acryloyloxy)propanoic acid (337 mg, 2.34 mmol).

LC/MS ESI(+) m/z: 332 (M+H)$^+$.

Reference Example 75

4-(2-tert-butyl-4-fluorophenoxy)piperidine hydrochloride

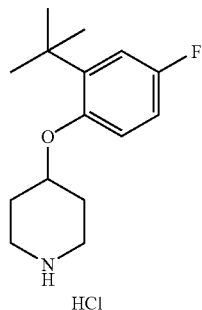 [SMILES: CC(C)(C)c1cc(F)ccc1OC1CCNCC1 ; Cl]

4-(2-tert-Butyl-4-fluorophenoxy)piperidine (8.9 g, 35.5 mmol) obtained in Reference Example 63 and 4N hydrochloric acid ethyl acetate solution (15 ml, 60 mmol) were mixed, and the mixture was stirred at room temperature for 16 hr. The reaction mixture was concentrated to give the title compound (9.42 g, 92%) as a white solid.

$^1$H NMR (300 MHz, DMSO-d$_6$) δ 9.02 (br s, 2H), 7.10-6.93 (m, 3H), 4.80-4.63 (m, 1H), 3.28-3.15 (m, 2H), 3.15-2.98 (m, 2H), 2.30-2.07 (m, 2H), 1.97-1.75 (m, 2H), 1.37 (s, 9H).

Reference Example 76

1-{2-[4-(2-tert-butyl-4-fluorophenoxy)piperidin-1-yl]-2-oxoethoxy}-1H-benzotriazole

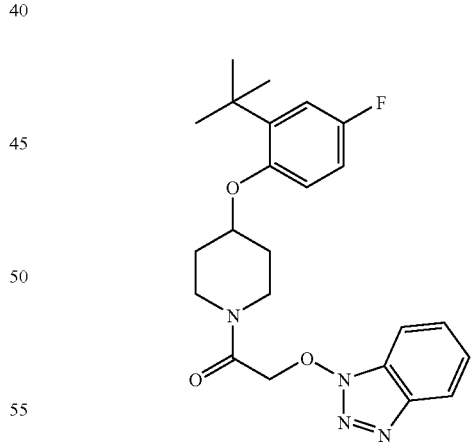

According to a method similar to that in Example 9, a mixture (7.58 g) of the title compound and a byproduct was obtained as a colorless amorphous form from 4-(2-tert-butyl-4-fluorophenoxy)piperidine hydrochloride (5.0 g, 17.4 mmol) obtained in Reference Example 75 and bromoacetic acid (3.14 g, 22.6 mmol).

$^1$H NMR (300 MHz, CDCl$_3$) δ 7.99 (d, J=8.7 Hz, 1H), 7.84 (d, J=8.3 Hz, 2H), 7.55 (t, J=7.6 Hz, 1H), 7.43-7.35 (m, 1H), 7.02 (dd, J=11.0, 3.0 Hz, 1H), 6.88-6.76 (m, 1H), 6.76-6.64

(m, 1H), 5.40-5.26 (m, 2H), 4.68-4.56 (m, 1H), 3.83-3.64 (m, 3H), 3.61-3.42 (m, 1H), 2.16-1.84 (m, 4H), 1.37 (s, 9H).

Reference Example 77

1-(2-{3-[(2-tert-butylphenoxy)methyl]azetidin-1-yl}-2-oxoethoxy)-1H-benzotriazole

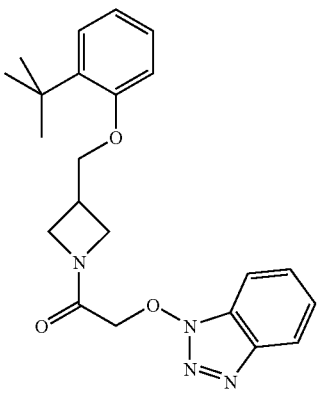 [SMILES: CC(C)(C)c1ccccc1OCC1CN(C(=O)COn2nnc3ccccc32)C1]

According to a method similar to that in Example 9, a mixture (7.58 g) of the title compound and a byproduct was obtained as a colorless amorphous form from 3-[(2-tert-butylphenoxy)methyl]azetidine hydrochloride (1.0 g, 3.9 mmol) obtained in Reference Example 32 and bromoacetic acid (706 mg, 5.1 mmol).

¹H NMR (300 MHz, CDCl₃) δ 8.05-7.92 (m, 1H), 7.84-7.76 (m, 1H), 7.58-7.50 (m, 1H), 7.44-7.35 (m, 1H), 7.35-7.27 (m, 1H), 7.23-7.13 (m, 1H), 6.99-6.88 (m, 1H), 6.88-6.78 (m, 1H), 5.16-5.00 (m, 2H), 4.56-4.43 (m, 1H), 4.31-4.19 (m, 2H), 4.19-4.06 (m, 2H), 4.06-3.94 (m, 1H), 3.31-3.05 (m, 1H), 1.31 (s, 9H).

Reference Example 78

2,6-di-tert-butyl-4-fluorophenol

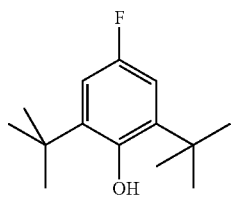 [SMILES: CC(C)(C)c1cc(F)cc(C(C)(C)C)c1O]

Concentrated sulfuric acid (30 mL) was added to 4-fluorophenol (50 g, 446 mmol) and tert-butanol (60 g, 810 mmol), and the mixture was stirred at room temperature for 16 hr. The reaction mixture was partitioned between hexane and water, and the hexane layer was washed with saturated brine, dried over anhydrous magnesium sulfate and filtered. The filtrate was concentrated under reduced pressure, and the obtained residue was purified by silica gel column chromatography (hexane) to give the title compound (6.8 g, 7%) as a colorless oil.

¹H NMR (300 MHz, CDCl₃) δ 6.87 (d, J=10.2 Hz, 2H), 4.93 (s, 1H), 1.40 (s, 18H).

Reference Example 79 tert-butyl 4-[(2,6-di-tert-butyl-4-fluorophenoxy)methyl]piperidine-1-carboxylate

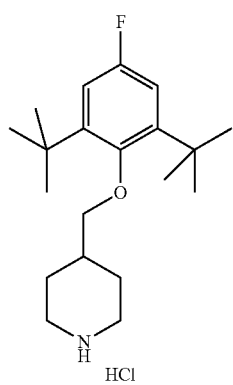 [SMILES: CC(C)(C)c1cc(F)cc(C(C)(C)C)c1OCC1CCNCC1 ; Cl]

According to a method similar to that in Reference Example 11, the title compound (4.16 g, 74%) was obtained as a yellow solid from 2,6-di-tert-butyl-4-fluorophenol (3.0 g, 13.4 mmol) obtained in Reference Example 78 and tert-butyl 4-({[(4-methylphenyl)sulfonyl]oxy}methyl)piperidine-1-carboxylate (5.9 g, 16.1 mmol) obtained in Reference Example 22.

¹H NMR (300 MHz, CDCl₃) δ 6.92 (d, J=10.4 Hz, 2H), 4.34-3.96 (m, 1H), 3.59 (d, J=7.2 Hz, 2H), 3.48-3.34 (m, 1H), 2.87-2.59 (m, 2H), 2.21-1.98 (m, 1H), 1.93-1.75 (m, 2H), 1.47 (s, 9H), 1.41 (s, 18H), 1.34-1.02 (m, 2H).

Reference Example 80

4-[(2,6-di-tert-butyl-4-fluorophenoxy)methyl]piperidine

According to a method similar to that in Reference Example 7, the title compound (3.41 g, 97%) was obtained as a yellow solid from tert-butyl-4-[(2,6-di-tert-butyl-4-fluorophenoxy)methyl]piperidine-1-carboxylate (4.16 g, 9.87 mmol) obtained in Reference Example 79.

$^1$H NMR (300 MHz, DMSO-$d_6$) δ 8.92 (br s, 1H), 8.60 (br s, 1H), 7.05 (d, J=10.2 Hz, 2H), 3.65-3.49 (m, 2H), 3.28 (br s, 1H), 3.03-2.76 (m, 2H), 2.25 (td, J=7.6, 4.2 Hz, 1H), 2.01-1.94 (m, 1H), 1.94-1.87 (m, 2H), 1.59-1.40 (m, 2H), 1.40-1.28 (m, 18H).

Reference Example 81 tert-butyl 2-[(2-tert-butylphenoxy)methyl]pyrrolidine-1-carboxylate

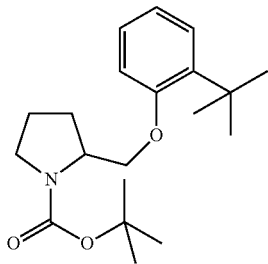 [SMILES: CC(C)(C)OC(=O)N1CCCC1COc1ccccc1C(C)(C)C]

A solution of tert-butyl 2-({[(4-methylphenyl)sulfonyl]oxy}methyl)pyrrolidine-1-carboxylate (7.91 g, 52.7 mmol) obtained in Reference Example 71, 2-tert-butylphenol (20.6 g, 58.0 mmol) and potassium phosphate (33.6 g, 158.1 mmol) in DMF (500 mL) was stirred at 80° C. for 16 hr. The reaction mixture was cooled to room temperature, concentrated under reduced pressure, and the residue was partitioned between ethyl acetate and water. The ethyl acetate layer was washed with water and saturated brine, dried over anhydrous magnesium sulfate, and filtered. The filtrate was concentrated under reduced pressure. The obtained residue was purified by silica gel column chromatography (hexane:ethyl acetate 95:5-90:10) to give the title compound (12.0 g, 69%) as a brown oil.

$^1$H NMR (300 MHz, CDCl$_3$) δ 7.22-7.12 (m, 1H), 7.11-7.01 (m, 1H), 6.97-6.80 (m, 2H), 4.33-4.05 (m, 2H), 4.01-3.74 (m, 1H), 3.55-3.32 (m, 2H), 2.16-2.06 (m, 2H), 2.00-1.78 (m, 2H), 1.47 (s, 9H), 1.38 (s, 9H).

Reference Example 82

2-[(2-tert-butylphenoxy)methyl]pyrrolidine

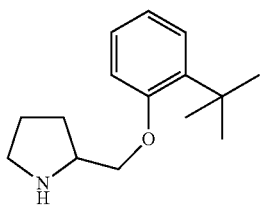 [SMILES: CC(C)(C)c1ccccc1OCC1CCCN1]

According to a method similar to that in Reference Example 12, hydrochloride of the title compound was obtained from tert-butyl 2-[(2-tert-butylphenoxy)methyl]pyrrolidine-1-carboxylate (12.0 g, 36.0 mmol) obtained in Reference Example 81. This was partitioned between ethyl acetate and 1N sodium hydroxide, and the ethyl acetate layer was washed with water and saturated brine, dried over anhydrous magnesium sulfate and filtered. The filtrate was concentrated. The obtained residue was dissolved in toluene (50 mL), and the mixture was concentrated under reduced pressure at 80° C. to give the title compound (9.36 g, quant.) as a brown oil mixture. This was used for the next reaction without further purification.

LC/MS ESI(+) m/z: 234 (M+H)$^+$.

Reference Example 83

3-(2-tert-butyl-4-methylphenoxy)-1-(diphenylmethyl)azetidine

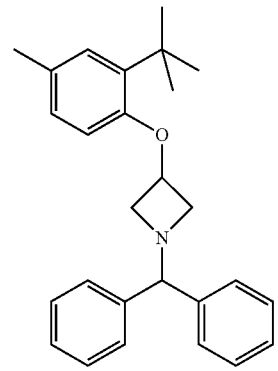 [SMILES: Cc1ccc(OC2CN(C(c3ccccc3)c3ccccc3)C2)c(C(C)(C)C)c1]

A solution of 3-(4-bromo-2-tert-butylphenoxy)-1-(diphenylmethyl)azetidine (6.96 g, 15.5 mmol) obtained in is Reference Example 45, methylboronic acid (3.70 g, 61.8 mmol), potassium phosphate (14.8 g, 69.8 mmol) and tetrakis(triphenylphosphine)palladium(0) (0.90 g, 0.78 mmol) in THF (140 mL) was stirred under an argon atmosphere at 80° C. for 24 hr. The reaction mixture was cooled to room temperature, concentrated under reduced pressure, and the residue was partitioned between ethyl acetate and water. The ethyl acetate layer was washed with saturated brine, dried over anhydrous magnesium sulfate and filtered. The filtrate was concentrated under reduced pressure. The obtained residue was purified by silica gel column chromatography (hexane:ethyl acetate 90:10-80:20) to give a pale yellow oil. To complete the reaction, the obtained yellow oil was further subjected to the above-mentioned reactions twice, and purified by silica gel column chromatography (hexane:ethyl acetate 100:0-80:20) to give the title compound (4.19 g, 70%) as a pale yellow oil.

$^1$H NMR (300 MHz, CDCl$_3$) δ 7.49-7.35 (m, 4H), 7.33-7.25 (m, 4H), 7.22-7.13 (m, 2H), 7.06 (d, J=2.3 Hz, 1H), 6.86 (dd, J=8.3, 1.5 Hz, 1H), 6.43 (d, J=8.3 Hz, 1H), 4.85-4.69 (m, 1H), 4.46-4.39 (m, 1H), 3.82-3.69 (m, 2H), 3.16-3.04 (m, 2H), 2.25 (s, 3H), 1.37 (s, 9H).

Reference Example 84

3-(2-tert-butyl-4-methylphenoxy)azetidine

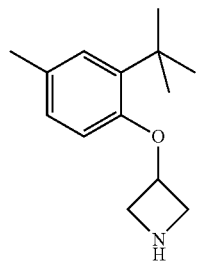 [SMILES: Cc1ccc(OC2CNC2)c(C(C)(C)C)c1]

According to a method similar to that in Reference Example 48, the title compound (1.12 g, 48%) was obtained as a colorless oil from 3-(2-tert-butyl-4-methylphenoxy)-1-(diphenylmethyl)azetidine (4.10 g, 10.6 mmol) obtained in Reference Example 83.

$^1$H NMR (300 MHz, CDCl$_3$) δ 7.23-7.14 (m, 1H), 7.11-7.06 (m, 1H), 6.96-6.88 (m, 1H), 6.42 (d, J=7.9 Hz, 1H), 5.03-4.93 (m, 1H), 4.00-3.90 (m, 2H), 3.88-3.80 (m, 2H), 2.27 (s, 3H), 1.39 (s, 9H).

Example 1

(3-(2-tert-butylphenoxy)azetidin-1-yl)(phenyl)methanone

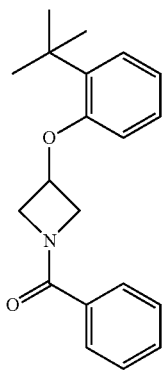

To a stirred solution of 3-(2-tert-butylphenoxy)azetidine (0.30 g, 1.46 mmol) and triethylamine (0.16 g, 1.61 mmol) in THF (10.0 mL) was added benzoyl chloride (0.23 g, 1.61 mmol). After stirring for 16 h at room temperature, the reaction mixture was diluted with ethyl acetate, washed with water, saturated sodium chloride, dried (Na$_2$SO$_4$), filtered and concentrated under reduced pressure. Purification by flash column chromatography (silica gel; 85:15 to 50:50 heptane/ethyl acetate) provided (3-(2-tert-butylphenoxy)azetidin-1-yl)(phenyl)methanone (0.21 g, 46%) as a yellow solid.

$^1$H NMR (500 MHz, CDCl$_3$) δ 7.66-7.65 (m, 2H), 7.49-7.46 (m, 1H), 7.43-7.40 (m, 2H), 7.33-7.32 (m, 1H), 7.15-7.12 (m, 1H), 6.96-6.93 (m, 1H), 6.47-6.45 (m, 1H), 5.06-5.02 (m, 1H), 4.67-4.63 (m, 2H), 4.37-4.34 (m, 2H), 1.41 (s, 9H).

Example 2

3-(2-tert-butylphenoxy)-1-(phenylsulfonyl)azetidine

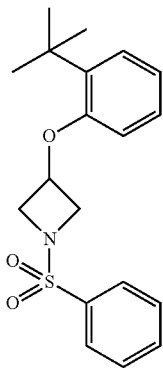

To a stirred solution of 3-(2-tert-butylphenoxy)azetidine (0.30 g, 1.46 mmol) in pyridine (5.0 mL) was added benzenesulfonyl chloride (0.28 g, 1.61 mmol). After stirring for 16 h at room temperature, the reaction mixture was concentrated under reduced pressure and the residue was dissolved in ethyl acetate. The organic layer was washed with 1.0 N hydrochloric acid, water, saturated sodium chloride, dried (Na$_2$SO$_4$), filtered and concentrated under reduced pressure. The resulting yellow solid was recrystallized from heptane/ethyl acetate to provide 3-(2-tert-butylphenoxy)-1-(phenylsulfonyl)azetidine (0.29 g, 57%) as a pale brown powder.

$^1$H NMR (500 MHz, CDCl$_3$) δ 7.87-7.85 (m, 2H), 7.64-7.61 (m, 1H), 7.58-7.55 (m, 2H), 7.26-7.23 (m, 1H), 7.11-7.08 (m, 1H), 6.92-6.87 (m, 1H), 6.32 (d, J=8.1 Hz, 1H), 4.86-4.84 (m, 1H), 4.30-4.27 (m, 2H), 3.79-3.76 (m, 2H), 1.16 (s, 9H).

Example 3

(3-(2-tert-butylphenoxy)azetidin-1-yl)(pyridin-2-yl)methanone

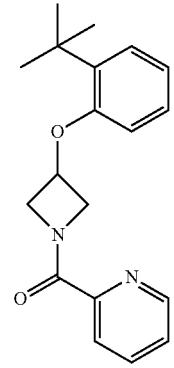 [SMILES: CC(C)(C)c1ccccc1OC1CN(C(=O)c2ccccn2)C1]

To an ice-cold stirred solution of 3-(2-tert-butylphenoxy)azetidine (2.00 g, 9.74 mmol) in pyridine (20.0 ml) was added picolinoyl chloride hydrochloride (2.08 g, 11.7 mmol). After stirring for 16 h at room temperature, the reaction mixture was concentrated under reduced pressure. The residue was partitioned between ethyl acetate and 10% aqueous Na$_2$CO$_3$ and separated. The organic layer was washed with saturated sodium chloride, dried (Na$_2$SO$_4$), filtered by a pad of silica gel and concentrated under reduced pressure. The residue was purified with flash column chromatography (silica gel, 90:10 to 50:50 heptane/ethyl acetate) to provide a yellow solid. The solid was recrystallized from heptane/ethyl acetate to provide (3-(2-tert-butylphenoxy)azetidin-1-yl)(pyridin-2-yl)methanone (0.94 g, 31%) as a off-white solid.

$^1$H NMR (500 MHz, CDCl$_3$) δ 8.59-8.57 (m, 1H), 8.08 (d, J=8.2 Hz, 1H), 7.83-7.80 (m, 1H), 7.38-7.32 (m, 2H), 7.18-7.15 (m, 1H), 6.96-6.93 (m, 1H), 6.54-6.52 (m, 1H), 5.19-5.15 (m, 1H), 5.07-5.04 (m, 1H), 4.80-4.77 (m, 1H), 4.68-4.64 (m, 1H), 4.37-4.33 (m, 1H), 1.40 (s, 9H).

Example 4 ethyl 2-(3-(2-tert-butylphenoxy)azetidin-1-yl)-2-oxoacetate

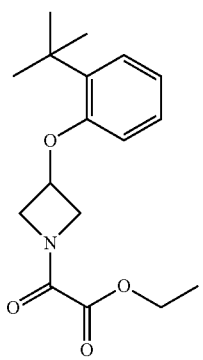 [SMILES: CCOC(=O)C(=O)N1CC(Oc2ccccc2C(C)(C)C)C1]

To an ice-cold stirred solution of 3-(2-tert-butylphenoxy)azetidine (2.20 g, 10.7 mmol) and triethylamine (1.73 g, 17.1 mmol) in THF (50.0 mL) was added ethyl oxalyl chloride (2.20 g, 16.1 mmol). After stirring for 16 h at room temperature the reaction mixture was diluted with ethyl acetate, washed with saturated sodium chloride, dried ($Na_2SO_4$), filtered and concentrated under reduced pressure. Purification by flash column chromatography (silica gel, 90:10 to 60:40 heptane/ethyl acetate) provided ethyl 2-(3-(2-tert-butylphenoxy)azetidin-1-yl)-2-oxoacetate (2.35 g, 72%) as a yellow oil.

$^1$H NMR (500 MHz, $CDCl_3$) δ 7.34-7.32 (m, 1H), 7.17-7.13 (m, 1H), 6.97-6.94 (m, 1H), 6.46-6.44 (m, 1H), 5.04-5.00 (m, 1H), 4.95-4.91 (m, 1H), 4.61-4.53 (m, 2H), 4.28 (q, J=7.2 Hz, 2H), 4.25-4.22 (m, 1H), 1.40 (s, 9H), 1.38 (t, J=7.2 Hz, 3H).

Example 5

2-(3-(2-tert-butylphenoxy)azetidin-1-yl)-2-oxoacetic acid

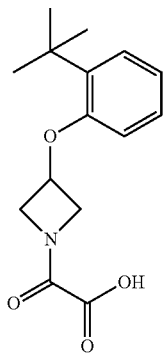

To a stirred solution of ethyl 2-(3-(2-tert-butylphenoxy)azetidin-1-yl)-2-oxoacetate (1.65 g, 5.40 mmol) in ethanol (60.0 ml) was added lithium hydroxide (16.2 mL of 1.0 M solution in water, 16.2 mmol) at room temperature. After 1 h the reaction mixture was concentrated under reduced pressure, the resulting residue was diluted with water, cooled to 0° C., adjusted to about pH 1 with 1.0 N hydrochloric acid and the resulting solution was extracted with ethyl acetate. The organic layer was washed with saturated sodium chloride, dried ($Na_2SO_4$), filtered and concentrated under reduced pressure. The residue was recrystallized from heptane/ethyl acetate to provide 2-(3-(2-tert-butylphenoxy)azetidin-1-yl)-2-oxoacetic acid (0.97 g, 65%) as a white powder.

$^1$H NMR (500 MHz, $CDCl_3$) δ 7.35-7.33 (m, 1H), 7.17-7.14 (m, 1H), 6.99-6.96 (m, 1H), 6.45-6.43 (m, 1H), 5.11-5.06 (m, 2H), 4.76-4.72 (m, 1H), 4.64-4.60 (m, 1H), 4.32-4.29 (m, 1H), 1.40 (s, 9H).

Example 6

(3-(2-tert-butyl-4-fluorophenoxy)azetidin-1-yl)(pyridin-2-yl)methanone

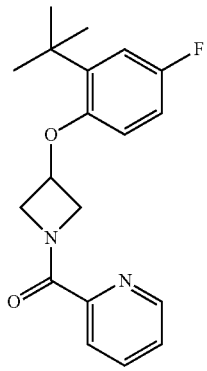 [SMILES: CC(C)(C)c1cc(F)ccc1OC1CN(C(=O)c2ccccn2)C1]

The title compound was prepared by a procedure similar to the one described for (3-(2-tert-butylphenoxy)azetidin-1-yl)(pyridin-2-yl)methanone to provide (3-(2-tert-butyl-4-fluorophenoxy)azetidin-1-yl)(pyridin-2-yl)methanone (0.11 g, 29%) as a colorless crystalline powder.

$^1$H NMR (500 MHz, $CDCl_3$) δ 8.59-8.58 (m, 1H), 8.14 (d, J=7.9 Hz, 1H), 7.84-7.80 (m, 1H), 7.39-7.36 (m, 1H), 7.05-7.02 (m, 1H), 6.85-6.81 (m, 1H), 6.45-6.43 (m, 1H), 5.18-5.14 (m, 1H), 5.02-4.98 (m, 1H), 4.78-4.75 (m, 1H), 4.66-4.62 (m, 1H), 4.34-4.31 (m, 1H), 1.38 (s, 9H).

Example 7 ethyl 2-(3-(2-tert-butyl-4-fluorophenoxy)azetidin-1-yl)-2-oxoacetate

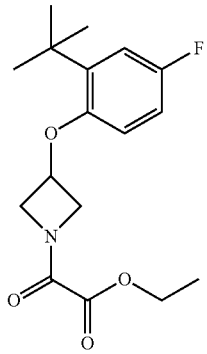 [SMILES: CCOC(=O)C(=O)N1CC(Oc2ccc(F)cc2C(C)(C)C)C1]

The title compound was prepared by a procedure similar to the one described for ethyl 2-(3-(2-tert-butylphenoxy)azetidin-1-yl)-2-oxoacetate to provide ethyl 2-(3-(2-tert-butyl-4-fluorophenoxy)azetidin-1-yl)-2-oxoacetate (0.40 g, 79%) as a yellow oil.

$^1$H NMR (500 MHz, CDCl$_3$) δ 7.06-7.03 (m, 1H), 6.84-6.80 (m, 1H), 6.39-6.36 (m, 1H), 4.99-4.90 (m, 2H), 4.59-4.52 (m, 2H), 4.35-4.31 (m, 2H), 4.23-4.20 (m, 1H), 1.42-1.31 (m, 12H).

Example 8

2-(3-(2-tert-butyl-4-fluorophenoxy)azetidin-1-yl)-2-oxoacetic acid

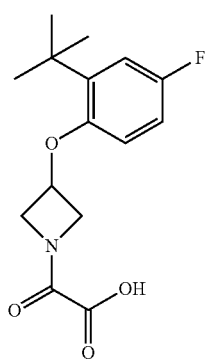 [SMILES: CC(C)(C)c1cc(F)ccc1OC1CN(C(=O)C(=O)O)C1]

The title compound was prepared by a similar procedure to the one described for 2-(3-(2-tert-butylphenoxy)azetidin-1-yl)-2-oxoacetic acid to provide 2-(3-(2-tert-butyl-4-fluorophenoxy)azetidin-1-yl)-2-oxoacetic acid (0.18 g, 58%) as a colorless crystalline powder.

$^1$H NMR (500 MHz, CDCl$_3$) δ 7.07-7.04 (m, 1H), 6.85-6.81 (m, 1H), 6.38-6.35 (m, 1H), 5.09-5.01 (m, 2H), 4.75-4.71 (m, 1H), 4.62-4.58 (m, 1H), 4.30-4.27 (m, 1H), 1.38 (s, 9H).

Example 9 ethyl 3-(3-(2-tert-butylphenoxy)azetidin-1-yl)-3-oxopropanoate

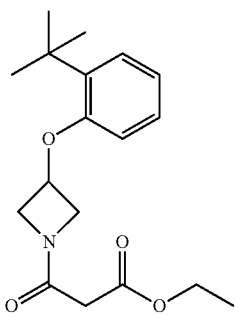 [SMILES: CCOC(=O)CC(=O)N1CC(Oc2ccccc2C(C)(C)C)C1]

To a stirred solution of 3-(2-tert-butylphenoxy)azetidine (0.35 g, 1.70 mmol), ethyl hydrogen malonate (0.25 g, 1.87 mmol) in methylene chloride (20.0 mL) was added EDCI (0.36 g, 1.87 mmol) and HOBt (0.25 g, 1.87 mmol) at room temperature. After 16 h the reaction mixture was concentrated under reduced pressure, the resulting residue was partitioned between ethyl acetate and water and separated. The organic layer was washed with 10% sodium bicarbonate, saturated sodium chloride, dried (Na$_2$SO$_4$), filtered and concentrated under reduced pressure. The residue was purified by flash column chromatography (silica gel, 50:50 heptane/ethyl acetate) to provide ethyl 3-(3-(2-tert-butylphenoxy)azetidin-1-yl)-3-oxopropanoate (0.29 g, 53%) as a colorless oil.

$^1$H NMR (500 MHz, CDCl$_3$) δ 7.34-7.32 (m, 1H), 7.16-7.13 (m, 1H). 6.97-6.94 (m, 1H), 6.47-6.45 (m, 1H), 5.02-5.00 (m, 1H), 4.62-4.59 (m, 1H), 4.50-4.46 (m, 1H), 4.29-4.26 (m, 1H), 4.23-4.15 (m, 3H), 3.25 (s, 2H), 1.39 (s, 9H), 1.29 (t, J=7.1 Hz, 3H).

Example 10

3-(3-(2-tert-butylphenoxy)azetidin-1-yl)-3-oxopropanoic acid

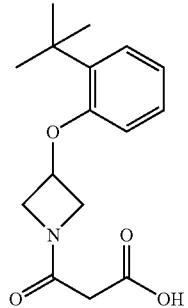 [SMILES: CC(C)(C)c1ccccc1OC1CN(C(=O)CC(=O)O)C1]

To an ice-cold stirred solution of ethyl 3-(3-(2-tert-butylphenoxy)azetidin-1-yl)-3-oxopropanoate (0.26 g, 0.81 mmol) in ethanol (10.0 mL) was added lithium hydroxide (2.44 ml of 1.0 M solution in water, 2.44 mmol) and the mixture was warmed at room temperature. After 2 h the reaction mixture was adjusted to about pH 1 with 1.0 M hydrochloric acid and concentrated under reduced pressure. The resulting residue was partitioned between ethyl acetate and water and separated. The organic layer was washed with saturated sodium chloride, dried (Na$_2$SO$_4$), filtered and concentrated under reduced pressure. The yellow residue was recrystallized from heptane/ethyl acetate to provide 3-(3-(2-tert-butylphenoxy)azetidin-1-yl)-3-oxopropanoic acid (0.12 g, 51%) as a white powder.

$^1$H NMR (500 MHz, CDCl$_3$) δ 13.10 (s, 1H), 7.36-7.34 (m, 1H), 7.26 (overlapping, 1H), 7.00-6.97 (m, 1H), 6.44 (d, J=8.1 Hz, 1H), 5.10-5.06 (m, 1H), 4.63-4.54 (m, 2H), 4.31-4.22 (m, 2H), 3.22 (s, 2H), 1.40 (s, 9H).

Example 11 ethyl 4-(3-(2-tert-butylphenoxy)azetidin-1-yl)-4-oxobutanoate

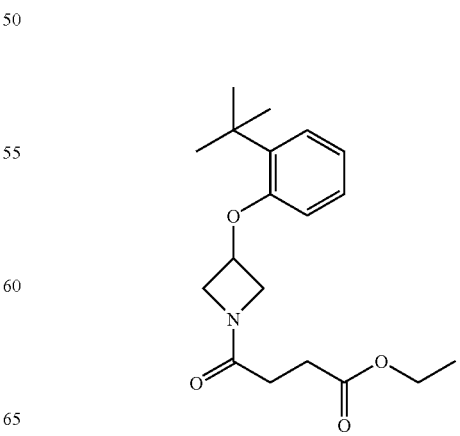

To an ice-cold stirred solution of 4-ethoxy-4-oxobutanoic acid (0.42 g, 2.56 mmol) and DMF (0.03 ml) in THF (15 mL) was added oxalyl chloride (0.35 g, 2.72 mmol). After 1 h the reaction mixture was concentrated under reduced pressure. The resulting residue was dissolved in THF (5.0 mL) and the solution was added to an ice-cold solution of 3-(2-tert-butylphenoxy)azetidine (0.35 g, 1.70 mmol) and triethylamine (0.31 g, 3.06 mmol) in THF (30.0 ml) and the resulting reaction mixture was warmed to room temperature. After 16 h the reaction mixture was filtered, the filtrate was partitioned between ethyl acetate and water and separated. The organic layer was washed with 10% sodium bicarbonate, saturated sodium chloride, dried ($Na_2SO_4$), filtered and concentrated under reduced pressure. The residue was purified by flash column chromatography (silica gel, 50:50 heptane/ethyl acetate) to provide ethyl 4-(3-(2-tert-butylphenoxy)azetidin-1-yl)-4-oxobutanoate (0.51 g, 90%) as a colorless oil.

$^1$H NMR (500 MHz, $CDCl_3$) δ 7.33-7.31 (m, 1H), 7.16-7.13 (m, 1H), 6.96-6.93 (m, 1H), 6.48-6.46 (m, 1H), 5.02-4.98 (m, 1H), 4.62-4.59 (m, 1H), 4.45-4.42 (m, 1H), 4.27-4.25 (m, 1H), 4.18-4.10 (m, 3H), 2.74-2.60 (m, 2H), 2.48-2.37 (m, 2H), 1.39 (s, 9H), 1.26 (t, J=7.1 Hz, 3H).

Example 12

4-(3-(2-tert-butylphenoxy)azetidin-1-yl)-4-oxobutanoic acid

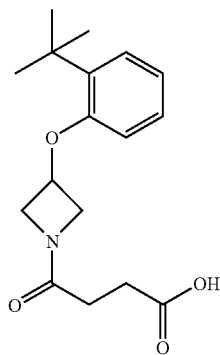 [SMILES: CC(C)(C)c1ccccc1OC1CN(C(=O)CCC(=O)O)C1]

To a solution of ethyl 4-(3-(2-tert-butylphenoxy)azetidin-1-yl)-4-oxobutanoate (0.47 g, 1.41 mmol) obtained in Example 11 in ethanol (20.0 mL) was added lithium hydroxide (1.0M aqueous solution, 4.23 ml, 4.23 mmol) under ice-cooling, and the mixture was stirred at room temperature. After 2 hr, the reaction mixture was adjusted to about pH 1 with 1.0M hydrochloric acid, and the mixture was concentrated under reduced pressure. The obtained residue was partitioned to between ethyl acetate and water, and the organic layer was washed with saturated sodium chloride, dried ($Na_2SO_4$), filtered, and concentrated under reduced pressure. The residue was recrystallized from heptane/ethyl acetate to give the title compound (0.28 g, 65%) as a white powder.

$^1$H NMR (500 MHz, $CDCl_3$) δ 7.34-7.32 (m, 1H), 7.17-7.13 (m, 1H), 6.98-6.94 (m, 1H), 6.47-6.45 (m, 1H), 5.03-5.00 (m, 1H), 4.61-4.58 (m, 1H), 4.49-4.46 (m, 1H), 4.28-4.25 (m, 1H), 4.17-4.14 (m, 1H), 2.77-2.66 (m, 2H), 2.50-2.45 (m, 2H), 1.39 (s, 9H).

Example 13 methyl 1-(3-(2-tert-butylphenoxy)azetidine-1-carbonyl)-cyclopropanecarboxylate

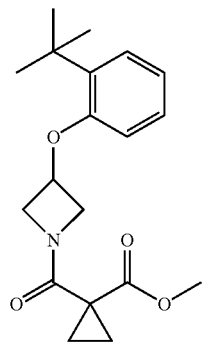 [SMILES: COC(=O)C1(C(=O)N2CC(Oc3ccccc3C(C)(C)C)C2)CC1]

The title compound was prepared by a procedure similar to the one described for ethyl 3-(3-(2-tert-butylphenoxy)azetidin-1-yl)-3-oxopropanoate to provide methyl 1-(3-(2-tert-butylphenoxy)azetidine-1-carbonyl)cyclopropanecarboxylate (0.42 g, 75%) as a colorless oil.

$^1$H NMR (500 MHz, $CDCl_3$) δ 7.34-7.32 (m, 1H), 7.17-7.13 (m, 1H), 6.97-6.94 (m, 1H), 6.47 (d, J=8.0 Hz, 1H), 5.04-5.00 (m, 1H), 4.54-4.46 (m, 2H), 4.19-4.16 (m, 2H), 3.73 (s, 3H), 1.46-1.43 (m, 2H), 1.40 (s, 9H), 1.36-1.32 (m, 2H).

Example 14

1-(3-(2-tert-butylphenoxy)azetidine-1-carbonyl)cyclopropanecarboxylic acid

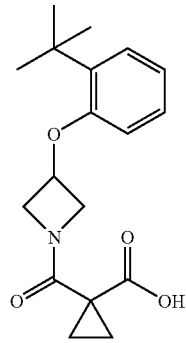 [SMILES: CC(C)(C)c1ccccc1OC1CN(C(=O)C2(C(=O)O)CC2)C1]

The title compound was prepared by a procedure similar to the one described for 3-(3-(2-tert-butylphenoxy)azetidin-1-yl)-3-oxopropanoic acid to provide 1-(3-(2-tert-butylphenoxy)azetidine-1-carbonyl)cyclopropanecarboxylic acid (0.27 g, 77%) as a white powder.

$^1$H NMR (500 MHz, $CDCl_3$) δ 7.34-7.32 (m, 1H), 7.17-7.13 (m, 1H), 6.98-6.95 (m, 1H), 6.45-6.43 (m, 1H), 5.03-4.98 (m, 1H), 4.56 (m, 2H), 4.25-4.23 (m, 2H), 1.68-1.67 (m, 2H), 1.51-1.49 (m, 2H), 1.39 (s, 9H).

Example 15 methyl 4-(3-(2-tert-butylphenoxy)azetidine-1-carbonyl)benzoate

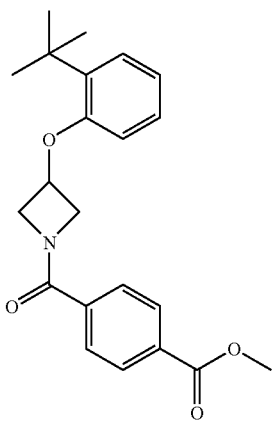 [SMILES: COC(=O)c1ccc(C(=O)N2CC(Oc3ccccc3C(C)(C)C)C2)cc1]

The title compound was prepared by a procedure similar to the one described for ethyl 3-(3-(2-tert-butylphenoxy)azetidin-1-yl)-3-oxopropanoate to provide methyl 4-(3-(2-tert-butylphenoxy)azetidine-1-carbonyl)benzoate (0.30 g, 42%) as a white powder.

$^1$H NMR (500 MHz, CDCl$_3$) δ 8.09 (d, J=8.5 Hz, 2H), 7.71 (d, J=8.5 Hz, 2H), 7.34-7.32 (m, 1H), 7.15-7.12 (m, 1H), 6.97-6.94 (m, 1H), 6.46-6.45 (m, 1H), 5.08-5.03 (m, 1H), 4.68-4.64 (m, 2H), 4.38-4.33 (m, 2H), 3.94 (s, 3H), 1.41 (s, 9H).

Example 16

4-(3-(2-tert-butylphenoxy)azetidine-1-carbonyl)benzoic acid

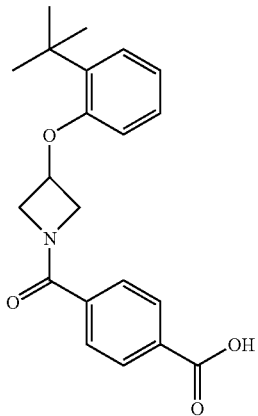 [SMILES: CC(C)(C)c1ccccc1OC1CN(C(=O)c2ccc(C(=O)O)cc2)C1]

The title compound was prepared by a procedure similar to the one described for 3-(3-(2-tert-butylphenoxy)azetidin-1-yl)-3-oxopropanoic acid to provide 4-(3-(2-tert-butylphenoxy)azetidine-1-carbonyl)benzoic acid (0.15 g, 71%) as a white powder.

$^1$H NMR (500 MHz, DMSO-d$_6$) δ 8.00 (d, J=8.4 Hz, 2H), 7.77 (d, J=8.4 Hz, 2H), 7.27-7.25 (m, 1H), 7.17-7.13 (m, 1H), 6.93-6.90 (m, 1H), 6.67 (d, J=7.5 Hz, 1H), 5.16-5.11 (m, 1H), 4.76-4.73 (m, 1H), 4.61-4.58 (m, 1H), 4.33-4.32 (m, 1H), 4.05-4.01 (m, 1H), 1.37 (s, 9H).

Example 17

(3-(2-tert-butylphenylthio)azetidin-1-yl)(pyridin-2-yl)methanone

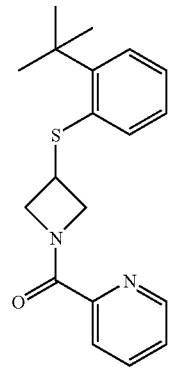

To an ice-cold stirred solution of 3-(2-tert-butylphenylthio)azetidine hydrochloride (0.25 g, 0.97 mmol) in pyridine (10.0 mL) was added picolinoyl chloride hydrochloride (0.21 g, 1.16 mmol) and the resulting reaction mixture was warmed at room temperature.

After 16 h the reaction mixture was concentrated under reduced pressure, the residue was partitioned between ethyl acetate and water and separated. The organic layer was washed with saturated sodium chloride, dried (Na$_2$SO$_4$), filtered and concentrated under reduced pressure. The residue was purified by flash column chromatography (silica gel, 80:20 to 50:50% heptane/ethyl acetate) to provide a yellow solid. Trituration of the solid with heptane and collection of the resulting solids by filtration provided (3-(2-tert-butylphenylthio)azetidin-1-yl)(pyridin-2-yl)methanone (1.80 g, 55%) as a yellow powder.

$^1$H NMR (500 MHz, CDCl$_3$) δ 8.57-8.56 (m, 1H), 8.12 (d, J=7.9 Hz, 1H), 7.82-7.79 (m, 1H), 7.41-7.35 (m, 2H), 7.17-7.14 (m, 2H), 7.10-7.07 (m, 1H), 5.22-5.18 (m, 1H), 4.71-4.65 (m, 2H), 4.25-4.16 (m, 2H), 1.50 (s, 9H).

Example 18

(3-(2-tert-butylphenylthio)azetidin-1-yl)(phenyl)methanone

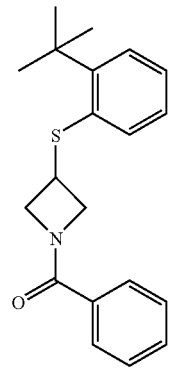

The title compound was prepared by a procedure similar to the one described for (3-(2-tert-butylphenylthio)azetidin-1-yl)(pyridin-2-yl)methanone to provide (3-(2-tert-butylphenylthio)azetidin-1-yl)(phenyl)methanone (0.50 g, 88%) as an off-white powder.

¹H NMR (500 MHz, CDCl₃) δ 7.64-7.61 (m, 2H), 7.48-7.45 (m, 1H), 7.42-7.39 (m, 3H), 7.17-7.11 (m, 2H), 7.04-7.02 (m, 1H), 4.69-4.65 (m, 2H), 4.24-4.14 (m, 3H), 1.49 (s, 9H).

Example 19

(3-(2-tert-butylphenylsulfinyl)azetidin-1-yl)(phenyl)methanone

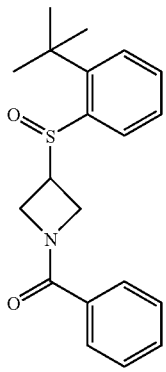

To an ice-cold stirred solution of (3-(2-tert-butylphenylthio)azetidin-1-yl)(phenyl)methanone (0.18 g, 0.55 mmol) in methylene chloride (10.0 mL) was added m-CPBA (0.15 g, 0.61 mmol). After 10 min a saturated solution of sodium thiosulfate and sodium hydrogen carbonate was added to the reaction mixture and the resulting reaction mixture was warmed to room temperature. After 30 min the reaction mixture was diluted with methylene chloride and separated. The organic layer was washed with saturated sodium chloride, dried (Na₂SO₄), filtered and concentrated under reduced pressure. The residue was purified by flash column chromatography (silica gel, 50:50 heptane/ethyl acetate) to provide (3-(2-tert-butylphenylsulfinyl)azetidin-1-yl)(phenyl)methanone (0.17 g, 66%) as a white powder.

¹H NMR (500 MHz, CDCl₃) δ 8.05-7.91 (m, 1H), 7.63 (m, 2H), 7.48-7.42 (m, 6H), 5.03-4.89 (m, 1H), 4.58-4.45 (m, 2H), 4.11-4.09 (m, 1H), 3.89-3.83 (m, 1H), 1.46 (s, 9H).

Example 20

(3-(2-tert-butylphenylsulfonyl)azetidin-1-yl)(phenyl)methanone

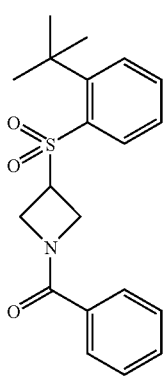

To an ice-cold stirring solution of (3-(2-tert-butylphenylthio)azetidin-1-yl)(phenyl)methanone (0.21 g, 0.65 mmol) in methylene chloride (10 mL) was added m-CPBA (0.18 g, 0.71 mmol). After 10 min additional m-CPBA (0.36 g, 1.42 mmol) was added and the resulting reaction mixture was stirred at room temperature for 20 h. Then, a saturated solution of sodium thiosulfate and sodium hydrogen carbonate was added and the resulting reaction mixture were stirred at room temperature. After 30 min the reaction mixture was diluted with methylene chloride and separated. The organic layer was washed with saturated sodium chloride, dried (Na₂SO₄), filtered and concentrated under reduced pressure. The residue was purified by flash column chromatography (silica gel, 60:40 to 50:50 heptane/ethyl acetate) provided (3-(2-tert-butylphenylsulfonyl)azetidin-1-yl)(phenyl)methanone (0.17 g, 73%) as a white powder.

¹H NMR (500 MHz, CDCl₃) δ 8.08-8.06 (m, 1H), 7.71-7.69 (m, 1H), 7.63-7.62 (m, 2H), 7.59-7.55 (m, 1H), 7.51-7.47 (m, 1H), 7.44-7.38 (m, 3H), 4.73 (m, 1H), 4.53 (m, 1H), 4.38-4.28 (m, 3H), 1.59 (s, 9H).

Example 21

(3-(2-tert-butylphenoxy)azetidin-1-yl)(5-methylisoxazol-3-yl)methanone

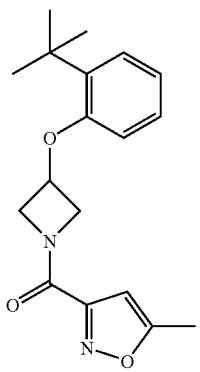 [SMILES: Cc1cc(C(=O)N2CC(Oc3ccccc3C(C)(C)C)C2)no1]

To a stirred solution of 3-(2-tert-butylphenoxy)azetidine (0.18 g, 0.80 mmol) and triethylamine (0.24 g, 2.4 mmol) in methylene chloride (4.0 mL) was added 5-methylisoxazole-3-carbonyl chloride (0.12 g, 0.80 mmol) at room temperature. After 2 h the reaction mixture was directly purified by flash column chromatography (silica gel, 80:20 heptane/ethyl acetate) to provide (3-(2-tert-butylphenoxy)azetidin-1-yl)(5-methylisoxazol-3-yl)methanone (0.21 g, 83%) as a white solid.

¹H NMR (300 MHz, DMSO-d₆) δ 7.26 (dd, J=7.8, 1.6 Hz, 1H), 7.17 (dt, J=7.4, 1.6 Hz, 1H), 6.92 (t, J=7.6 Hz, 1H), 6.70 (d, J=8.0 Hz, 1H), 6.55 (d, J=0.78 Hz, 1H), 5.17-5.12 (m, 1H), 4.94-4.88 (m, 1H), 4.60-4.54 (m, 1H), 4.37-4.32 (m, 1H), 4.04-3.98 (m, 1H), 2.45 (s, 3H), 1.35 (s, 9H).

Example 22

(3-(2-tert-butylphenoxy)azetidin-1-yl)(2,5-dimethyloxazol-4-yl)methanone

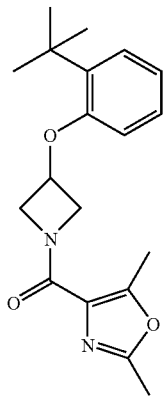

The title compound was prepared by a procedure similar to the one described for (3-(2-tert-butylphenoxy)azetidin-1-yl)(5-methylisoxazol-3-yl)methanone to provide (3-(2-tert-butylphenoxy)azetidin-1-yl)(2,5-dimethyloxazol-4-yl)methanone (0.20 g, 74%) as a colorless viscous oil.

$^{1}$H NMR (300 MHz, DMSO-d$_{6}$) δ 7.26 (dd, J=7.7, 1.5 Hz, 1H), 7.17 (dt, J=7.8, 1.5 Hz, 1H), 6.92 (t, J=7.8 Hz, 1H), 6.70 (d, J=7.7 Hz, 1H), 5.14-5.07 (m, 1H), 4.95-4.89 (m, 1H), 4.50-4.45 (m, 1H), 4.37-4.32 (m, 1H), 3.95-3.90 (m, 1H), 2.49 (s, 3H), 2.36 (s, 3H), 1.35 (s, 9H).

Example 23

(3-(2-tert-butylphenoxy)azetidin-1-yl)(thiazol-2-yl)methanone

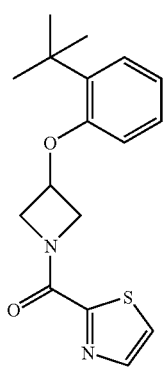

The title compound was prepared by a procedure similar to the one described for (3-(2-tert-butylphenoxy)azetidin-1-yl)(5-methylisoxazol-3-yl)methanone to provide (3-(2-tert-butylphenoxy)azetidin-1-yl)(thiazol-2-yl)methanone (0.17 g, 66%) as an off-white solid.

$^{1}$H NMR (500 MHz, DMSO-d$_{6}$) δ 8.05-8.03 (m, 2H), 7.28 (dd, J=7.8, 1.6 Hz, 1H), 7.17 (dt, J=7.4, 1.6 Hz, 1H), 6.93 (t, J=7.6 Hz, 1H), 6.72 (d, J=8.0 Hz, 1H), 5.19-5.17 (m, 1H), 5.12-5.10 (m, 1H), 4.63-4.61 (m, 1H), 4.54-4.51 (m, 1H), 4.08-4.05 (m, 1H), 1.36 (s, 9H).

Example 24 benzo[d]thiazol-2-yl(3-(2-tert-butylphenoxy)azetidin-1-yl)methanone

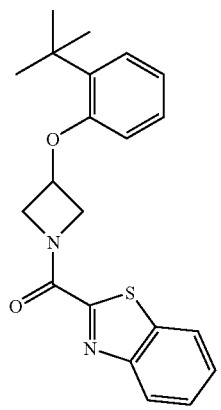 [SMILES: CC(C)(C)c1ccccc1OC1CN(C(=O)c2nc3ccccc3s2)C1]

The title compound was prepared by a procedure similar to the one described for (3-(2-tert-butylphenoxy)azetidin-1-yl)(5-methylisoxazol-3-yl)methanone to provide benzo[d]thiazol-2-yl(3-(2-tert-butylphenoxy)azetidin-1-yl)methanone (0.14 g, 48%) as an off-white solid.

$^{1}$H NMR (500 MHz, DMSO-d$_{6}$) δ 8.22 (dd, J=7.8, 1.6 Hz, 1H), 8.16 (d, J=8.5 Hz, 1H), 7.62-7.58 (m, 2H), 7.28 (dd, J=7.8, 1.5 Hz, 1H), 7.25-7.17 (m, 1H), 6.98-6.92 (m, 1H), 6.76 (d, J=8.0 Hz, 1H), 5.26-5.21 (m, 2H), 4.71-4.63 (m, 2H), 4.14-4.12 (m, 1H), 1.38 (s, 9H).

Example 25

(3-(2-tert-butylphenoxy) azetidin-1-yl) (oxazol-4-yl) methanone

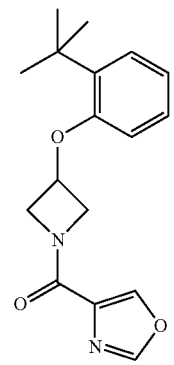 [SMILES: CC(C)(C)c1ccccc1OC1CN(C(=O)c2cocn2)C1]

To a stirred solution of oxazole-4-carboxylic acid (0.18 g, 1.60 mmol) and DMF (2 drops) in THF (3.0 mL) was added oxalyl chloride (0.22 g, 1.76 mmol) dropwise. After the addition was complete the mixture was stirred at room temperature for 0.5 h. Then, the reaction mixture was concentrated under reduced pressure to provide oxazole-4-carbonyl chloride which was dissolved in methylene chloride (3.0 mL) and added to a stirred solution of 3-(2-tert-butylphenoxy)azetidine (0.37 g, 1.60 mmol) and triethylamine (0.49 g, 4.80 mmol) in methylene chloride (6.0 mL) at room temperature. After 16 h reaction mixture was directly purified by flash column chromatography (silica gel, 50:50 heptane/ethyl acetate) to provide (3-(2-tert-butylphenoxy)azetidin-1-yl)(oxazol-4-yl)methanone (0.27 g, 56%) as a yellow orange solid.

$^1$H NMR (500 MHz, DMSO-d$_6$) δ 8.69 (d, J=0.8 Hz, 1H), 8.49 (d, J=0.8 Hz, 1H), 7.27 (dd, J=7.8, 1.6 Hz, 1H), 7.17 (dt, J=7.4, 1.6 Hz, 1H), 6.92 (t, J=7.6 Hz, 1H), 6.70 (d, J=8.0 Hz, 1H), 5.17-5.13 (m, 1H), 4.99-4.95 (m, 1H), 4.55-4.51 (m, 1H), 4.43-4.40 (m, 1H), 3.99-3.96 (m, 1H), 1.36 (s, 9H).

Example 26

(3-(2-tert-butylphenoxy)azetidin-1-yl) (5-methyl-isoxazol-4-yl)methanone

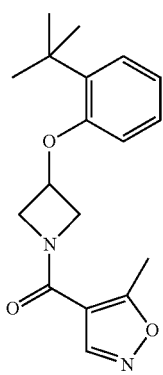

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(5-methylisoxazol-4-yl)methanone (0.12 g, 37%) as a pale brown viscous oil.

$^1$H NMR (300 MHz, DMSO-d$_6$) δ 8.86 (d, J=0.5 Hz, 1H), 7.27 (dd, J=7.8, 1.6 Hz, 1H), 7.16 (dt, J=7.4, 1.6 Hz, 1H), 6.93 (t, J=7.6 Hz, 1H), 6.67 (d, J=8.0 Hz, 1H), 5.16-5.09 (m, 1H), 4.80-4.78 (m, 1H), 4.55-4.50 (m, 1H), 4.43-4.40 (m, 1H), 3.99-3.96 (m, 1H), 2.61 (s, 3H), 1.36 (s, 9H).

Example 27

(3-(2-tert-butylphenoxy)azetidin-1-yl)(2-methylthi-azol-4-yl)methanone

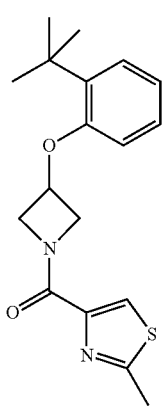

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(2-methylthiazol-4-yl)methanone (0.12 g, 37%) as a pale brown solid.

$^1$H NMR (300 MHz, DMSO-d$_6$) δ 8.17 (s, 1H), 7.26 (dd, J=7.8, 1.6 Hz, 1H), 7.18 (dt, J=7.4, 1.6 Hz, 1H), 6.93 (dt, J=7.6, 1.1 Hz, 1H), 6.71 (dd, J=8.1, 1.1 Hz, 1H), 5.17-5.10 (m, 1H), 5.95-5.01 (m, 1H), 4.56-4.50 (m, 1H), 4.44-4.40 (m, 1H), 4.00-3.95 (m, 1H), 2.68 (s, 3H), 1.36 (s, 9H).

Example 28

(3-(2-tert-butylphenoxy)azetidin-1-yl)(imidazo[2,1-b]thiazol-6-yl)methanone

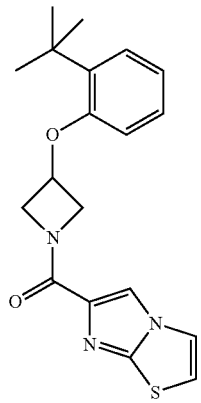 [SMILES: CC(C)(C)c1ccccc1OC1CN(C(=O)c2cn3ccsc3n2)C1]

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(imidazo[2,1-b]thiazol-6-yl)methanone (0.070 g, 20%) as an off-white solid.

$^1$H NMR (300 MHz, DMSO-d$_6$) δ 8.24 (s, 1H), 7.93 (d, J=4.5 Hz, 1H), 7.39 (d, J=4.5 Hz, 1H), 7.28-7.25 (m, 1H), 7.20-7.15 (m, 1H), 6.95-6.89 (m, 1H), 6.74-6.65 (m, 1H), 5.15-5.13 (m, 1H), 5.07-5.03 (m, 1H), 4.55-4.48 (m, 2H), 4.00-3.95 (m, 1H), 1.36 (s, 9H).

Example 29

(3-(2-tert-butylphenoxy)azetidin-1-yl)(thieno[2,3-b]pyrazin-6-yl)methanone

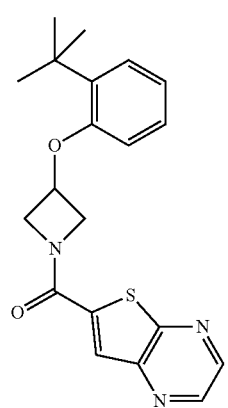 [SMILES: CC(C)(C)c1ccccc1OC1CN(C(=O)c2cc3nccnc3s2)C1]

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(thieno[2,3-b]pyrazin-6-yl)methanone (0.12 g, 32%) as an off-white solid.

¹H NMR (300 MHz, DMSO-d₆) δ 8.86 (d, J=2.3 Hz, 1H), 8.74 (d, J=2.3 Hz, 1H), 8.08 (s, 1H), 7.28 (dd, J=7.8, 1.6 Hz, 1H), 7.19 (dt, J=7.4, 1.6 Hz, 1H), 6.94 (dt, J=7.6, 1.1 Hz, 1H), 6.71 (dd, J=8.1, 1.1 Hz, 1H), 5.23-5.18 (m, 1H), 5.15-5.10 (m, 1H), 4.75-4.65 (m, 2H), 4.15-4.08 (m, 1H), 1.38 (s, 9H).

Example 30

(3-(2-tert-butylphenoxy)azetidin-1-yl)(pyrimidin-2-yl)methanone

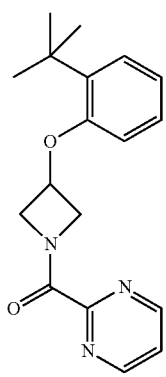

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(pyrimidin-2-yl)methanone (0.12 g, 47%) as a white solid.

¹H NMR (300 MHz, DMSO-d₆) δ 8.94 (d, J=4.9 Hz, 2H), 7.64 (t, J=4.9 Hz, 1H), 7.26 (dd, J=7.8, 1.6 Hz, 1H), 7.16 (dt, J=7.4, 1.6 Hz, 1H), 6.92 (dt, J=7.6, 1.1 Hz, 1H), 6.69 (dd, J=8.1, 1.1 Hz, 1H), 5.23-5.18 (m, 1H), 5.16-5.11 (m, 1H), 4.92-4.86 (m, 1H), 4.64-4.57 (m, 1H), 4.07-4.02 (m, 1H), 1.36 (s, 9H).

Example 31

(3-(2-tert-butylphenoxy)azetidin-1-yl)(pyrimidin-5-yl)methanone

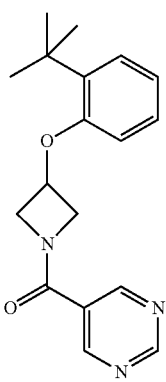 [SMILES: CC(C)(C)c1ccccc1OC1CN(C(=O)c2cncnc2)C1]

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(pyrimidin-5-yl)methanone (0.11 g, 34%) as a white solid.

¹H NMR (300 MHz, DMSO-d₆) δ 9.32 (s, 1H), 9.07 (s, 2H), 7.26 (dd, J=7.8, 1.6 Hz, 1H), 7.16 (dt, J=7.4, 1.6 Hz, 1H), 6.92 (dt, J=7.6, 1.1 Hz, 1H), 6.66 (dd, J=8.1, 1.1 Hz, 1H), 5.15-5.09 (m, 1H), 4.88-4.82 (m, 1H), 4.65-4.59 (m, 1H), 4.53-4.48 (m, 1H), 4.09-4.04 (m, 1H), 1.37 (s, 9H).

Example 32

(3-(2-tert-butylphenoxy)azetidin-1-yl)(pyrazolo[1,5-a]pyridin-2-yl)methanone

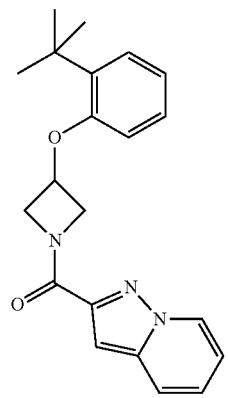 [SMILES: CC(C)(C)c1ccccc1OC1CN(C(=O)c2cc3ccccn3n2)C1]

The title compound was prepared by a procedure similar to the one described for (3-(2-tert-butylphenoxy)azetidin-1-yl)(oxazol-4-yl)methanone to provide (3-(2-tert-butylphenoxy)azetidin-1-yl)(pyrazolo[1,5-a]pyridin-2-yl)methanone (0.23 g, 66%) as a white solid.

¹H NMR (300 MHz, DMSO-d₆) δ 8.72 (dd, J=7.0, 0.8 Hz, 1H), 7.76 (d, J=8.9 Hz, 1H), 7.30-7.27 (m, 2H), 7.19 (dt, J=7.4, 1.6 Hz, 1H), 7.02-6.99 (m, 2H), 6.93 (dt, J=7.6, 0.6 Hz, 1H), 6.74 (dd, J=8.0, 0.5 Hz, 1H), 5.21-5.17 (m, 1H), 5.08-5.05 (m, 1H), 4.61-4.58 (m, 1H), 4.53-4.50 (m, 1H), 4.05-4.02 (m, 1H), 1.37 (s, 9H).

Example 33

(3-(2-tert-butylphenoxy)azetidin-1-yl)(imidazo[1,2-a]pyridin-2-yl)methanone

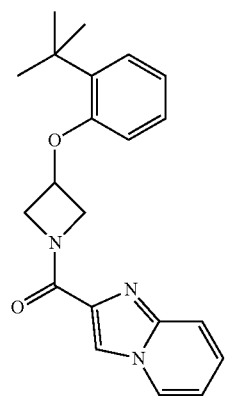 [SMILES: CC(C)(C)c1ccccc1OC1CN(C(=O)c2cn3ccccc3n2)C1]

To a stirred solution of sodium imidazo[1,2-a]pyridine-2-carboxylate (0.19 g, 1.0 mmol), 3-(2-tert-butylphenoxy)azetidine (0.21 g, 0.53 mmol) and DIPEA (0.39 g, 3.0 mmol) in DMF (5.0 mL) was added HBTU (0.76 g, 2.0 mmol) at room temperature. After 1 h the reaction mixture was diluted with ethyl acetate (50 mL) and washed with a 10% $K_2CO_3$ solution (3×20 mL), dried ($Na_2SO_4$), filtered and concentrated under reduced pressure. The residue was purified by flash column chromatography (silica gel, ethyl acetate to 95:5 methanol/ethyl acetate) to provide (3-(2-tert-butylphenoxy)azetidin-1-yl)(imidazo[1,2-a]pyridin-2-yl)methanone (0.18 g, 51%) as a white solid.

$^1$H NMR (300 MHz, DMSO-$d_6$) δ 8.58-8.52 (m, 1H), 8.42 (s, 1H), 7.62 (dd, J=9.1, 0.7 Hz, 1H), 7.34-7.25 (m, 2H), 7.23-7.16 (m, 1H), 7.00-6.90 (m, 2H), 6.74 (dd, J=7.8, 0.8 Hz, 1H), 5.21-5.02 (m, 2H), 4.60-4.54 (m, 2H), 4.04-4.00 (m, 1H), 1.37 (s, 9H).

Example 34

3-(2-tert-butylphenoxy)-N-ethylazetidine-1-carboxamide

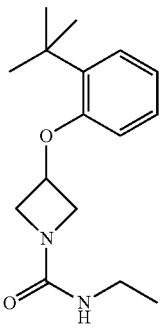

To a stirred solution of 3-(2-tert-Butylphenoxy)azetidine (0.21 g, 1.02 mmol) in pyridine (10 ml) was added ethyl isocyanate (0.078 g, 1.10 mmol) and the mixture was stirred at room temperature for 16 h. The reaction mixture was concentrated under reduced pressure and the resulting residue was partitioned between ethyl acetate and 1N hydrochloric acid. The organic layer was washed with water and saturated sodium chloride, dried ($MgSO_4$), filtered and concentrated under reduced pressure. The resulting residue was triturated with heptane/ethyl acetate to provide 3-(2-tert-Butylphenoxy)-N-ethylazetidine-1-carboxamide (0.15 g, 53%) as a white powder.

$^1$H NMR (500 MHz, CDCl$_3$) δ 7.33-7.31 (m, 1H), 7.15-7.12 (m, 1H), 6.95-6.92 (m, 1H), 6.48-6.46 (m, 1H), 4.97-4.95 (m, 1H), 4.35-4.32 (m, 2H), 4.07-4.04 (m, 3H), 3.29-3.24 (m, 2H), 1.39 (s, 9H), 1.14 (t, J=7.2 Hz, 3H).

Example 35

(3-(2-tert-butyl-4-fluorophenoxy)azetidin-1-yl)(2,5-dimethyloxazol-4-yl)methanone

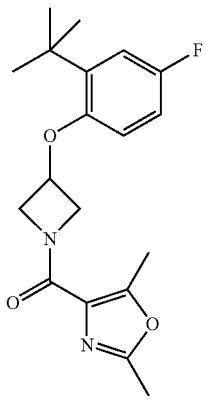 [SMILES: Cc1nc(C(=O)N2CC(Oc3ccc(F)cc3C(C)(C)C)C2)c(C)o1]

The title compound was prepared by a procedure similar to the one described for (3-(2-tert-butylphenoxy)azetidin-1-yl)(5-methylisoxazol-3-yl)methanone to provide (3-(2-tert-butyl-4-fluorophenoxy)azetidin-1-yl)(2,5-dimethyloxazol-4-yl)methanone (0.11 g, 54%) as a white solid.

$^1$H NMR (300 MHz, DMSO-$d_6$) δ 7.06-6.96 (m, 2H), 6.71 (dd, J=8.8, 4.9 Hz, 1H), 5.12-5.05 (m, 1H), 4.94-4.88 (m, 1H), 4.49-4.43 (m, 1H), 4.36-4.32 (m, 1H), 3.94-3.89 (m, 1H), 2.49 (s, 3H), 2.37 (s, 3H), 1.35 (s, 9H).

Example 36

(3-(2-tert-butyl-4-fluorophenoxy)azetidin-1-yl)(5-methylisoxazol-3-yl)methanone

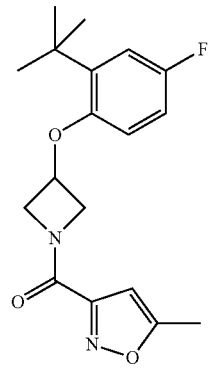 [SMILES: Cc1cc(C(=O)N2CC(Oc3ccc(F)cc3C(C)(C)C)C2)no1]

The title compound was prepared by a procedure similar to the one described for (3-(2-tert-butylphenoxy)azetidin-1-yl)(5-methylisoxazol-3-yl)methanone to provide (3-(2-tert-butyl-4-fluorophenoxy)azetidin-1-yl)(5-methylisoxazol-3-yl)methanone (0.16 g, 82%) as a white solid.

$^1$H NMR (300 MHz, DMSO-$d_6$) δ 7.06-6.97 (m, 2H), 6.71 (dd, J=8.8, 4.9 Hz, 1H), 6.55 (d, J=0.85 Hz, 1H), 5.15-5.11 (m, 1H), 4.92-4.87 (m, 1H), 4.59-4.53 (m, 1H), 4.36-4.31 (m, 1H), 4.03-3.98 (m, 1H), 2.45 (s, 3H), 1.35 (s, 9H).

Example 37

(3-(2-tert-butyl-4-fluorophenoxy)azetidin-1-yl)(thiazol-2-yl)methanone

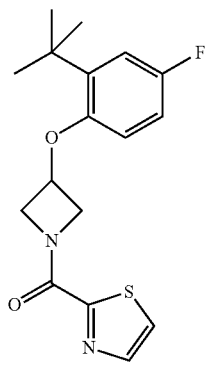 [SMILES: CC(C)(C)c1cc(F)ccc1OC1CN(C(=O)c2nccs2)C1]

The title compound was prepared by a procedure similar to the one described for (3-(2-tert-butylphenoxy)azetidin-1-yl)(5-methylisoxazol-3-yl)methanone to provide (3-(2-tert-butyl-4-fluorophenoxy)azetidin-1-yl)(thiazol-2-yl)methanone (0.16 g, 78%) as an off-white solid.

$^1$H NMR (300 MHz, DMSO-d$_6$) δ 8.06-8.03 (m, 2H), 7.07-6.97 (m, 2H), 6.74 (dd, J=8.8, 4.9 Hz, 1H), 5.19-5.06 (m, 2H), 4.64-4.58 (m, 1H), 4.54-4.49 (m, 1H), 4.08-4.03 (m, 1H), 1.35 (s, 9H

Example 38

(3-(2-tert-butyl-4-fluorophenoxy)azetidin-1-yl)(pyrazin-2-yl)methanone

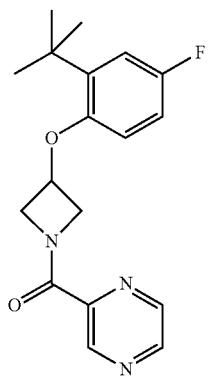 [SMILES: CC(C)(C)c1cc(F)ccc1OC1CN(C(=O)c2cnccn2)C1]

The title compound was prepared by a procedure similar to the one described for (3-(2-tert-butylphenoxy)azetidin-1-yl)(5-methylisoxazol-3-yl)methanone to (3-(2-tert-butyl-4-fluorophenoxy)azetidin-1-yl)(pyrazin-2-yl)methanone (0.11 g, 56%) as a pale yellow viscous oil.

$^1$H NMR (300 MHz, DMSO-d$_6$) δ 9.13 (d, J=1.4 Hz, 1H), 8.82 (d, J=2.5 Hz, 1H), 8.72-8.02 (m, 1H), 7.06-6.96 (m, 2H), 6.71 (dd, J=8.8, 4.9 Hz, 1H), 5.17-5.11 (m, 1H), 5.07-5.01 (m, 1H), 4.65-4.59 (m, 1H), 4.55-4.50 (m, 1H), 4.09-4.04 (m, 1H), 1.35 (s, 9H).

Example 39

3-(2-tert-butyl-4-fluorophenoxy)azetidin-1-yl)(oxazol-4-yl)methanone

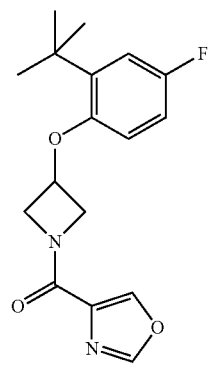 [SMILES: CC(C)(C)c1cc(F)ccc1OC1CN(C(=O)c2cocn2)C1]

The title compound was prepared by a procedure similar to the one described for (3-(2-tert-butylphenoxy)azetidin-1-yl)(imidazo[1,2-a]pyridin-2-yl)methanone to provide (3-(2-tert-butyl-4-fluorophenoxy)azetidin-1-yl)(oxazol-4-yl)methanone (0.044 g, 27%) as an off-white solid.

$^1$H NMR (500 MHz, DMSO-d$_6$) δ 8.69 (s, 1H), 8.49 (s, 1H), 7.04 (dd, J=10.9, 3.1 Hz, 1H), 7.02-6.98 (m, 1H), 6.71 (dd, J=8.9, 5.0 Hz, 1H), 5.14-5.10 (m, 1H), 4.97-4.94 (m, 1H), 4.53-4.50 (m, 1H), 4.42-4.39 (m, 1H), 3.98-3.95 (m, 1H), 1.35 (s, 9H)

Example 40

4-(3-(2-tert-butyl-4-fluorophenoxy)azetidine-1-carbonyl)benzonitrile

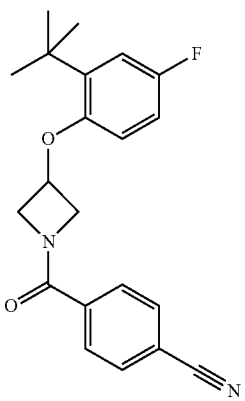 [SMILES: CC(C)(C)c1cc(F)ccc1OC1CN(C(=O)c2ccc(C#N)cc2)C1]

The title compound was prepared by a procedure similar to the one described for (3-(2-tert-butylphenoxy)azetidin-1-yl)(imidazo[1,2-a]pyridin-2-yl)methanone to provide 4-(3-(2-tert-butyl-4-fluorophenoxy)azetidine-1-carbonyl)benzonitrile (0.036 g, 22%) as an off-white solid.

$^1$H NMR (300 MHz, DMSO-d$_6$) δ 7.94 (dd, J=6.5, 1.9 Hz, 2H), 7.83 (dd, J=6.7, 1.9 Hz, 2H), 7.04 (dd, J=10.6, 3.0 Hz,

1H), 7.00-6.94 (m, 1H), 6.69 (dd, J=9.0, 4.9 Hz, 1H), 5.13-5.06 (m, 1H), 4.74-4.68 (m, 1H), 4.61-4.55 (m, 1H), 4.35-4.32 (m, 1H), 4.06-4.01 (m, 1H), 1.35 (s, 9H).

Example 41

3-(2-tert-butyl-4-fluorophenoxy) azetidin-1-yl)(5-methylisoxazol-4-yl)methanone

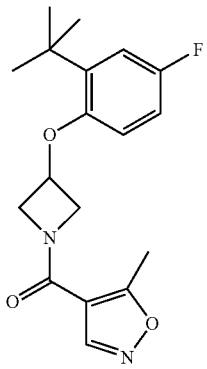 [SMILES: Cc1oncc1C(=O)N1CC(Oc2ccc(F)cc2C(C)(C)C)C1]

The title compound was prepared by a procedure similar to the one described for (3-(2-tert-butylphenoxy)azetidin-1-yl)(imidazo[1,2-a]pyridin-2-yl)methanone to provide 3-(2-tert-butyl-4-fluorophenoxy)azetidin-1-yl)(5-methylisoxazol-4-yl)methanone (0.12 g, 37%) as a pale yellow solid.

$^1$H NMR (500 MHz, DMSO-$d_6$) δ 8.84 (s, 1H), 7.04 (dd, J=10.9, 3.1 Hz, 1H), 7.01-6.98 (m, 1H), 6.69 (dd, J=8.8, 4.9 Hz, 1H), 5.12-5.08 (m, 1H), 4.80-4.78 (m, 1H), 4.52-4.49 (m, 1H), 4.43-4.40 (m, 1H), 4.03-3.94 (m, 1H), 2.61 (s, 3H), 1.35 (s, 9H).

Example 42

(3-(2-tert-butyl-4-fluorophenoxy)azetidin-1-yl)(pyrimidin-5-yl)methanone

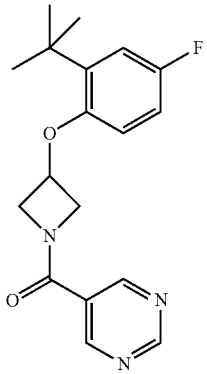 [SMILES: CC(C)(C)c1cc(F)ccc1OC1CN(C(=O)c2cncnc2)C1]

The title compound was prepared by a procedure similar to the one described for (3-(2-tert-butylphenoxy)azetidin-1-yl)(imidazo[1,2-a]pyridin-2-yl)methanone to provide (3-(2-tert-butyl-4-fluorophenoxy)azetidin-1-yl)(pyrimidin-5-yl)methanone (0.018 g, 6%) as an off-white solid.

$^1$H NMR (500 MHz, DMSO-$d_6$) δ 9.31 (s, 1H), 9.06 (s, 2H), 7.04 (dd, J=10.9, 2.6 Hz, 1H), 6.98-6.96 (m, 1H), 6.68 (dd, J=8.9, 5.0 Hz, 1H), 5.13-5.08 (m, 1H), 4.85-4.81 (m, 1H), 4.62-4.59 (m, 1H), 4.51-4.49 (m, 1H), 4.07-4.04 (m, 1H), 1.36 (s, 9H).

Example 43

(3-(2-tert-butyl-4-fluorophenoxy)azetidin-1-yl)(thieno[2,3-b]pyrazin-6-yl)methanone

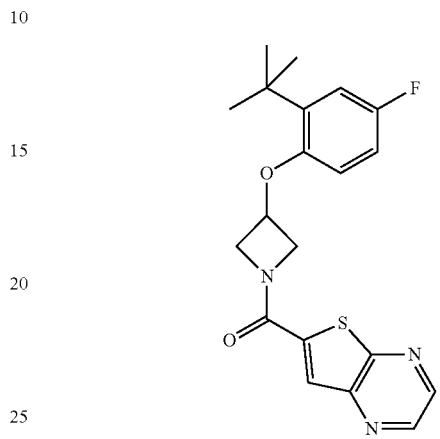

The title compound was prepared by a procedure similar to the one described for (3-(2-tert-butylphenoxy)azetidin-1-yl)(imidazo[1,2-a]pyridin-2-yl)methanone to provide (3-(2-tert-butyl-4-fluorophenoxy)azetidin-1-yl)(thieno[2,3-b]pyrazin-6-yl)methanone (0.024 g, 6%) as an off-white solid.

$^1$H NMR (500 MHz, DMSO-$d_6$) δ 8.86 (d, J=2.3 Hz, 1H), 8.73 (d, J=2.3 Hz, 1H), 8.08 (s, 1H), 7.05 (dd, J=10.8, 3.1 Hz, 1H), 7.03-6.99 (m, 1H), 6.74 (dd, J=8.9, 5.0 Hz, 1H), 5.20-5.16 (m, 1H), 5.12-5.09 (m, 1H), 4.75-4.72 (m, 1H), 4.68-4.64 (m, 1H), 4.11-4.10 (m, 1H), 1.37 (s, 9H).

Example 44

(3-(2-tert-butyl-4-fluorophenoxy)azetidin-1-yl)(imidazo[2,1-b]thiazol-6-yl)methanone

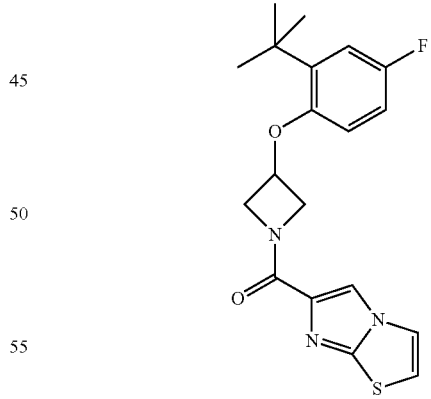

The title compound was prepared by a procedure similar to the one described for (3-(2-tert-butylphenoxy)azetidin-1-yl)(oxazol-4-yl)methanone to provide (3-(2-tert-butyl-4-fluorophenoxy)azetidin-1-yl)(imidazo[2,1-b]thiazol-6-yl)methanone (0.049 g, 27%) as an off-white solid.

$^1$H NMR (500 MHz, DMSO-$d_6$) δ 8.23 (s, 1H), 7.93 (d, J=4.5 Hz, 1H), 7.39 (d, J=4.5 Hz, 1H), 7.04 (dd, J=10.9, 3.1 Hz, 1H), 7.00-6.98 (m, 1H), 6.74 (dd, J=8.9, 5.0 Hz, 1H), 5.14-5.10 (m, 1H), 5.05-5.01 (m, 1H), 4.52-4.49 (m, 1H), 4.47-4.45 (m, 1H), 3.97-3.96 (m, 1H), 1.35 (s, 9H).

Example 45

1-(4-(3-(2-tert-butyl-4-fluorophenoxy)azetidine-1-carbonyl)phenyl)ethanone

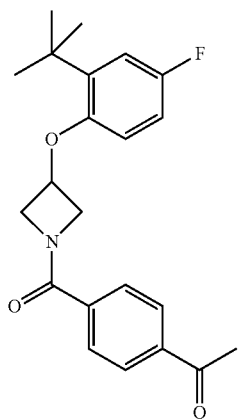 [SMILES: CC(=O)c1ccc(C(=O)N2CC(Oc3ccc(F)cc3C(C)(C)C)C2)cc1]

The title compound was prepared by a procedure similar to the one described for (3-(2-tert-butylphenoxy)azetidin-1-yl)(oxazol-4-yl)methanone to provide 1-(4-(3-(2-tert-butyl-4-fluorophenoxy)azetidine-1-carbonyl)phenyl)ethanone (0.31 g, 83%) as an off-white solid.

$^1$H NMR (500 MHz, DMSO-$d_6$) δ 8.01 (dd, J=6.7, 1.8 Hz, 2H), 7.78 (dd, J=6.7, 1.8 Hz, 2H), 7.03 (dd, J=10.9, 3.1 Hz, 1H), 6.97-6.95 (m, 1H), 6.68 (dd, J=9.0, 5.0 Hz, 1H), 5.13-5.09 (m, 1H), 4.74-4.71 (m, 1H), 4.59-4.56 (m, 1H), 4.33-4.30 (m, 1H), 4.04-4.03 (m, 1H), 2.61 (s, 3H), 1.35 (s, 9H).

Example 46

(3-(2-tert-Butyl-4-fluorophenoxy)azetidin-1-yl) (4-(2-hydroxypropan-2-yl)phenyl)methanone

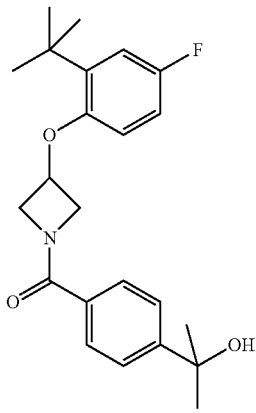 [SMILES: CC(C)(C)c1cc(F)ccc1OC1CN(C(=O)c2ccc(C(C)(C)O)cc2)C1]

To a stirred suspension of 1-(4-(3-(2-tert-butyl-4-fluorophenoxy)azetidin-1-carbonyl)phenyl)ethanone (0.14 g, 0.37 mmol) in diethyl ether (2.0 mL) was added methyl magnesium iodide (0.25 mL, 3.0 M in diethyl ether, 0.75 mmol) dropwise at room temperature. The resulting reaction mixture was heated to reflux for 1.5 h. After this reaction mixture was cooled to 0° C., diluted with diethyl ether, quenched with 1 N hydrochloric acid (2 ml) and the reaction mixture was stirred until the solids disappeared. The organic layer was separated and washed with water (2×2.0 mL), dried (Na$_2$SO$_4$), filtered and the filtrate was directly purified by flash column chromatography (silica gel, 50:50 ethyl acetate/heptane) to provide (3-(2-tert-butyl-4-fluorophenoxy)azetidin-1-yl)(4-(2-hydroxypropan-2-yl)phenyl)methanone (0.081 g, 57%) as a white solid.

$^1$H NMR (500 MHz, DMSO-$d_6$) δ 7.59 (d, J=8.3 Hz, 2H), 7.53 (d, J=8.0 Hz, 2H), 7.03 (dd, J=10.9, 3.0 Hz, 1H), 6.98-6.94 (m, 1H), 6.69 (dd, J=8.9, 5.0 Hz, 1H), 5.11-5.07 (m, 2H), 4.82-4.74 (m, 1H), 4.60-4.53 (m, 1H), 4.31-4.25 (m, 1H), 4.01-3.98 (m, 1H), 1.42 (s, 6H), 1.35 (s, 9H).

Example 47

(3-(2-isopropylphenoxy)azetidin-1-yl)(phenyl)methanone

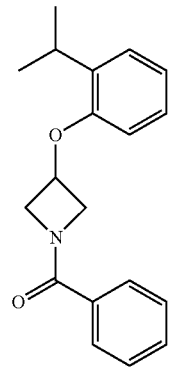 [SMILES: CC(C)c1ccccc1OC1CN(C(=O)c2ccccc2)C1]

The title compound was prepared by a procedure similar to the one described in Reference Example 39 for phenyl(3-(o-tolyloxy)azetidin-1-yl)methanone to provide (3-(2-isopropylphenoxy)azetidin-1-yl)(phenyl)methanone (0.23 g, 52%) as a colorless gum-like substance.

$^1$H NMR (500 MHz, CDCl$_3$) δ 7.67-7.65 (m, 2H), 7.49-7.40 (m, 3H), 7.26-7.24 (m, 1H), 7.12-7.09 (m, 1H), 6.99-6.96 (t, J=7.5 Hz, 1H), 6.46 (d, J=8.1 Hz, 1H), 5.03-4.99 (m, 1H), 4.65-4.61 (m, 2H), 4.35-4.30 (br m, 2H), 3.37-3.32 (m, 1H), 1.23 (d, J=6.9 Hz, 6H).

Example 48

(3-(2-tert-butylphenylamino)azetidin-1-yl)(phenyl)methanone

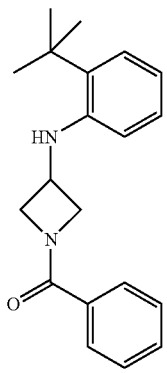 [SMILES: CC(C)(C)c1ccccc1NC1CN(C(=O)c2ccccc2)C1]

Starting from N-(2-tert-butylphenyl)azetidin-3-amine to give the title compound was prepared by a procedure similar to the one described in Example 1 for (3-(2-tert-Butylphenoxy)azetidin-1-yl)(phenyl)methanone to provide (3-(2-tert-butylphenylamino)azetidin-1-yl)(phenyl)methanone (0.22 g, 36%) as a light yellow gum-like substance.

¹H NMR (500 MHz, CDCl₃) δ 7.66-7.64 (m, 2H), 7.48-7.39 (m, 3H), 7.29-7.26 (m, 1H), 7.12-7.08 (m, 1H), 6.79-6.76 (m, 1H), 6.33-6.31 (m, 1H), 4.67-4.64 (m, 2H), 4.39-4.36 (m, 1H), 4.30-4.29 (br m, 1H), 4.06 (br s, 2H), 1.44 (s, 9H).

Example 49

(3-(2-tert-butylphenoxy)pyrrolidin-1-yl)(pyridin-2-yl)methanone

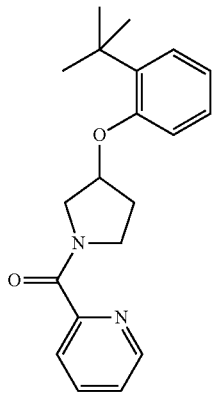 [SMILES: CC(C)(C)c1ccccc1OC1CCN(C(=O)c2ccccn2)C1]

To a stirred solution of 3-(2-tert-butylphenoxy)pyrrolidine hydrochloride (0.26 g, 1.00 mmol) in pyridine (2.5 mL) was added picolinoyl chloride hydrochloride (0.20 g, 1.10 mmol) at room temperature. After 16 h the reaction mixture was concentrated under reduced pressure, the residue partitioned between ethyl acetate (50.0 mL) and water (50.0 mL) and separated. The organic layer was washed with saturated sodium chloride (50.0 mL), dried (MgSO₄), filtered, and concentrated under reduced pressure. Purification by flash column chromatography (silica gel, 80:20 to 50:50 heptane/ethyl acetate) provided (3-(2-tert-butylphenoxy)pyrrolidin-1-yl)(pyridin-2-yl)methanone (0.14 g, 43%) as a pale yellow oil.

¹H NMR (500 MHz, CDCl₃) δ 8.61-8.56 (m, 1H), 7.89-7.85 (m, 1H), 7.81-7.76 (m, 1H), 7.36-7.26 (m, 2H), 7.19-7.12 (m, 1H), 6.92-6.76 (m, 2H), 5.09-5.06 (m, 1H), 4.27-3.90 (m, 4H), 2.39-2.35 (m, 1H), 2.30-2.21 (m, 1H), 1.36-1.32 (m, 9H).

Example 50

(4-(2-tert-butylphenoxy)piperidin-1-yl)(pyridin-2-yl)methanone

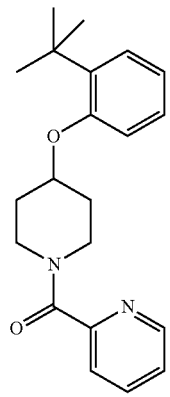 [SMILES: CC(C)(C)c1ccccc1OC1CCN(C(=O)c2ccccn2)CC1]

The title compound was prepared by a procedure similar to the one described for (3-(2-tert-butylphenoxy)pyrrolidin-1-yl) (pyridin-2-yl)methanone to provide (4-(2-tert-butylphenoxy)piperidin-1-yl)(pyridin-2-yl)methanone (0.13 g, 0.38 mmol, 38%) as a pale yellow powder.

¹H NMR (500 MHz, CDCl₃) δ 8.61-8.60 (m, 1H), 7.82-7.79 (m, 1H), 7.66 (d, J=7.5 Hz, 1H), 7.36-7.31 (m, 2H), 7.18-7.14 (m, 1H), 6.90-6.84 (m, 2H), 4.74-4.70 (m, 1H), 3.96-3.94 (m, 2H), 3.84-3.78 (m, 1H), 3.62-3.57 (m, 1H), 2.16-1.93 (m, 4H), 1.41 (s, 9H).

Example 51 methyl [4-(2-tert-butylphenoxy)piperidin-1-yl](oxo)acetate

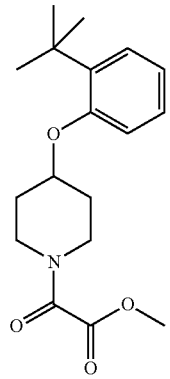 [SMILES: COC(=O)C(=O)N1CCC(Oc2ccccc2C(C)(C)C)CC1]

The title compound was prepared by a procedure similar to the one described for (3-(2-tert-butylphenoxy)azetidin-1-yl) (phenyl)methanone to provide methyl [4-(2-tert-butylphenoxy)piperidin-1-yl](oxo)acetate (0.47 g, 78%) as a white powder.

¹H NMR (300 MHz, CDCl₃) δ 7.34-7.31 (m, 1H), 7.20-7.13 (m, 1H), 6.93-6.86 (m, 1H), 6.84-6.78 (m, 1H), 4.77-

4.68 (m, 1H), 3.92-3.82 (m, 4H), 3.75-3.62 (m, 2H), 3.55-3.35 (m, 1H), 2.07-1.96 (m, 4H), 1.40 (s, 9H).

Example 52

[4-(2-tert-butylphenoxy)piperidin-1-yl](oxo)acetic acid

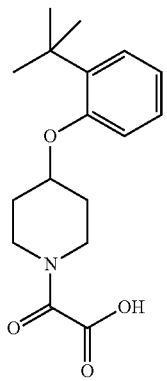

The title compound was prepared by a procedure similar to the one described for 2-(3-(2-tert-butylphenoxy)azetidin-1-yl)-2-oxoacetic acid to provide [4-(2-tert-butylphenoxy)piperidin-1-yl](oxo)acetic acid (0.45 g, 98%) as a white powder.

$^1$H NMR (300 MHz, CDCl$_3$) δ 7.35-7.30 (m, 1H), 7.21-7.13 (m, 1H), 6.94-6.87 (m, 1H), 6.84-6.80 (m, 1H), 4.77-4.71 (m, 1H), 4.56-4.46 (m, 1H), 4.30-4.18 (m, 1H), 4.00-3.90 (m, 1H), 3.83-3.72 (m, 1H), 2.14-2.02 (m, 4H), 1.41 (s, 9H).

Example 53 methyl 3-[4-(2-tert-butylphenoxy)piperidin-1-yl]-3-oxopropanoate

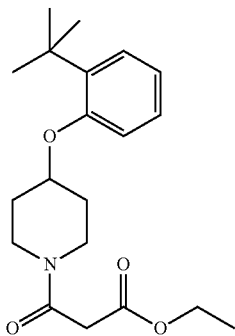 [SMILES: CCOC(=O)CC(=O)N1CCC(Oc2ccccc2C(C)(C)C)CC1]

The title compound was prepared by a procedure similar to the one described for ethyl 3-(3-(2-tert-butylphenoxy)azetidin-1-yl)-3-oxopropanoate to provide ethyl 3-[4-(2-tert-butylphenoxy)piperidin-1-yl]-3-oxopropanoate (0.44 g, 54%) as a colorless oil.

$^1$H NMR (300 MHz, CDCl$_3$) δ 7.34-7.28 (m, 1H), 7.19-7.12 (m, 1H), 6.92-6.85 (m, 1H), 6.85-6.80 (m, 1H), 4.72-

4.62 (m, 1H), 4.22 (q, J=7.2 Hz, 2H), 3.87-3.63 (m, 3H), 3.55-3.40 (m, $^3$H), 2.09-1.87 (m, 4H), 1.40 (s, 9H), 1.26 (t, J=7.2 Hz, 3H).

Example 54

3-[4-(2-tert-butylphenoxy)piperidin-1-yl]-3-oxopropanoic acid

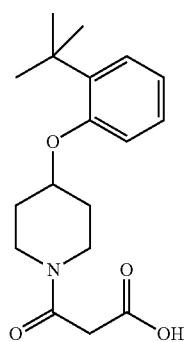 [SMILES: CC(C)(C)c1ccccc1OC1CCN(C(=O)CC(=O)O)CC1]

The title compound was prepared by a procedure similar to the one described for 2-(3-(2-tert-butylphenoxy)azetidin-1-yl)-2-oxoacetic acid to provide 3-[4-(2-tert-butylphenoxy)piperidin-1-yl]-3-oxopropanoic acid (0.35 g, 99%) as a white powder.

$^1$H NMR (300 MHz, CDCl$_3$) δ 14.30-14.10 (br s, 1H), 7.35-7.31 (m, 1H), 7.21-7.13 (m, 1H), 6.94-6.87 (m, 1H), 6.84-6.79 (m, 1H), 4.78-4.71 (m, 1H), 4.05-3.95 (m, 1H), 3.77-3.65 (m, 2H), 3.58-3.48 (m, 1H), 3.40 (s, 2H), 2.07-1.99 (m, 4H), 1.40 (s, 9H).

Example 55 methyl 4-[4-(2-tert-butylphenoxy)piperidin-1-yl]-4-oxobutanoate

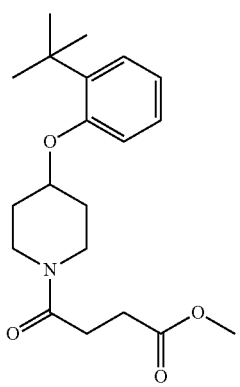

The title compound was prepared by a procedure similar to the one described for (3-(2-tert-butylphenoxy)azetidin-1-yl)(phenyl)methanone to provide methyl 4-[4-(2-tert-butylphenoxy)piperidin-1-yl]-4-oxobutanoate (0.36 g, 58%) as a colorless oil.

$^1$H NMR (300 MHz, CDCl$_3$) δ 7.34-7.29 (m, 1H), 7.19-7.12 (m, 1H), 6.92-6.85 (m, 1H), 6.85-6.80 (m, 1H), 4.71-

4.64 (m, 1H), 3.79-3.68 (m, 6H), 3.57-3.46 (m, 1H), 2.74-2.62 (m, 4H), 2.10-1.84 (m, 4H), 1.40 (s, 9H).

Example 56

4-[4-(2-tert-butylphenoxy)piperidin-1-yl]-4-oxobutanoic acid

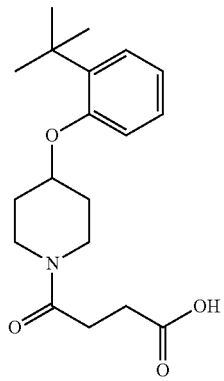 [SMILES: CC(C)(C)c1ccccc1OC1CCN(C(=O)CCC(=O)O)CC1]

The title compound was prepared by a procedure similar to the one described for 2-(3-(2-tert-butylphenoxy)azetidin-1-yl)-2-oxoacetic acid to provide 4-[4-(2-tert-butylphenoxy)piperidin-1-yl]-4-oxobutanoic acid (0.18 g, 61%) as a white powder.

$^1$H NMR (300 MHz, CDCl$_3$) δ 7.34-7.30 (m, 1H), 7.20-7.13 (m, 1H), 6.93-6.86 (m, 1H), 6.85-6.80 (m, 1H), 4.73-4.66 (m, 1H), 3.88-3.68 (m, 3H), 3.59-3.46 (m, 1H), 2.79-2.67 (m, 4H), 2.07-1.89 (m, 4H), 1.40 (s, 9H).

Example 57 methyl 1-{[4-(2-tert-butylphenoxy)piperidin-1-yl]carbonyl}cyclopropanecarboxylate

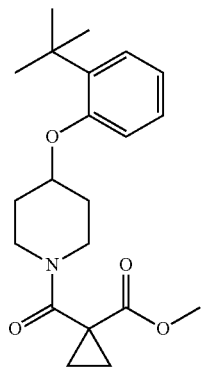 [SMILES: COC(=O)C1(C(=O)N2CCC(Oc3ccccc3C(C)(C)C)CC2)CC1]

The title compound was prepared by a procedure similar to the one described for ethyl 3-(3-(2-tert-butylphenoxy)azetidin-1-yl)-3-oxopropanoate to provide methyl 1-{[4-(2-tert-butylphenoxy)piperidin-1-yl]carbonyl}cyclopropanecarboxylate (0.64 g, 100%) as a colorless oil.

$^1$H NMR (300 MHz, CDCl$_3$) δ 7.34-7.30 (m, 1H), 7.20-7.13 (m, 1H), 6.92-6.86 (m, 1H), 6.85-6.81 (m, 1H), 4.72-

4.64 (m, 1H), 3.87-3.70 (m, 6H), 3.60-3.50 (m, 1H), 2.06-1.86 (m, 4H), 1.56-1.49 (m, 2H), 1.42-1.34 (m, 11H).

Example 58

1-{[4-(2-tert-butylphenoxy)piperidin-1-yl]carbonyl}cyclopropanecarboxylic acid

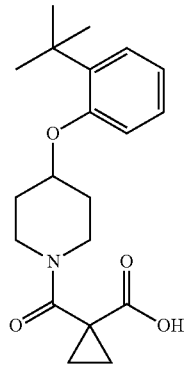 [SMILES: CC(C)(C)c1ccccc1OC1CCN(C(=O)C2(C(=O)O)CC2)CC1]

The title compound was prepared by a procedure similar to the one described for 2-(3-(2-tert-butylphenoxy)azetidin-1-yl)-2-oxoacetic acid to provide 1-{[4-(2-tert-butylphenoxy)piperidin-1-yl]carbonyl}cyclopropanecarboxylic acid (0.35 g, 21%) as a white powder.

$^1$H NMR (300 MHz, CDCl$_3$) δ 7.34-7.29 (m, 1H), 7.19-7.12 (m, 1H), 6.92-6.86 (m, 1H), 6.85-6.80 (m, 1H), 4.72-4.64 (m, 1H), 3.84-3.65 (m, 4H), 2.12-1.85 (m, 4H), 1.62-1.58 (m, 2H), 1.47-1.42 (m, 2H), 1.40 (s, 9H).

Example 59 ethyl (2E)-4-[4-(2-tert-butylphenoxy)piperidin-1-yl]-4-oxobut-2-enoate

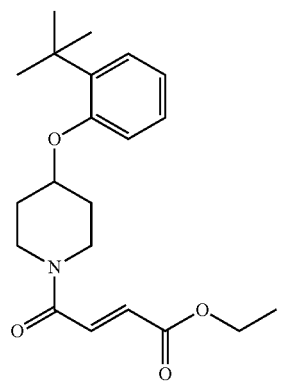 [SMILES: CCOC(=O)/C=C/C(=O)N1CCC(Oc2ccccc2C(C)(C)C)CC1]

The title compound was prepared by a procedure similar to the one described for ethyl 3-(3-(2-tert-butylphenoxy)azetidin-1-yl)-3-oxopropanoate to provide ethyl (2E)-4-[4-(2-tert-butylphenoxy)piperidin-1-yl]-4-oxobut-2-enoate (0.52 g, 96%) as a colorless oil.

$^1$H NMR (300 MHz, CDCl$_3$) δ 7.44 (d, J=15.5 Hz, 1H), 7.36-7.29 (m, 1H), 7.21-7.13 (m, 1H), 6.95-6.86 (m, 1H), 6.85-6.81 (m, 1H), 6.77 (d, J=15.5 Hz, 1H), 4.75-4.67 (m,

1H), 4.26 (q, J=7.2 Hz, 2H), 3.93-3.74 (m, 3H), 3.70-3.56 (m, 1H), 2.08-1.92 (m, 4H), 1.40 (s, 9H), 1.32 (t, J=7.2 Hz, 3H).

Example 60

(2E)-4-[4-(2-tert-butylphenoxy)piperidin-1-yl]-4-oxobut-2-enoic acid

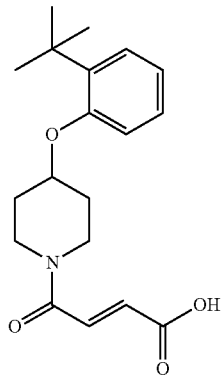 [SMILES: CC(C)(C)c1ccccc1OC1CCN(C(=O)/C=C/C(=O)O)CC1]

The title compound was prepared by a procedure similar to the one described for 2-(3-(2-tert-butylphenoxy)azetidin-1-yl)-2-oxoacetic acid to provide (2E)-4-[4-(2-tert-butylphenoxy)piperidin-1-yl]-4-oxobut-2-enoic acid (0.35 g, 99%) as a white powder.

$^1$H NMR (300 MHz, CDCl$_3$) δ 9.61 (br s, 1H), 7.49 (d, J=15.5 Hz, 1H), 7.36-7.28 (m, 1H), 7.36-7.11 (m, 1H), 6.98-6.86 (m, 1H), 6.79 (d, J=15.5 Hz, 1H), 6.85-6.75 (m, 1H), 4.82-4.63 (m, 1H), 3.98-3.71 (m, 2H), 3.69-3.56 (m, 1H), 3.40 (br m, 1H), 2.49-2.18 (m, 2H), 2.02-1.96 (m, 2H), 1.40 (s, 9H).

Example 61 methyl [4-(2-tert-butyl-4-fluorophenoxy)piperidin-1-yl](oxo)acetate

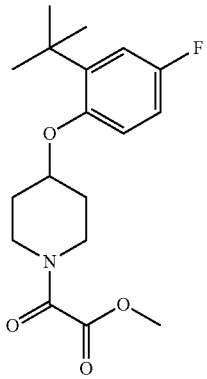 [SMILES: COC(=O)C(=O)N1CCC(Oc2ccc(F)cc2C(C)(C)C)CC1]

The title compound was prepared by a procedure similar to the one described for (3-(2-tert-butylphenoxy)azetidin-1-yl)(phenyl)methanone to provide methyl [4-(2-tert-butyl-4-fluorophenoxy)piperidin-1-yl](oxo)acetate (0.62 g, 99%) as a white powder.

$^1$H NMR (300 MHz, CDCl$_3$) δ 7.06-7.00 (m, 1H), 6.87-6.79 (m, 1H), 6.75-6.68 (m, 1H), 4.69-4.61 (m, 1H), 3.92-3.82 (m, 6H), 3.49-3.39 (m, 1H), 2.12-1.90 (m, 4H), 1.38 (s, 9H).

Example 62

[4-(2-tert-butyl-4-fluorophenoxy)piperidin-1-yl](oxo)acetic acid

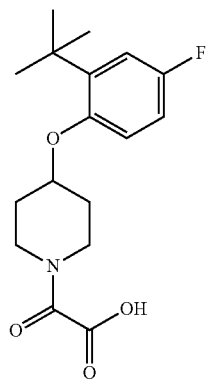 [SMILES: CC(C)(C)c1cc(F)ccc1OC1CCN(C(=O)C(=O)O)CC1]

The title compound was prepared by a procedure similar to the one described for 2-(3-(2-tert-butylphenoxy)azetidin-1-yl)-2-oxoacetic acid to provide [4-(2-tert-butyl-4-fluorophenoxy)piperidin-1-yl](oxo)acetic acid (0.23 g, 80%) as a white powder.

$^1$H NMR (300 MHz, CDCl$_3$) δ 7.10-7.00 (m, 1H), 6.89-6.78 (m, 1H), 6.77-6.67 (m, 1H), 4.70-4.61 (m, 1H), 4.41-4.29 (m, 1H), 4.29-4.16 (m, 1H), 3.95-3.74 (m, 2H), 2.16-1.96 (m, 4H), 1.38 (s, 9H).

Example 63 ethyl 3-[4-(2-tert-butyl-4-fluorophenoxy)piperidin-1-yl]-3-oxopropanoate

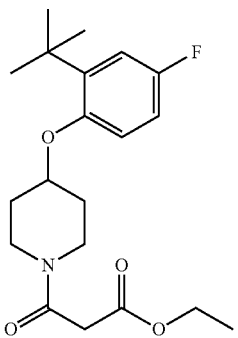 [SMILES: CCOC(=O)CC(=O)N1CCC(Oc2ccc(F)cc2C(C)(C)C)CC1]

The title compound was prepared by a procedure similar to the one described for ethyl 3-(3-(2-tert-butylphenoxy)azetidin-1-yl)-3-oxopropanoate to provide ethyl 3-[4-(2-tert-butyl-4-fluorophenoxy)piperidin-1-yl]-3-oxopropanoate (0.50 g, 74%) as a colorless oil.

$^1$H NMR (300 MHz, CDCl$_3$) δ 7.08-6.98 (m, 1H), 6.87-6.78 (m, 1H), 6.76-6.68 (m, 1H), 4.66-4.55 (m, 1H), 4.22 (q,

J=7.2 Hz, 2H), 3.86-3.61 (m, 3H), 3.54-3.39 (m, 3H), 2.12-1.85 (m, 4H), 1.38 (s, 9H), 1.29 (t, J=7.2 Hz, 3H).

Example 64

3-[4-(2-tert-butyl-4-fluorophenoxy)piperidin-1-yl]-3-oxopropanoic acid

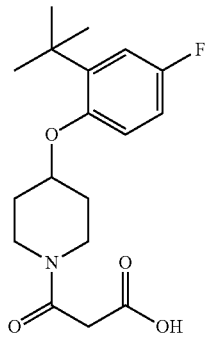 [SMILES: CC(C)(C)c1cc(F)ccc1OC1CCN(C(=O)CC(=O)O)CC1]

The title compound was prepared by a procedure similar to the one described for 2-(3-(2-tert-butylphenoxy)azetidin-1-yl)-2-oxoacetic acid to provide 3-[4-(2-tert-butyl-4-fluorophenoxy)piperidin-1-yl]-3-oxopropanoic acid (0.35 g, 99%) as a white powder.

$^1$H NMR (300 MHz, CDCl$_3$) δ 14.40-13.80 (br s, 1H), 7.07-7.01 (m, 1H), 6.88-6.80 (m, 1H), 6.75-6.69 (m, 1H), 4.71-4.63 (m, 1H), 3.99-3.89 (m, 1H), 3.81-3.65 (m, 2H), 3.58-3.47 (m, 1H), 3.40 (s, 2H), 2.06-1.98 (m, 4H), 1.38 (s, 9H).

Example 65 methyl 4-[4-(2-tert-butylphenoxy)piperidin-1-yl]-4-oxobutanoate

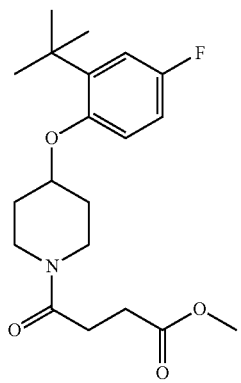 [SMILES: COC(=O)CCC(=O)N1CCC(Oc2ccc(F)cc2C(C)(C)C)CC1]

The title compound was prepared by a procedure similar to the one described for (3-(2-tert-butylphenoxy)azetidin-1-yl)(phenyl)methanone to provide methyl 4-[4-(2-tert-butyl-4-fluorophenoxy)piperidin-1-yl]-4-oxobutanoate (0.61 g, 91%) as a pale yellow oil.

$^1$H NMR (300 MHz, CDCl$_3$) δ 7.06-6.97 (m, 1H), 6.87-6.76 (m, 1H), 6.76-6.68 (m, 1H), 4.64-4.54 (m, 1H), 3.86-3.61 (m, 6H), 3.55-3.43 (m, 1H), 2.75-2.60 (m, 4H), 2.10-1.77 (m, 4H), 1.38 (s, 9H).

Example 66

4-[4-(2-tert-butyl-4-fluorophenoxy)piperidin-1-yl]-4-oxobutanoic acid

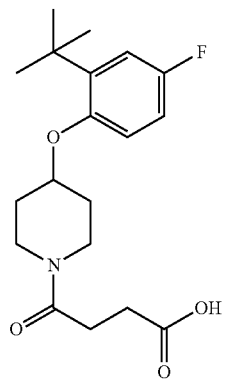 [SMILES: CC(C)(C)c1cc(F)ccc1OC1CCN(C(=O)CCC(=O)O)CC1]

The title compound was prepared by a procedure similar to the one described for 2-(3-(2-tert-butylphenoxy)azetidin-1-yl)-2-oxoacetic acid to provide 4-[4-(2-tert-butyl-4-fluorophenoxy)piperidin-1-yl]-4-oxobutanoic acid (0.30 g, 98%) as a white powder.

$^1$H NMR (300 MHz, CDCl$_3$) δ 7.08-6.98 (m, 1H), 6.88-6.77 (m, 1H), 6.77-6.68 (m, 1H), 4.67-4.51 (m, 1H), 3.81-3.67 (m, 3H), 3.57-3.45 (m, 1H), 2.82-2.62 (m, 4H), 2.11-1.81 (m, 4H), 1.38 (s, 9H).

Example 67 methyl 1-{[4-(2-tert-butyl-4-fluorophenoxy)piperidin-1-yl]carbonyl}cyclopropanecarboxylate

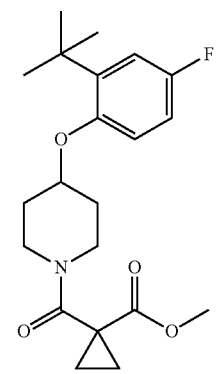 [SMILES: COC(=O)C1(C(=O)N2CCC(Oc3ccc(F)cc3C(C)(C)C)CC2)CC1]

The title compound was prepared by a procedure similar to the one described for ethyl 3-(3-(2-tert-butylphenoxy)azetidin-1-yl)-3-oxopropanoate to provide methyl 1-{[4-(2-tert-butyl-4-fluorophenoxy)piperidin-1-yl]carbonyl}cyclopropanecarboxylate (0.64 g, 100%) as a colorless oil.

$^1$H NMR (300 MHz, CDCl$_3$) δ 7.08-6.95 (m, 1H), 6.84-6.77 (m, 1H), 6.77-6.60 (m, 1H), 4.67-4.52 (m, 1H), 3.91-

3.64 (m, 6H), 3.58-3.45 (m, 1H), 2.11-1.95 (m, 2H), 1.96-1.79 (m, 2H), 1.55-1.47 (m, 2H), 1.40-1.34 (m, 11H).

Example 68

1-{[4-(2-tert-butyl-4-fluorophenoxy)piperidin-1-yl]carbonyl}cyclopropanecarboxylic acid

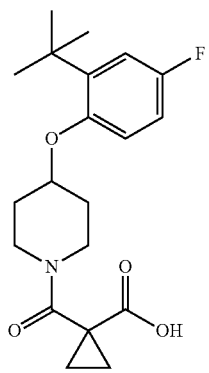 [SMILES: CC(C)(C)c1cc(F)ccc1OC1CCN(C(=O)C2(C(=O)O)CC2)CC1]

The title compound was prepared by a procedure similar to the one described for 2-(3-(2-tert-butylphenoxy)azetidin-1-yl)-2-oxoacetic acid to provide 1-{[4-(2-tert-butyl-4-fluorophenoxy)piperidin-1-yl]carbonyl}cyclopropanecarboxylic acid (0.30 g, 100%) as a white powder.

$^1$H NMR (300 MHz, CDCl$_3$) δ 7.06-6.97 (m, 1H), 6.88-6.77 (m, 1H), 6.77-6.66 (m, 1H), 4.66-4.52 (m, 1H), 3.87-3.72 (m, 2H), 3.72-3.57 (m, 2H), 2.11-1.96 (m, 2H), 1.95-1.84 (m, 2H), 1.64-1.53 (m, 2H), 1.47-1.40 (m, 2H), 1.38 (s, 9H).

Example 69 ethyl (2E)-4-[4-(2-tert-butyl-4-fluorophenoxy)piperidin-1-yl]-4-oxobut-2-enoate

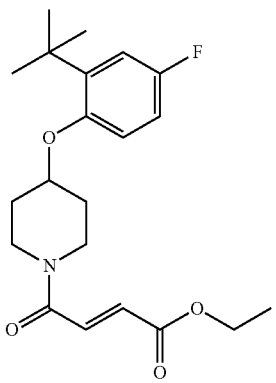 [SMILES: CCOC(=O)/C=C/C(=O)N1CCC(Oc2ccc(F)cc2C(C)(C)C)CC1]

The title compound was prepared by a procedure similar to the one described for ethyl 3-(3-(2-tert-butylphenoxy)azetidin-1-yl)-3-oxopropanoate to provide ethyl (2E)-4-[4-(2-tert-butyl-4-fluorophenoxy)piperidin-1-yl]-4-oxobut-2-enoate (0.62 g, 91%) as a colorless oil.

$^1$H NMR (300 MHz, CDCl$_3$) δ 7.43 (d, J=15.5 Hz, 1H), 7.06-7.00 (m, 1H), 6.87-6.69 (m, 3H), 4.67-4.58 (m, 1H), 4.26 (q, J=7.2 Hz, 2H), 3.92-3.70 (m, 3H), 3.69-3.50 (m, 1H), 2.09-1.86 (m, 4H), 1.38 (s, 9H), 1.32 (t, J=7.2 Hz, 3H).

Example 70

(2E)-4-[4-(2-tert-butyl-4-fluorophenoxy)piperidin-1-yl]-4-oxobut-2-enoic acid

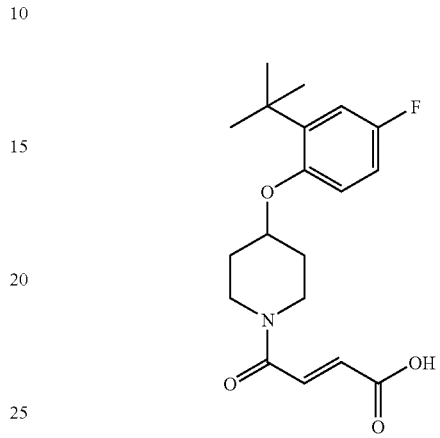

The title compound was prepared by a procedure similar to the one described for 2-(3-(2-tert-butylphenoxy)azetidin-1-yl)-2-oxoacetic acid to provide (2E)-4-[4-(2-tert-butyl-4-fluorophenoxy)piperidin-1-yl]-4-oxobut-2-enoic acid (0.29 g, 99%) as a white powder.

$^1$H NMR (300 MHz, CDCl$_3$) δ 7.50 (d, J=15.5 Hz, 1H), 7.08-6.98 (m, 1H), 6.89-6.67 (m, 3H), 4.71-4.54 (m, 1H), 3.88-3.70 (m, 3H), 3.68-3.54 (m, 1H), 2.10-1.87 (m, 4H), 1.38 (s, 9H).

Example 71

3-(2-tert-butylphenoxy)-1-[(4-chlorophenyl)acetyl]azetidine

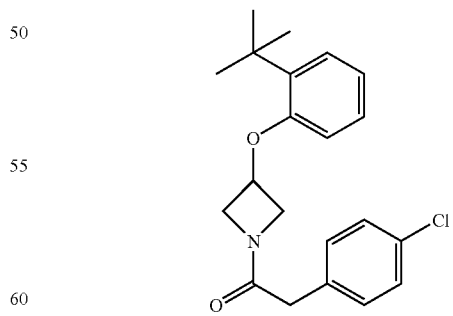

The title compound was prepared by a procedure similar to the one described for ethyl 3-(3-(2-tert-butylphenoxy)azetidin-1-yl)-3-oxopropanoate to provide 3-(2-tert-butylphenoxy)-1-[(4-chlorophenyl)acetyl]azetidine (0.43 g, 61%) as a colorless oil.

¹H NMR (300 MHz, CDCl₃) δ 7.37-7.17 (m, 5H), 7.17-7.10 (m, 1H), 6.99-6.91 (m, 1H), 6.47-6.40 (m, 1H), 5.01-4.92 (m, 1H), 4.53-4.39 (m, 2H), 4.23-4.07 (m, 2H), 3.48 (s, 2H), 1.38 (s, 9H).

Example 72

3-(2-tert-butylphenoxy)-1-(3-phenylpropanoyl)azetidine

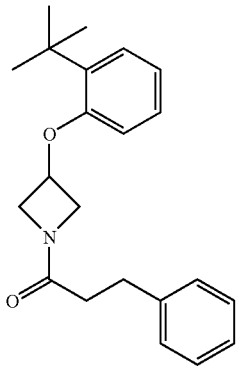 [SMILES: CC(C)(C)c1ccccc1OC1CN(C(=O)CCc2ccccc2)C1]

The title compound was prepared by a procedure similar to the one described for ethyl 3-(3-(2-tert-butylphenoxy)azetidin-1-yl)-3-oxopropanoate to provide 3-(2-tert-butylphenoxy)-1-(3-phenylpropanoyl)azetidine (0.48 g, 72%) as a colorless oil.

¹H NMR (300 MHz, CDCl₃) δ 7.34-7.16 (m, 6H), 7.16-7.09 (m, 1H), 6.97-6.90 (m, 1H), 6.43-6.37 (m, 1H), 4.92-4.82 (m, 1H), 4.44-4.34 (m, 1H), 4.31-4.22 (m, 1H), 4.13-4.04 (m, 1H), 4.03-3.95 (m, 1H), 2.96 (t, J=7.8 Hz, 2H), 2.42 (t, J=7.8 Hz, 2H), 1.37 (s, 9H).

Example 73 ethyl (2E)-3-(4-{[3-(2-tert-butylphenoxy)azetidin-1-yl]carbonyl}phenyl)acrylate

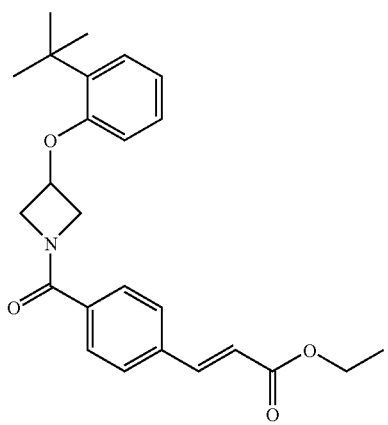 [SMILES: CCOC(=O)/C=C/c1ccc(C(=O)N2CC(Oc3ccccc3C(C)(C)C)C2)cc1]

The title compound was prepared by a procedure similar to the one described for ethyl 3-(3-(2-tert-butylphenoxy)azetidin-1-yl)-3-oxopropanoate to provide ethyl (2E)-3-(4-{[3-(2-tert-butylphenoxy)azetidin-1-yl]carbonyl}phenyl)acrylate (0.51 g, 64%) as a colorless powder.

¹H NMR (300 MHz, CDCl₃) δ 7.72-7.64 (m, 3H), 7.60-7.54 (m, 2H), 7.35-7.30 (m, 1H), 7.17-7.10 (m, 1H), 6.98-6.91 (m, 1H), 6.52-6.43 (m, 2H), 5.10-5.01 (m, 1H), 4.70-4.61 (m, 2H), 4.45-4.23 (m, 4H), 1.41 (s, 9H), 1.34 (t, J=7.2 Hz, 3H).

Example 74

(2E)-3-(4-{[3-(2-tert-butylphenoxy)azetidin-1-yl]carbonyl}phenyl)acrylic acid

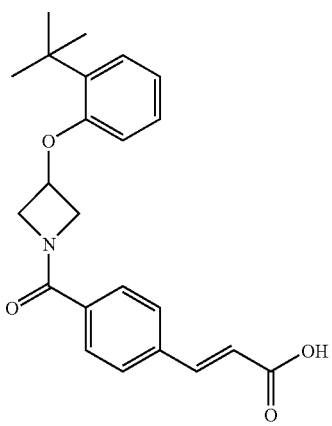 [SMILES: CC(C)(C)c1ccccc1OC1CN(C(=O)c2ccc(/C=C/C(=O)O)cc2)C1]

The title compound was prepared by a procedure similar to the one described for 2-(3-(2-tert-butylphenoxy)azetidin-1-yl)-2-oxoacetic acid to provide (2E)-3-(4-{[3-(2-tert-butylphenoxy)azetidin-1-yl]carbonyl}phenyl)acrylic acid (0.29 g, 100%) as a white powder.

¹H NMR (300 MHz, CDCl₃) δ 7.77 (d, J=16.3 Hz, 1H), 7.73-7.67 (m, 2H), 7.62-7.56 (m, 2H), 7.36-7.30 (m, 1H), 7.17-7.10 (m, 1H), 6.98-6.91 (m, 1H), 6.55-6.43 (m, 2H), 5.11-5.01 (m, 1H), 4.72-4.62 (m, 2H), 4.45-4.28 (m, 2H), 1.41 (s, 9H).

Example 75 ethyl 3-(4-{[3-(2-tert-butylphenoxy)azetidin-1-yl]carbonyl}phenyl)propanoate

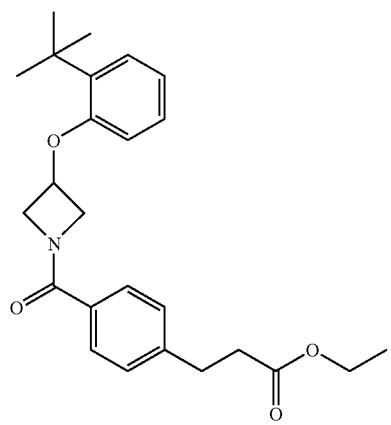 [SMILES: CCOC(=O)CCc1ccc(C(=O)N2CC(Oc3ccccc3C(C)(C)C)C2)cc1]

The title compound was prepared by a procedure similar to the one described for ethyl 3-(3-(2-tert-butylphenoxy)azetidin-1-yl)-3-oxopropanoate to provide ethyl 3-(4-{[3-(2-tert-butylphenoxy)azetidin-1-yl]carbonyl}phenyl)propanoate (0.63 g, 79%) as a colorless oil.

$^1$H NMR (300 MHz, CDCl$_3$) δ 7.62-7.56 (m, 2H), 7.35-7.30 (m, 1H), 7.29-7.23 (m, 2H), 7.17-7.10 (m, 1H), 6.98-6.90 (m, 1H), 6.59-6.43 (m, 1H), 5.08-4.99 (m, 1H), 4.70-4.60 (m, 2H), 4.43-4.26 (m, 2H), 4.12 (q, J=7.2 Hz, 2H), 2.98 (t, J=7.6 Hz, 2H), 2.53 (t, J=7.6 Hz, 2H), 1.40 (s, 9H), 1.24 (t, J=7.2 Hz, 3H).

Example 76

3-(4-{[3-(2-tert-butylphenoxy)azetidin-1-yl]carbonyl}phenyl)propanoic acid

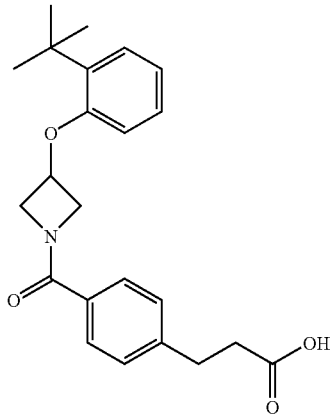 [SMILES: CC(C)(C)c1ccccc1OC1CN(C(=O)c2ccc(CCC(=O)O)cc2)C1]

The title compound was prepared by a procedure similar to the one described for 2-(3-(2-tert-butylphenoxy)azetidin-1-yl)-2-oxoacetic acid to provide 3-(4-{[3-(2-tert-butylphenoxy)azetidin-1-yl]carbonyl}phenyl)propanoic acid (0.43 g, 100%) as a white powder.

$^1$H NMR (300 MHz, CDCl$_3$) δ 7.66-7.55 (m, 2H), 7.35-7.30 (m, 1H), 7.30-7.23 (m, 2H), 7.18-7.10 (m, 1H), 6.98-6.89 (m, 1H), 6.49-6.42 (m, 1H), 5.08-4.98 (m, 1H), 4.71-4.56 (m, 2H), 4.44-4.24 (m, 2H), 3.00 (t, J=7.6 Hz, 2H), 2.69 (t, J=7.6 Hz, 2H), 1.40 (s, 9H).

Example 77 ethyl 3-[3-(2-tert-butyl-4-fluorophenoxy)azetidin-1-yl]-3-oxopropanoate

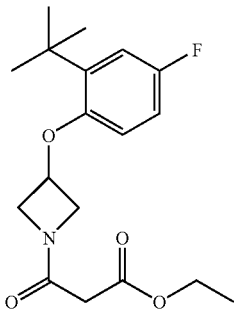 [SMILES: CCOC(=O)CC(=O)N1CC(Oc2ccc(F)cc2C(C)(C)C)C1]

The title compound was prepared by a procedure similar to the one described for ethyl 3-(3-(2-tert-butylphenoxy)azeti-din-1-yl)-3-oxopropanoate to provide ethyl 3-[3-(2-tert-butyl-4-fluorophenoxy)azetidin-1-yl]-3-oxopropanoate (6.77 g, 76%) as a colorless oil.

$^1$H NMR (300 MHz, CDCl$_3$) δ 7.07-7.00 (m, 1H), 6.86-6.76 (m, 1H), 6.41-6.35 (m, 1H), 5.01-4.91 (m, 1H), 4.65-4.56 (m, 1H), 4.53-4.42 (m, 1H), 4.30-4.10 (m, 4H), 3.25 (s, 2H), 1.37 (s, 9H), 1.29 (t, J=7.2 Hz, 3H).

Example 78

3-[3-(2-tert-butyl-4-fluorophenoxy)azetidin-1-yl]-3-oxopropanoic acid

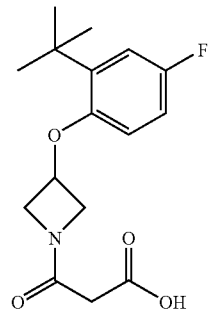 [SMILES: CC(C)(C)c1cc(F)ccc1OC1CN(C(=O)CC(=O)O)C1]

The title compound was prepared by a procedure similar to the one described for 2-(3-(2-tert-butylphenoxy)azetidin-1-yl)-2-oxoacetic acid to provide 3-[3-(2-tert-butyl-4-fluorophenoxy)azetidin-1-yl]-3-oxopropanoic acid (0.28 g, 50%) as a white powder.

$^1$H NMR (300 MHz, CDCl$_3$) δ 7.09-7.02 (m, 1H), 6.87-6.79 (m, 1H), 6.40-6.34 (m, 1H), 5.07-4.98 (m, 1H), 4.63-4.49 (m, 2H), 4.32-4.17 (m, 2H), 3.21 (s, 2H), 1.38 (s, 9H).

Example 79 methyl 4-[3-(2-tert-butyl-4-fluorophenoxy)azetidin-1-yl]-4-oxobutanoate

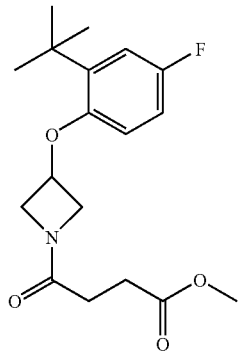 [SMILES: COC(=O)CCC(=O)N1CC(Oc2ccc(F)cc2C(C)(C)C)C1]

The title compound was prepared by a procedure similar to the one described for (3-(2-tert-butylphenoxy)azetidin-1-yl)(phenyl)methanone to provide methyl 4-[3-(2-tert-butyl-4-fluorophenoxy)azetidin-1-yl]-4-oxobutanoate (0.37 g, 44%) as a colorless powder.

$^1$H NMR (300 MHz, CDCl$_3$) δ 7.07-7.00 (m, 1H), 6.86-6.77 (m, 1H), 6.42-6.36 (m, 1H), 4.99-4.91 (m, 1H), 4.63-

4.55 (m, 1H), 4.46-4.38 (m, 1H), 4.28-4.21 (m, 1H), 4.16-4.06 (m, 1H), 3.69 (s, 3H), 2.80-2.57 (m, 2H), 2.52-2.32 (m, 2H), 1.38 (s, 9H).

Example 80

4-[3-(2-tert-butyl-4-fluorophenoxy)azetidin-1-yl]-4-oxobutanoic acid

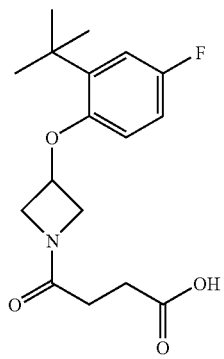 [SMILES: CC(C)(C)c1cc(F)ccc1OC1CN(C(=O)CCC(=O)O)C1]

To a stirred solution of methyl 4-[3-(2-tert-butyl-4-fluorophenoxy)azetidin-1-yl]-4-oxobutanoate (214 mg, 0.63 mmol) obtained in Example 79 in methanol (6.0 mL) was added lithium hydroxide (1.0M aqueous solution, 1.9 mL, 1.9 mmol) at 0° C. The reaction mixture was warmed to room temperature, and stirred for 1 h. After cooling to 0° C., the mixture was adjusted to about pH 1 with 1.0N hydrochloric acid. The obtained solution was extracted with ethyl acetate. The organic layer was washed with saturated sodium chloride, dried (Na$_2$SO$_4$), filtered, and concentrated under reduced pressure to give 4-[3-(2-tert-butyl-4-fluorophenoxy)azetidin-1-yl]-4-oxobutanoic acid (0.19 g, 92%) as a white powder.

$^1$H NMR (300 MHz, CDCl$_3$) δ 7.07-7.01 (m, 1H), 6.86-6.78 (m, 1H), 6.42-6.34 (m, 1H), 5.02-4.92 (m, 1H), 4.62-4.54 (m, 1H), 4.50-4.42 (m, 1H), 4.30-4.22 (m, 1H), 4.16-4.10 (m, 1H), 2.76-2.67 (m, 2H), 2.54-2.44 (m, 2H), 1.38 (s, 9H).

Example 81 ethyl 1-{[3-(2-tert-butyl-4-fluorophenoxy)azetidin-1-yl]carbonyl}cyclopropanecarboxylate

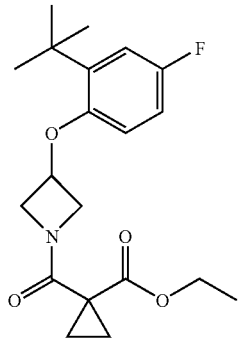 [SMILES: CCOC(=O)C1(C(=O)N2CC(Oc3ccc(F)cc3C(C)(C)C)C2)CC1]

The title compound was prepared by a procedure similar to the one described for ethyl 3-(3-(2-tert-butylphenoxy)azetidin-1-yl)-3-oxopropanoate to provide ethyl 1-{[3-(2-tert-butyl-4-fluorophenoxy)azetidin-1-yl]carbonyl}cyclopropanecarboxylate (0.37 g, 38%) as a colorless powder.

$^1$H NMR (300 MHz, CDCl$_3$) δ 7.07-7.00 (m, 1H), 6.87-6.77 (m, 1H), 6.42-6.35 (m, 1H), 5.01-4.92 (m, 1H), 4.57-4.41 (m, 2H), 4.24-4.10 (m, 4H), 1.45-1.22 (m, 16H).

Example 82

1-{[3-(2-tert-butyl-4-fluorophenoxy)azetidin-1-yl]carbonyl}cyclopropanecarboxylic acid

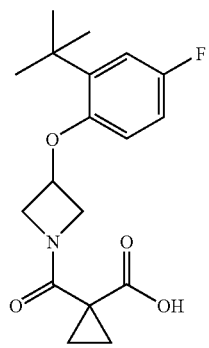 [SMILES: CC(C)(C)c1cc(F)ccc1OC1CN(C(=O)C2(C(=O)O)CC2)C1]

The title compound was prepared by a procedure similar to the one described for 2-(3-(2-tert-butylphenoxy)azetidin-1-yl)-2-oxoacetic acid to provide 1-{[3-(2-tert-butyl-4-fluorophenoxy)azetidin-1-yl]carbonyl}cyclopropanecarboxylic acid (0.26 g, 99%) as a white powder.

$^1$H NMR (300 MHz, CDCl$_3$) δ 7.08-7.01 (m, 1H), 6.86-6.78 (m, 1H), 6.39-6.33 (m, 1H), 4.99-4.91 (m, 1H), 4.61-4.50 (m, 2H), 4.27-4.19 (m, 2H), 1.73-1.67 (m, 2H), 1.54-1.48 (m, 2H), 1.37 (s, 9H).

Example 83 ethyl (2E)-4-[3-(2-tert-butyl-4-fluorophenoxy)azetidin-1-yl]-4-oxobut-2-enoate

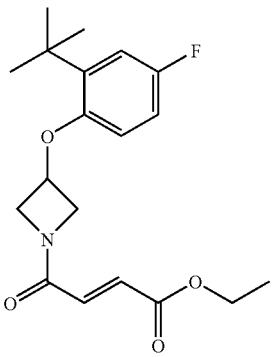 [SMILES: CCOC(=O)/C=C/C(=O)N1CC(Oc2ccc(F)cc2C(C)(C)C)C1]

The title compound was prepared by a procedure similar to the one described for ethyl 3-(3-(2-tert-butylphenoxy)azetidin-1-yl)-3-oxopropanoate to provide ethyl (2E)-4-[3-(2-tert-butyl-4-fluorophenoxy)azetidin-1-yl]-4-oxobut-2-enoate (0.53 g, 74%) as a white powder.

$^1$H NMR (300 MHz, CDCl$_3$) δ 7.07-7.02 (m, 1H), 6.99 (d, J=15.5 Hz, 1H), 6.88-6.79 (m, 1H), 6.42-6.36 (m, 1H), 5.04-4.96 (m, 1H), 4.72-4.55 (m, 1H), 4.56-4.48 (m, 1H), 4.39-4.33 (m, 4H), 4.25 (q, J=7.2 Hz, 2H), 1.37 (s, 9H), 1.32 (t, J=7.2 Hz, 3H).

Example 84

2-[3-(2-tert-butyl-4-fluorophenoxy)azetidin-1-yl]-N-ethyl-2-oxoacetamide

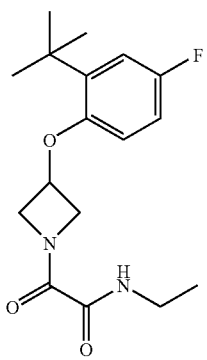 [SMILES: CCNC(=O)C(=O)N1CC(Oc2ccc(F)cc2C(C)(C)C)C1]

To a stirred solution of [3-(2-tert-butyl-4-fluorophenoxy)azetidin-1-yl](oxo)acetic acid (0.27 g, 0.93 mmol) and ethylamine hydrochloride (89 mg, 1.1 mmol) in acetonitrile (20.0 mL) were added EDCI (0.21 g, 1.1 mmol) and HOBt (0.17 g, 1.1 mmol) at room temperature. After 16 h the reaction mixture was concentrated under reduced pressure, the resulting residue was partitioned between ethyl acetate and water and separated. The organic layer was washed with 10% sodium bicarbonate, saturated sodium chloride, dried (MgSO$_4$), filtered and concentrated under reduced pressure. The residue was purified by flash column chromatography (silica gel, 66:34 to 34:66 hexane/ethyl acetate) to provide 2-[3-(2-tert-butyl-4-fluorophenoxy)azetidin-1-yl]-N-ethyl-2-oxoacetamide (0.14 g, 48%) as a white powder.

$^1$H NMR (300 MHz, CDCl$_3$) δ 7.50-7.32 (br s, 1H), 7.07-6.98 (m, 1H), 6.87-6.76 (m, 1H), 6.41-6.32 (m, 1H), 5.12-4.90 (m, 2H), 4.76-4.60 (m, 1H), 4.56-4.43 (m, 1H), 4.24-4.10 (m, 1H), 3.37-3.25 (m, 2H), 1.37 (s, 9H), 1.19 (t, J=7.3 Hz, 3H).

Example 85

2-[3-(2-tert-butyl-4-fluorophenoxy)azetidin-1-yl]-N-cyclohexyl-2-oxoacetamide

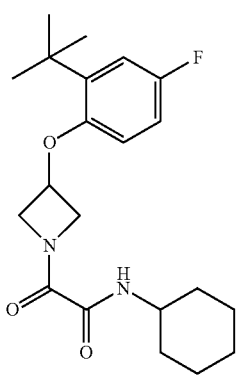 [SMILES: CC(C)(C)c1cc(F)ccc1OC1CN(C(=O)C(=O)NC2CCCCC2)C1]

The title compound was prepared by a procedure similar to the one described for 2-[3-(2-tert-butyl-4-fluorophenoxy)azetidin-1-yl]-N-ethyl-2-oxoacetamide to provide 2-[3-(2-tert-butyl-4-fluorophenoxy)azetidin-1-yl]-N-cyclohexyl-2-oxoacetamide (0.29 g, 91%) as a white powder.

$^1$H NMR (300 MHz, CDCl$_3$) δ 7.45-7.25 (m, 1H), 7.06-7.00 (m, 1H), 6.85-6.77 (m, 1H), 6.40-6.33 (m, 1H), 5.11-5.03 (m, 1H), 5.00-4.91 (m, 1H), 4.76-4.68 (m, 1H), 4.55-4.47 (m, 1H), 4.22-4.15 (m, 1H), 3.77-3.62 (m, 1H), 1.95-1.84 (m, 2H), 1.80-1.68 (m, 2H), 1.68-1.14 (m, 15H).

Example 86

2-[3-(2-tert-butyl-4-fluorophenoxy)azetidin-1-yl]-2-oxo-N-phenylacetamide

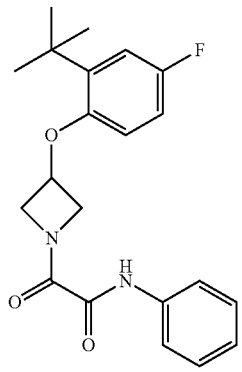 [SMILES: CC(C)(C)c1cc(F)ccc1OC1CN(C(=O)C(=O)Nc2ccccc2)C1]

The title compound was prepared by a procedure similar to the one described for 2-[3-(2-tert-butyl-4-fluorophenoxy)azetidin-1-yl]-N-ethyl-2-oxoacetamide to provide 2-[3-(2-tert-butyl-4-fluorophenoxy)azetidin-1-yl]-2-oxo-N-phenylacetamide (0.19 g, 61%) as a white powder.

$^1$H NMR (300 MHz, CDCl$_3$) δ 9.30-9.15 (br s, 1H), 7.65-7.56 (m, 2H), 7.42-7.32 (m, 2H), 7.22-7.13 (m, 1H), 7.09-7.02 (m, 1H), 6.87-6.77 (m, 1H), 6.42-6.36 (m, 1H), 5.20-5.11 (m, 1H), 5.05-4.96 (m, 1H), 4.85-4.76 (m, 1H), 4.64-4.55 (m, 1H), 4.31-4.22 (m, 1H), 1.38 (m, 9H).

Example 87

N-benzyl-2-[3-(2-tert-butyl-4-fluorophenoxy)azetidin-1-yl]-2-oxoacetamide

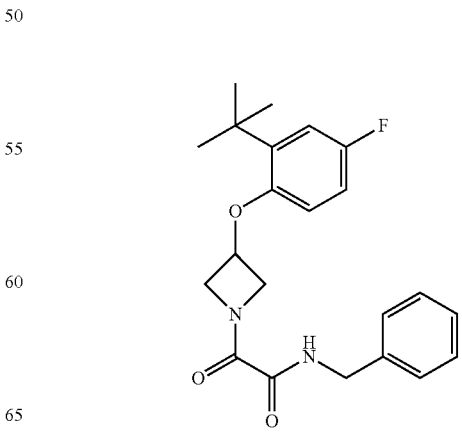

The title compound was prepared by a procedure similar to the one described for 2-[3-(2-tert-butyl-4-fluorophenoxy)azetidin-1-yl]-N-ethyl-2-oxoacetamide to provide N-benzyl-2-[3-(2-tert-butyl-4-fluorophenoxy)azetidin-1-yl]-2-oxoacetamide (0.19 g, 50%) as a white powder.

$^1$H NMR (300 MHz, CDCl$_3$) δ 7.80-7.68 (br s, 1H), 7.39-7.25 (m, 5H), 7.07-7.00 (m, 1H), 6.86-6.77 (m, 1H), 6.40-6.34 (m, 1H), 5.14-5.05 (m, 1H), 5.01-4.92 (m, 1H), 4.79-4.70 (m, 1H), 4.57-4.47 (m, 1H), 4.45 (d, J=6.2 Hz, 2H), 4.24-4.16 (m, 1H), 1.38 (m, 9H).

Example 88

4-{4-[(2-tert-butylphenoxy)methyl]piperidin-1-yl}-2,2-dimethyl-4-oxobutanoic acid

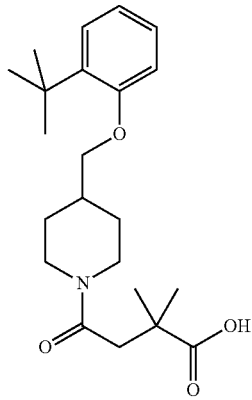 [SMILES: CC(C)(CC(=O)N1CCC(COc2ccccc2C(C)(C)C)CC1)C(=O)O]

To an ice-cold stirred solution of 4-[(2-tert-butylphenoxy)methyl]piperidine hydrochloride (0.20 g, 0.71 mmol) and triethylamine (0.10 g, 1.0 mmol) in THF (20.0 mL) was added 3,3-dimethyldihydrofuran-2,5-dione (0.11 g, 0.87 mmol) and the resulting mixture was warmed to room temperature. After 16 h the reaction mixture was concentrated under reduced pressure. The residue was partitioned between ethyl acetate and 1N hydrochloric acid and separated. The organic layer was washed with saturated sodium chloride, dried (MgSO$_4$), filtered and concentrated under reduced pressure to give a white solid. The solid was recrystallized from hexane/ethyl acetate to provide 4-{4-[(2-tert-butylphenoxy)methyl]piperidin-1-yl}-2,2-dimethyl-4-oxobutanoic acid (0.19 g, 72%) as a white powder.

$^1$H NMR (300 MHz, CDCl$_3$) δ 7.33-7.25 (m, 1H), 7.21-7.14 (m, 1H), 6.95-6.87 (m, 1H), 6.86-6.81 (m, 1H), 4.79-4.70 (m, 3H), 4.05-3.95 (m, 1H), 3.93-3.80 (m, 2H), 3.23-3.10 (m, 1H), 2.77-2.60 (m, 3H), 2.25-1.75 (m, 3H), 1.38 (s, 9H), 1.33 (s, 6H).

Example 89 methyl {4-[(2-tert-butyl-4-fluorophenoxy)methyl]piperidin-1-yl}(oxo)acetate

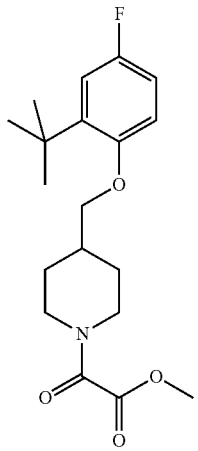 [SMILES: COC(=O)C(=O)N1CCC(COc2ccc(F)cc2C(C)(C)C)CC1]

The title compound was prepared by a procedure similar to the one described for (3-(2-tert-butylphenoxy)azetidin-1-yl)(phenyl)methanone to provide methyl {4-[(2-tert-butyl-4-fluorophenoxy)methyl]piperidin-1-yl}(oxo)acetate (0.43 g, 74%) as a white powder.

$^1$H NMR (300 MHz, CDCl$_3$) δ 7.04-6.97 (m, 1H), 6.87-6.78 (m, 1H), 6.77-6.71 (m, 1H), 4.65-4.55 (m, 1H), 3.88 (s, 3H), 3.86-3.70 (m, 3H), 3.25-3.12 (m, 1H), 2.84-2.72 (m, 1H), 2.25-2.07 (m, 1H), 2.06-1.94 (m, 2H), 1.54-1.32 (m, 11H).

Example 90

{4-[(2-tert-butyl-4-fluorophenoxy)methyl]piperidin-1-yl}(oxo)acetic acid

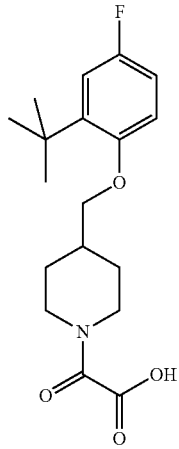 [SMILES: CC(C)(C)c1cc(F)ccc1OCC1CCN(C(=O)C(=O)O)CC1]

The title compound was prepared by a procedure similar to the one described for 2-(3-(2-tert-butylphenoxy)azetidin-1-yl)-2-oxoacetic acid to provide {4-[(2-tert-butyl-4-fluorophenoxy)methyl]piperidin-1-yl}(oxo)acetic acid (0.21 g, 95%) as a white powder.

¹H NMR (300 MHz, CDCl₃) δ 7.04-6.97 (m, 1H), 6.87-6.79 (m, 1H), 6.77-6.71 (m, 1H), 5.14-5.05 (m, 1H), 4.69-4.58 (m, 1H), 3.82 (d, J=6.4 Hz, 2H), 3.30-3.17 (m, 1H), 2.98-2.82 (m, 1H), 2.27-2.12 (m, 1H), 2.10-2.00 (m, 2H), 1.57-1.40 (m, 2H), 1.36 (s, 9H).

Example 91 methyl 4-{4-[(2-tert-butyl-4-fluorophenoxy)methyl]piperidin-1-yl}-4-oxobutanoate

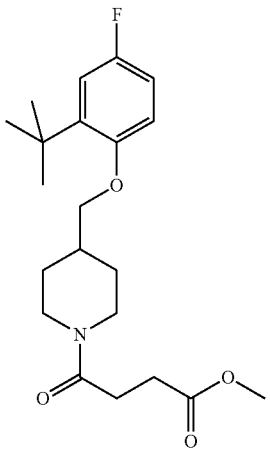 [SMILES: COC(=O)CCC(=O)N1CCC(COc2ccc(F)cc2C(C)(C)C)CC1]

The title compound was prepared by a procedure similar to the one described for (3-(2-tert-butylphenoxy)azetidin-1-yl)(phenyl)methanone to provide methyl 4-{4-[(2-tert-butyl-4-fluorophenoxy)methyl]piperidin-1-yl}-4-oxobutanoate (0.43 g, 69%) as a pale yellow oil.

¹H NMR (300 MHz, CDCl₃) δ 7.03-6.97 (m, 1H), 6.86-6.77 (m, 1H), 6.77-6.71 (m, 1H), 4.75-4.62 (m, 1H), 4.03-3.92 (m, 1H), 3.87-3.74 (m, 2H), 3.70 (s, 3H), 3.17-3.04 (m, 1H), 2.71-2.57 (m, 5H), 2.20-2.04 (m, 1H), 2.04-1.85 (m, 2H), 1.45-1.25 (m, 11H).

Example 92

2-{2-[(1-benzoylazetidin-3-yl)oxy]phenyl}propan-2-ol

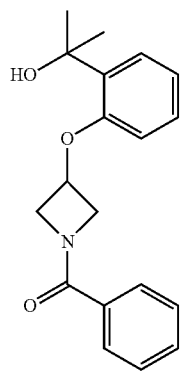 [SMILES: CC(C)(O)c1ccccc1OC1CN(C(=O)c2ccccc2)C1]

The title compound was prepared by a procedure similar to the one described for (3-(2-tert-butylphenoxy)azetidin-1-yl)(phenyl)methanone to provide 2-{2-[(1-benzoylazetidin-3-yl)oxy]phenyl}propan-2-ol (77 mg, 15%) as a colorless amorphous.

¹H NMR (300 MHz, CDCl₃) δ 7.68-7.62 (m, 2H), 7.52-7.38 (m, 4H), 7.24-7.16 (m, 1H), 7.05-6.97 (m, 1H), 6.54-6.49 (m, 1H), 5.16-5.06 (m, 1H), 4.74-4.63 (m, 2H), 4.45-4.25 (br m, 2H), 3.48 (s, 1H), 1.65 (s, 6H).

Example 93 methyl {4-[(2-tert-butylphenoxy)methyl]piperidin-1-yl}(oxo)acetate

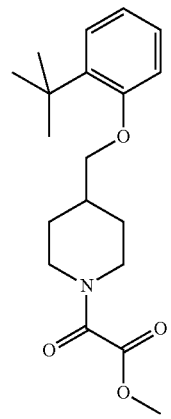

The title compound was prepared by a procedure similar to the one described for (3-(2-tert-butylphenoxy)azetidin-1-yl)(pyridin-2-yl)methanone to provide methyl {4-[(2-tert-butylphenoxy)methyl]piperidin-1-yl}(oxo)acetate (840 mg, 72%) as a colorless solid.

¹H NMR (300 MHz, CDCl₃) δ 7.29-7.26 (m, 1H), 7.18-7.12 (m, 1H), 6.91-6.81 (m, 2H), 4.60-4.55 (m, 1H), 3.86-3.84 (m, 5H), 3.75-3.70 (m, 1H), 3.21-3.12 (m, 1H), 2.81-2.72 (m, 1H), 2.19-2.16 (m, 1H), 2.02-1.95 (m, 2H), 1.48-1.42 (m, 2H), 1.38 (s, 9H).

Example 94 methyl 4-{4-[(2-tert-Butylphenoxy)methyl]piperidin-1-yl}-4-oxobutanoate

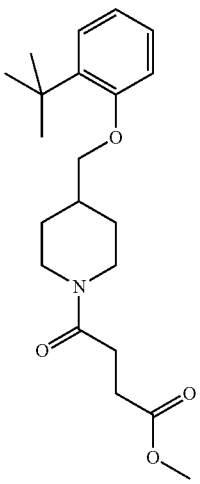 [SMILES: COC(=O)CCC(=O)N1CCC(COc2ccccc2C(C)(C)C)CC1]

The title compound was prepared by a procedure similar to the one described for (3-(2-tert-butylphenoxy)azetidin-1-yl)(pyridin-2-yl)methanone to provide methyl 4-{4-[(2-tert-butylphenoxy)methyl]piperidin-1-yl}-4-oxobutanoate (732 mg, 58%) as a colorless oil.

$^1$H NMR (300 MHz, CDCl$_3$) δ 7.30-7.25 (m, 1H), 7.18-7.13 (m, 1H), 6.91-6.82 (m, 2H), 4.70-4.66 (m, 1H), 4.00-3.94 (m, 1H), 3.86-3.82 (m, 2H), 3.69 (s, 3H), 3.15-3.04 (m, 1H), 2.69-2.65 (m, 4H), 2.64-2.60 (m, 1H), 2.15-2.09 (m, 1H), 1.99-1.88 (m, 2H), 1.38 (s, 9H), 1.35-1.25 (m, 2H).

Example 95

4-{4-[(2-tert-butylphenoxy)methyl]piperidin-1-yl}-4-oxobutanoic acid

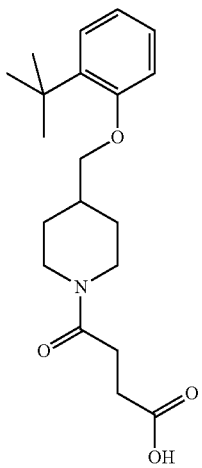 [SMILES: CC(C)(C)c1ccccc1OCC1CCN(C(=O)CCC(=O)O)CC1]

The title compound was prepared by a procedure similar to the one described for 2-(3-(2-tert-butylphenoxy)azetidin-1-yl)-2-oxoacetic acid to provide 4-{4-[(2-tert-butylphenoxy)methyl]piperidin-1-yl}-4-oxobutanoic acid (450 mg, 67%) as a colorless solid.

$^1$H NMR (300 MHz, CDCl$_3$) δ 13.42 (br s, 1H), 7.30-7.25 (m, 1H), 7.18-7.13 (m, 1H), 6.92-6.82 (m, 2H), 4.71-4.67 (m, 1H), 3.97-3.90 (m, 1H), 3.87-3.80 (m, 2H), 3.17-3.08 (m, 1H), 2.71-2.65 (m, 5H), 2.16-2.14 (m, 1H), 2.01-1.91 (m, 2H), 1.43-1.26 (m, 2H), 1.38 (s, 9H).

Example 96

{4-[(2-tert-butylphenoxy)methyl]piperidin-1-yl}(oxo)acetic acid

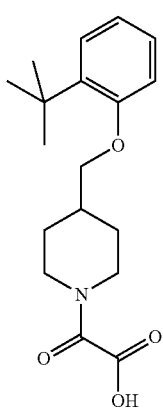 [SMILES: CC(C)(C)c1ccccc1OCC1CCN(C(=O)C(=O)O)CC1]

The title compound was prepared by a procedure similar to the one described for 2-(3-(2-tert-butylphenoxy)azetidin-1-yl)-2-oxoacetic acid to provide {4-[(2-tert-butylphenoxy)methyl]piperidin-1-yl}(oxo)acetic acid (690 mg, 96%) as a colorless solid.

$^1$H NMR (300 MHz, CDCl$_3$) δ 13.24 (br s, 1H), 7.30-7.25 (m, 1H), 7.19-7.13 (m, 1H), 6.92-6.82 (m, 2H), 4.82-4.60 (m, 2H), 3.86 (d, J=6.3 Hz, 2H), 3.29-3.19 (m, 1H), 2.92-2.83 (m, 1H), 2.22-2.18 (m, 1H), 2.08-2.04 (m, 2H), 1.58-1.43 (m, 2H), 1.38 (s, 9H).

Example 97

3-[3-(2-tert-butylphenoxy)azetidin-1-yl]-3-oxopropanenitrile

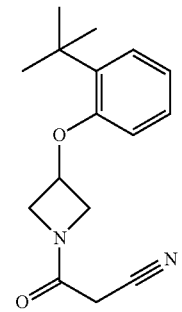 [SMILES: CC(C)(C)c1ccccc1OC1CN(C(=O)CC#N)C1]

The title compound was prepared by a procedure similar to the one described for ethyl 3-(3-(2-tert-butylphenoxy)azetidin-1-yl)-3-oxopropanoate to provide 3-[3-(2-tert-butylphenoxy)azetidin-1-yl]-3-oxopropanenitrile (900% mg, 55%) as a colorless solid.

$^1$H NMR (300 MHz, CDCl$_3$) δ 7.34-7.31 (m, 1H), 7.17-7.12 (m, 1H), 6.98-6.93 (m, 1H), 6.46-6.43 (m, 1H), 5.06-5.00 (m, 1H), 4.73-4.68 (m, 1H), 4.53-4.47 (m, 1H), 4.38-4.33 (m, 1H), 4.21-4.16 (m, 1H), 3.33 (s, 2H), 1.39 (s, 9H).

Example 98

4-[3-(2-tert-butylphenoxy)azetidin-1-yl]-N-(methylsulfonyl)-4-oxobutanamide

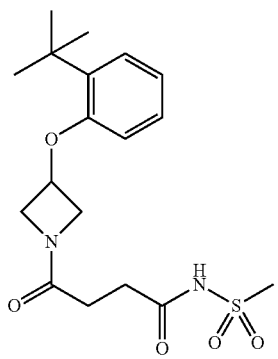 [SMILES: CC(C)(C)c1ccccc1OC1CN(C(=O)CCC(=O)NS(C)(=O)=O)C1]

To a stirred solution of 4-[3-(2-tert-butylphenoxy)azetidin-1-yl]-4-oxobutanoic acid (610 mg, 2.00 mmol), methanesulfonamide (200 mg, 2.10 mmol) and triethylamine (0.84 ml, 6.00 mmol) in acetonitrile (5.0 mL) was added 2-methyl-6-nitrobenzoic anhydride (883 mg, 2.56 mmol) and N,N-dimethylpyridin-4-amine (244 mg, 2.00 mmol) at room temperature. After 16 h, the reaction mixture was partitioned between ethyl acetate and water and separated. The organic layer was washed with saturated sodium chloride, dried (Na$_2$SO$_4$), filtered and concentrated under reduced pressure. The residue was purified by flash column chromatography (silica gel, 10:90 hexane/ethyl acetate) to provide 4-[3-(2-tert-butylphenoxy)azetidin-1-yl]-N-(methylsulfonyl)-4-oxobutanamide (628 mg, 82%) as a colorless solid.

$^1$H NMR (300 MHz, CDCl$_3$) δ 10.63 (br s, 1H), 7.33-7.30 (m, 1H), 7.17-7.11 (m, 1H), 6.97-6.92 (m, 1H), 6.46-6.44 (m, 1H), 5.04-4.97 (m, 1H), 4.63-4.57 (m, 1H), 4.52-4.46 (m, 1H), 4.29-4.25 (m, 1H), 4.15-4.10 (m, 1H), 3.25 (s, 3H), 2.84-2.72 (m, 2H), 2.63-2.47 (m, 2H), 1.39 (s, 9H).

Example 99

4-[3-(2-tert-butylphenoxy)azetidin-1-yl]-4-oxo-N-(pentylsulfonyl)butanamide

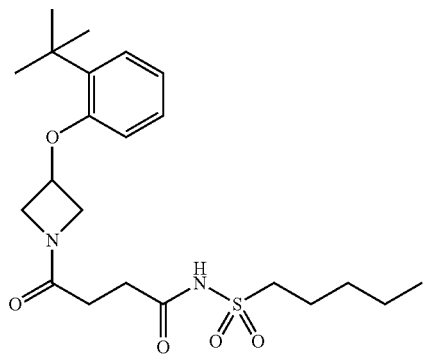 [SMILES: CCCCCS(=O)(=O)NC(=O)CCC(=O)N1CC(Oc2ccccc2C(C)(C)C)C1]

The title compound was prepared by a procedure similar to the one described for 4-[3-(2-tert-butylphenoxy)azetidin-1-yl]-N-(methylsulfonyl)-4-oxobutanamide to provide 4-[3-(2-tert-butylphenoxy)azetidin-1-yl]-4-oxo-N-(pentylsulfonyl)butanamide (493 mg, 69%) as a colorless solid.

$^1$H NMR (300 MHz, CDCl$_3$) δ 10.13 (br s, 1H), 7.32-7.30 (m, 1H), 7.16-7.11 (m, 1H), 6.96-6.91 (m, 1H), 6.46-6.43 (m, 1H), 5.01-4.98 (m, 1H), 4.66-4.64 (m, 1H), 4.49-4.47 (m, 1H), 4.31-4.29 (m, 1H), 4.14-4.12 (m, 1H), 3.39-3.34 (m, 2H), 2.82-2.52 (m, 4H), 1.80-1.77 (m, 2H), 1.39 (s, 9H), 1.35-1.26 (m, 4H), 0.88 (t, J=6.9 Hz, 3H).

Example 100

4-{[3-(2-tert-butylphenoxy)azetidin-1-yl]carbonyl}benzaldehyde

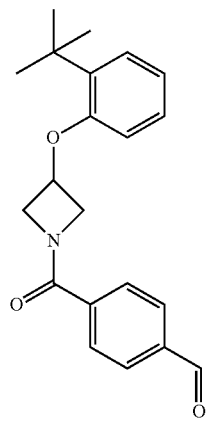 [SMILES: CC(C)(C)c1ccccc1OC1CN(C(=O)c2ccc(C=O)cc2)C1]

The title compound was prepared by a procedure similar to the one described for ethyl 3-(3-(2-tert-butylphenoxy)azetidin-1-yl)-3-oxopropanoate to provide 4-{[3-(2-tert-butylphenoxy)azetidin-1-yl]carbonyl}benzaldehyde (480 mg, 47%) as a colorless oil.

$^1$H NMR (300 MHz, CDCl$_3$) δ 10.05 (s, 1H), 7.94-7.91 (m, 2H), 7.81-7.78 (m, 2H), 7.33-7.30 (m, 1H), 7.15-7.10 (m, 1H), 6.97-6.91 (m, 1H), 6.47-6.43 (m, 1H), 5.08-5.04 (m, 1H), 4.67-4.62 (m, 2H), 4.38-4.34 (m, 2H), 1.41 (s, 9H).

Example 101

5-(4-{[3-(2-tert-butylphenoxy)azetidin-1-yl]carbonyl}benzylidene)-1,3-thiazolidine-2,4-dione

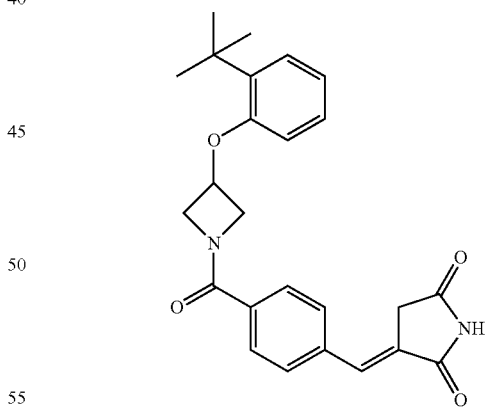

To a stirred solution of 4-{[3-(2-tert-butylphenoxy)azetidin-1-yl]carbonyl} benzaldehyde (480 mg, 1.42 mmol) and piperidine (70 μl, 0.71 mmol) in EtOH (15.0 mL) was added 1,3-thiazolidine-2,4-dione (200 mg, 1.70 mmol) and acetic acid (17 μl) at 80° C. After 16 h the reaction mixture was diluted with ethyl acetate, washed with saturated sodium chloride, dried (Na$_2$SO$_4$), filtered and concentrated under reduced pressure. The resulting mixture was washed with acetonitrile and diethyl ether to provided 5-(4-{[3-(2-tert-butylphenoxy)azetidin-1-yl]carbonyl}benzylidene)-1,3-thiazolidine-2,4-dione (308 mg, 56%) as a colorless solid.

$^1$H NMR (300 MHz, DMSO-d$_6$) δ 12.69 (br s, 1H), 7.82-7.79 (m, 3H), 7.67 (d, J=8.1 Hz, 2H), 7.27-7.24 (m, 1H), 7.17-7.12 (m, 1H), 6.93-6.88 (m, 1H), 6.68-6.65 (m, 1H), 5.13-5.09 (m, 1H), 4.77-4.75 (m, 1H), 4.59-4.57 (m, 1H), 4.36-4.34 (m, 1H), 4.05-4.03 (m, 1H), 1.37 (s, 9H).

Example 102

4-[3-(2-tert-butylphenoxy)azetidin-1-yl]-4-oxo-N-2H-tetrazol-5-ylbutanamide

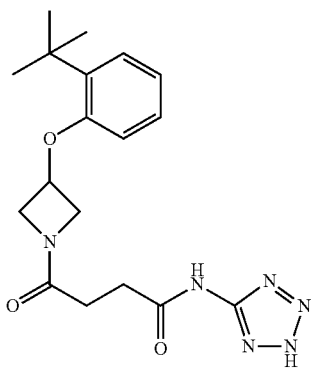 [SMILES: CC(C)(C)c1ccccc1OC1CN(C(=O)CCC(=O)Nc2nn[nH]n2)C1]

The title compound was prepared by a procedure similar to the one described for ethyl 3-(3-(2-tert-butylphenoxy)azetidin-1-yl)-3-oxopropanoate to provide 4-[3-(2-tert-butylphenoxy)azetidin-1-yl]-4-oxo-N-2H-tetrazol-5-ylbutanamide (361 mg, 32%) as a colorless solid.

$^1$H NMR (300 MHz, DMSO-d$_6$) δ 12.00 (br s, 2H), 7.27-7.24 (m, 1H), 7.18-7.13 (m, 1H), 6.94-6.89 (m, 1H), 6.68-6.65 (m, 1H), 5.08-5.06 (m, 1H), 4.66-4.61 (m, 1H), 4.36-4.30 (m, 1H), 4.16-4.12 (m, 1H), 3.82-3.77 (m, 1H), 2.67 (t, J=6.9 Hz, 2H), 2.49-2.44 (m, 1H), 1.36 (s, 9H).

Example 103

1-{[3-(2-tert-butylphenoxy)azetidin-1-yl]carbonyl}cyclopropanecarbonitrile

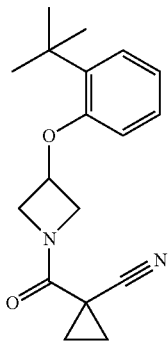 [SMILES: CC(C)(C)c1ccccc1OC1CN(C(=O)C2(C#N)CC2)C1]

The title compound was prepared by a procedure similar to the one described for ethyl 3-(3-(2-tert-butylphenoxy)azetidin-1-yl)-3-oxopropanoate to provide 1-{[3-(2-tert-butylphenoxy)azetidin-1-yl]carbonyl}cyclopropanecarbonitrile (1.42 g, 80%) as a colorless solid.

$^1$H NMR (300 MHz, CDCl$_3$) δ 7.34-7.31 (m, 1H), 7.17-7.11 (m, 1H), 6.97-6.92 (m, 1H), 6.47-6.44 (m, 1H), 5.09-4.99 (m, 2H), 4.68-4.66 (m, 1H), 4.51-4.46 (m, 1H), 4.21-4.17 (m, 1H), 1.72-1.48 (m, 4H), 1.40 (s, 9H).

Example 104

4-{[3-(2-tert-butylphenoxy)azetidin-1-yl]carbonyl}benzonitrile

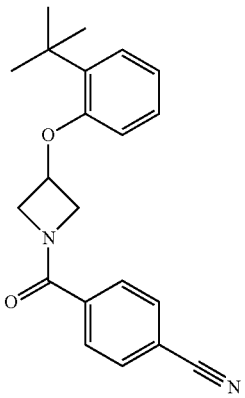 [SMILES: CC(C)(C)c1ccccc1OC1CN(C(=O)c2ccc(C#N)cc2)C1]

The title compound was prepared by a procedure similar to the one described for (3-(2-tert-butylphenoxy)azetidin-1-yl)(phenyl)methanone to provide 4-{[3-(2-tert-butylphenoxy)azetidin-1-yl]carbonyl}benzonitrile (2.00 g, 100%) as a colorless solid.

$^1$H NMR (300 MHz, CDCl$_3$) δ 7.77-7.70 (m, 4H), 7.34-7.25 (m, 1H), 7.16-7.10 (m, 1H), 6.98-6.92 (m, 1H), 6.46-6.43 (m, 1H), 5.08-5.05 (m, 1H), 4.66-4.63 (m, 2H), 4.37-4.35 (m, 2H), 1.40 (s, 9H).

Example 105 methyl 4-{4-[2-(2-tert-butylphenoxy)ethyl]piperidin-1-yl}-4-oxobutanoate

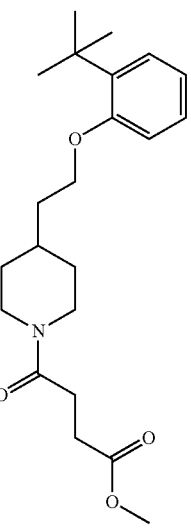

The title compound was prepared by a procedure similar to the one described for (3-(2-tert-butylphenoxy)azetidin-1-yl)(pyridin-2-yl)methanone to provide methyl 4-{4-[2-(2-tert-butylphenoxy)ethyl]piperidin-1-yl}-4-oxobutanoate (1.25 g, 83%) as a colorless oil.

$^1$H NMR (300 MHz, CDCl$_3$) δ 7.30-7.25 (m, 1H), 7.19-7.13 (m, 1H), 6.91-6.84 (m, 2H), 4.60-4.56 (m, 1H), 4.03 (t,

J=6.3 Hz, 2H), 3.97-3.93 (m, 1H), 3.69 (s, 3H), 3.10-3.06 (m, 1H), 2.69-2.67 (m, 4H), 2.67-2.65 (m, 1H), 2.11-2.06 (m, 1H), 1.88-1.81 (m, 4H), 1.38 (s, 9H), 1.32-1.24 (m, 2H).

Example 106 methyl {4-[2-(2-tert-butylphenoxy)ethyl]piperidin-1-yl}(oxo)acetate

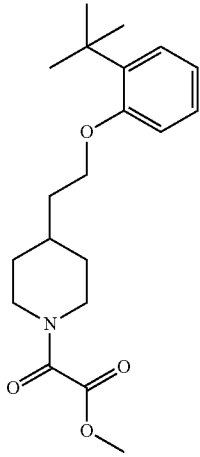 [SMILES: COC(=O)C(=O)N1CCC(CCOc2ccccc2C(C)(C)C)CC1]

The title compound was prepared by a procedure similar to the one described for (3-(2-tert-butylphenoxy)azetidin-1-yl)(pyridin-2-yl)methanone to provide methyl {4-[2-(2-tert-butylphenoxy)ethyl]piperidin-1-yl}(oxo)acetate (1.39 g, 100%) as a colorless oil.

$^1$H NMR (300 MHz, CDCl$_3$) δ 7.29-7.25 (m, 1H), 7.18-7.12 (m, 1H), 6.91-6.83 (m, 2H), 4.54-4.48 (m, 1H), 4.03 (t, J=6.0 Hz, 2H), 3.86 (s, 3H), 3.69-3.63 (m, 1H), 3.14-3.04 (m, 1H), 2.95-2.65 (m, 1H), 1.94-1.79 (m, 5H), 1.38 (s, 9H), 1.37-1.23 (m, 2H).

Example 107

4-{4-[2-(2-tert-butylphenoxy)ethyl]piperidin-1-yl}-4-oxobutanoic acid

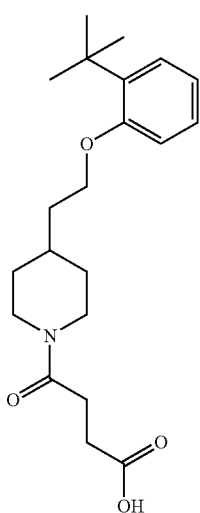 [SMILES: CC(C)(C)c1ccccc1OCCC1CCN(C(=O)CCC(=O)O)CC1]

The title compound was prepared by a procedure similar to the one described for 2-(3-(2-tert-butylphenoxy)azetidin-1-yl)-2-oxoacetic acid to provide 4-{4-[(2-tert-butylphenoxy)ethyl]piperidin-1-yl}-4-oxobutanoic acid (694 m 60%) as a yellow oil.

$^1$H NMR (300 MHz, CDCl$_3$) δ 9.58 (br s, 1H), 7.29-7.25 (m, 1H), 7.18-7.13 (m, 1H), 6.90-6.83 (m, 2H), 4.61-4.56 (m, 1H), 4.03 (t, J=6.6 Hz, 2H), 3.91-3.87 (m, 1H), 3.54-3.48 (m, 1H), 3.10-2.98 (m, 1H), 2.69 (s, 4H), 2.66-2.57 (m, 1H), 1.84-1.80 (m, 4H), 1.38 (s, 9H), 1.25-1.17 (m, 2H).

Example 108

{4-[2-(2-tert-butylphenoxy)ethyl]piperidin-1-yl}(oxo)acetic acid

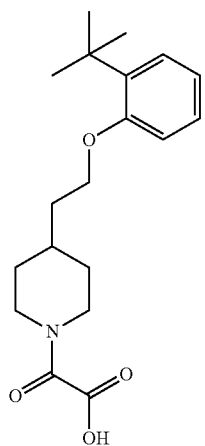 [SMILES: CC(C)(C)c1ccccc1OCCC1CCN(C(=O)C(=O)O)CC1]

The title compound was prepared by a procedure similar to the one described for 2-(3-(2-tert-butylphenoxy)azetidin-1-yl)-2-oxoacetic acid to provide {4-[2-(2-tert-butylphenoxy)ethyl]piperidin-1-yl}(oxo)acetic acid (742 mg, 55%) as a colorless solid.

$^1$H NMR (300 MHz, CDCl$_3$) δ 9.17 (br s, 1H), 7.29-7.24 (m, 1H), 7.19-7.13 (m, 1H), 6.91-6.83 (m, 2H), 4.56-4.46 (m, 2H), 4.03 (t, J=6.0 Hz, 2H), 3.20-3.12 (m, 1H), 2.83-2.74 (m, 1H), 1.93-1.82 (m, 5H), 1.38 (s, 9H), 1.34-1.26 (m, 2H).

Example 109 methyl 4-{3-[(2-tert-butylphenoxy)methyl]pyrrolidin-1-yl}-4-oxobutanoate

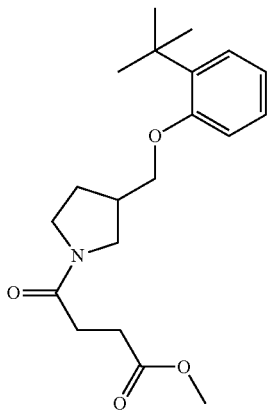 [SMILES: COC(=O)CCC(=O)N1CCC(COc2ccccc2C(C)(C)C)C1]

The title compound was prepared by a procedure similar to the one described for (3-(2-tert-butylphenoxy)azetidin-1-yl)(pyridin-2-yl)methanone to provide methyl 4-{3-[(2-tert-butylphenoxy)methyl]pyrrolidin-1-yl}-4-oxobutanoate (1.39 g, 90%) as a colorless oil.

$^1$H NMR (300 MHz, CDCl$_3$) δ 7.30-7.26 (m, 1H), 7.18-7.12 (m, 1H), 6.92-6.81 (m, 2H), 3.95 (d, J=6.9 Hz, 2H), 3.91-3.71 (m, 1H), 3.68 (s, 3H), 3.67-3.26 (m, 3H), 2.90-2.73 (m, 1H), 2.71-2.66 (m, 2H), 2.60-2.54 (m, 2H), 2.29-2.12 (m, 1H), 2.04-1.76 (m, 1H), 1.39 (s, 9H).

Example 110

4-{3-[(2-tert-butylphenoxy)methyl]pyrrolidin-1-yl}-4-oxobutanoic acid

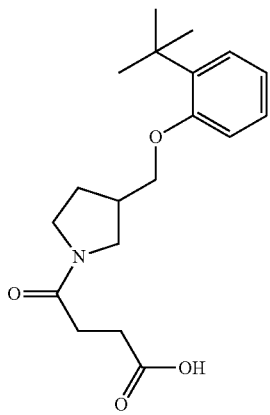 [SMILES: CC(C)(C)c1ccccc1OCC1CCN(C(=O)CCC(=O)O)C1]

The title compound was prepared by a procedure similar to the one described for 2-(3-(2-tert-butylphenoxy)azetidin-1-yl)-2-oxoacetic acid to provide 4-{3-[(2-tert-butylphenoxy)methyl]pyrrolidin-1-yl}-4-oxobutanoic acid (1.00 g, 75%) as a colorless solid.

$^1$H NMR (300 MHz, CDCl$_3$) δ 8.05 (br s, 1H), 7.30-7.25 (m, 1H), 7.18-7.13 (m, 1H), 6.92-6.81 (m, 2H), 4.04-3.27 (m, 6H), 2.93-2.54 (m, 5H), 2.33-2.11 (m, 1H), 2.02-1.77 (m, 1H), 1.39 (s, 9H).

Example 111

3-(4-{[3-(2-tert-butylphenoxy)azetidin-1-yl]carbonyl}phenyl)-1,2,4-oxadiazol-5(4H)-one

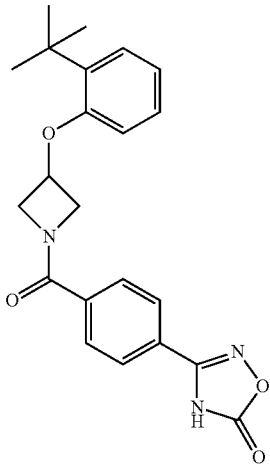 [SMILES: CC(C)(C)c1ccccc1OC1CN(C(=O)c2ccc(-c3noc(=O)[nH]3)cc2)C1]

To a stirred solution of 4-{[3-(2-tert-butylphenoxy)azetidin-1-yl]carbonyl}benzonitrile (2.00 g, 6.00 mmol) in DMSO (5.0 mL) was added hydroxylammonium chloride (2.08 g, 30.0 mmol) and sodium hydrogen carbonate (2.52 g, 30.0 mmol) at 90° C. After 1 h the reaction mixture was partitioned between ethyl acetate and water and separated. The organic layer was washed with saturated sodium chloride, dried (Na$_2$SO$_4$), filtered and concentrated under reduced pressure. The residue was dissolved in THF (10.0 mL), added to a stirred solution of 1,1'-carbonylbis-1H-imidazole (1.07 g, 6.6 mmol) and 1,8-diazabicyclo[5.4.0]undec-7-ene (1.07 g, 6.6 mmol) in THF (10.0 mL) and the resulting reaction mixture was stirred at room temperature for 2 h. Then, the reaction mixture was poured into 1N HCl water solution (150.0 mL) and extracted with ethyl acetate (2×100.0 ml). The combined organics were washed with water (2×150 mL), saturated sodium chloride (100 mL), dried (MgSO$_4$), filtered, and concentrated under reduced pressure. The resulting mixture was washed with acetonitrile and diethyl ether to provide 3-(4-{[3-(2-tert-butylphenoxy)azetidin-1-yl]carbonyl}phenyl)-1,2,4-oxadiazol-5(4H)-one (1.40 g, 59%) as a colorless solid.

$^1$H NMR (300 MHz, CDCl$_3$) δ 11.73 (br s, 1H), 7.88 (d, J=8.1 Hz, 2H), 7.74 (d, J=8.1 Hz, 2H), 7.34-7.30 (m, 1H), 7.15-7.10 (m, 1H), 6.97-6.92 (m, 1H), 6.45 (d, J=8.1 Hz, 1H), 5.09-5.05 (m, 1H), 4.74-4.67 (m, 2H), 4.44-4.34 (m, 2H), 1.40 (s, 9H).

Example 112

4-{[3-(2-tert-butylphenoxy)azetidin-1-yl]carbonyl}piperidine-2,6-dione

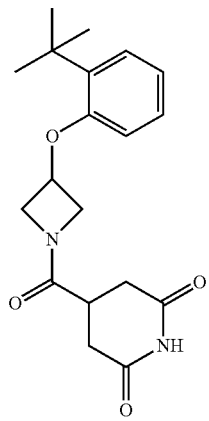 [SMILES: CC(C)(C)c1ccccc1OC1CN(C(=O)C2CC(=O)NC(=O)C2)C1]

The title compound was prepared by a procedure similar to the one described for ethyl 3-(3-(2-tert-butylphenoxy)azetidin-1-yl)-3-oxopropanoate to provide 4-{[3-(2-tert-butylphenoxy)azetidin-1-yl]carbonyl}piperidine-2,6-dione (437.0 mg, 58%) as a colorless solid.

$^1$H NMR (300 MHz, DMSO-d$_6$) δ 10.68 (s, 1H), 7.27-7.24 (m, 1H), 7.18-7.13 (m, 1H), 6.91 (t, J=6.6 Hz, 1H), 6.65 (d, J=6.6 Hz, 1H), 5.10-5.05 (m, 1H), 4.71-4.65 (m, 1H), 4.38-4.32 (m, 1H), 4.22-4.17 (m, 1H), 3.84-3.80 (m, 1H), 3.16-3.11 (m, 1H), 2.59-2.47 (m, 1H), 1.36 (s, 9H).

Example 113

2-{[3-(2-tert-butylphenoxy)azetidin-1-yl]carbonyl}cyclopropanecarbaldehyde

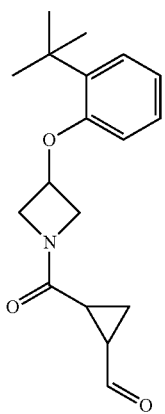

The title compound was prepared by a procedure similar to the one described for ethyl 3-(3-(2-tert-butylphenoxy)azetidin-1-yl)-3-oxopropanoate to provide 2-{[3-(2-tert-butylphenoxy)azetidin-1-yl]carbonyl}cyclopropanecarbaldehyde (1.00 g, 57%) as a colorless solid.

$^1$H NMR (300 MHz, CDCl$_3$) δ 9.46-9.39 (m, 1H), 7.33-7.30 (m, 1H), 7.16-7.11 (m, 1H), 6.96-6.91 (m, 1H), 6.48-6.45 (m, 1H), 5.04-5.00 (m, 1H), 4.69-4.64 (m, 1H), 4.47-4.42 (m, 1H), 4.38-4.32 (m, 1H), 4.14-4.07 (m, 1H), 2.50-2.44 (m, 1H), 2.16-2.10 (m, 1H), 1.63-1.57 (m, 1H), 1.48-1.41 (m, 1H), 1.39 (s, 9H).

Example 114

5-[(2-{[3-(2-tert-butylphenoxy)azetidin-1-yl]carbonyl}cyclopropyl)methylene]-1,3-thiazolidine-2,4-dione

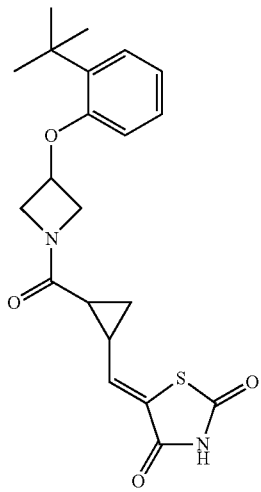 [SMILES: CC(C)(C)c1ccccc1OC1CN(C(=O)C2CC2/C=C2\SC(=O)NC2=O)C1]

The title compound was prepared by a procedure similar to the one described in Example 101 for 5-(4-{[3-(2-tert-butylphenoxy)azetidin-1-yl]carbonyl}benzylidene)-1,3-thiazolidine-2,4-dione to provide 5-[(2-{[3-(2-tert-butylphenoxy)azetidin-1-yl]carbonyl}cyclopropyl)methylene]-1,3-thiazolidine-2,4-dione (630.0 mg, 47%) as a colorless solid.

$^1$H NMR (300 MHz, DMSO-d$_6$) δ 12.34 (s, 1H), 7.25 (d, J=7.8 Hz, 1H), 7.15 (d, J=7.8 Hz, 1H), 6.91 (t, J=7.8 Hz, 1H), 6.67% (d, J=7.8 Hz, 1H), 6.54 (d, J=7.8 Hz, 1H), 5.12-5.08 (m, 1H), 4.77-4.69 (m, 1H), 4.40-4.35 (m, 1H), 4.24-4.16 (m, 1H), 3.85-3.81 (m, 1H), 2.27-2.21 (m, 1H), 1.69-1.64 (m, 1H), 1.43-1.32 (m, 2H), 1.36 (s, 9H).

Example 115

4-[3-(2-tert-butylphenoxy)azetidin-1-yl]-N-{[4-(1,3-oxazol-5-yl)phenyl]sulfonyl}-4-oxobutanamide

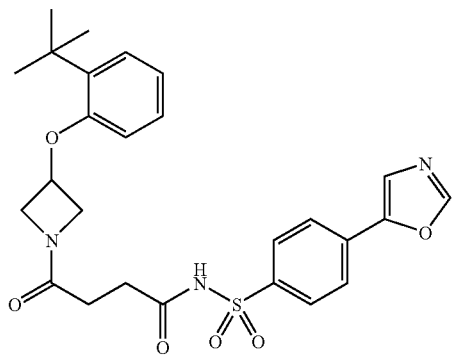 [SMILES: CC(C)(C)c1ccccc1OC1CN(C(=O)CCC(=O)NS(=O)(=O)c2ccc(-c3cnco3)cc2)C1]

The title compound was prepared by a procedure similar to the one described for 4-[3-(2-tert-butylphenoxy)azetidin-1-yl]-N-(methylsulfonyl)-4-oxobutanamide to provide 4-[3-(2-tert-butylphenoxy)azetidin-1-yl]-N-{[4-(1,3-oxazol-5-yl)phenyl]sulfonyl}-4-oxobutanamide (665 mg, 79%) as a colorless solid.

$^1$H NMR (300 MHz, DMSO-d$_6$) δ 12.10 (s, 1H), 8.56 (s, 1H), 8.00-7.91 (m, 5H), 7.24 (t, J=7.5 Hz, 1H), 7.14 (t, J=7.5 Hz, 1H), 6.90 (d, J=7.5 Hz, 1H), 6.62 (d, J=7.5 Hz, 1H), 5.08-5.01 (m, 1H), 4.56-4.51 (m, 1H), 4.29-4.24 (m, 1H), 4.08-4.04 (m, 1H), 3.76-3.71 (m, 1H), 2.50-2.45 (m, 2H), 2.28-2.24 (m, 2H), 1.34 (s, 9H).

Example 116 methyl {3-[(2-tert-butylphenoxy)methyl]azetidin-1-yl}(oxo)acetate

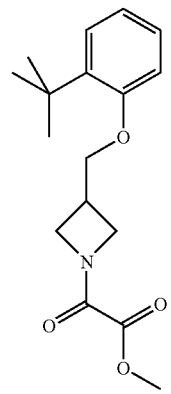

The title compound was prepared by a procedure similar to the one described for (3-(2-tert-butylphenoxy)azetidin-1-yl)(pyridin-2-yl)methanone to provide methyl {3-[(2-tert-butylphenoxy)methyl]azetidin-1-yl}(oxo)acetate (1.10 g, 92%) as a colorless oil.

$^1$H NMR (300 MHz, CDCl$_3$) δ 7.31-7.28 (m, 1H), 7.20-7.15 (m, 1H), 6.95-6.89 (m, 1H), 6.86-6.38 (m, 1H), 4.75-4.68 (m, 1H), 4.49-4.43 (m, 1H), 4.36-4.29 (m, 1H), 4.14 (d, J=6.0 Hz, 2H), 4.11-4.05 (m, 1H), 3.86 (s, 3H), 3.25-3.15 (m, 1H), 1.35 (s, 9H).

Example 117

{3-[(2-tert-butylphenoxy)methyl]azetidin-1-yl}(oxo)acetic acid

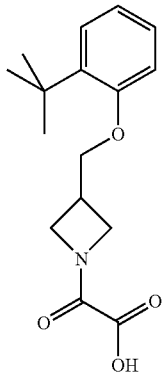 [SMILES: CC(C)(C)c1ccccc1OCC1CN(C(=O)C(=O)O)C1]

The title compound was prepared by a procedure similar to the one described for 2-(3-(2-tert-butylphenoxy)azetidin-1-yl)-2-oxoacetic acid to provide {3-[(2-tert-butylphenoxy)methyl]azetidin-1-yl}(oxo)acetic acid (762 mg, 800) as a colorless solid.

$^1$H NMR (300 MHz, CDCl$_3$) δ 12.04 (br s, 1H), 7.30 (dd, J=7.5, 1.5 Hz, 1H), 7.21-7.15 (m, 1H), 6.95-6.90 (m, 1H), 6.84 (d, J=8.4 Hz, 1H), 4.88-4.81 (m, 1H), 4.65-4.59 (m, 1H), 4.42-4.35 (m, 1H), 4.18-4.13 (m, 3H), 3.30-3.23 (m, 1H), 1.35 (s, 9H).

Example 118 methyl {3-[(2-tert-butylphenoxy)methyl]pyrrolidin-1-yl}(oxo)acetate

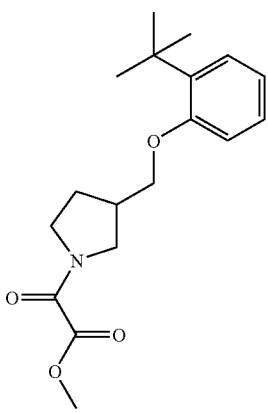 [SMILES: COC(=O)C(=O)N1CCC(COc2ccccc2C(C)(C)C)C1]

The title compound was prepared by a procedure similar to the one described for (3-(2-tert-butylphenoxy)azetidin-1-yl)(pyridin-2-yl)methanone to provide methyl {3-[(2-tert-butylphenoxy)methyl]pyrrolidin-1-yl}(oxo)acetate (2.33 g, 99%) as a colorless oil.

$^1$H NMR (300 MHz, CDCl$_3$) δ 7.31-7.28 (m, 1H), 7.19-7.14 (m, 1H), 6.93-6.88 (m, 1H), 6.84-6.81 (m, 1H), 4.13-4.02 (m, 2H), 4.00-3.90 (m, 1H), 3.88-3.85 (m, 3H), 3.79-3.68 (m, 1H), 3.62-3.53 (m, 1H), 3.45-3.39 (m, 1H), 2.90-2.79 (m, 1H), 2.30-2.19 (m, 1H), 2.02-1.83 (m, 1H), 1.39 (s, 9H).

Example 119

{3-[(2-tert-butylphenoxy)methyl]pyrrolidin-1-yl}(oxo)acetic acid

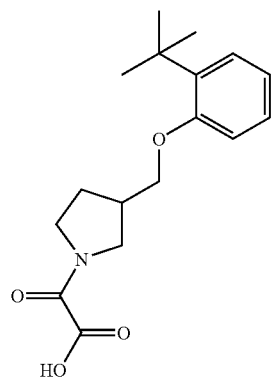 [SMILES: CC(C)(C)c1ccccc1OCC1CCN(C(=O)C(=O)O)C1]

The title compound was prepared by a procedure similar to the one described for 2-(3-(2-tert-butylphenoxy)azetidin-1-yl)-2-oxoacetic acid to provide {3-[(2-tert-butylphenoxy)methyl]pyrrolidin-1-yl}(oxo)acetic acid (378 mg, 86%) as a colorless solid.

$^1$H NMR (300 MHz, DMSO-d$_6$) δ 12.23 (br s, 1H), 7.23-7.13 (m, 2H), 6.95 (d, J=8.4 Hz, 1H), 6.86 (t, J=8.4 Hz, 1H), 4.01-3.98 (m, 2H), 3.85-3.21 (m, 4H), 2.81-2.71 (m, 1H), 2.18-2.10 (m, 1H), 1.87-1.74 (m, 1H), 1.34 (s, 9H).

Example 120

2-{4-[(2-tert-butylphenoxy)methyl]piperidin-1-yl}-2-oxo-N-[(pentylamino)sulfonyl]acetamide

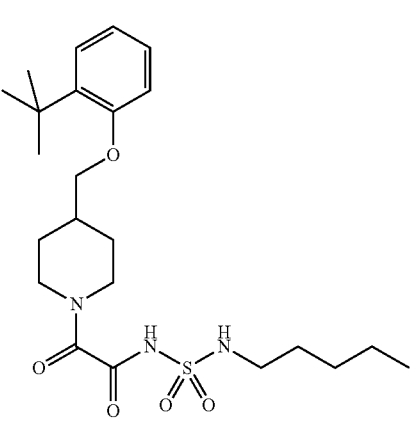 [SMILES: CCCCCNS(=O)(=O)NC(=O)C(=O)N1CCC(COc2ccccc2C(C)(C)C)CC1]

The title compound was prepared by a procedure similar to the one described for 4-[3-(2-tert-butylphenoxy)azetidin-1-yl]-N-(methylsulfonyl)-4-oxobutanamide to provide 2-{4-[(2-tert-butylphenoxy)methyl]piperidin-1-yl}-2-oxo-N-[(pentylamino)sulfonyl]acetamide (303 mg, 41%) as a colorless solid.

¹H NMR (300 MHz, DMSO-d₆) δ 12.16 (br s, 1H), 8.01 (br s, 1H), 7.22-7.12 (m, 2H), 6.95 (d, J=7.8 Hz, 1H), 6.85 (t, J=7.8 Hz, 1H), 4.29-4.25 (m, 1H), 3.88-3.85 (m, 2H), 3.59-3.55 (m, 1H), 3.26-3.18 (m, 1H), 2.95-2.89 (m, 2H), 2.84-2.76 (m, 1H), 2.19-2.14 (m, 1H), 1.92-1.88 (m, 2H), 1.49-1.40 (m, 2H), 1.34 (s, 9H), 1.29-1.22 (m, 6H), 0.85 (t, J=6.9 Hz, 3H).

Example 121

2-{4-[(2-tert-butylphenoxy)methyl]piperidin-1-yl}-2-oxo-N-(pentylsulfonyl)acetamide

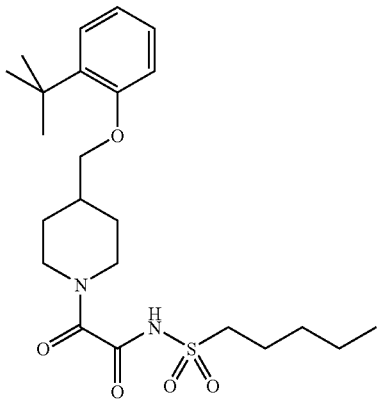 [SMILES: CCCCCS(=O)(=O)NC(=O)C(=O)N1CCC(COc2ccccc2C(C)(C)C)CC1]

The title compound was prepared by a procedure similar to the one described for 4-[3-(2-tert-butylphenoxy)azetidin-1-yl]-N-(methylsulfonyl)-4-oxobutanamide to provide 2-{4-[(2-tert-butylphenoxy)methyl]piperidin-1-yl}-2-oxo-N-(pentylsulfonyl)acetamide (467 mg, 66%) as a colorless solid.

¹H NMR (300 MHz, DMSO-d₆) δ 12.12 (br s, 1H), 7.22-7.12 (m, 2H), 6.95 (d, J=8.1 Hz, 1H), 6.85 (t, J=8.1 Hz, 1H), 4.29-4.25 (m, 1H), 3.88-3.85 (m, 2H), 3.59-3.55 (m, 1H), 3.47-3.42 (m, 2H), 3.27-3.19 (m, 1H), 2.85-2.77 (m, 1H), 2.18-2.15 (m, 1H), 1.92-1.88 (m, 2H), 1.70-1.63 (m, 2H), 1.40-1.23 (m, 6H), 1.34 (s, 9H), 0.86 (t, J=6.9 Hz, 3H).

Example 122 methyl 4-[4-(2-tert-Butyl-5-methylphenoxy)piperidin-1-yl]-4-oxobutanoate

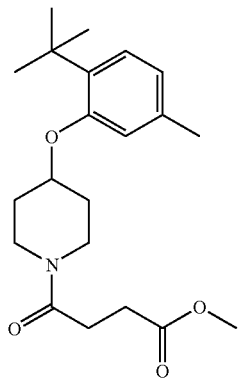

The title compound was prepared by a procedure similar to the one described for (3-(2-tert-butylphenoxy)azetidin-1-yl)(pyridin-2-yl)methanone to provide methyl 4-[4-(2-tert-butyl-5-methylphenoxy)piperidin-1-yl]-4-oxobutanoate (490 mg, 64%) as a colorless oil.

¹H NMR (300 MHz, CDCl₃) δ 7.18 (d, J=7.8 Hz, 1H), 6.68 (d, J=7.8 Hz, 1H), 6.63 (s, 1H), 4.67-4.66 (m, 1H), 3.77-3.73 (m, 2H), 3.70 (s, 3H), 3.56-3.49 (m, 2H), 2.73-2.64 (m, 4H), 2.31 (s, 3H), 2.04-1.88 (m, 4H), 1.38 (s, 9H).

Example 123

4-[4-(2-tert-butyl-5-methylphenoxy)piperidin-1-yl]-4-oxobutanoic acid

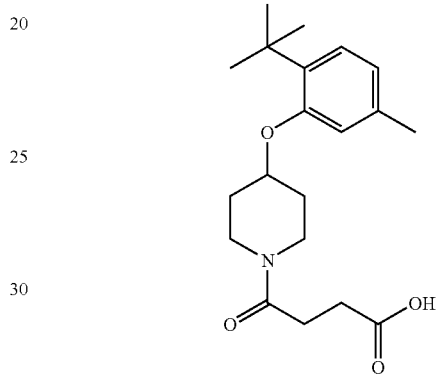

The title compound was prepared by a procedure similar to the one described for 2-(3-(2-tert-butylphenoxy)azetidin-1-yl)-2-oxoacetic acid to provide 4-[4-(2-tert-butyl-5-methylphenoxy)piperidin-1-yl]-4-oxobutanoic acid (382 g, 85%) as a colorless solid.

¹H NMR (300 MHz, CDCl₃) δ 13.42 (br s, 1H), 7.18 (d, J=8.1 Hz, 1H), 6.69 (d, J=8.1 Hz, 1H), 6.63 (s, 1H), 4.69-4.67 (m, 1H), 3.82-3.68 (m, 3H), 3.60-3.55 (m, 1H), 2.72 (m, 4H), 2.31 (s, 3H), 2.04-1.94 (m, 4H), 1.37 (s, 9H).

Example 124 methyl [3-(2-tert-butylphenoxy)pyrrolidin-1-yl](oxo)acetate

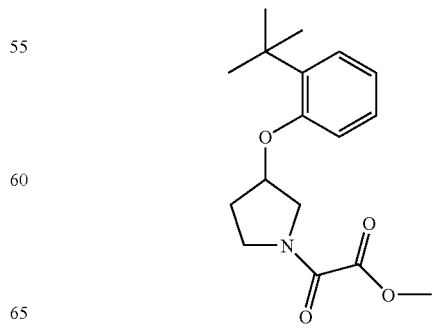

To a solution of 3-(2-tert-butylphenoxy)pyrrolidine hydrochloride (0.40 g, 1.56 mmol) obtained in Reference Example 53 in THF (16 mL) were added triethylamine (0.35 g, 3.43 mmol) and methyl chloro(oxo)acetate (0.21 g, 1.71 mmol) at 0° C., and the mixture was stirred for 30 min. The mixture was further stirred at room temperature for 3 hr, and the precipitate was collected by filtration. The filtrate was partitioned between ethyl acetate-water, the ethyl acetate layer was washed with saturated brine, dried over anhydrous magnesium sulfate and filtered. The filtrate was concentrated under reduced pressure, and the obtained residue was purified by silica gel column chromatography (hexane:ethyl acetate 80:20-10:90) to give the title compound (0.39 g, 82%) as a colorless oil.

$^1$H NMR (300 MHz, CDCl$_3$) δ 7.33-7.29 (m, 1H), 7.22-7.09 (m, 1H), 6.99-6.85 (m, 1H), 6.83-6.71 (m, 1H), 5.17-4.98 (m, 1H), 4.56-4.26 (m, 1H), 4.04-3.89 (m, 2H), 3.89-3.84 (m, 3H), 3.84-3.66 (m, 1H), 2.52-2.09 (m, 2H), 1.38-1.31 (m, 9H).

Example 125 ethyl 3-[3-(2-tert-butylphenoxy)pyrrolidin-1-yl]-3-oxopropanoate

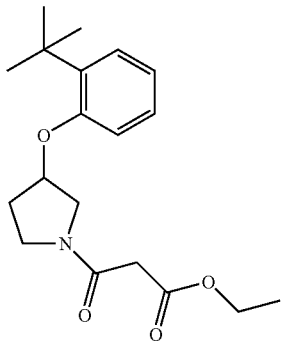 [SMILES: CCOC(=O)CC(=O)N1CCC(Oc2ccccc2C(C)(C)C)C1]

According to a method similar to that in Example 9, the title compound (0.28 g, 54%) was obtained as a colorless oil from 3-(2-tert-butylphenoxy)pyrrolidine hydrochloride (0.40 g, 1.56 mmol) obtained in Reference Example 53 and 3-ethoxy-3-oxopropanoic acid (0.31 g, 2.34 mmol).

$^1$H NMR (300 MHz, CDCl$_3$) δ 7.38-7.27 (m, 1H), 7.22-7.09 (m, 1H), 6.99-6.85 (m, 1H), 6.83-6.71 (m, 1H), 5.16-4.93 (m, 1H), 4.26-4.06 (m, 2H), 3.97-3.58 (m, 4H), 3.47-3.33 (m, 2H), 2.47-2.11 (m, 2H), 1.34 (s, 9H), 1.32-1.18 (m, 3H).

Example 126 ethyl 4-[3-(2-tert-butylphenoxy)pyrrolidin-1-yl]-4-oxobutanoate

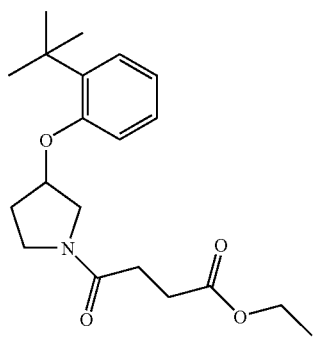 [SMILES: CCOC(=O)CCC(=O)N1CCC(Oc2ccccc2C(C)(C)C)C1]

According to a method similar to that in Example 124, the title compound (0.47 g, 87%) was obtained as a colorless oil from 3-(2-tert-butylphenoxy)pyrrolidine hydrochloride (0.40 g, 1.56 mmol) obtained in Reference Example 53 and ethyl 4-chloro-4-oxobutanoate (0.31 g, 1.88 mmol).

$^1$H NMR (300 MHz, CDCl$_3$) δ 7.35-7.27 (m, 1H), 7.22-7.09 (m, 1H), 6.96-6.84 (m, 1H), 6.81-6.74 (m, 1H), 5.18-4.89 (m, 1H), 4.32-4.21 (m, 1H), 4.21-4.07 (m, 2H), 3.98-3.54 (m, 3H), 2.77-2.09 (m, 6H), 1.34 (s, 9H), 1.30-1.20 (m, 3H).

Example 127

[3-(2-tert-butylphenoxy)pyrrolidin-1-yl](oxo)acetic acid

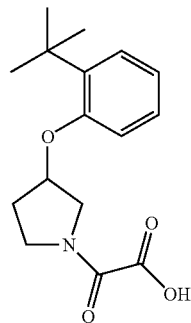 [SMILES: CC(C)(C)c1ccccc1OC1CCN(C(=O)C(=O)O)C1]

According to a method similar to that in Example 5, the title compound (0.27 g, 83%) was obtained as a white solid from methyl [3-(2-tert-butylphenoxy)pyrrolidin-1-yl](oxo)acetate (0.34 g, 1.11 mmol) obtained in Example 124.

$^1$H NMR (300 MHz, DMSO-d$_6$) δ 13.98 (br s, 1H), 7.33-7.09 (m, 2H), 7.03-6.93 (m, 1H), 6.87 (t, J=7.6 Hz, 1H), 5.36-4.98 (m, 1H), 4.00-3.26 (m, 4H), 2.40-2.09 (m, 2H), 1.32-1.23 (m, 9H).

Example 128

3-[3-(2-tert-butylphenoxy)pyrrolidin-1-yl]-3-oxopropanoic acid

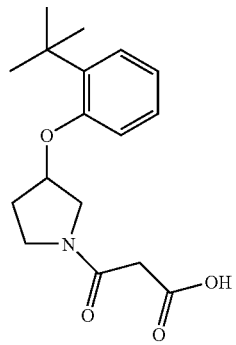 [SMILES: CC(C)(C)c1ccccc1OC1CCN(C(=O)CC(=O)O)C1]

To a solution of ethyl 3-[3-(2-tert-butylphenoxy)pyrrolidin-1-yl]-3-oxopropanoate (0.26 g, 0.78% mmol) obtained in Example 125 in ethanol (10.0 mL) was added lithium hydroxide (1.0M aqueous solution, 2.34 mL, 2.34 mmol) under ice-cooling, and the mixture was stirred at room temperature for 2 hr. The reaction mixture was adjusted to about pH 1 with 1.0M hydrochloric acid, and concentrated under reduced pressure. The obtained residue was partitioned between ethyl acetate and water, and the organic layer was washed with saturated sodium chloride, dried (Na$_2$SO$_4$), filtered, and the filtrate was concentrated under reduced pressure. The residue was recrystallized from hexane/diethyl ether to give the title compound (0.16 g, 48%) as a white solid.

$^1$H NMR (300 MHz, DMSO-d$_6$) δ 12.58 (br s, 1H), 7.23 (dd, J=7.6, 1.5 Hz, 1H), 7.21-7.11 (m, 1H), 6.96 (d, J=8.3 Hz, 1H), 6.91-6.80 (m, 1H), 5.25-5.03 (m, 1H), 3.92-3.50 (m, 3H), 3.50-3.23 (m, 3H), 2.37-2.00 (m, 2H), 1.30 (s, 9H).

Example 129

4-[3-(2-tert-butylphenoxy)pyrrolidin-1-yl]-4-oxobutanoic acid

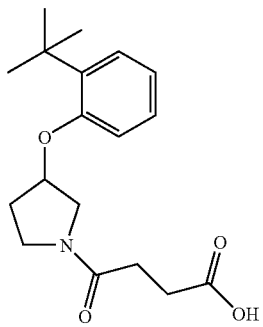 [SMILES: CC(C)(C)c1ccccc1OC1CCN(C(=O)CCC(=O)O)C1]

According to a method similar to that in Example 5, the title compound (0.27 g, 72%) was obtained as a white solid from ethyl 4-[3-(2-tert-butylphenoxy)pyrrolidin-1-yl]-4-oxobutanoate (0.41 g, 1.18 mmol) obtained in Example 126.

$^1$H NMR (300 MHz, DMSO-d$_6$) δ 12.01 (br s, 1H), 7.28-7.11 (m, 2H), 6.97 (t, J=7.6 Hz, 1H), 6.86 (t, J=7.4 Hz, 1H), 5.32-4.90 (m, 1H), 3.94-3.14 (m, 5H), 2.48-1.90 (m, 5H), 1.29 (s, 9H).

Example 130 methyl [3-(4-bromo-2-tert-butylphenoxy)azetidin-1-yl](oxo)acetate

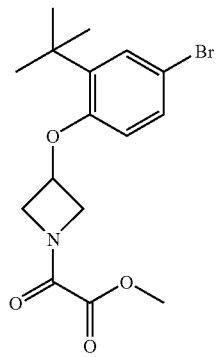 [SMILES: COC(=O)C(=O)N1CC(Oc2ccc(Br)cc2C(C)(C)C)C1]

According to a method similar to that in Example 124, the title compound (0.24 g, 53%) was obtained from 3-(2-tert-butyl-4-bromophenoxy)azetidine (0.35 g, 1.23 mmol) obtained in Reference Example 46 and methyl chloro(oxo)acetate (0.17 g, 1.35 mmol).

$^1$H NMR (300 MHz, CDCl$_3$) δ 7.41 (d, J=2.4 Hz, 1H), 7.29-7.21 (m, 2H), 6.32 (d, J=8.7 Hz, 1H), 5.07-4.84 (m, 2H), 4.68-4.45 (m, 2H), 3.87 (s, 3H), 1.37 (s, 9H).

Example 131

[3-(4-bromo-2-tert-butylphenoxy)azetidin-1-yl](oxo)acetic acid

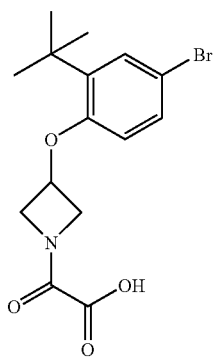 [SMILES: CC(C)(C)c1cc(Br)ccc1OC1CN(C(=O)C(=O)O)C1]

According to a method similar to that in Example 5, the title compound (0.15 g, 78%) was obtained as a white solid from methyl [3-(4-bromo-2-tert-butylphenoxy)azetidin-1-yl](oxo)acetate (0.20 g, 0.54 mmol) obtained in Example 130.

$^1$H NMR (300 MHz, DMSO-d$_6$) δ 13.98 (br s, 1H), 7.39-7.29 (m, 2H), 6.67 (d, J=8.3 Hz, 1H), 5.15-5.03 (m, 1H), 4.94-4.81 (m, 1H), 4.54-4.41 (m, 1H), 4.36-4.25 (m, 1H), 3.97-3.86 (m, 1H), 1.35 (s, 9H).

Example 132

3-[3-(4-bromo-2-tert-butylphenoxy)azetidin-1-yl]-3-oxopropanoic acid

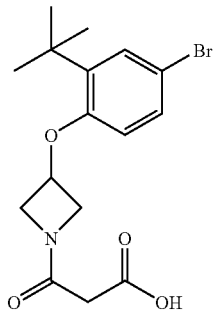 [SMILES: CC(C)(C)c1cc(Br)ccc1OC1CN(C(=O)CC(=O)O)C1]

According to a method similar to that in Example 9, ethyl 3-[3-(4-bromo-2-tert-butylphenoxy)azetidin-1-yl]-3-oxopropanoate (0.18 g, 40%) was obtained from 3-(2-tert-butyl-4-bromophenoxy)azetidine (0.33 g, 1.16 mmol) obtained in Reference Example 46 and 3-ethoxy-3-oxopropanoic acid (0.23 g, 1.74 mmol). This was treated by a method similar to that in Example 5 to give the title compound (0.10 g, 60%) as a white solid.

¹H NMR (300 MHz, DMSO-d₆) δ 12.60 (br s, 1H), 7.38-7.28 (m, 2H), 6.67 (d, J=8.3 Hz, 1H), 5.19-4.89 (m, 1H), 4.70-4.54 (m, 1H), 4.45-4.28 (m, 1H), 4.22-4.03 (m, 1H), 3.90-3.67 (m, 1H), 3.20 (s, 2H), 1.35 (s, 9H).

Example 133

4-[3-(4-bromo-2-tert-butylphenoxy)azetidin-1-yl]-4-oxobutanoic acid

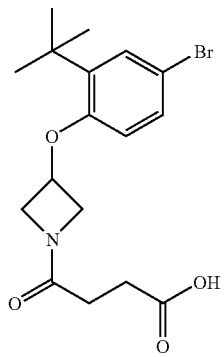 [SMILES: CC(C)(C)c1cc(Br)ccc1OC1CN(C(=O)CCC(=O)O)C1]

According to a method similar to that in Example 124, ethyl 4-[3-(4-bromo-2-tert-butylphenoxy)azetidin-1-yl]-4-oxobutanoate (0.18 g, 35%) was obtained from 3-(2-tert-butyl-4-bromophenoxy)azetidine (0.35 g, 1.23 mmol) obtained in Reference Example 46 and ethyl 4-chloro-4-oxobutanoate (0.22 g, 1.35 mmol). This was treated by a method similar to that in Example 5 to give the title compound (0.10 g, 59%) as a white solid.

¹H NMR (300 MHz, DMSO-d₆) δ 12.08 (br s, 1H), 7.40-7.28 (m, 2H), 6.67 (d, J=8.3 Hz, 1H), 5.16-4.97 (m, 1H), 4.67-4.54 (m, 1H), 4.39-4.25 (m, 1H), 4.17-4.06 (m, 1H), 3.83-3.71 (m, 1H), 2.46-2.36 (m, 2H), 2.35-2.22 (m, 2H), 1.35 (s, 9H).

Example 134 ethyl 3-{4-[(2-tert-butyl-4-fluorophenoxy)methyl]piperidin-1-yl}-3-oxopropanoate

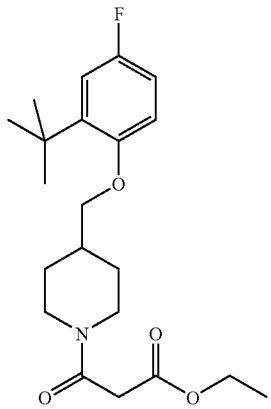 [SMILES: CCOC(=O)CC(=O)N1CCC(COc2ccc(F)cc2C(C)(C)C)CC1]

According to a method similar to that in Example 9, the title compound (432 mg, 69%) was obtained as a colorless oil from 4-[(2-tert-butyl-4-fluorophenoxy)methyl]piperidine hydrochloride (500 mg, 1.66 mmol) obtained in Reference Example 18 and 3-ethoxy-3-oxopropanoic acid (291 mg, 2.0 mmol).

¹H NMR (300 MHz, CDCl₃) δ 7.00 (dd, J=10.9, 3.0 Hz, 1H), 6.88-6.78 (m, 1H), 6.74 (dd, J=9.0, 5.1 Hz, 1H), 4.77-4.67 (m, 1H), 4.21 (q, J=7.2 Hz, 2H), 3.91-3.73 (m, 3H), 3.49 (s, 2H), 3.22-3.08 (m, 1H), 2.68 (td, J=13.0, 2.9 Hz, 1H), 2.20-2.04 (m, 1H), 2.04-1.84 (m, 2H), 1.36 (s, 9H), 1.44-1.25 (m, 2H), 1.29 (t, J=7.2 Hz, 3H).

Example 135

3-{4-[(2-tert-butyl-4-fluorophenoxy)methyl]piperidin-1-yl}-3-oxopropanoic acid

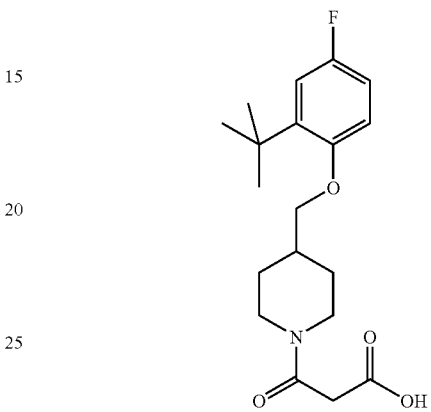

According to a method similar to that in Example 5, the title compound (342 mg, 99%) was obtained as a white solid from ethyl 3-{4-[(2-tert-butyl-4-fluorophenoxy)methyl]piperidin-1-yl}-3-oxopropanoate (371 mg, 0.98 mmol) obtained in Example 134.

¹H NMR (300 MHz, CDCl₃) δ 7.01 (dd, J=11.0, 3.0 Hz, 1H), 6.88-6.78 (m, 1H), 6.74 (dd, J=9.1, 4.9 Hz, 1H), 4.80-4.67 (m, 1H), 3.95-3.75 (m, 3H), 3.39 (s, 2H), 3.18 (td, J=13.2, 2.8 Hz, 1H), 2.78 (td, J=13.2, 2.8 Hz, 1H), 2.28-2.12 (m, 1H), 2.12-1.93 (m, 2H), 1.49-1.21 (m, 11H).

Example 136 methyl 3-{4-[(2-tert-butyl-4-fluorophenoxy)methyl]piperidin-1-yl}carbonyl)cyclopropanecarboxylate

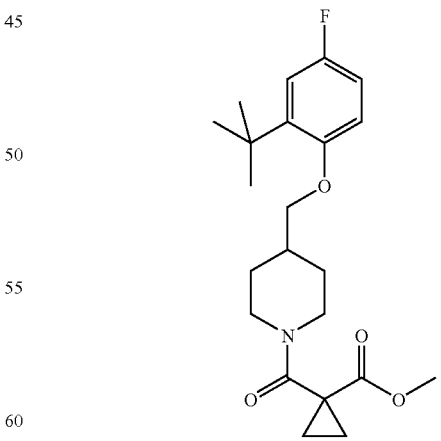

According to a method similar to that in Example 9, the title compound (463 mg, 71%) was obtained as a white solid from 4-[(2-tert-butyl-4-fluorophenoxy)methyl]piperidine hydrochloride (500 mg, 1.66 mmol) obtained in Reference Example 18 and 1-(methoxycarbonyl)cyclopropanecarboxylic acid (288 mg, 2.0 mmol).

¹H NMR (300 MHz, CDCl₃) δ 7.00 (dd, J=10.9, 3.0 Hz, 1H), 6.88-6.78 (m, 1H), 6.74 (dd, J=8.9, 4.9 Hz, 1H), 4.75-4.61 (m, 1H), 4.12-3.98 (m, 1H), 3.89-3.76 (m, 2H), 3.73 (s, 3H), 3.09 (td, J=13.0, 2.5 Hz, 1H), 2.73 (td, J=13.2, 2.5 Hz, 1H), 2.22-2.02 (m, 1H), 2.02-1.83 (m, 2H), 1.55-1.45 (m, 2H), 1.45-1.22 (m, 13H).

Example 137

1-({4-[(2-tert-butyl-4-fluorophenoxy)methyl]piperidin-1-yl}carbonyl)cyclopropanecarboxylic acid

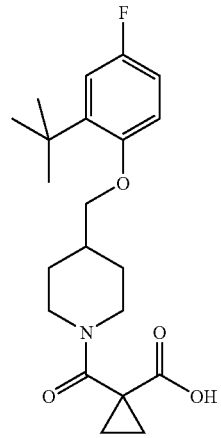 [SMILES: CC(C)(C)c1cc(F)ccc1OCC1CCN(C(=O)C2(C(=O)O)CC2)CC1]

According to a method similar to that in Example 5, the title compound (326 mg, quant.) was obtained as a white solid from methyl 3-{4-[(2-tert-butyl-4-fluorophenoxy)methyl]piperidin-1-yl}carbonyl)cyclopropanecarboxylate (311 mg, 0.79 mmol) obtained in Example 136.

¹H NMR (300 MHz, CDCl₃) δ 7.00 (dd, J=11.0, 3.0 Hz, 1H), 6.88-6.78 (m, 1H), 6.74 (dd, J=9.1, 4.9 Hz, 1H), 4.51-4.26 (m, 2H), 3.82 (d, J=6.1 Hz, 2H), 3.09-2.79 (m, 2H), 2.20-2.01 (m, 1H), 2.00-1.85 (m, 2H), 1.62-1.51 (m, 2H), 1.48-1.30 (m, 13H).

Example 138

4-{4-[(2-tert-butyl-4-fluorophenoxy)methyl]piperidin-1-yl}-4-oxobutanoic acid

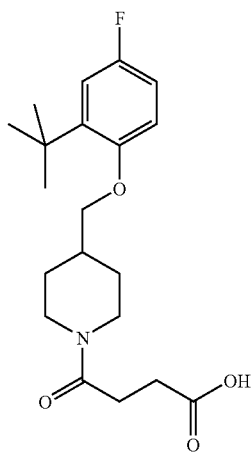 [SMILES: CC(C)(C)c1cc(F)ccc1OCC1CCN(C(=O)CCC(=O)O)CC1]

According to a method similar to that in Example 5, the title compound (220 mg, 62%) was obtained as a white solid from methyl 4-{4-[(2-tert-butyl-4-fluorophenoxy)methyl]piperidin-1-yl}-4-oxobutanoate (367 mg, 0.97 mmol) obtained in Example 253.

¹H NMR (300 MHz, CDCl₃) δ 7.00 (dd, J=10.9, 3.0 Hz, 1H), 6.90-6.79 (m, 1H), 6.74 (dd, J=8.9, 4.7 Hz, 1H), 4.78-4.63 (m, 1H), 4.01-3.90 (m, 1H), 3.90-3.75 (m, 2H), 3.24-3.06 (m, 1H), 2.77-2.62 (m, 5H), 2.22-2.08 (m, 1H), 2.08-1.89 (m, 2H), 1.43-1.28 (m, 11H).

Example 139

4-{[3-(2-tert-butylphenoxy)azetidin-1-yl]carbonyl}phenol

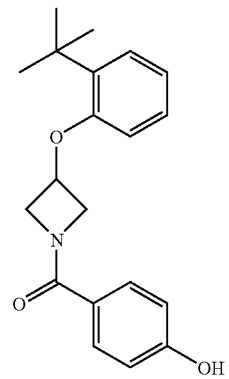 [SMILES: CC(C)(C)c1ccccc1OC1CN(C(=O)c2ccc(O)cc2)C1]

According to a method similar to that in Example 9, the title compound (1.03 g, 65%) was obtained as a white solid from 3-(2-tert-butylphenoxy)azetidine (1.0 g, 4.87 mmol) obtained in Reference Example 2 and 4-hydroxybenzoic acid (751 mg, 5.0 mmol).

¹H NMR (300 MHz, CDCl₃) δ 7.58 (m, 2H), 7.33 (dd, J=7.7, 1.7 Hz, 1H), 7.14 (td, 1.7 Hz, 1H), 6.94 (td, J=7.6, 1.2 Hz, 1H), 6.85 (m, 2H), 6.46 (dd, J=7.9, 0.9 Hz, 1H), 5.11-4.97 (m, 1H), 4.73-4.59 (m, 2H), 4.50-4.22 (m, 2H), 1.40 (s, 9H).

Example 140 methyl 4-{3-[(2-tert-butyl-4-fluorophenoxy)methyl]azetidin-1-yl}-4-oxobutanoate

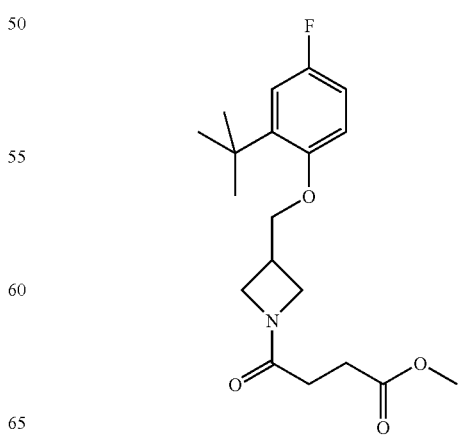

According to a method similar to that in Example 124, the title compound (386 mg, 65%) was obtained as a colorless oil from 3-[(2-tert-butyl-4-fluorophenoxy)methyl]azetidine (400 mg, 1.69 mmol) obtained in Reference Example 48 and methyl 4-chloro-4-oxobutanoate (303 mg, 2.02 mmol).

$^1$H NMR (300 MHz, CDCl$_3$) δ 7.01 (dd, J=10.7, 3.0 Hz, 1H), 6.90-6.80 (m, 1H), 6.76 (dd, J=8.9, 4.7 Hz, 1H), 4.38 (t, J=8.4 Hz, 1H), 4.19 (t, J=9.2 Hz, 1H), 4.14-4.02 (m, 3H), 3.90 (dd, J=10.0, 5.5 Hz, 1H), 3.69 (s, 3H), 3.23-3.03 (m, 1H), 2.80-2.55 (m, 2H), 2.49-2.25 (m, 2H), 1.34 (s, 9H).

Example 141

4-{3-[(2-tert-butyl-4-fluorophenoxy)methyl]azetidin-1-yl}-4-oxobutanoic acid

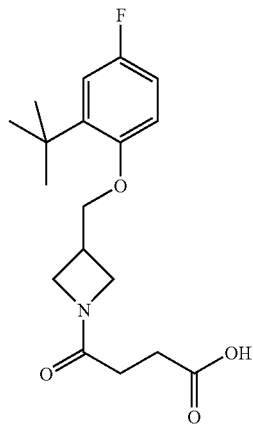 [SMILES: CC(C)(C)c1cc(F)ccc1OCC1CN(C(=O)CCC(=O)O)C1]

According to a method similar to that in Example 5, the title compound (336 mg, quant.) was obtained as a white solid from methyl 4-{3-[(2-tert-butyl-4-fluorophenoxy)methyl]azetidin-1-yl}-4-oxobutanoate (331 mg, 0.94 mmol) obtained in Example 140.

$^1$H NMR (300 MHz, CDCl$_3$) δ 7.02 (dd, J=10.9, 3.0 Hz, 1H), 6.90-6.80 (m, 1H), 6.76 (dd, J=8.9, 4.9 Hz, 1H), 4.38 (t, J=8.9 Hz, 1H), 4.22 (t, J=9.6 Hz, 1H), 4.13-4.05 (m, 3H), 3.98 (dd, J=10.4, 5.7 Hz, 1H), 3.26-3.07 (m, 1H), 2.75-2.62 (m, 2H), 2.51-2.40 (m, 2H), 1.34 (s, 9H).

Example 142 ethyl 3-{3-[(2-tert-butyl-4-fluorophenoxy)methyl]azetidin-1-yl}-3-oxopropanoate

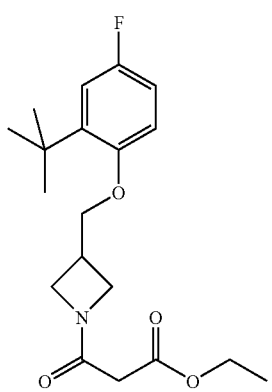 [SMILES: CCOC(=O)CC(=O)N1CC(COc2ccc(F)cc2C(C)(C)C)C1]

According to a method similar to that in Example 9, the title compound (398 mg, 67%) was obtained as a white solid from 3-[(2-tert-butyl-4-fluorophenoxy)methyl]azetidine (400 mg, 1.69 mmol) obtained in Reference Example 48 and 3-ethoxy-3-oxopropanoic acid (266 mg, 2.02 mmol).

$^1$H NMR (300 MHz, CDCl$_3$) δ 7.01 (dd, J=10.7, 3.0 Hz, 1H), 6.90-6.80 (m, 1H), 6.75 (dd, J=9.0, 4.9 Hz, 1H), 4.39 (t, J=8.5 Hz, 1H), 4.30-4.15 (m, 3H), 4.15-4.10 (m, 3H), 3.95 (dd, J=10.2, 5.5 Hz, 1H), 3.26-3.04 (m, 3H), 1.34 (s, 9H), 1.29 (t, J=7.2 Hz, 3H).

Example 143

3-{3-[(2-tert-butyl-4-fluorophenoxy)methyl]azetidin-1-yl}-3-oxopropanoic acid

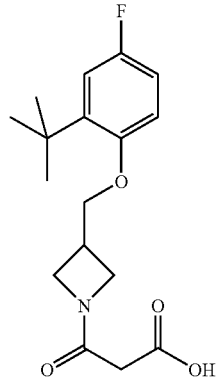 [SMILES: CC(C)(C)c1cc(F)ccc1OCC1CN(C(=O)CC(=O)O)C1]

To a stirred solution of ethyl 3-[(3-[(2-tert-butyl-4-fluorophenoxy)methyl]azetidin-1-yl]-3-oxopropanoate (4.40 g, 12.5 mmol) obtained in Example 142 in THF (50.0 mL) was added lithium hydroxide (1.0M aqueous solution, 40.0 ml, 40.0 mmol) at room temperature. After 3 hr, the reaction mixture was adjusted to about pH 1 with 1.0 N hydrochloric acid. The obtained solution was concentrated under reduced pressure, and the mixture was extracted with ethyl acetate. The organic layer was washed with saturated sodium chloride, dried (MgSO$_4$), filtered, and concentrated under reduced pressure to give the title compound (3.62 g, 90%) as a white solid.

$^1$H NMR (300 MHz, CDCl$_3$) δ 7.03 (dd, J=10.7, 3.0 Hz, 1H), 6.92-6.80 (m, 1H), 6.76 (dd, J=8.9, 4.7 Hz, 1H), 4.38 (t, J=8.7 Hz, 1H), 4.29 (t, J=10.0 Hz, 1H), 4.16-4.03 (m, 4H), 3.30-3.19 (m, 1H), 3.17 (s, 2H), 1.34 (s, 9H).

Example 144

1-({3-[(2-tert-butyl-4-fluorophenoxy)methyl]azetidin-1-yl}carbonyl)cyclopropanecarboxylic acid

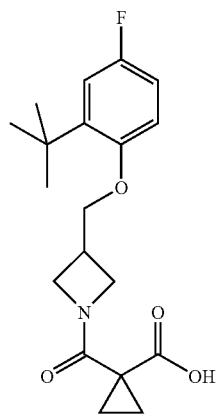 [SMILES: CC(C)(C)c1cc(F)ccc1OCC1CN(C(=O)C2(C(=O)O)CC2)C1]

According to a method similar to that in Example 5, the title compound (414 mg, quant.) was obtained as a white solid from methyl 1-({3-[(2-tert-butyl-4-fluorophenoxy)methyl]azetidin-1-yl}carbonyl)cyclopropanecarboxylate (390 mg, 1.07 mmol) obtained in Example 147.

$^1$H NMR (300 MHz, CDCl$_3$) δ 7.02 (dd, J=10.9, 3.0 Hz, 1H), 6.90-6.80 (m, 1H), 6.75 (dd, J=8.9, 4.7 Hz, 1H), 4.43-4.28 (m, 2H), 4.19-4.04 (m, 4H), 3.23-3.10 (m, 1H), 1.78-1.69 (m, 2H), 1.57-1.50 (m, 2H), 1.34 (s, 9H).

Example 145 methyl (4-{[3-(2-tert-butylphenoxy)azetidin-1-yl]carbonyl}phenoxy)acetate

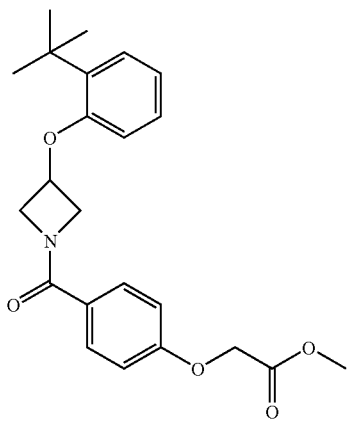 [SMILES: COC(=O)COc1ccc(C(=O)N2CC(Oc3ccccc3C(C)(C)C)C2)cc1]

To a solution of 4-{[3-(2-tert-butylphenoxy)azetidin-1-yl]carbonyl}phenol (552 mg, 1.7 mmol) obtained in Example 139 in DMF (20 mL) were added potassium carbonate (1.04 g, 7.5 mmol) and methyl bromoacetate (352 mg, 2.3 mmol), and the mixture was stirred at 70° C. for 3 hr. The reaction mixture was cooled to room temperature, partitioned between ethyl acetate and water, and the ethyl acetate layer was washed with water and saturated brine, dried over anhydrous magnesium sulfate and filtered. The filtrate was concentrated under reduced pressure, and the obtained residue was purified by silica gel column chromatography (hexane:ethyl acetate 85:15-40:60) to give the title compound (578 mg, 69%) as a colorless solid.

$^1$H NMR (300 MHz, CDCl$_3$) δ 7.65 (m, 2H), 7.33 (dd, J=7.7, 1.7 Hz, 1H), 7.14 (td, J=7.7, 1.7 Hz, 1H), 7.01-6.86 (m, 3H), 6.46 (dd, J=8.1, 1.1 Hz, 1H), 5.12-4.88 (m, 1H), 4.76-4.64 (m, 4H), 4.36 (br s, 2H), 3.82 (s, 3H), 1.40 (s, 9H).

Example 146

(4-{[3-(2-tert-butylphenoxy)azetidin-1-yl]carbonyl}phenoxy)acetic acid

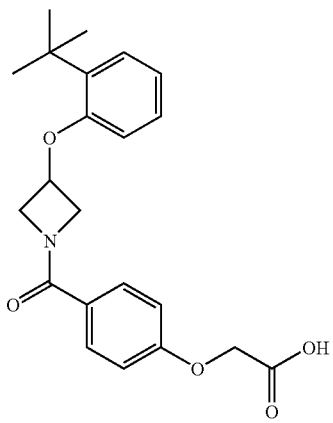 [SMILES: CC(C)(C)c1ccccc1OC1CN(C(=O)c2ccc(OCC(=O)O)cc2)C1]

According to a method similar to that in Example 5, the title compound (226 mg, 80%) was obtained as a white solid from methyl (4-{[3-(2-tert-butylphenoxy)azetidin-1-yl]carbonyl}phenoxy)acetate (282 mg, 0.71 mmol) obtained in Example 145.

$^1$H NMR (300 MHz, CDCl$_3$) δ 7.70-7.55 (m, 2H), 7.30-7.21 (m, 1H), 7.15 (td, J=7.8, 1.0 Hz, 1H), 7.02-6.86 (m, 3H), 6.67 (d, J=7.9 Hz, 1H), 5.18-5.04 (m, 1H), 4.89-4.64 (m, 3H), 4.64-4.39 (m, 1H), 4.39-4.13 (m, 1H), 4.11-3.89 (m, 1H), 1.36 (s, 9H).

Example 147 methyl 1-({3-[(2-tert-butyl-4-fluorophenoxy)methyl]azetidin-1-yl}carbonyl)cyclopropanecarboxylate

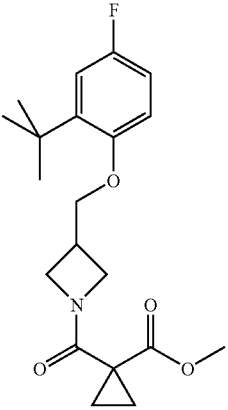 [SMILES: COC(=O)C1(C(=O)N2CC(COc3ccc(F)cc3C(C)(C)C)C2)CC1]

According to a method similar to that in Example 9, the title compound (452 mg, 74%) was obtained as a colorless oil from 3-[(2-tert-butyl-4-fluorophenoxy)methyl]azetidine (400 mg, 1.69 mmol) obtained in Reference Example 48 and 1-(methoxycarbonyl)cyclopropanecarboxylic acid (291 mg, 2.02 mmol).

¹H NMR (300 MHz, CDCl₃) δ 7.01 (dd, J=11.0, 3.4 Hz, 1H), 6.91-6.81 (m, 1H), 6.76 (dd, J=9.1, 4.9 Hz, 1H), 4.39-4.17 (m, 2H), 4.11 (d, J=6.4 Hz, 2H), 4.06-3.88 (m, 2H), 3.73 (s, 3H), 3.27-3.01 (m, 1H), 1.47-1.19 (m, 13H).

Example 148 methyl {3-[(2-tert-butyl-4-fluorophenoxy)methyl]azetidin-1-yl}(oxo)acetate

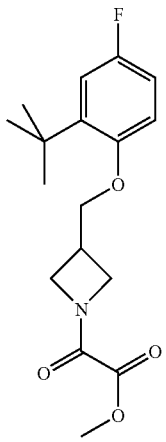 [SMILES: COC(=O)C(=O)N1CC(COc2ccc(F)cc2C(C)(C)C)C1]

According to a method similar to that in Example 124, the title compound (413 mg, 76%) was obtained from 3-[(2-tert-butyl-4-fluorophenoxy)methyl]azetidine (400 mg, 1.69 mmol) obtained in Reference Example 48 and methyl chloro(oxo)acetate (248 mg, 2.0 mmol).

¹H NMR (300 MHz, CDCl₃) δ 7.02 (dd, J=10.7, 3.0 Hz, 1H), 6.90-6.80 (m, 1H), 6.75 (dd, J=8.9, 4.7 Hz, 1H), 4.78-4.62 (m, 1H), 4.46 (ddd, J=10.7, 5.5, 1.1 Hz, 1H), 4.39-4.27 (m, 1H), 4.18-3.99 (m, 3H), 3.86 (s, 3H), 3.27-3.10 (m, 1H), 1.33 (s, 9H).

Example 149

{3-[(2-tert-butyl-4-fluorophenoxy)methyl]azetidin-1-yl}(oxo)acetic acid

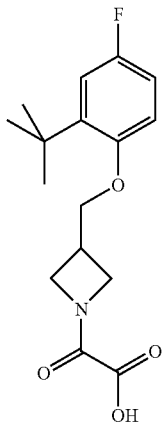 [SMILES: CC(C)(C)c1cc(F)ccc1OCC1CN(C(=O)C(=O)O)C1]

According to a method similar to that in Example 5, the title compound (345 mg, 87%) was obtained as a white solid from methyl {3-[(2-tert-butyl-4-fluorophenoxy)methyl]azetidin-1-yl}(oxo)acetate (413 mg, 1.28 mmol) obtained in Example 148.

¹H NMR (300 MHz, CDCl₃) δ 7.02 (dd, J=10.6, 3.0 Hz, 1H), 6.90-6.80 (m, 1H), 6.76 (dd, J=8.7, 4.5 Hz, 1H), 4.92-4.78 (m, 1H), 4.61 (ddd, J=11.4, 5.7, 1.1 Hz, 1H), 4.45-4.33 (m, 1H), 4.15-4.07 (m, 3H), 3.34-3.17 (m, 1H), 1.33 (s, 9H).

Example 150

1-[3-(2-tert-butylphenoxy)azetidin-1-yl]-2-methyl-1-oxopropan-2-ol

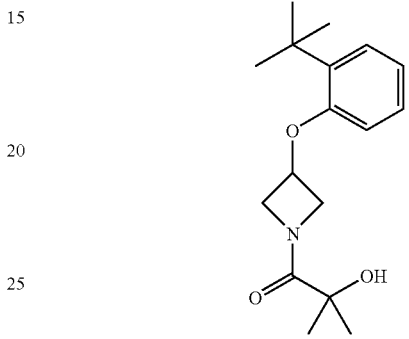

According to a method similar to that in Example 9, the title compound (97 mg, 69%) was obtained as a white solid from 3-(2-tert-butylphenoxy)azetidine (200 mg, 0.98 mmol) obtained in Reference Example 2 and 2-hydroxy-2-methylpropanoic acid (112 mg, 1.1 mmol).

¹H NMR (300 MHz, CDCl₃) δ 7.33 (dd, J=7.6, 1.5 Hz, 1H), 7.14 (td, J=8.0, 1.5 Hz, 1H), 7.01-6.91 (m, 1H), 6.47 (dd, J=8.0, 1.1 Hz, 1H), 5.08-4.93 (m, 1H), 4.86-4.67 (m, 1H), 4.55-4.32 (m, 2H), 4.28-4.08 (m, 1H), 3.41 (s, 1H), 1.43 (s, 6H), 1.40 (s, 9H).

Example 151

2-[3-(2-tert-butylphenoxy)azetidin-1-yl]-2-oxoethanol

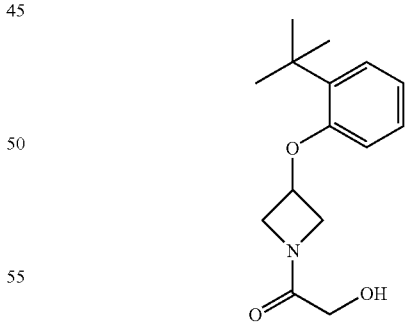

According to a method similar to that in Example 9, the title compound (64 mg, 250) was obtained as a white solid from 3-(2-tert-butylphenoxy)azetidine (200 mg, 0.97 mmol) obtained in Reference Example 2 and hydroxyacetic acid (80 mg, 1.05 mmol).

¹H NMR (300 MHz, CDCl₃) δ 7.33 (dd, J=7.7, 1.7 Hz, 1H), 7.20-7.11 (m, 1H), 6.98 (td, J=7.5, 1.3 Hz, 1H), 6.45 (dd, J=8.1, 1.1 Hz, 1H), 5.13-5.01 (m, 1H), 4.59-4.46 (m, 2H), 4.22-4.13 (m, 2H), 4.04 (d, J=4.5 Hz, 2H), 3.05 (t, J=4.5 Hz, 1H), 1.39 (s, 9H).

Example 152

4-[3-(2-tert-butylphenoxy)azetidin-1-yl]-2-methyl-4-oxobutan-2-ol

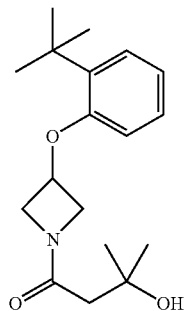 [SMILES: CC(C)(O)CC(=O)N1CC(Oc2ccccc2C(C)(C)C)C1]

According to a method similar to that in Example 9, the title compound (147 mg, 50%) was obtained as a white solid from 3-(2-tert-butylphenoxy)azetidine (200 mg, 0.97 mmol) obtained in Reference Example 2 and 3-hydroxy-3-methylbutanoic acid (124 mg, 1.05 mmol).

$^1$H NMR (300 MHz, CDCl$_3$) δ 7.33 (dd, J=7.6, 1.5 Hz, 1H), 7.20-7.10 (m, 1H), 6.96 (td, J=7.6, 1.1 Hz, 1H), 6.46 (dd, J=8.1, 0.9 Hz, 1H), 5.07-4.95 (m, 1H), 4.82 (s, 1H), 4.59-4.39 (m, 2H), 4.25-4.10 (m, 2H), 2.26 (s, 2H), 1.39 (s, 9H), 1.28 (s, 3H), 1.27 (s, 3H).

Example 153 methyl {4-[(2-tert-butyl-4-chlorophenoxy)methyl]piperidin-1-yl}(oxo)acetate

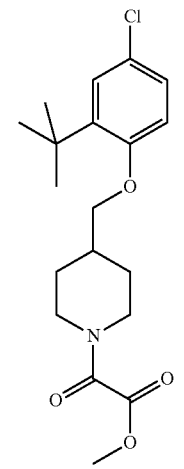 [SMILES: COC(=O)C(=O)N1CCC(COc2ccc(Cl)cc2C(C)(C)C)CC1]

According to a method similar to that in Example 124, the title compound (335 mg, 72%) was obtained as a white solid from 4-[(2-tert-butyl-4-chlorophenoxy)methyl]piperidine hydrochloride (400 mg, 1.26 mmol) obtained in Reference Example 67 and methyl chloro(oxo)acetate (185 mg, 1.51 mmol).

$^1$H NMR (300 MHz, CDCl$_3$) δ 7.23 (d, J=2.4 Hz, 1H), 7.11 (dd, J=8.7, 2.6 Hz, 1H), 6.75 (d, J=8.7 Hz, 1H), 4.66-4.54 (m, 1H), 3.88 (s, 3H), 3.87-3.80 (m, 2H), 3.80-3.70 (m, 1H), 3.26-3.10 (m, 1H), 2.85-2.70 (m, 1H), 2.28-2.07 (m, 1H), 2.00-1.89 (m, 2H), 1.39-1.29 (m, 11H).

Example 154

{4-[(2-tert-butyl-4-chlorophenoxy)methyl]piperidin-1-yl}(oxo)acetic acid

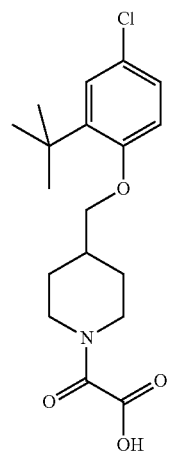

According to a method similar to that in Example 5, the title compound (213 mg, 98%) was obtained as a white solid from methyl {4-[(2-tert-butyl-4-chlorophenoxy)methyl]piperidin-1-yl}(oxo)acetate (226 mg, 0.614 mmol) obtained in Example 153.

$^1$H NMR (300 MHz, CDCl$_3$) δ 7.23 (d, J=2.6 Hz, 1H), 7.12 (dd, J=8.7, 2.6 Hz, 1H), 6.75 (d, J=8.7 Hz, 1H), 5.23-5.06 (m, 1H), 4.72-4.56 (m, 1H), 3.83 (d, J=6.4 Hz, 2H), 3.33-3.17 (m, 1H), 2.95-2.86 (m, 1H), 2.30-2.12 (m, 1H), 2.12-1.98 (m, 2H), 1.57-1.25 (m, 11H).

Example 155

2-({4-[(2-tert-butyl-4-chlorophenoxy)methyl]piperidin-1-yl}carbonyl)pyridine

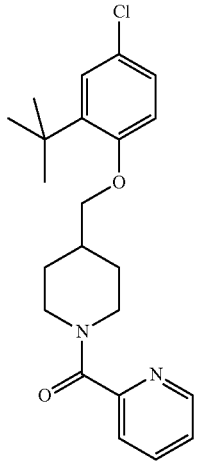 [SMILES: CC(C)(C)c1cc(Cl)ccc1OCC1CCN(C(=O)c2ccccn2)CC1]

According to a method similar to that in Example 124, the title compound (198 mg, 820) was obtained as a white solid from 4-[(2-tert-butyl-4-chlorophenoxy)methyl]piperidine hydrochloride (200 mg, 0.63 mmol) obtained in Reference Example 67 and pyridine-2-carboxylic acid chloride hydrochloride (134 mg, 0.75 mmol).

$^1$H NMR (300 MHz, CDCl$_3$) δ 8.60 (br s, 1H), 7.79 (t, J=7.7 Hz, 1H), 7.62 (d, J=7.0 Hz, 1H), 7.40-7.30 (m, 1H), 7.22 (d, J=2.4 Hz, 1H), 7.11 (dd, J=8.7, 2.4 Hz, 1H), 6.76 (d, J=8.7 Hz, 1H), 4.93-4.74 (m, 1H), 4.10-3.93 (m, 1H), 3.93-3.71 (m, 2H), 3.23-3.05 (m, 1H), 2.98-2.77 (m, 1H), 2.29-2.09 (m, 1H), 2.10-1.95 (m, 1H), 1.95-1.83 (m, 1H), 1.41-1.21 (m, 11H).

Example 156 ethyl (2E)-3-(3-{[3-(2-tert-butylphenoxy)azetidin-1-yl]carbonyl}phenyl)prop-2-enoate

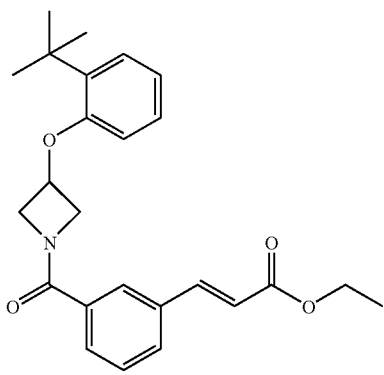 [SMILES: CCOC(=O)/C=C/c1cccc(C(=O)N2CC(Oc3ccccc3C(C)(C)C)C2)c1]

According to a method similar to that in Example 9, the title compound (532 mg, 67%) was obtained as a pale yellow solid from 3-(2-tert-butylphenoxy)azetidine (400 mg, 1.95 mmol) obtained in Reference Example 2 and 3-[(1E)-3-ethoxy-3-oxoprop-1-en-1-yl]benzoic acid (472 mg, 2.14 mmol) obtained in Reference Example 72.

$^1$H NMR (300 MHz, CDCl$_3$) δ 7.84-7.77 (m, 1H), 7.73-7.59 (m, 3H), 7.45 (t, J=7.6 Hz, 1H), 7.33 (dd, J=8.0, 1.9 Hz, 1H), 7.14 (td, J=7.7, 1.7 Hz, 1H), 6.95 (td, J=7.5, 1.3 Hz, 1H), 6.53-6.43 (m, 2H), 5.11-4.99 (m, 1H), 4.72-4.60 (m, 2H), 4.37 (br s, 2H), 4.28 (q, J=7.2 Hz, 2H), 1.41 (s, 9H), 1.34 (t, J=7.0 Hz, 3H).

Example 157

(2E)-3-(3-{[3-(2-tert-butylphenoxy)azetidin-1-yl]carbonyl}phenyl)prop-2-enoic acid

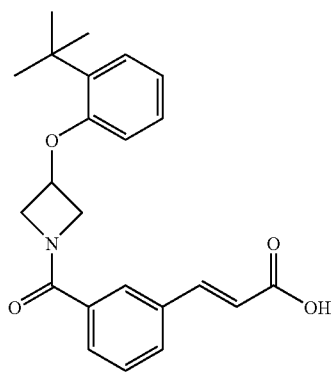 [SMILES: CC(C)(C)c1ccccc1OC1CN(C(=O)c2cccc(/C=C/C(=O)O)c2)C1]

According to a method similar to that in Example 5, the title compound (296 mg, quant.) was obtained as a white solid from ethyl (2E)-3-(3-{[3-(2-tert-butylphenoxy)azetidin-1-yl]carbonyl}phenyl)prop-2-enoate (294 mg, 0.72 mmol) obtained in Example 156.

$^1$H NMR (300 MHz, CDCl$_3$) δ 7.88-7.83 (m, 1H), 7.79 (d, J=16.0 Hz, 1H), 7.71-7.63 (m, 2H), 7.47 (t, J=7.7 Hz, 1H), 7.33 (dd, J=7.7, 1.7 Hz, 1H), 7.14 (td, J=7.7, 1.7 Hz, 1H), 6.97 (td, J=7.5, 1.1 Hz, 1H), 6.56-6.43 (m, 2H), 5.13-5.00 (m, 1H), 4.76-4.60 (m, 2H), 4.38 (br s, 2H), 1.41 (s, 9H).

Example 158 ethyl 3-(3-{[3-(2-tert-butylphenoxy)azetidin-1-yl]carbonyl}phenyl)propanoate

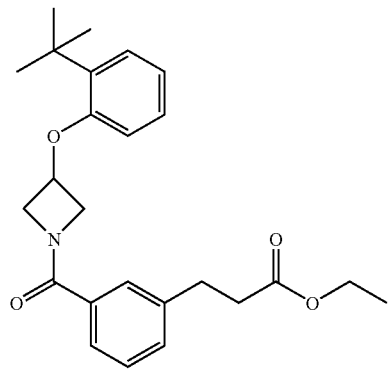 [SMILES: CCOC(=O)CCc1cccc(C(=O)N2CC(Oc3ccccc3C(C)(C)C)C2)c1]

According to a method similar to that in Example 9, the title compound (512 mg, 64%) was obtained as a colorless oil from 3-(2-tert-butylphenoxy)azetidine (400 mg, 1.95 mmol) obtained in Reference Example 2 and 3-(3-ethoxy-3-oxopropyl)benzoic acid (520 mg, 2.34 mmol) obtained in Reference Example 73.

$^1$H NMR (300 MHz, CDCl$_3$) δ 7.52 (s, 1H), 7.50-7.42 (m, 1H), 7.38-7.29 (m, 3H), 7.13 (td, J=7.7, 1.7 Hz, 1H), 6.99-6.89 (m, 1H), 6.46 (dd, J=8.3, 1.1 Hz, 1H), 5.10-4.97 (m, 1H), 4.71-4.57 (m, 2H), 4.41-4.23 (m, 2H), 4.11 (q, J=7.2 Hz, 2H), 2.98 (t, J=7.8 Hz, 2H), 2.63 (t, J=7.8 Hz, 2H), 1.41 (s, 9H), 1.22 (t, J=7.2 Hz, 3H).

Example 159

3-(3-{[3-(2-tert-butylphenoxy)azetidin-1-yl]carbonyl}phenyl)propanoic acid

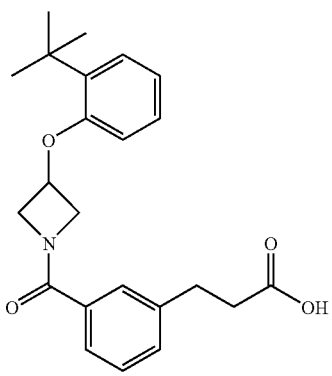

According to a method similar to that in Example 5, the title compound (163 mg, 63%) was obtained as a white solid from ethyl 3-(3-{[3-(2-tert-butylphenoxy)azetidin-1-yl]carbonyl}phenyl)propanoate (280 mg, 0.68 mmol) obtained in Example 158.

$^1$H NMR (300 MHz, CDCl$_3$) δ 7.53 (s, 1H), 7.51-7.41 (m, 1H), 7.39-7.29 (m, 3H), 7.13 (td, J=7.7, 1.7 Hz, 1H), 7.00-6.87 (m, 1H), 6.46 (dd, J=8.3, 1.1 Hz, 1H), 5.10-4.98 (m, 1H), 4.71-4.59 (m, 2H), 4.34 (br s, 2H), 2.99 (t, J=7.6 Hz, 2H), 2.69 (t, J=7.6 Hz, 2H), 1.40 (s, 9H).

Example 160

2-{[3-(2-tert-butylphenoxy)azetidin-1-yl]carbonyl}phenol

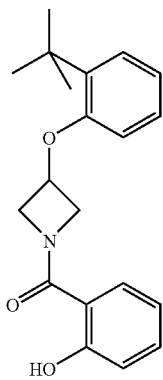 [SMILES: CC(C)(C)c1ccccc1OC1CN(C(=O)c2ccccc2O)C1]

According to a method similar to that in Example 9, the title compound (757 mg, 68%) was obtained from 3-(2-tert-butylphenoxy)azetidine (700 mg, 3.41 mmol) obtained in Reference Example 2 and 2-hydroxybenzoic acid (518 mg, 3.75 mmol).

$^1$H NMR (300 MHz, CDCl$_3$) δ 12.04 (s, 1H), 7.43-7.31 (m, 3H), 7.16 (td, J=7.7, 1.7 Hz, 1H), 7.03-6.90 (m, 2H), 6.88-6.75 (m, 1H), 6.48 (dd, J=8.1, 1.1 Hz, 1H), 5.15-5.04 (m, 1H), 4.81 (br s, 2H), 4.50 (br s, 2H), 1.41 (s, 9H).

Example 161

2-{4-[(2-tert-butylphenoxy)methyl]piperidin-1-yl}-N-(2-methoxyethyl)-2-oxoacetamido

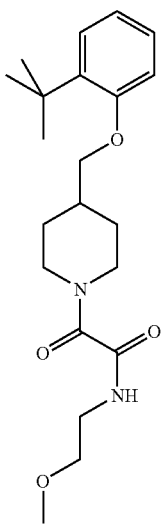 [SMILES: COCCNC(=O)C(=O)N1CCC(COc2ccccc2C(C)(C)C)CC1]

According to a method similar to that in Example 9, the title compound (199 mg, 93%) was obtained as a colorless oil from {4-[(2-tert-butylphenoxy)methyl]piperidin-1-yl}(oxo)acetic acid (200 mg, 0.565 mmol) obtained in Example 96 and 2-methoxyethaneamine (43 mg, 0.57 mmol).

$^1$H NMR (300 MHz, CDCl$_3$) δ 7.39 (br s, 1H), 7.33-7.26 (m, 1H), 7.17 (td, J=7.7, 1.3 Hz, 1H), 6.90 (td, J=7.5, 0.7 Hz, 1H), 6.86 (d, J=8.3 Hz, 1H), 5.10-4.89 (m, 1H), 4.70-4.54 (m, 1H), 3.85 (d, J=6.4 Hz, 2H), 3.56-3.44 (m, 4H), 3.37 (s, 3H), 3.14 (td, J=13.2, 2.8 Hz, 1H), 2.78 (td, J=12.9, 2.8 Hz, 1H), 2.30-2.09 (m, 1H), 2.09-1.91 (m, 2H), 1.52-1.32 (m, 11H).

Example 162

2-{4-[(2-tert-butylphenoxy)methyl]piperidin-1-yl}-N-(2-hydroxyethyl)-2-oxoacetamido

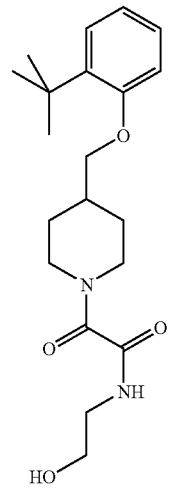

According to a method similar to that in Example 9, the title compound (58 mg, 38%) was obtained as a white solid from {4-[(2-tert-butylphenoxy)methyl]piperidin-1-yl}(oxo)acetic acid (150 mg, 0.42 mmol) obtained in Example 96 and 2-aminoethanol (27 mg, 0.44 mmol).

$^1$H NMR (300 MHz, CDCl$_3$) δ 7.50 (br s, 1H), 7.34-7.27 (m, 1H), 7.22-7.11 (m, 1H), 6.90 (td, J=7.5, 1.3 Hz, 1H), 6.84 (dd, J=8.1, 0.9 Hz, 1H), 5.08-4.94 (m, 1H), 4.70-4.53 (m, 1H), 3.86 (d, J=6.4 Hz, 2H), 3.83-3.73 (m, 2H), 3.55-3.42 (m, 2H), 3.22-3.06 (m, 1H), 2.88-2.72 (m, 1H), 2.33-2.09 (m, 2H), 2.09-1.89 (m, 2H), 1.56-1.29 (m, 11H).

Example 163

2-{4-[(2-tert-butylphenoxy)methyl]piperidin-1-yl}-N-methoxy-2-oxoacetamido

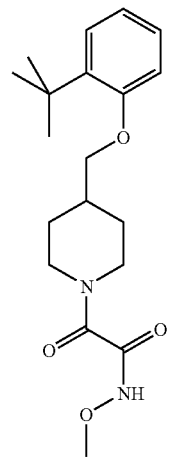

According to a method similar to that in Example 9, the title compound (60 mg, 41%) was obtained as a white solid from {4-[(2-tert-butylphenoxy)methyl]piperidin-1-yl}(oxo)acetic acid (150 mg, 0.42 mmol) obtained in Example 96 and (aminooxy)methane hydrochloride (37 mg, 0.44 mmol).

$^1$H NMR (300 MHz, CDCl$_3$) δ 9.39 (br s, 1H), 7.32-7.23 (m, 1H), 7.17 (td, J=7.7, 1.7 Hz, 1H), 6.94-6.86 (m, 1H), 6.84 (d, J=8.3 Hz, 1H), 5.01-4.87 (m, 1H), 4.66-4.50 (m, 1H), 3.86 (d, J=6.1 Hz, 2H), 3.83 (s, 3H), 3.24-3.10 (m, 1H), 2.78 (td, J=12.8, 2.8 Hz, 1H), 2.30-2.10 (m, 1H), 2.09-1.94 (m, 2H), 1.52-1.21 (m, 11H).

Example 164

2-{[3-(2-tert-butyl-4-chlorophenoxy)azetidin-1-yl]carbonyl}pyridine

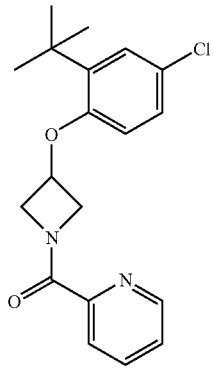 [SMILES: CC(C)(C)c1cc(Cl)ccc1OC1CN(C(=O)c2ccccn2)C1]

A solution of 3-(2-tert-butyl-4-chlorophenoxy)azetidine (200 mg, 0.83 mmol) obtained in Reference Example 44, pyridine-2-carboxylic acid chloride hydrochloride (178 mg, 1.0 mmol) and triethylamine (307 μl, 2.2 mmol) in THF (10 mL) was stirred at room temperature for 16 hr. Saturated brine was added to the reaction mixture, and the mixture was extracted with ethyl acetate. The ethyl acetate layer was washed with saturated brine, dried over anhydrous magnesium sulfate and filtered. The filtrate was concentrated under reduced pressure, and the obtained residue was purified by silica gel column chromatography (hexane:ethyl acetate 40:60-20:80) to give the title compound (200 mg, 70%) as a white solid.

$^1$H NMR (300 MHz, CDCl$_3$) δ 8.66-8.48 (m, 1H), 8.26-8.06 (m, 1H), 7.82 (td, J=7.8, 1.5 Hz, 1H), 7.38 (ddd, J=6.9, 5.6, 1.1 Hz, 1H), 7.28-7.23 (m, 1H), 7.12 (dd, J=8.7, 2.7 Hz, 1H), 6.44 (d, J=8.7 Hz, 1H), 5.15 (ddd, J=11.4, 5.7, 1.5 Hz, 1H), 5.06-4.97 (m, 1H), 4.76 (ddd, J=11.4, 3.8, 1.5 Hz, 1H), 4.64 (ddd, J=11.4, 6.6, 1.7 Hz, 1H), 4.37-4.28 (m, 1H), 1.38 (s, 9H).

Example 165 methyl [3-(2-tert-butyl-4-chlorophenoxy)azetidin-1-yl](oxo)acetate

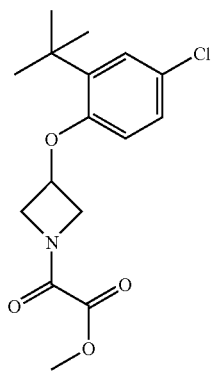 [SMILES: COC(=O)C(=O)N1CC(Oc2ccc(Cl)cc2C(C)(C)C)C1]

According to a method similar to that in Example 124, the title compound (398 mg, 73%) was obtained as a white solid from 3-(2-tert-butyl-4-chlorophenoxy)azetidine (400 mg, 1.67 mmol) obtained in Reference Example 44 and methyl chloro(oxo)acetate (245 mg, 2.0 mmol).

$^1$H NMR (300 MHz, CDCl$_3$) δ 7.28 (d, J=2.6 Hz, 1H), 7.11 (dd, J=8.7, 2.6 Hz, 1H), 6.37 (d, J=8.7 Hz, 1H), 5.06-4.87 (m, 2H), 4.64-4.49 (m, 2H), 4.27-4.16 (m, 1H), 3.87 (s, 3H), 1.38 (s, 9H).

Example 166

[3-(2-tert-butyl-4-chlorophenoxy)azetidin-1-yl](oxo)acetic acid

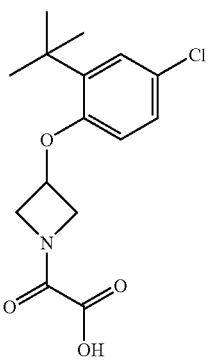 [SMILES: CC(C)(C)c1cc(Cl)ccc1OC1CN(C(=O)C(=O)O)C1]

According to a method similar to that in Example 5, the title compound (32 mg, 11%) was obtained as a white solid from methyl[3-(2-tert-butyl-4-chlorophenoxy)azetidin-1-yl](oxo)acetate (299 mg, 0.92 mmol) obtained in Example 165.

$^1$H NMR (300 MHz, CDCl$_3$) δ 7.28 (d, J=2.6 Hz, 1H), 7.12 (dd, J=8.7, 2.6 Hz, 1H), 6.36 (d, J=8.5 Hz, 1H), 5.13-4.96 (m, 2H), 4.78-4.67 (m, 1H), 4.65-4.55 (m, 1H), 4.34-4.21 (m, 1H), 1.38 (s, 9H).

Example 167

3-{[3-(2-tert-butylphenoxy)azetidin-1-yl]carbonyl}phenol

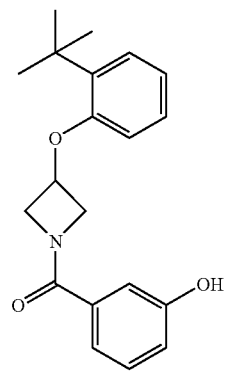 [SMILES: CC(C)(C)c1ccccc1OC1CN(C(=O)c2cccc(O)c2)C1]

According to a method similar to that in Example 9, the title compound (503 mg, 45%) was obtained as a white solid from 3-(2-tert-butylphenoxy)azetidine (700 mg, 3.41 mmol) obtained in Reference Example 2 and 3-hydroxybenzoic acid (518 mg, 3.75 mmol).

¹H NMR (300 MHz, CDCl₃) δ 7.36-7.23 (m, 3H), 7.19-7.09 (m, 2H), 7.00-6.87 (m, 2H), 6.46 (dd, J=8.3, 1.1 Hz, 1H), 5.81 (br s, 1H), 5.10-4.98 (m, 1H), 4.73-4.56 (m, 2H), 4.46-4.19 (m, 2H), 1.40 (s, 9H).

Example 168 methyl (3-{[3-(2-tert-butylphenoxy)azetidin-1-yl]carbonyl}phenoxy)acetate

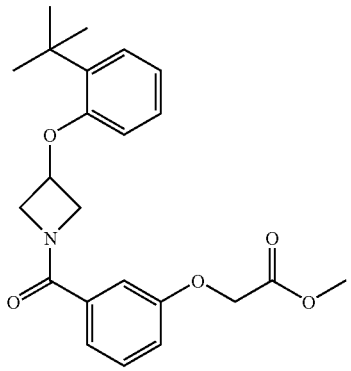 [SMILES: COC(=O)COc1cccc(C(=O)N2CC(Oc3ccccc3C(C)(C)C)C2)c1]

According to a method similar to that in Example 145, the title compound (380 mg, 92%) was obtained as a colorless oil from 3-{[3-(2-tert-butylphenoxy)azetidin-1-yl]carbonyl}phenol (339 mg, 1.04 mmol) obtained in Example 167.

¹H NMR (300 MHz, CDCl₃) δ 7.38-7.28 (m, 2H), 7.28-7.25 (m, 2H), 7.17-7.08 (m, 1H), 7.04 (ddd, J=8.1, 2.7, 0.9 Hz, 1H), 6.94 (td, J=7.4, 1.1 Hz, 1H), 6.46 (dd, J=8.0, 1.1 Hz, 1H), 5.10-4.94 (m, 1H), 4.70-4.54 (m, 4H), 4.45-4.20 (m, 2H), 3.80 (s, 3H), 1.40 (s, 9H).

Example 169

(3-{[3-(2-tert-butylphenoxy)azetidin-1-yl]carbonyl}phenoxy)acetic acid

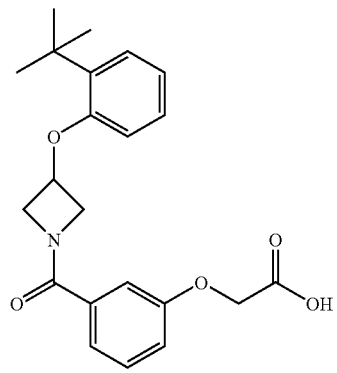 [SMILES: CC(C)(C)c1ccccc1OC1CN(C(=O)c2cccc(OCC(=O)O)c2)C1]

According to a method similar to that in Example 5, the title compound (327 mg, quant.) was obtained as a white solid from methyl (3-{[3-(2-tert-butylphenoxy)azetidin-1-yl]carbonyl}phenoxy)acetate (311 mg, 0.78 mmol) obtained in Example 168.

¹H NMR (300 MHz, CDCl₃) δ 7.37-7.30 (m, 2H), 7.29-7.19 (m, 2H), 7.18-7.02 (m, 2H), 6.95 (td, J=7.5, 1.1 Hz, 1H), 6.45 (dd, J=8.1, 1.1 Hz, 1H), 5.09-4.96 (m, 1H), 4.75-4.60 (m, 4H), 4.34 (br s, 2H), 1.40 (s, 9H).

Example 170 methyl (2-{[3-(2-tert-butylphenoxy)azetidin-1-yl]carbonyl}phenoxy)acetate

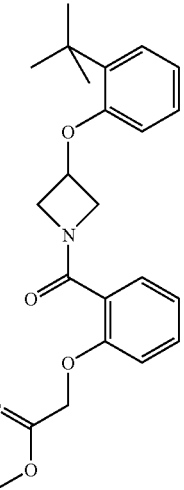

According to a method similar to that in Example 145, the title compound (582 mg, 83%) was obtained as a white solid from 2-{[3-(2-tert-butylphenoxy)azetidin-1-yl]carbonyl}phenol (571 mg, 1.75 mmol) obtained in Example 160.

¹H NMR (300 MHz, CDCl₃) δ 7.42 (dd, J=7.6, 1.9 Hz, 1H), 7.39-7.27 (m, 2H), 7.12 (td, J=15.5, 1.5 Hz, 1H), 7.04 (t, J=7.6 Hz, 1H), 6.92 (td, J=7.5, 1.3 Hz, 1H), 6.77 (d, J=8.3 Hz, 1H), 6.46 (dd, J=8.1, 0.9 Hz, 1H), 5.08-4.96 (m, 1H), 4.70 (s, 2H), 4.66-4.54 (m, 1H), 4.54-4.42 (m, 1H), 4.29 (ddd, J=10.9, 3.9, 1.1 Hz, 1H), 4.20 (ddd, J=9.9, 4.1, 1.1 Hz, 1H), 3.75 (s, 3H), 1.39 (s, 9H).

Example 171

(2-{[3-(2-tert-butylphenoxy)azetidin-1-yl]carbonyl}phenoxy)acetic acid

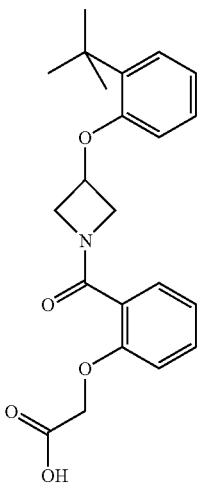 [SMILES: CC(C)(C)c1ccccc1OC1CN(C(=O)c2ccccc2OCC(=O)O)C1]

According to a method similar to that in Example 5, the title compound (302 mg, 97%) was obtained as a white solid from methyl (2-{[3-(2-tert-butylphenoxy)azetidin-1-yl]carbonyl}phenoxy)acetate (321 mg, 0.81 mmol) obtained in Example 170.

¹H NMR (300 MHz, CDCl₃) δ 7.73-7.41 (m, 1H), 7.34 (ddd, J=7.8, 3.8, 1.8 Hz, 2H), 7.20-7.04 (m, 3H), 7.01-6.89 (m, 1H), 6.49-6.37 (m, 1H), 5.13-4.99 (m, 1H), 4.82 (s, 2H), 4.76-4.65 (m, 1H), 4.65-4.49 (m, 1H), 4.43-4.25 (m, 2H), 1.41 (s, 9H).

Example 172

1-acryloyl-3-(2-tert-butylphenoxy)azetidine

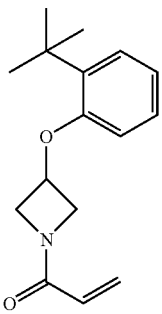 [SMILES: C=CC(=O)N1CC(Oc2ccccc2C(C)(C)C)C1]

The oily residue obtained according to a method similar to that in Example 5 from 3-[3-(2-tert-butylphenoxy)azetidin-1-yl]-3-oxopropylprop-2-enoate (150 mg, 0.45 mmol) obtained in Reference Example 74 was purified by silica gel column chromatography (hexane:ethyl acetate 20:80-10:90) to give the title compound (91 mg, 2 steps, 17%) as a white solid.

¹H NMR (300 MHz, CDCl₃) δ 7.33 (dd, J=7.7, 1.7 Hz, 1H), 7.15 (td, J=7.7, 1.7 Hz, 1H), 6.95 (td, J=7.5, 1.1 Hz, 1H), 6.48 (dd, J=8.1, 1.1 Hz, 1H), 6.37 (dd, J=17.0, 2.1 Hz, 1H), 6.21 (dd, J=17.0, 10.2 Hz, 1H), 5.71 (dd, J=10.2, 1.9 Hz, 1H), 5.09-4.95 (m, 1H), 4.69-4.58 (m, 1H), 4.58-4.42 (m, 1H), 4.36-4.27 (m, 1H), 4.27-4.11 (m, 1H), 1.39 (s, 9H).

Example 173

2-[4-(2-tert-butylphenoxy)piperidin-1-yl]-N-(2-hydroxyethyl)-2-oxoacetamido

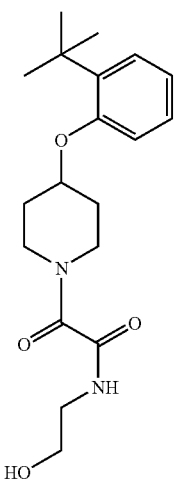 [SMILES: CC(C)(C)c1ccccc1OC1CCN(C(=O)C(=O)NCCO)CC1]

According to a method similar to that in Example 9, the title compound (331 mg, 97%) was obtained as a colorless oil from [4-(2-tert-butylphenoxy)piperidin-1-yl](oxo)acetic acid (300 mg, 0.98 mmol) obtained in Example 52 and 2-aminoethanol (60 mg, 0.98 mmol).

¹H NMR (300 MHz, CDCl₃) δ 7.59 (br s, 1H), 7.32 (dd, J=7.7, 1.7 Hz, 1H), 7.22-7.09 (m, 1H), 6.89 (td, J=7.5, 1.1 Hz, 1H), 6.83 (d, J=8.1 Hz, 1H), 4.79-4.67 (m, 1H), 4.28-4.12 (m, 2H), 3.79 (dd, J=7.3, 4.7 Hz, 4H), 3.50 (t, J=5.1 Hz, 2H), 2.34 (br s, 1H), 2.18-1.87 (m, 4H), 1.40 (s, 9H).

Example 174 benzyl 3-[4-(2-tert-butylphenoxy)piperidin-1-yl]-3-oxo-2-phenylpropanoate

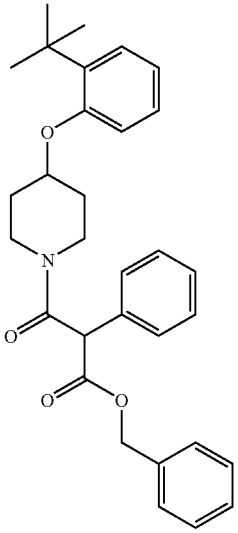 [SMILES: CC(C)(C)c1ccccc1OC1CCN(C(=O)C(C(=O)OCc2ccccc2)c2ccccc2)CC1]

According to a method similar to that in Example 9, the title compound (565 mg, 63%) was obtained as a white solid from 4-(2-tert-butylphenoxy)piperidine hydrochloride (500 mg, 1.85 mmol) obtained in Reference Example 15 and 3-(benzyloxy)-3-oxo-2-phenylpropanoic acid (514 mg, 1.90 mmol).

¹H NMR (300 MHz, CDCl₃) δ 7.48-7.22 (m, 11H), 7.17-7.04 (m, 1H), 6.90-6.79 (m, 1H), 6.79-6.61 (m, 1H), 5.22 (q, J=12.5 Hz, 2H), 4.92 (s, 1H), 4.66-4.38 (m, 1H), 4.07-3.84 (m, 1H), 3.70-3.45 (m, 2H), 3.45-3.22 (m, 1H), 2.08-1.86 (m, 1H), 1.86-1.70 (m, 2H), 1.38 (s, 5H), 1.31 (s, 4H), 1.29-1.13 (m, 1H).

Example 175

3-[4-(2-tert-butylphenoxy)piperidin-1-yl]-3-oxo-2-phenylpropan-1-ol

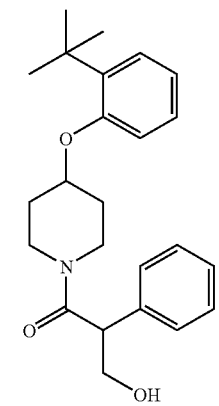 [SMILES: CC(C)(C)c1ccccc1OC1CCN(C(=O)C(CO)c2ccccc2)CC1]

Benzyl 3-[4-(2-tert-butylphenoxy)piperidin-1-yl]-3-oxo-2-phenylpropanoate (167 mg, 0.34 mmol) obtained in Example 174 and lithium tetrahydroborate (2.0M, THF solution, 0.41 mL, 0.82 mmol) were stirred at room temperature for 3 days. The reaction mixture was partitioned between ethyl acetate and saturated aqueous ammonium chloride, and the ethyl acetate layer was dried over anhydrous magnesium sulfate, and filtered. The filtrate was concentrated under reduced pressure, and the obtained residue was purified by silica gel column chromatography (hexane:ethyl acetate 75:25-25:75) to give the title compound (32 mg, 24%) as a colorless oil.

$^1$H NMR (300 MHz, CDCl$_3$) δ 7.40-7.18 (m, 6H), 7.16-7.04 (m, 1H), 6.90-6.80 (m, 1H), 6.80-6.63 (m, 1H), 4.62-4.43 (m, 1H), 4.18-3.90 (m, 3H), 3.84-3.66 (m, 1H), 3.64-3.42 (m, 2H), 3.42-3.13 (m, 2H), 2.09-1.88 (m, 1H), 1.88-1.57 (m, 2H), 1.38 (s, 5H), 1.29 (s, 4H), 1.24-1.05 (m, 1H).

Example 176

6-{[4-(2-tert-butylphenoxy)piperidin-1-yl]carbonyl}piperidin-2-one

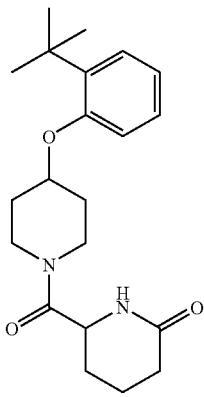 [SMILES: CC(C)(C)c1ccccc1OC1CCN(C(=O)C2CCCC(=O)N2)CC1]

According to a method similar to that in Example 9, the title compound (158 mg, 60%) was obtained as a white solid from 4-(2-tert-butylphenoxy)piperidine hydrochloride (200 mg, 0.74 mmol) obtained in Reference Example 15 and 6-oxopiperidine-2-carboxylic acid (111 mg, 0.78 mmol).

$^1$H NMR (300 MHz, CDCl$_3$) δ 7.33 (dd, J=8.0, 1.9 Hz, 1H), 7.21-7.10 (m, 1H), 6.99-6.86 (m, 1H), 6.82 (d, J=8.0 Hz, 1H), 6.02 (br s, 1H), 4.76-4.63 (m, 1H), 4.43-4.28 (m, 1H), 3.90-3.62 (m, 3H), 3.61-3.39 (m, 1H), 2.42 (t, J=6.8 Hz, 2H), 2.03-1.87 (m, 6H), 1.87-1.78 (m, 1H), 1.78-1.64 (m, 1H), 1.40 (s, 9H).

Example 177

4-(2-tert-butylphenoxy)-1-(phenylacetyl)piperidine

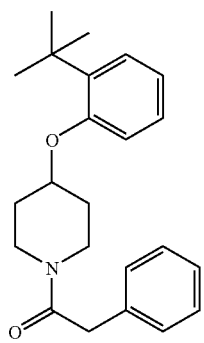 [SMILES: CC(C)(C)c1ccccc1OC1CCN(C(=O)Cc2ccccc2)CC1]

The oily residue obtained by a method similar to that in Example 5 from benzyl 3-[4-(2-tert-butylphenoxy)piperidin-1-yl]-3-oxo-2-phenylpropanoate (203 mg, 0.42 mmol) obtained in Example 174 was purified by preparative HPLC (device: Gilson Inc., High Throughput Purification system; column: YMC Combiprep ODS-A, S-5 µm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), 5.60 min (SOLUTION A/SOLUTION B=90/10); flow rate: 25 mL/min; detection method: UV 220 nm) to give the title compound (136 mg, 93%) as a white solid.

$^1$H NMR (300 MHz, CDCl$_3$) δ 7.41-7.30 (m, 3H), 7.30-7.19 (m, 3H), 7.18-7.07 (m, 1H), 6.87 (td, J=7.6, 1.1 Hz, 1H), 6.76 (d, J=8.0 Hz, 1H), 4.68-4.54 (m, 1H), 3.97-3.80 (m, 3H), 3.80-3.59 (m, 2H), 3.58-3.42 (m, 1H), 2.00-1.92 (m, 2H), 1.79-1.59 (m, 2H), 1.37 (s, 9H).

Example 178

3-[3-(2-tert-butylphenoxy)azetidin-1-yl]-3-oxopropane-1,2-diol

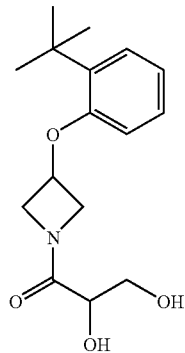 [SMILES: CC(C)(C)c1ccccc1OC1CN(C(=O)C(O)CO)C1]

According to a method similar to that in Example 9, the title compound (104 mg, 36%) was obtained as a white solid from 3-(2-tert-butylphenoxy)azetidine (200 mg, 0.97 mmol) obtained in Reference Example 2 and 2,3-dihydroxypropanoic acid (103 mg, 0.97 mmol).

$^1$H NMR (300 MHz, CDCl$_3$) δ 7.33 (dd, J=7.6, 1.5 Hz, 1H), 7.15 (td, J=7.6, 1.5 Hz, 1H), 6.96 (td, J=7.6, 1.1 Hz, 1H), 6.45 (dd, J=8.0, 0.8 Hz, 1H), 5.16-4.98 (m, 1H), 4.75-4.42 (m, 2H), 4.42-4.09 (m, 3H), 3.85-3.63 (m, 2H), 3.48 (d, J=6.8 Hz, 1H), 2.28 (t, J=6.2 Hz, 1H), 1.39 (s, 9H).

Example 179

3-{[4-(2-tert-butylphenoxy)piperidin-1-yl]carbonyl}pyridin-2(1H)-on

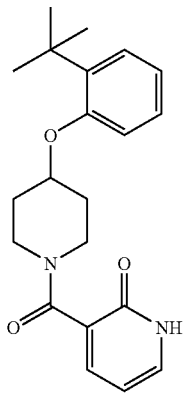 [SMILES: CC(C)(C)c1ccccc1OC1CCN(C(=O)c2ccc[nH]c2=O)CC1]

According to a method similar to that in Example 9, the title compound (54 mg, 21%) was obtained as a white solid from 4-(2-tert-butylphenoxy)piperidine hydrochloride (194 mg, 0.72 mmol) obtained in Reference Example 15 and 2-oxo-1,2-dihydropyridine-3-carboxylic acid (100 mg, 0.72 mmol).

$^1$H NMR (300 MHz, CDCl$_3$) δ 12.93 (br s, 1H), 7.64 (dd, J=7.0, 2.3 Hz, 1H), 7.44 (dd, J=6.4, 2.1 Hz, 1H), 7.31 (dd, J=7.7, 1.7 Hz, 1H), 7.22-7.10 (m, 1H), 6.94-6.78 (m, 2H), 6.36 (t, J=6.6 Hz, 1H), 4.81-4.60 (m, 1H), 4.04-3.80 (m, 2H), 3.73-3.53 (m, 1H), 3.52-3.25 (m, 1H), 2.13-1.88 (m, 4H), 1.40 (s, 9H).

Example 180

6-{[4-(2-tert-butylphenoxy)piperidin-1-yl]carbonyl}pyridin-2-ol

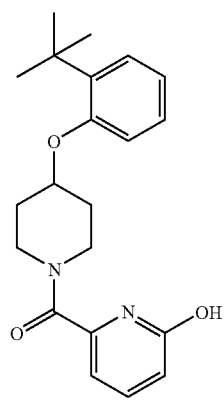 [SMILES: CC(C)(C)c1ccccc1OC1CCN(C(=O)c2cccc(O)n2)CC1]

According to a method similar to that in Example 9, the title compound (189 mg, 72%) was obtained as a white solid from 4-(2-tert-butylphenoxy)piperidine hydrochloride (200 mg, 0.741 mmol) obtained in Reference Example 15 and 6-hydroxypyridine-2-carboxylic acid (108 mg, 0.79 mmol).

$^1$H NMR (300 MHz, CDCl$_3$) δ 10.38 (br s, 1H), 7.42 (dd, J=9.1, 6.4 Hz, 1H), 7.33 (dd, J=7.6, 1.5 Hz, 1H), 7.17 (td, J=15.5, 1.9 Hz, 1H), 6.90 (t, J=7.6 Hz, 1H), 6.83 (d, J=8.0 Hz, 1H), 6.66 (d, J=10.2 Hz, 1H), 6.37 (d, J=6.8 Hz, 1H), 4.81-4.67 (m, 1H), 3.92-3.67 (m, 4H), 2.17-1.92 (m, 4H), 1.41 (s, 9H).

Example 181

4-(2-tert-butylphenoxy)-1-[(1,1-dioxidoisothiazolidin-3-yl)carbonyl]piperidine

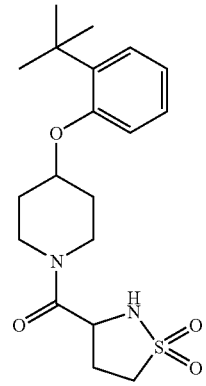 [SMILES: CC(C)(C)c1ccccc1OC1CCN(C(=O)C2CCS(=O)(=O)N2)CC1]

According to a method similar to that in Example 9, the title compound (172 mg, 61%) was obtained as a white solid from 4-(2-tert-butylphenoxy)piperidine hydrochloride (200 mg, 0.741 mmol) obtained in Reference Example 15 and isothiazolidine-3-carboxylic acid 1,1-dioxide (122 mg, 0.741 mmol).

$^1$H NMR (300 MHz, CDCl$_3$) δ 7.33 (d, J=6.4 Hz, 1H), 7.16 (t, J=7.2 Hz, 1H), 6.91 (t, J=7.2 Hz, 1H), 6.82 (d, J=8.3 Hz, 1H), 5.49 (br s, 1H), 4.88-4.56 (m, 1H), 4.54-4.22 (m, 1H), 4.09-3.59 (m, 3H), 3.58-3.38 (m, 1H), 3.28-3.13 (m, 1H), 3.05-2.86 (m, 1H), 2.86-2.65 (m, 1H), 2.48-2.21 (m, 1H), 2.13-1.88 (m, 4H), 1.47-1.33 (m, 9H).

Example 182

6-{[3-(2-tert-butyl-4-fluorophenoxy)azetidin-1-yl]carbonyl}pyridin-2-ol

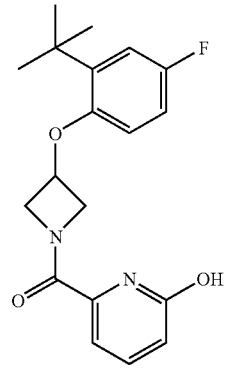 [SMILES: CC(C)(C)c1cc(F)ccc1OC1CN(C(=O)c2cccc(O)n2)C1]

According to a method similar to that in Example 9, the title compound (182 mg, 39%) was obtained as a white solid from 3-(2-tert-butyl-4-fluorophenoxy)azetidine (300 mg, 1.34 mmol) obtained in Reference Example 5 and 6-hydroxy-pyridine-2-carboxylic acid (187 mg, 1.34 mmol).

¹H NMR (300 MHz, CDCl₃) δ 9.68 (br s, 1H), 7.41 (dd, J=9.5, 6.8 Hz, 1H), 7.06 (dd, J=10.6, 3.0 Hz, 1H), 6.90-6.77 (m, 1H), 6.74 (d, J=9.5 Hz, 1H), 6.43 (d, J=6.8 Hz, 1H), 6.39 (dd, J=9.1, 4.9 Hz, 1H), 5.13-4.98 (m, 1H), 4.98-4.76 (m, 1H), 4.76-4.62 (m, 1H), 4.62-4.45 (m, 1H), 4.45-4.12 (m, 1H), 1.39 (s, 9H).

Example 183

6-{[3-(2-tert-butyl-4-fluorophenoxy)azetidin-1-yl]carbonyl}piperidin-2-one

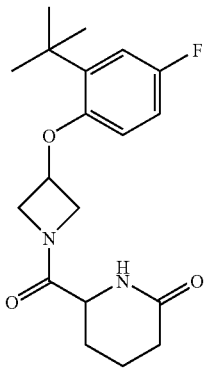 [SMILES: CC(C)(C)c1cc(F)ccc1OC1CN(C(=O)C2CCCC(=O)N2)C1]

According to a method similar to that in Example 9, the title compound (330 mg, 70%) was obtained as a white solid from 3-(2-tert-butyl-4-fluorophenoxy)azetidine (300 mg, 1.34 mmol) obtained in Reference Example 5 and 6-oxopiperidine-2-carboxylic acid (192 mg, 1.34 mmol).

¹H NMR (300 MHz, CDCl₃) δ 7.05 (dd, J=10.6, 3.0 Hz, 1H), 6.87-6.76 (m, 1H), 6.37 (dd, J=8.7, 4.5 Hz, 1H), 6.04-5.87 (m, 1H), 5.05-4.84 (m, 1H), 4.66-4.40 (m, 2H), 4.19-4.00 (m, 3H), 2.48-2.33 (m, 2H), 2.20-1.88 (m, 2H), 1.88-1.65 (m, 2H), 1.38 (s, 9H).

Example 184 ethyl 3-{4-[(2-tert-butyl-4-chlorophenoxy)methyl]piperidin-1-yl}-3-oxopropanoate

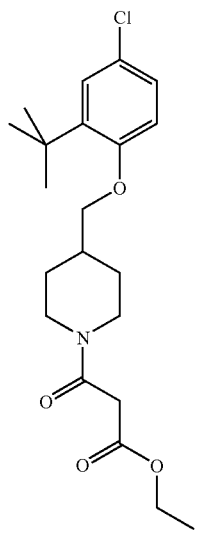 [SMILES: CCOC(=O)CC(=O)N1CCC(COc2ccc(Cl)cc2C(C)(C)C)CC1]

According to a method similar to that in Example 9, the title compound (327 mg, 83%) was obtained as a colorless oil from methyl {4-[(2-tert-butyl-4-chlorophenoxy)methyl]piperidin-1-yl}(oxo)acetate (318 mg, 1.0 mmol) obtained in Example 153 and 3-ethoxy-3-oxopropanoic acid (159 mg, 1.20 mmol).

¹H NMR (300 MHz, CDCl₃) δ 7.23 (d, J=2.7 Hz, 1H), 7.11 (dd, J=8.7, 2.7 Hz, 1H), 6.75 (d, J=8.7 Hz, 1H), 4.78-4.63 (m, 1H), 4.21 (q, J=7.2 Hz, 2H), 3.90-3.74 (m, 3H), 3.48 (s, 2H), 3.15 (td, J=13.1, 2.7 Hz, 1H), 2.68 (td, J=12.9, 3.0 Hz, 1H), 2.22-2.05 (m, 1H), 2.04-1.83 (m, 2H), 1.36 (s, 9H), 1.29 (t, J=7.2 Hz, 3H), 1.48-1.25 (m, 2H).

Example 185

3-{4-[(2-tert-butyl-4-chlorophenoxy)methyl]piperidin-1-yl}-3-oxopropanoic acid

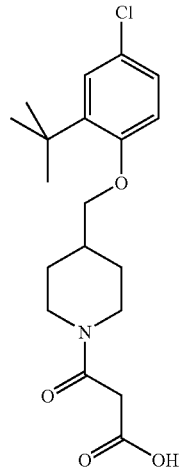 [SMILES: CC(C)(C)c1cc(Cl)ccc1OCC1CCN(C(=O)CC(=O)O)CC1]

According to a method similar to that in Example 5, the title compound (261 mg, 93%) was obtained as a white solid from ethyl 3-{4-[(2-tert-butyl-4-chlorophenoxy)methyl]piperidin-1-yl}-3-oxopropanoate (301 mg, 0.761 mmol) obtained in Example 184.

¹H NMR (300 MHz, CDCl₃) δ 7.24 (d, J=2.6 Hz, 1H), 7.12 (dd, J=8.7, 2.6 Hz, 1H), 6.75 (d, J=8.7 Hz, 1H), 4.80-4.68 (m, 1H), 3.95-3.77 (m, 3H), 3.39 (s, 2H), 3.18 (td, J=13.0, 2.6 Hz, 1H), 2.78 (td, J=13.0, 3.2 Hz, 1H), 2.29-2.13 (m, 1H), 2.08-1.95 (m, 2H), 1.36 (s, 9H), 1.49-1.26 (m, 2H).

Example 186 methyl 4-{4-[(2-tert-butyl-4-chlorophenoxy)methyl]piperidin-1-yl}-4-oxobutanoate

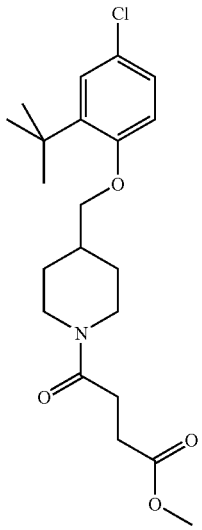 [SMILES: COC(=O)CCC(=O)N1CCC(COc2ccc(Cl)cc2C(C)(C)C)CC1]

According to a method similar to that in Example 124, the title compound (276 mg, 70%) was obtained as a colorless oil from methyl {4-[(2-tert-butyl-4-chlorophenoxy)methyl]piperidin-1-yl}(oxo)acetate (318 mg, 1.0 mmol) obtained in Example 0.153 and methyl 4-chloro-4-oxobutanoate (181 mg, 1.2 mmol).

$^1$H NMR (300 MHz, CDCl$_3$) δ 7.25-7.20 (m, 1H), 7.11 (dd, J=8.7, 2.7 Hz, 1H), 6.75 (d, J=8.7 Hz, 1H), 4.75-4.63 (m, 1H), 4.05-3.92 (m, 1H), 3.88-3.75 (m, 2H), 3.70 (s, 3H), 3.19-3.03 (m, 1H), 2.67 (s, 4H), 2.73-2.54 (m, 1H), 2.22-2.05 (m, 1H), 2.04-1.94 (m, 1H), 1.94-1.83 (m, 1H), 1.36 (s, 9H), 1.45-1.30 (m, 2H).

Example 187

4-{4-[(2-tert-butyl-4-chlorophenoxy)methyl]piperidin-1-yl}-4-oxobutanoic acid

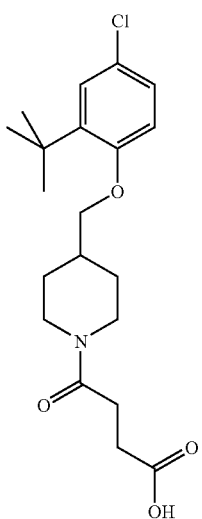 [SMILES: CC(C)(C)c1cc(Cl)ccc1OCC1CCN(C(=O)CCC(=O)O)CC1]

According to a method similar to that in Example 5, the title compound (260 mg, quant.) was obtained as a white solid from methyl 4-{4-[(2-tert-butyl-4-chlorophenoxy)methyl]piperidin-1-yl}-4-oxobutanoate (246 mg, 0.62 mmol) obtained in Example 186.

$^1$H NMR (300 MHz, CDCl$_3$) δ 7.23 (d, J=2.6 Hz, 1H), 7.12 (dd, J=8.7, 2.6 Hz, 1H), 6.75 (d, J=8.7 Hz, 1H), 4.78-4.66 (m, 1H), 4.01-3.89 (m, 1H), 3.88-3.76 (m, 2H), 3.15 (td, J=13.1, 3.0 Hz, 1H), 2.77-2.63 (m, 5H), 2.24-2.08 (m, 1H), 2.08-1.86 (m, 2H), 1.36 (s, 9H), 1.46-1.22 (m, 2H).

Example 188 methyl 4-[3-(2-tert-butyl-4-chlorophenoxy)azetidin-1-yl]-4-oxobutanoate

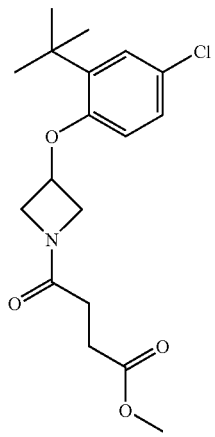 [SMILES: COC(=O)CCC(=O)N1CC(Oc2ccc(Cl)cc2C(C)(C)C)C1]

According to a method similar to that in Example 124, the title compound (338 mg, 46%) was obtained as a white solid from 3-(2-tert-butyl-4-chlorophenoxy)azetidine (500 mg, 2.09 mmol) obtained in Reference Example 44 and methyl 4-chloro-4-oxobutanoate (378 mg, 2.51 mmol).

$^1$H NMR (300 MHz, CDCl$_3$) δ 7.28-7.24 (m, 1H), 7.10 (dd, J=8.7, 2.7 Hz, 1H), 6.39 (d, J=8.7 Hz, 1H), 5.02-4.91 (m, 1H), 4.65-4.52 (m, 1H), 4.42 (dd, J=10.6, 6.8 Hz, 1H), 4.24 (dd, J=9.1, 3.4 Hz, 1H), 4.18-4.03 (m, 1H), 3.69 (s, 3H), 2.81-2.53 (m, 2H), 2.53-2.27 (m, 2H), 1.37 (s, 9H).

Example 189

4-[3-(2-tert-butyl-4-chlorophenoxy)azetidin-1-yl]-4-oxobutanoic acid

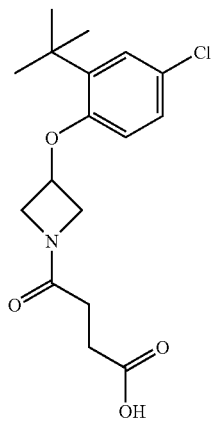 [SMILES: CC(C)(C)c1cc(Cl)ccc1OC1CN(C(=O)CCC(=O)O)C1]

To a stirred solution of methyl 4-[3-(2-tert-butyl-4-chlorophenoxy)azetidin-1-yl]-4-oxobutanoate (236 mg, 0.67 mmol) obtained in Example 188 in THF (5.0 ml) was added lithium hydroxide (1.0M aqueous solution, 5.0 mL, 5.0 mmol) at room temperature. After 3 hr, the reaction mixture was adjusted to about pH 1 with 1.0N hydrochloric acid. The obtained solution was concentrated under reduced pressure, and the mixture was extracted with ethyl acetate. The organic layer was washed with saturated sodium chloride, dried (MgSO$_4$), filtered, and concentrated under reduced pressure to give the title compound (222 mg, 98%) as a white solid.

$^1$H NMR (300 MHz, CDCl$_3$) δ 7.27 (d, J=2.6 Hz, 1H), 7.11 (dd, J=8.5, 2.6 Hz, 1H), 6.38 (d, J=8.7 Hz, 1H), 5.03-4.93 (m, 1H), 4.64-4.54 (m, 1H), 4.46 (dd, J=10.0, 5.8 Hz, 1H), 4.25 (dd, J=9.4, 3.0 Hz, 1H), 4.14 (dd, J=11.3, 4.1 Hz, 1H), 2.82-2.61 (m, 2H), 2.56-2.36 (m, 2H), 1.37 (s, 9H).

Example 190 ethyl 3-[3-(2-tert-butyl-4-chlorophenoxy)azetidin-1-yl]-3-oxopropanoate

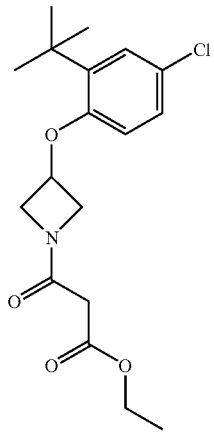 [SMILES: CCOC(=O)CC(=O)N1CC(Oc2ccc(Cl)cc2C(C)(C)C)C1]

According to a method similar to that in Example 9, the title compound (480 mg, 65%) was obtained as a colorless oil from 3-(2-tert-butyl-4-chlorophenoxy)azetidine (500 mg, 2.09 mmol) obtained in Reference Example 44 and 3-ethoxy-3-oxopropanoic acid (330 mg, 2.50 mmol).

$^1$H NMR (300 MHz, CDCl$_3$) δ 7.29-7.26 (m, 1H), 7.10 (dd, J=8.7, 2.7 Hz, 1H), 6.38 (d, J=8.7 Hz, 1H), 5.04-4.91 (m, 1H), 4.66-4.55 (m, 1H), 4.53-4.41 (m, 1H), 4.20 (q, J=7.2 Hz, 2H), 4.31-4.09 (m, 2H), 3.25 (s, 2H), 1.37 (s, 9H), 1.28 (t, J=7.2 Hz, 3H).

Example 191

3-[3-(2-tert-butyl-4-chlorophenoxy)azetidin-1-yl]-3-oxopropanoic acid

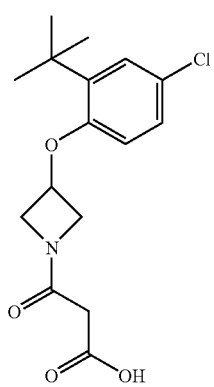 [SMILES: CC(C)(C)c1cc(Cl)ccc1OC1CN(C(=O)CC(=O)O)C1]

According to a method similar to that in Example 5, the title compound (378 mg, 98%) was obtained as a white solid from ethyl 3-[3-(2-tert-butyl-4-chlorophenoxy)azetidin-1-yl]-3-oxopropanoate (420 mg, 1.19 mmol) obtained in Example 190.

$^1$H NMR (300 MHz, CDCl$_3$) δ 7.29 (d, J=2.6 Hz, 1H), 7.12 (dd, J=8.7, 2.6 Hz, 1H), 6.36 (d, J=8.7 Hz, 1H), 5.09-4.99 (m, 1H), 4.67-4.48 (m, 2H), 4.34-4.25 (m, 1H), 4.20 (dd, J=11.7, 4.0 Hz, 1H), 3.22 (s, 2H), 1.38 (s, 9H).

Example 192 methyl 4-{3-[(2-tert-butylphenoxy)methyl]azetidin-1-yl}-4-oxobutanoate

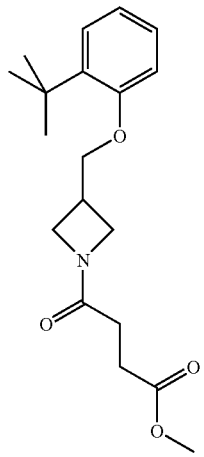 [SMILES: COC(=O)CCC(=O)N1CC(COc2ccccc2C(C)(C)C)C1]

According to a method similar to that in Example 124, the title compound (552 mg, 91%) was obtained as a colorless oil from 3-[(2-tert-butylphenoxy)methyl]azetidine hydrochloride (500 mg, 1.83 mmol) obtained in Reference Example 32 and methyl 4-chloro-4-oxobutanoate (330 mg, 2.19 mmol).

$^1$H NMR (300 MHz, CDCl$_3$) δ 7.30 (dd, J=7.6, 1.5 Hz, 1H), 7.22-7.14 (m, 1H), 6.92 (td, J=7.6, 1.1 Hz, 1H), 6.86 (dd, J=8.3, 1.1 Hz, 1H), 4.43-4.33 (m, 1H), 4.24-4.13 (m, 3H), 4.09 (dd, J=8.7, 5.3 Hz, 1H), 3.92 (dd, J=10.0, 5.5 Hz, 1H), 3.69 (s, 3H), 3.23-3.04 (m, 1H), 2.79-2.56 (m, 2H), 2.50-2.28 (m, 2H), 1.36 (s, 9H).

Example 193

4-{3-[(2-tert-butylphenoxy)methyl]azetidin-1-yl}-4-oxobutanoic acid

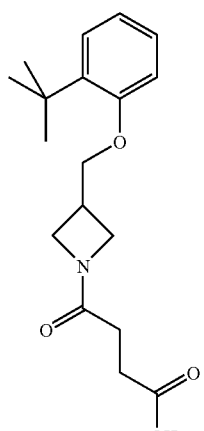

According to a method similar to that in Example 5, the title compound (466 mg, quant.) was obtained as a white solid from methyl 4-{3-[(2-tert-butylphenoxy)methyl]azetidin-1-yl}-4-oxobutanoate (462 mg, 1.38 mmol) obtained in Example 192.

¹H NMR (300 MHz, CDCl₃) δ 7.31 (dd, J=7.7, 1.7 Hz, 1H), 7.23-7.15 (m, 1H), 6.94 (td, J=7.5, 1.1 Hz, 1H), 6.85 (dd, J=8.1, 1.1 Hz, 1H), 4.38 (t, J=8.6 Hz, 1H), 4.25 (t, J=9.4 Hz, 1H), 4.19-4.10 (m, 3H), 4.03 (dd, J=10.4, 5.5 Hz, 1H), 3.27-3.10 (m, 1H), 2.74-2.65 (m, 2H), 2.51-2.45 (m, 2H), 1.36 (s, 9H).

Example 194 ethyl 3-{3-[(2-tert-butylphenoxy)methyl]azetidin-1-yl}-3-oxopropanoate

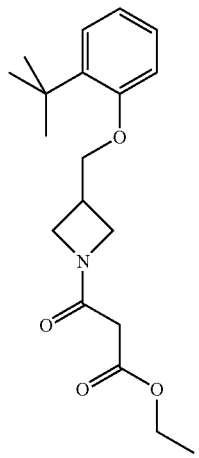 [SMILES: CCOC(=O)CC(=O)N1CC(COc2ccccc2C(C)(C)C)C1]

According to a method similar to that in Example 9, the title compound (576 mg, 95%) was obtained as a white solid from 3-[(2-tert-butylphenoxy)methyl]azetidine hydrochloride (500 mg, 1.83 mmol) obtained in Reference Example 32 and 3-ethoxy-3-oxopropanoic acid (289 mg, 2.19 mmol).

¹H NMR (300 MHz, CDCl₃) δ 7.30 (dd, J=8.0, 1.9 Hz, 1H), 7.23-7.14 (m, 1H), 6.93 (td, J=7.5, 1.3 Hz, 1H), 6.85 (dd, J=8.1, 0.9 Hz, 1H), 4.45-4.33 (m, 1H), 4.29-4.07 (m, 6H), 3.97 (dd, J=10.2, 5.3 Hz, 1H), 3.26-3.08 (m, 3H), 1.36 (s, 9H), 1.29 (t, J=7.2 Hz, 3H).

Example 195

3-{3-[(2-tert-butylphenoxy)methyl]azetidin-1-yl}-3-oxopropanoic acid

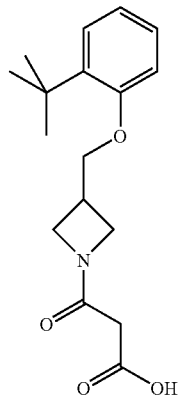 [SMILES: CC(C)(C)c1ccccc1OCC1CN(C(=O)CC(=O)O)C1]

According to a method similar to that in Example 5, the title compound (378 mg, 86%) was obtained as a white solid from ethyl 3-{3-[(2-tert-butylphenoxy)methyl]azetidin-1-yl}-3-oxopropanoate (480 mg, 1.44 mmol) obtained in Example 194.

¹H NMR (300 MHz, CDCl₃) δ 7.32 (dd, J=7.9, 1.7 Hz, 1H), 7.24-7.15 (m, 1H), 6.95 (td, J=7.5, 1.3 Hz, 1H), 6.85 (dd, J=8.1, 1.1 Hz, 1H), 4.40 (t, J=8.7 Hz, 1H), 4.31 (t, J=9.6 Hz, 1H), 4.24-4.05 (m, 4H), 3.32-3.19 (m, 1H), 3.17 (s, 2H), 1.36 (s, 9H)

Example 196 ethyl 3-{3-[(2-tert-butylphenoxy)methyl]pyrrolidin-1-yl}-3-oxopropanoate

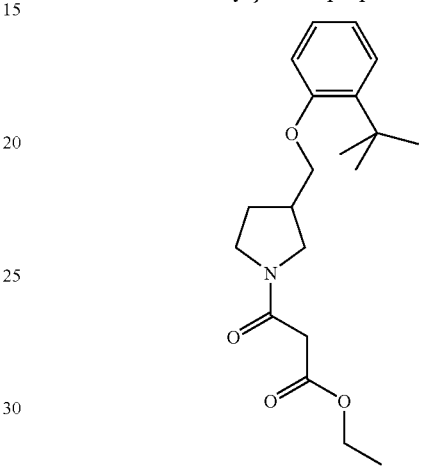

According to a method similar to that in Example 9, the title compound (565 mg, 88%) was obtained as a colorless oil from 3-[(2-tert-butylphenoxy)methyl]pyrrolidine hydrochloride (500 mg, 1.85 mmol) obtained in Reference Example 30 and 3-ethoxy-3-oxopropanoic acid (310 mg, 2.35 mmol).

¹H NMR (300 MHz, CDCl₃) δ 7.30 (dt, J=7.7, 2.0 Hz, 1H), 7.22-7.12 (m, 1H), 6.97-6.87 (m, 1H), 6.83 (dd, J=8.1, 1.1 Hz, 1H), 4.21 (quin, J=7.1 Hz, 2H), 4.08-3.47 (m, 5H), 3.45-3.27 (m, 3H), 2.98-2.70 (m, 1H), 2.36-2.09 (m, 1H), 2.06-1.77 (m, 1H), 1.38 (s, 9H), 1.28 (q, J=7.2 Hz, 3H).

Example 197

3-{3-[(2-tert-butylphenoxy)methyl]pyrrolidin-1-yl}-3-oxopropanoic acid

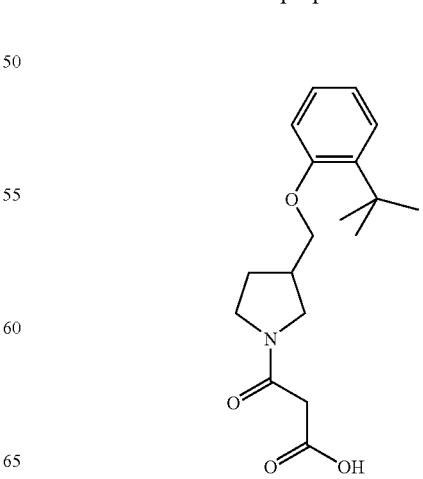

To a stirred solution of ethyl 3-{3-[(2-tert-butylphenoxy)methyl]pyrrolidin-1-yl}-3-oxopropanoate (500 mg, 1.44 mmol) obtained in Example 196 in THF (5.0 mL) was added lithium hydroxide (1.0M aqueous solution, 5.0 mL, 5.0 mmol) at room temperature. After 3 hr, the reaction mixture was adjusted to about pH 1 with 1.0N hydrochloric acid. The obtained solution was concentrated under reduced pressure, and the mixture was extracted with ethyl acetate. The organic layer was washed with saturated sodium chloride, dried (MgSO$_4$), filtered, and concentrated under reduced pressure to give the title compound (451 mg, 98%) as a white solid.

$^1$H NMR (300 MHz, CDCl$_3$) δ 14.11 (br s, 1H), 7.31 (dt, J=7.7, 1.7 Hz, 1H), 7.22-7.14 (m, 1H), 6.98-6.88 (m, 1H), 6.83 (d, J=8.3 Hz, 1H), 4.13-3.48 (m, 5H), 3.48-3.30 (m, 3H), 3.02-2.76 (m, 1H), 2.42-2.15 (m, 1H), 2.13-1.80 (m, 1H), 1.38 (s, 9H).

Example 198 ethyl {3-[(2-tert-butyl-4-chlorophenoxy)methyl]pyrrolidin-1-yl}(oxo)acetate

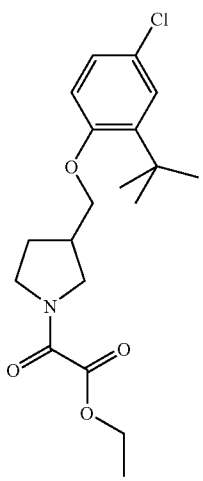 [SMILES: CCOC(=O)C(=O)N1CCC(COc2ccc(Cl)cc2C(C)(C)C)C1]

According to a method similar to that in Example 124, the title compound (576 mg, 95%) was obtained as a colorless oil from 3-[(2-tert-butyl-4-chlorophenoxy)methyl]pyrrolidine hydrochloride (500 mg, 1.64 mmol) obtained in Reference Example 61 and ethyl chloro(oxo)acetate (292 mg, 2.13 mmol).

$^1$H NMR (300 MHz, CDCl$_3$) δ 7.24 (d, J=2.6 Hz, 1H), 7.12 (dd, J=8.7, 2.4 Hz, 1H), 6.74 (dd, J=8.7, 1.9 Hz, 1H), 4.40-4.27 (m, 2H), 4.03-3.28 (m, 6H), 2.97-2.70 (m, 1H), 2.36-2.14 (m, 1H), 2.02-1.76 (m, 1H), 1.42-1.31 (m, 9H), 1.42-1.31 (m, 3H).

Example 199 ethyl 3-{3-[(2-tert-butyl-4-chlorophenoxy)methyl]pyrrolidin-1-yl}-3-oxopropanoate

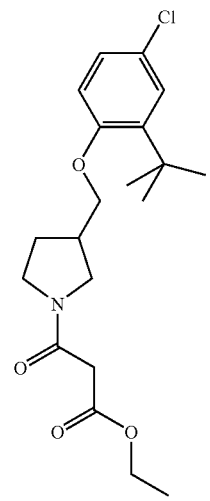 [SMILES: CCOC(=O)CC(=O)N1CCC(COc2ccc(Cl)cc2C(C)(C)C)C1]

According to a method similar to that in Example 9, the title compound (470 mg, 75%) was obtained as a colorless oil from 3-[(2-tert-butyl-4-chlorophenoxy)methyl]pyrrolidine hydrochloride (500 mg, 1.64 mmol) obtained in Reference Example 61 and 3-ethoxy-3-oxopropanoic acid (260 mg, 1.97 mmol).

$^1$H NMR (300 MHz, CDCl$_3$) δ 7.23 (t, J=2.3 Hz, 1H), 7.12 (dt, J=8.5, 2.6 Hz, 1H), 6.74 (d, J=8.7 Hz, 1H), 4.20 (quin, J=7.1 Hz, 2H), 4.06-3.25 (m, 8H), 2.99-2.69 (m, 1H), 2.35-2.10 (m, 1H), 2.04-1.74 (m, 1H), 1.36 (s, 9H), 1.28 (q, J=7.2 Hz, 3H).

Example 200

3-{3-[(2-tert-butyl-4-chlorophenoxy)methyl]pyrrolidin-1-yl}-3-oxopropanoic acid

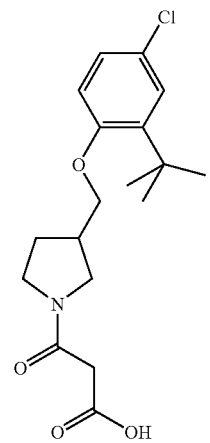 [SMILES: CC(C)(C)c1cc(Cl)ccc1OCC1CCN(C(=O)CC(=O)O)C1]

According to a method similar to that in Example 5, the title compound (380 mg, 98%) was obtained as a white solid from ethyl 3-[(3-[(2-tert-butyl-4-chlorophenoxy)methyl]pyrrolidin-1-yl]-3-oxopropanoate (421 mg, 1.10 mmol) obtained in Example 199.

¹H NMR (300 MHz, CDCl₃) δ 14.05 (br s, 1H), 7.27-7.23 (m, 1H), 7.17-7.07 (m, 1H), 6.74 (d, 1H), 4.11-3.25 (m, 8H), 3.04-2.75% (m, 1H), 2.41-2.16 (m, 1H), 2.08-1.81 (m, 1H), 1.36 (s, 9H).

Example 201 methyl 4-{3-[(2-tert-butyl-4-chlorophenoxy)methyl]pyrrolidin-1-yl}-4-oxobutanoate

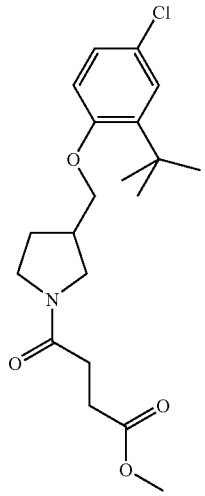 [SMILES: COC(=O)CCC(=O)N1CCC(COc2ccc(Cl)cc2C(C)(C)C)C1]

According to a method similar to that in Example 124, the title compound (478 mg, 76%) was obtained as a colorless oil from 3-[(2-tert-butyl-4-chlorophenoxy)methyl]pyrrolidine hydrochloride (500 mg, 1.64 mmol) obtained in Reference Example 61 and methyl 4-chloro-4-oxobutanoate (322 mg, 2.14 mmol).

¹H NMR (300 MHz, CDCl₃) δ 7.25-7.20 (m, 1H), 7.16-7.06 (m, 1H), 6.80-6.68 (m, 1H), 4.05-3.19 (m, 9H), 2.96-2.47 (m, 5H), 2.35-2.08 (m, 1H), 2.02-1.70 (m, 1H), 1.42-1.32 (m, 9H).

Example 202

4-{3-[(2-tert-butyl-4-chlorophenoxy)methyl]pyrrolidin-1-yl}-4-oxobutanoic acid

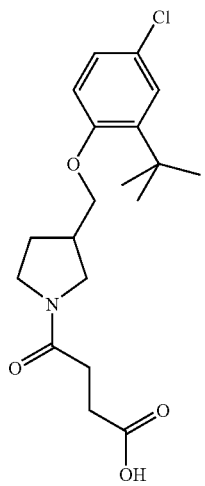 [SMILES: CC(C)(C)c1cc(Cl)ccc1OCC1CCN(C(=O)CCC(=O)O)C1]

According to a method similar to that in Example 5, the title compound (384 mg, quant.) was obtained as a white solid from methyl 4-{3-[(2-tert-butyl-4-chlorophenoxy)methyl]pyrrolidin-1-yl}-4-oxobutanoate (379 mg, 0.99 mmol) obtained in Example 201.

¹H NMR (300 MHz, CDCl₃) δ 7.26-7.23 (m, 1H), 7.12 (dt, J=8.7, 2.6 Hz, 1H), 6.75 (dd, J=8.7, 1.5 Hz, 1H), 4.06-3.46 (m, 5H), 3.44-3.26 (m, 1H), 2.93-2.61 (m, 5H), 2.39-2.11 (m, 1H), 2.06-1.73 (m, 1H), 1.36 (s, 9H).

Example 203 ethyl 3-{4-[(2-tert-butylphenoxy)methyl]piperidin-1-yl}-3-oxopropanoate

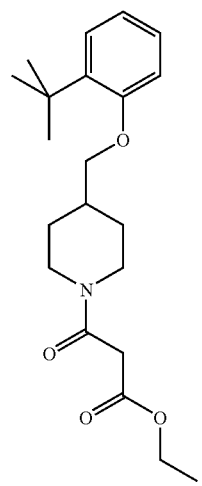 [SMILES: CCOC(=O)CC(=O)N1CCC(COc2ccccc2C(C)(C)C)CC1]

According to a method similar to that in Example 9, the title compound (330 mg, 74%) was obtained as a colorless oil from 4-[(2-tert-butylphenoxy)methyl]piperidine hydrochloride (350 mg, 1.23 mmol) obtained in Reference Example 24 and 3-ethoxy-3-oxopropanoic acid (196 mg, 1.48 mmol).

¹H NMR (300 MHz, CDCl₃) δ 7.33-7.23 (m, 1H), 7.17 (td, J=7.7, 1.7 Hz, 1H), 6.90 (td, J=7.5, 1.1 Hz, 1H), 6.84 (dd, J=8.2, 1.0 Hz, 1H), 4.80-4.64 (m, 1H), 4.28-4.15 (m, 2H), 3.92-3.75 (m, 3H), 3.56-3.43 (m, 2H), 3.16 (td, J=13.1, 2.8 Hz, 1H), 2.69 (td, J=12.9, 3.0 Hz, 1H), 2.14 (br s, 1H), 2.06-1.87 (m, 2H), 1.46-1.24 (m, 14H).

Example 204

3-{4-[(2-tert-butylphenoxy)methyl]piperidin-1-yl}-3-oxopropanoic acid

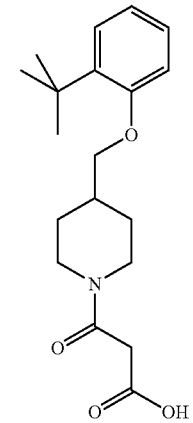 [SMILES: CC(C)(C)c1ccccc1OCC1CCN(C(=O)CC(=O)O)CC1]

According to a method similar to that in Example 5, the title compound (254 mg, 99%) was obtained as a white solid from ethyl 3-{4-[(2-tert-butylphenoxy)methyl]piperidin-1-yl}-3-oxopropanoate (278 mg, 0.77 mmol) obtained in Example 203.

$^1$H NMR (300 MHz, CDCl$_3$) δ 14.34 (br s, 1H), 7.31 (dd, J=7.7, 1.7 Hz, 1H), 7.17 (td, J=7.7, 1.7 Hz, 1H), 6.91 (td, J=7.5, 1.3 Hz, 1H), 6.84 (dd, J=8.1, 1.1 Hz, 1H), 4.79-4.69 (m, 1H), 3.96-3.78 (m, 3H), 3.39 (s, 2H), 3.18 (td, J=13.2, 2.8 Hz, 1H), 2.79 (td, J=13.0, 2.9 Hz, 1H), 2.32-2.14 (m, 1H), 2.14-1.97 (m, 2H), 1.49-1.29 (m, 11H).

Example 205

{3-[(2-tert-butyl-4-chlorophenoxy)methyl]pyrrolidin-1-yl}(oxo)acetic acid

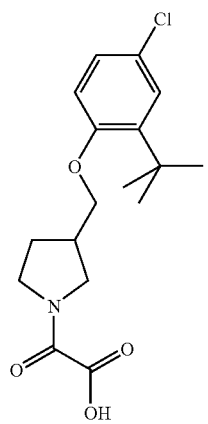 [SMILES: CC(C)(C)c1cc(Cl)ccc1OCC1CCN(C(=O)C(=O)O)C1]

According to a method similar to that in Example 5, the title compound (514 mg, quant.) was obtained as a white solid from ethyl {3-[(2-tert-butyl-4-chlorophenoxy)methyl]pyrrolidin-1-yl}(oxo)acetate (512 mg, 1.39 mmol) obtained in Example 198.

$^1$H NMR (300 MHz, CDCl$_3$) δ 7.23 (d, J=2.7 Hz, 1H), 7.12 (dd, J=8.7, 2.7 Hz, 1H), 6.74 (dd, J=8.7, 0.8 Hz, 1H), 4.48-4.22 (m, 1H), 4.09-3.78 (m, 4H), 3.74-3.43 (m, 1H), 3.02-2.72 (m, 1H), 2.41-2.15 (m, 1H), 2.06-1.79 (m, 1H), 1.37 (s, 9H).

Example 206 methyl {3-[(2-tert-butyl-4-chlorophenoxy)methyl]azetidin-1-yl}(oxo)acetate

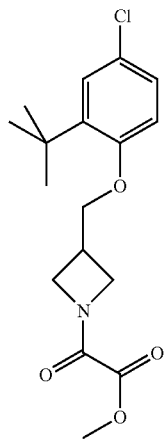

According to a method similar to that in Example 124, the title compound (287 mg, 54%) was obtained as a yellow oil from 3-[(2-tert-butyl-4-chlorophenoxy)methyl]azetidine (400 mg, 1.58 mmol) obtained in Reference Example 50 and methyl chloro(oxo)acetate (251 mg, 2.05 mmol).

$^1$H NMR (300 MHz, CDCl$_3$) δ 7.24 (d, J=2.7 Hz, 1H), 7.13 (dd, J=8.7, 2.7 Hz, 1H), 6.76 (d, J=8.7 Hz, 1H), 4.79-4.65 (m, 1H), 4.45 (dd, J=10.8, 5.5 Hz, 1H), 4.39-4.25 (m, 1H), 4.19-3.99 (m, 3H), 3.91-3.80 (m, 3H), 3.28-3.10 (m, 1H), 1.37-1.30 (m, 9H).

Example 207

{3-[(2-tert-butyl-4-chlorophenoxy)methyl]azetidin-1-yl}(oxo)acetic acid

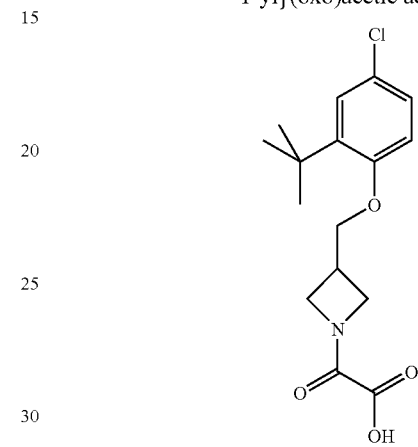

To a stirred solution of methyl {3-[(2-tert-butyl-4-chlorophenoxy)methyl]azetidin-1-yl}(oxo)acetate (232 mg, 0.68 mmol) obtained in Example 206 in THF (5.0 mL) was added lithium hydroxide (1.0M aqueous solution, 5.0 mL, 5.0 mmol) at 0° C. After stirring at 0° C. for 3 hr, the reaction mixture was adjusted to about pH 1 with 1.0N hydrochloric acid. The obtained solution was concentrated under reduced pressure, and the mixture was extracted with ethyl acetate. The organic layer was washed with saturated sodium chloride, dried (MgSO$_4$), filtered, and concentrated under reduced pressure to give the title compound (214 mg, 96%) as a white solid.

$^1$H NMR (300 MHz, CDCl$_3$) δ 7.27-7.24 (m, 1H), 7.14 (dd, J=8.7, 2.6 Hz, 1H), 6.77 (d, J=8.7 Hz, 1H), 4.91-4.77 (m, 1H), 4.66-4.54 (m, 1H), 4.48-4.33 (m, 1H), 4.21-4.05 (m, 3H), 3.35-3.14 (m, 1H), 1.33 (s, 9H).

Example 208 ethyl 3-{3-[(2-tert-butyl-4-chlorophenoxy)methyl]azetidin-1-yl}-3-oxopropanoate

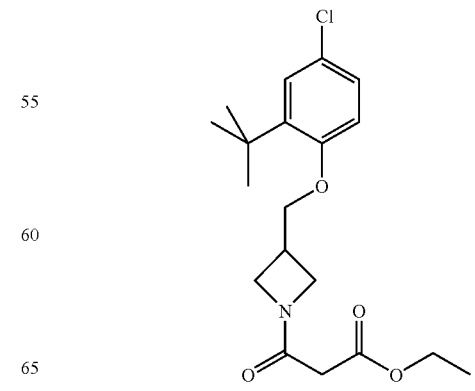

According to a method similar to that in Example 9, the title compound (361 mg, 62%) was obtained as a white solid from 3-[(2-tert-butyl-4-chlorophenoxy)methyl]azetidine (400 mg, 1.58 mmol) obtained in Reference Example 50 and 3-ethoxy-3-oxopropanoic acid (271 mg, 2.05 mmol).

$^1$H NMR (300 MHz, CDCl$_3$) δ 7.24 (d, J=2.7 Hz, 1H), 7.13 (dd, J=8.7, 2.7 Hz, 1H), 6.76 (d, J=8.7 Hz, 1H), 4.40 (t, J=8.3 Hz, 1H), 4.29-4.21 (m, 1H), 4.20 (q, J=7.2 Hz, 2H), 4.15-4.05 (m, 3H), 3.95 (dd, J=10.2, 5.3 Hz, 1H), 3.22 (s, 2H), 3.25-3.06 (m, 1H), 1.34 (s, 9H), 1.28 (t, J=7.2 Hz, 3H).

Example 209

3-{3-[(2-tert-butyl-4-chlorophenoxy)methyl]azetidin-1-yl}-3-oxopropanoic acid

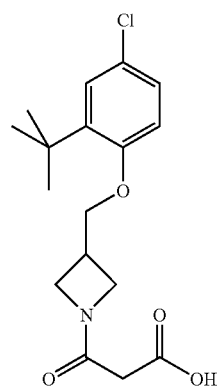 [SMILES: CC(C)(C)c1cc(Cl)ccc1OCC1CN(C(=O)CC(=O)O)C1]

To a stirred solution of ethyl 3-{3-[(2-tert-butyl-4-chlorophenoxy)methyl]azetidin-1-yl}-3-oxopropanoate (285 mg, 0.78 mmol) obtained in Example 208 in THF (5.0 ml) was added lithium hydroxide (1.0M aqueous solution, 5.0 mL, 5.0 mmol) at room temperature. After 3 hr, the reaction mixture was adjusted to about pH 1 with 1.0N hydrochloric acid. The obtained solution was concentrated under reduced pressure, and the mixture was extracted with ethyl acetate. The organic layer was washed with saturated sodium chloride, dried (MgSO$_4$), filtered, and concentrated under reduced pressure to give the title compound (203 mg, 77%) as a white solid.

$^1$H NMR (300 MHz, CDCl$_3$) δ 13.37 (br s, 1H), 7.27-7.22 (m, 1H), 7.14 (dd, J=8.7, 2.6 Hz, 1H), 6.76 (d, J=8.7 Hz, 1H), 4.40 (t, J=8.8 Hz, 1H), 4.31 (t, J=9.6 Hz, 1H), 4.21-4.07 (m, 4H), 3.32-3.19 (m, 1H), 3.16 (s, 2H), 1.34 (s, 9H).

Example 210 methyl 4-{3-[(2-tert-butyl-4-chlorophenoxy)methyl]azetidin-1-yl}-4-oxobutanoate

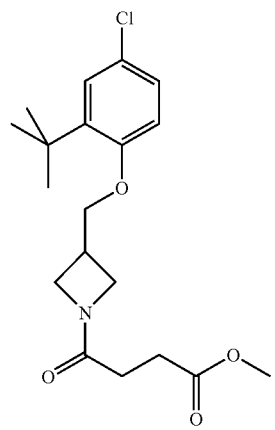 [SMILES: COC(=O)CCC(=O)N1CC(COc2ccc(Cl)cc2C(C)(C)C)C1]

According to a method similar to that in Example 124, the title compound (268 mg, 46%) was obtained as a pale yellow oil from 3-[(2-tert-butyl-4-chlorophenoxy)methyl]azetidine (400 mg, 1.58 mmol) obtained in Reference Example 50 and methyl 4-chloro-4-oxobutanoate (309 mg, 2.05 mmol).

$^1$H NMR (300 MHz, CDCl$_3$) δ 7.24 (d, J=2.7 Hz, 1H), 7.13 (dd, J=8.5, 2.5 Hz, 1H), 6.76 (d, J=8.7 Hz, 1H), 4.38 (t, J=8.5 Hz, 1H), 4.19 (t, J=9.3 Hz, 1H), 4.12 (d, J=6.4 Hz, 2H), 4.07 (dd, J=8.5, 5.5 Hz, 1H), 3.90 (dd, J=9.8, 5.3 Hz, 1H), 3.69 (s, 3H), 3.22-3.03 (m, 1H), 2.77-2.56 (m, 2H), 2.50-2.25 (m, 2H), 1.34 (s, 9H).

Example 211

4-{3-[(2-tert-butyl-4-chlorophenoxy)methyl]azetidin-1-yl}-4-oxobutanoic acid

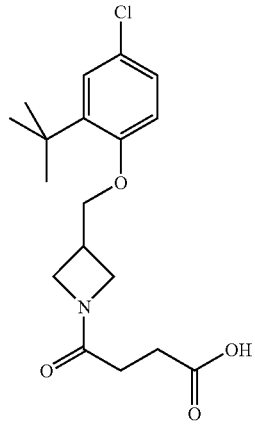 [SMILES: CC(C)(C)c1cc(Cl)ccc1OCC1CN(C(=O)CCC(=O)O)C1]

According to a method similar to that in Example 5, the title compound (223 mg, quant.) was obtained as a white solid from methyl 4-{3-[(2-tert-butyl-4-chlorophenoxy)methyl]azetidin-1-yl}-4-oxobutanoate (217 mg, 0.59 mmol) obtained in Example 210.

$^1$H NMR (300 MHz, CDCl$_3$) δ 7.29-7.23 (m, 1H), 7.14 (dd, J=8.3, 2.7 Hz, 1H), 6.76 (d, J=8.3 Hz, 1H), 4.38 (t, J=8.7 Hz, 1H), 4.24 (t, J=9.5 Hz, 1H), 4.19-4.07 (m, 3H), 3.98 (dd, J=10.0, 5.5 Hz, 1H), 3.32-3.0.7 (m, 1H), 2.76-2.62 (m, 2H), 2.52-2.37 (m, 2H), 1.34 (s, 9H).

Example 212 methyl {3-[(2-tert-butyl-4-fluorophenoxy)methyl]pyrrolidin-1-yl}(oxo)acetate

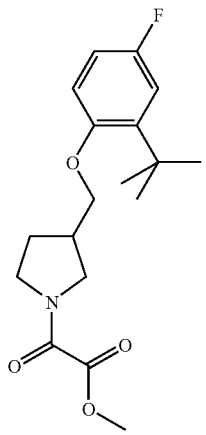 [SMILES: COC(=O)C(=O)N1CCC(COc2ccc(F)cc2C(C)(C)C)C1]

According to a method similar to that in Example 124, the title compound (552 mg, 94%) was obtained from 3-[(2-tert-butyl-4-fluorophenoxy)methyl]pyrrolidine hydrochloride (500 mg, 1.74 mmol) obtained in Reference Example 59 and methyl chloro(oxo)acetate (277 mg, 2.26 mmol).

$^1$H NMR (300 MHz, CDCl$_3$) δ 7.05-6.97 (m, 1H), 6.88-6.78 (m, 1H), 6.76-6.68 (m, 1H), 4.06-3.34 (m, 9H), 2.96-2.70 (m, 1H), 2.34-2.13 (m, 1H), 2.02-1.75 (m, 1H), 1.36 (s, 9H).

Example 213

{3-[(2-tert-butyl-4-fluorophenoxy)methyl]pyrrolidin-1-yl}(oxo)acetic acid

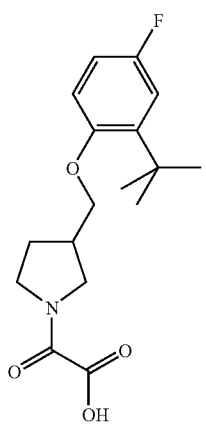 [SMILES: CC(C)(C)c1cc(F)ccc1OCC1CCN(C(=O)C(=O)O)C1]

According to a method similar to that in Example 5, the title compound (453 mg, 99%) was obtained as a white solid from methyl {3-[(2-tert-butyl-4-fluorophenoxy)methyl]pyrrolidin-1-yl}(oxo)acetate (473 mg, 1.40 mmol) obtained in Example 212.

$^1$H NMR (300 MHz, CDCl$_3$) δ 7.07-6.95 (m, 1H), 6.90-6.79 (m, 1H), 6.79-6.56 (m, 1H), 4.48-4.22 (m, 1H), 4.11-3.81 (m, 4H), 3.73-3.43 (m, 1H), 3.05-2.72 (m, 1H), 2.41-2.13 (m, 1H), 2.08-1.77 (m, 1H), 1.37 (s, 9H).

Example 214 ethyl 3-{3-[(2-tert-butyl-4-fluorophenoxy)methyl]pyrrolidin-1-yl}-3-oxopropanoate

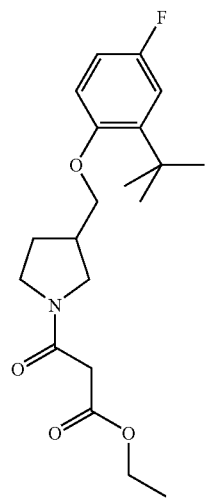 [SMILES: CCOC(=O)CC(=O)N1CCC(COc2ccc(F)cc2C(C)(C)C)C1]

According to a method similar to that in Example 9, the title compound (539 mg, 85%) was obtained as a colorless oil from 3-[(2-tert-butyl-4-fluorophenoxy)methyl]pyrrolidine hydrochloride (500 mg, 1.74 mmol) obtained in Reference Example 59 and 3-ethoxy-3-oxopropanoic acid (299 mg, 2.26 mmol).

$^1$H NMR (300 MHz, CDCl$_3$) δ 7.05-6.96 (m, 1H), 6.89-6.78 (m, 1H), 6.78-6.70 (m, 1H), 4.21 (quin, J=7.0 Hz, 2H), 4.04-3.29 (m, 8H), 2.97-2.68 (m, 1H), 2.34-2.10 (m, 1H), 2.06-1.74 (m, 1H), 1.36 (s, 9H), 1.28 (q, J=7.1 Hz, 3H).

Example 215

3-{3-[(2-tert-butyl-4-fluorophenoxy)methyl]pyrrolidin-1-yl}-3-oxopropanoic acid

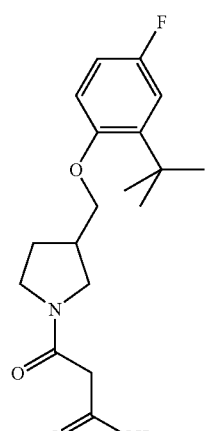

To a stirred solution of ethyl 3-{3-[(2-tert-butyl-4-fluorophenoxy)methyl]pyrrolidin-1-yl}-3-oxopropanoate (434 mg, 1.19 mmol) obtained in Example 214 in THF (5.0 ml) was added lithium hydroxide (1.0M aqueous solution, 5.0 mL, 5.0 mmol) at room temperature. After 3 hr, the reaction mixture was adjusted to about pH 1 with 1.0N hydrochloric acid. The obtained solution was concentrated under reduced pressure, and to the mixture was extracted with ethyl acetate. The organic layer was washed with saturated sodium chloride, dried (MgSO$_4$), filtered, and concentrated under reduced pressure to give the title compound (392 mg, 98%) as a white solid.

$^1$H NMR (300 MHz, CDCl$_3$) δ 14.08 (br s, 1H), 7.07-6.97 (m, 1H), 6.89-6.78 (m, 1H), 6.78-6.69 (m, 1H), 4.10-3.86 (m, 3H), 3.86-3.71 (m, 1H), 3.71-3.47 (m, 1H), 3.47-3.25 (m, 3H), 3.03-2.71 (m, 1H), 2.41-2.13 (m, 1H), 2.11-1.79 (m, 1H), 1.36 (s, 9H).

Example 216 methyl 4-{3-[(2-tert-butyl-4-fluorophenoxy)methyl]pyrrolidin-1-yl}-4-oxobutanoate

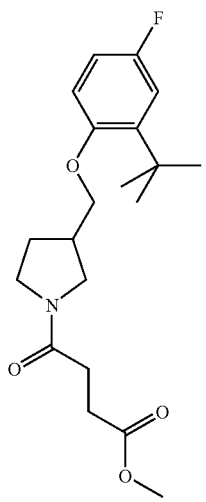 [SMILES: COC(=O)CCC(=O)N1CCC(COc2ccc(F)cc2C(C)(C)C)C1]

According to a method similar to that in Example 124, the title compound (566 mg, 89%) was obtained as a colorless oil from 3-[(2-tert-butyl-4-fluorophenoxy)methyl]pyrrolidine hydrochloride (500 mg, 1.74 mmol) obtained in Reference Example 59 and methyl 4-chloro-4-oxobutanoate (340 mg, 2.26 mmol).

$^1$H NMR (300 MHz, CDCl$_3$) δ 7.05-6.96 (m, 1H), 6.89-6.78 (m, 1H), 6.78-6.69 (m, 1H), 4.04-3.21 (m, 9H), 2.96-2.48 (m, 5H), 2.35-2.06 (m, 1H), 1.99-1.67 (m, 1H), 1.37 (s, 4H), 1.36 (s, 5H).

Example 217

4-{3-[(2-tert-butyl-4-fluorophenoxy)methyl]pyrrolidin-1-yl}-4-oxobutanoic acid

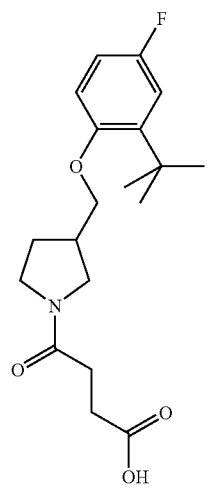 [SMILES: CC(C)(C)c1cc(F)ccc1OCC1CCN(C(=O)CCC(=O)O)C1]

According to a method similar to that in Example 5, the title compound (410 mg, 99%) was obtained as a white solid from methyl 4-{3-[(2-tert-butyl-4-fluorophenoxy)methyl]pyrrolidin-1-yl}-4-oxobutanoate (431 mg, 1.18 mmol) obtained in Example 216.

$^1$H NMR (300 MHz, CDCl$_3$) δ 7.08-6.94 (m, 1H), 6.89-6.79 (m, 1H), 6.79-6.67 (m, 1H), 4.05-3.26 (m, 6H), 2.95-2.61 (m, 5H), 2.38-2.09 (m, 1H), 2.03-1.74 (m, 1H), 1.37 (s, 4H), 1.34 (s, 5H).

Example 218 calcium bis(4-{3-[(2-tert-butyl-4-fluorophenoxy)methyl]pyrrolidin-1-yl}-4-oxobutanoate)

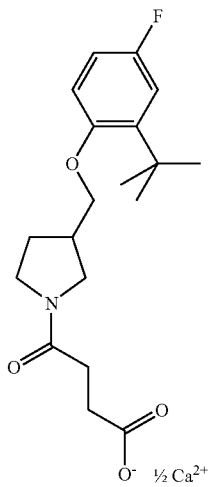 [SMILES: CC(C)(C)c1cc(F)ccc1OCC1CCN(C(=O)CCC(=O)[O-])C1]

To a solution of 4-{3-[(2-tert-butyl-4-fluorophenoxy)methyl]pyrrolidin-1-yl}-4-oxobutanoic acid (260 mg, 0.74 mmol) obtained in Example 217 in methanol (10 mL) was added aqueous solution (10 mL) of potassium hydrogen carbonate (78 mg, 0.78 mmol). The reaction mixture was concentrated under reduced pressure, the residue was dissolved in methanol (10 mL), and aqueous solution (10 mL) of calcium chloride (43 g, 0.39 mmol) was added. The reaction mixture was concentrated under reduced pressure, and the residue was diluted with THF. The resulting precipitate was filtered, and the filtrate was concentrated to give the title compound (248 mg, 90%) as a white solid.

$^1$H NMR (300 MHz, DMSO-$d_6$) δ 6.99-6.86 (m, 3H), 4.07-3.85 (m, 2H), 3.78-3.55 (m, 1H), 3.55-3.38 (m, 1H), 3.38-3.18 (m, 2H), 2.82-2.56 (m, 1H), 2.47-2.28 (m, 2H), 2.28-1.97, 1.92-1.60 (m, 1H), 1.36-1.26 (m, 9H).

Example 219 methyl [4-(2-tert-butyl-4-chlorophenoxy)piperidin-1-yl](oxo)acetate

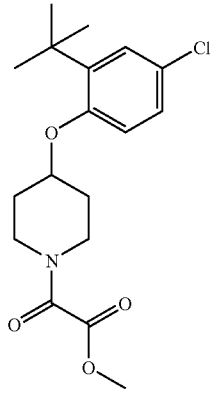 [SMILES: COC(=O)C(=O)N1CCC(Oc2ccc(Cl)cc2C(C)(C)C)CC1]

According to a method similar to that in Example 124, the title compound (550 mg, quant.) was obtained from 4-(2-tert-butyl-4-chlorophenoxy)piperidine hydrochloride (450 mg, 1.48 mmol) obtained in Reference Example 65 and methyl chloro(oxo)acetate (236 mg, 1.92 mmol).

$^1$H NMR (300 MHz, CDCl$_3$) δ 7.26-7.24 (m, 1H), 7.16-7.06 (m, 1H), 6.76-6.70 (m, 1H), 4.71-4.61 (m, 1H), 3.94-3.60 (m, 6H), 3.53-3.35 (m, 1H), 2.13-1.88 (m, 4H), 1.38 (s, 9H).

Example 220

[4-(2-tert-butyl-4-chlorophenoxy)piperidin-1-yl](oxo) acetic acid

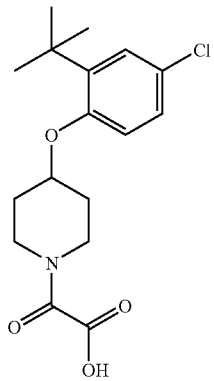 [SMILES: CC(C)(C)c1cc(Cl)ccc1OC1CCN(C(=O)C(=O)O)CC1]

According to a method similar to that in Example 5, the title compound (421 mg, quant.) was obtained as a white solid from methyl [4-(2-tert-butyl-4-chlorophenoxy)piperidin-1-yl](oxo)acetate (430 mg, 1.22 mmol) obtained in Example 219.

$^1$H NMR (300 MHz, CDCl$_3$) δ 7.28-7.25 (m, 1H), 7.16-7.09 (m, 1H), 6.78-6.69 (m, 1H), 4.74-4.62 (m, 1H), 4.49-4.36 (m, 1H), 4.32-4.18 (m, 1H), 4.00-3.72 (m, 2H), 2.19-1.91 (m, 4H), 1.38 (s, 9H).

Example 221 ethyl 3-[4-(2-tert-butyl-4-chlorophenoxy)piperidin-1-yl]-3-oxopropanoate

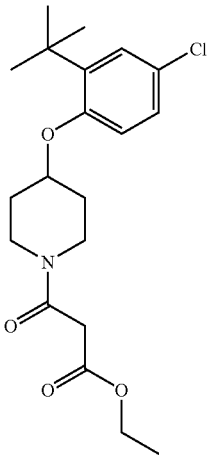 [SMILES: CCOC(=O)CC(=O)N1CCC(Oc2ccc(Cl)cc2C(C)(C)C)CC1]

According to a method similar to that in Example 9, the title compound (530 mg, 94%) was obtained as a colorless oil from 4-(2-tert-butyl-4-chlorophenoxy)piperidine hydrochloride (450 mg, 1.48 mmol) obtained in Reference Example 65 and 3-24 ethoxy-3-oxopropanoic acid (254 mg, 1.92 mmol).

$^1$H NMR (300 MHz, CDCl$_3$) δ 7.26-7.24 (m, 1H), 7.15-7.07 (m, 1H), 6.77-6.71 (m, 1H), 4.69-4.55 (m, 1H), 4.22 (q, J=7.2 Hz, 2H), 3.84-3.61 (m, 3H), 3.57-3.33 (m, 3H), 2.12-1.82 (m, 4H), 1.37 (s, 9H), 1.29 (t, J=7.1 Hz, 3H).

Example 222

3-[4-(2-tert-butyl-4-chlorophenoxy)piperidin-1-yl]-3-oxopropanoic acid

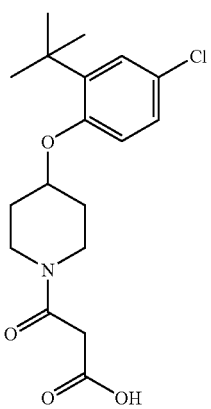 [SMILES: CC(C)(C)c1cc(Cl)ccc1OC1CCN(C(=O)CC(=O)O)CC1]

According to a method similar to that in Example 5, the title compound (418 mg, quant.) was obtained as a white solid from ethyl 3-[4-(2-tert-butyl-4-chlorophenoxy)piperidin-1-yl]-3-oxopropanoate (446 mg, 1.17 mmol) obtained in Example 221.

$^1$H NMR (300 MHz, CDCl$_3$) δ 14.03 (br s, 1H), 7.28-7.24 (m, 1H), 7.16-7.06 (m, 1H), 6.77-6.67 (m, 1H), 4.75-4.60 (m, 1H), 3.94 (dt, J=13.6, 5.3 Hz, 1H), 3.82-3.61 (m, 2H), 3.59-3.45 (m, 1H), 3.40 (s, 2H), 2.10-1.87 (m, 4H), 1.38 (s, 9H).

Example 223 methyl 4-[4-(2-tert-butyl-4-chlorophenoxy)piperidin-1-yl]-4-oxobutanoate

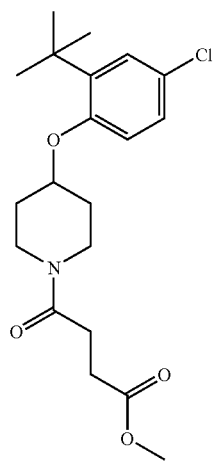 [SMILES: COC(=O)CCC(=O)N1CCC(Oc2ccc(Cl)cc2C(C)(C)C)CC1]

According to a method similar to that in Example 124, the title compound (499 mg, 88%) was obtained as a colorless oil from 4-(2-tert-butyl-4-chlorophenoxy)piperidine hydrochloride (450 mg, 1.48 mmol) obtained in Reference Example 65 and methyl 4-chloro-4-oxobutanoate (290 mg, 1.92 mmol).

$^1$H NMR (300 MHz, CDCl$_3$) δ 7.26-7.22 (m, 1H), 7.15-7.05 (m, 1H), 6.78-6.71 (m, 1H), 4.70-4.54 (m, 1H), 3.87-3.62 (m, 6H), 3.60-3.41 (m, 1H), 2.80-2.54 (m, 4H), 2.10-1.76 (m, 4H), 1.37 (s, 9H).

Example 224

4-[4-(2-tert-butyl-4-chlorophenoxy)piperidin-1-yl]-4-oxobutanoic acid

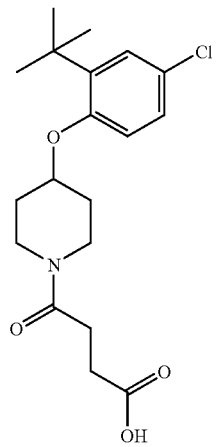 [SMILES: CC(C)(C)c1cc(Cl)ccc1OC1CCN(C(=O)CCC(=O)O)CC1]

According to a method similar to that in Example 5, the title compound (363 mg, 98%) was obtained as a white solid from methyl 4-[4-(2-tert-butyl-4-chlorophenoxy)piperidin-1-yl]-4-oxobutanoate (384 mg, 1.01 mmol) obtained in Example 223.

$^1$H NMR (300 MHz, CDCl$_3$) δ 7.27-7.23 (m, 1H), 7.17-7.07 (m, 1H), 6.80-6.66 (m, 1H), 4.70-4.57 (m, 1H), 3.85-3.75 (m, 2H), 3.75-3.65 (m, 1H), 3.60-3.44 (m, 1H), 2.82-2.63 (m, 4H), 2.14-1.82 (m, 4H), 1.38 (s, 9H).

Example 225 methyl [3-(2-tert-butyl-4-chlorophenoxy)pyrrolidin-1-yl](oxo)acetate

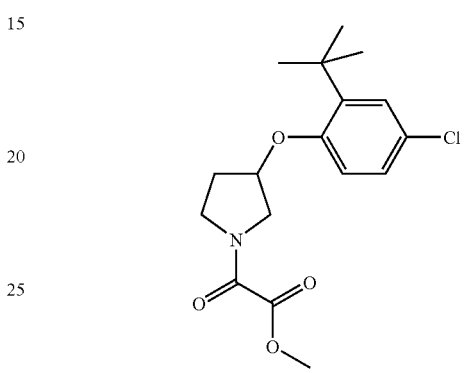

According to a method similar to that in Example 124, the title compound (250 mg, 61%) was obtained from 3-(2-tert-butyl-4-chlorophenoxy)pyrrolidine (285 mg, 1.20 mmol) obtained in Reference Example 57 and methyl chloro(oxo)acetate (213 mg, 1.56 mmol).

$^1$H NMR (300 MHz, CDCl$_3$) δ 7.26-7.20 (m, 1H), 7.17-7.08 (m, 1H), 6.69 (dd, J=8.7, 3.4 Hz, 1H), 5.09-4.95 (m, 1H), 4.06-3.68 (m, 7H), 2.47-2.09 (m, 2H), 1.32 (s, 4H), 1.31 (s, 5H).

Example 226

[3-(2-tert-butyl-4-chlorophenoxy)pyrrolidin-1-yl](oxo)acetic acid

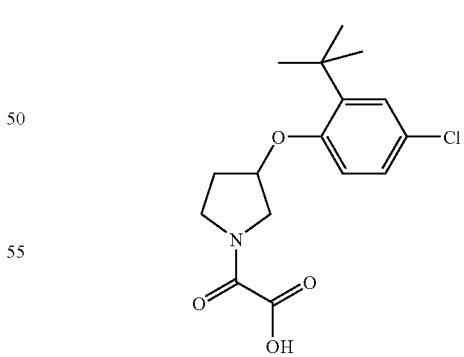

According to a method similar to that in Example 5, the title compound (213 mg, quant.) was obtained as a white solid from methyl [3-(2-tert-butyl-4-chlorophenoxy)pyrrolidin-1-yl](oxo)acetate (213 mg, 0.63 mmol) obtained in Example 225.

$^1$H NMR (300 MHz, CDCl$_3$) δ 7.41-7.20 (m, 1H), 7.14 (dd, J=8.7, 2.7 Hz, 1H), 6.70 (d, J=8.7 Hz, 1H), 5.25-4.90 (m, 1H), 4.60-4.30 (m, 1H), 4.30-4.07 (m, 1H), 4.01-3.72 (m, 2H), 2.52-2.27 (m, 1H), 2.24-2.11 (m, 1H), 1.27 (s, 9H).

Example 227 ethyl 3-[3-(2-tert-butyl-4-chlorophenoxy)pyrrolidin-1-yl]-3-oxopropanoate

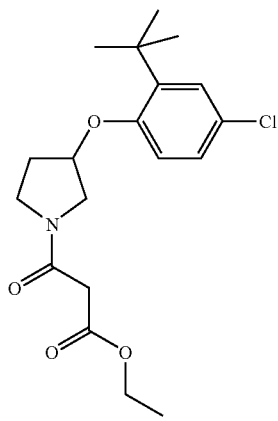 [SMILES: CCOC(=O)CC(=O)N1CCC(Oc2ccc(Cl)cc2C(C)(C)C)C1]

According to a method similar to that in Example 9, the title compound (322 mg, 73%) was obtained as a colorless oil from 3-(2-tert-butyl-4-chlorophenoxy)pyrrolidine (285 mg, 1.2 mmol) obtained in Reference Example 57 and 3-ethoxy-3-oxopropanoic acid (206 mg, 1.56 mmol).

$^1$H NMR (300 MHz, CDCl$_3$) δ 7.29-7.22 (m, 1H), 7.17-7.07 (m, 1H), 6.68 (d, J=8.7 Hz, 1H), 5.09-4.95 (m, 1H), 4.26-4.11 (m, 2H), 3.95-3.57 (m, 4H), 3.50-3.34 (m, 2H), 2.45-2.11 (m, 2H), 1.36-1.18 (m, 12H).

Example 228

3-[3-(2-tert-butyl-4-chlorophenoxy)pyrrolidin-1-yl]-3-oxopropanoic acid

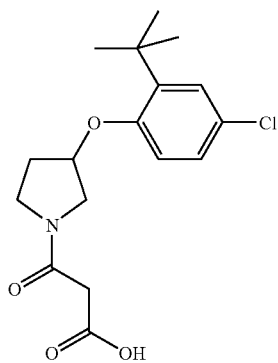 [SMILES: CC(C)(C)c1cc(Cl)ccc1OC1CCN(C(=O)CC(=O)O)C1]

According to a method similar to that in Example 5, the title compound (251 mg, quant.) was obtained as a white solid from ethyl 3-[3-(2-tert-butyl-4-chlorophenoxy)pyrrolidin-1-yl]-3-oxopropanoate (254 mg, 0.69 mmol) obtained in Example 227.

$^1$H NMR (300 MHz, CDCl$_3$) δ 7.31-7.24 (m, 1H), 7.14 (dt, J=8.7, 3.0 Hz, 1H), 6.73-6.65 (m, 1H), 5.16-5.01 (m, 1H), 4.05-3.82 (m, 1H), 3.82-3.60 (m, 3H), 3.46-3.20 (m, 2H), 2.54-2.15 (m, 2H), 1.31 (s, 9H).

Example 229 methyl 4-[3-(2-tert-butyl-4-chlorophenoxy)pyrrolidin-1-yl]-4-oxobutanoate

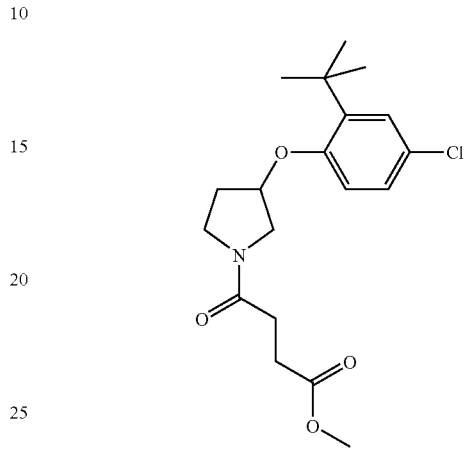

According to a method similar to that in Example 124, the title compound (308 mg, 70%) was obtained as a pale yellow oil from 3-(2-tert-butyl-4-chlorophenoxy)pyrrolidine (285 mg, 1.20 mmol) obtained in Reference Example 57 and methyl 4-chloro-4-oxobutanoate (235 mg, 1.56 mmol).

$^1$H NMR (300 MHz, CDCl$_3$) δ 7.26-7.22 (m, 1H), 7.16-7.07 (m, 1H), 6.69 (dd, J=8.9, 2.1 Hz, 1H), 5.10-4.93 (m, 1H), 3.94-3.55 (m, 7H), 2.80-2.46 (m, 4H), 2.44-2.12 (m, 2H), 1.29 (s, 9H).

Example 230

4-[3-(2-tert-butyl-4-chlorophenoxy)pyrrolidin-1-yl]-4-oxobutanoic acid

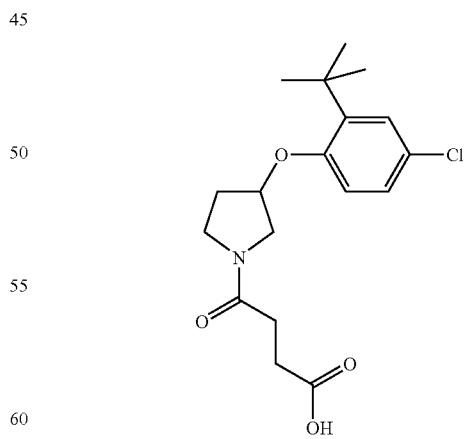

According to a method similar to that in Example 5, the title compound (232 mg, 96%) was obtained as a white solid from methyl 4-[3-(2-tert-butyl-4-chlorophenoxy)pyrrolidin-1-yl]-4-oxobutanoate (251 mg, 0.68 mmol) obtained in Example 229.

¹H NMR (300 MHz, CDCl₃) δ 7.29-7.21 (m, 1H), 7.16-7.07 (m, 1H), 6.69 (d, J=8.7 Hz, 1H), 5.11-4.95 (m, 1H), 3.97-3.57 (m, 4H), 2.82-2.49 (m, 4H), 2.49-2.11 (m, 2H), 1.27 (s, 9H).

Example 231 methyl [3-(2-tert-butyl-4-fluorophenoxy)pyrrolidin-1-yl](oxo)acetate

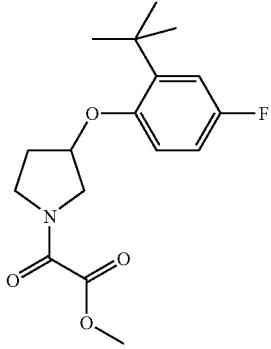 [SMILES: COC(=O)C(=O)N1CCC(Oc2ccc(F)cc2C(C)(C)C)C1]

According to a method similar to that in Example 124, the title compound (426 mg, 63%) was obtained from 3-(2-tert-butyl-4-fluorophenoxy)pyrrolidine (500 mg, 2.10 mmol) obtained in Reference Example 55 and methyl chloro(oxo)acetate (336 mg, 2.74 mmol).

¹H NMR (300 MHz, CDCl₃) δ 7.03 (dt, J=10.8, 2.8 Hz, 1H), 6.89-6.79 (m, 1H), 6.68 (dt, J=8.7, 4.4 Hz, 1H), 5.07-4.97 (m, 1H), 4.05-3.66 (m, 7H), 2.47-2.10 (m, 2H), 1.41-1.22 (m, 9H).

Example 232

[3-(2-tert-butyl-4-fluorophenoxy)pyrrolidin-1-yl](oxo) acetic acid

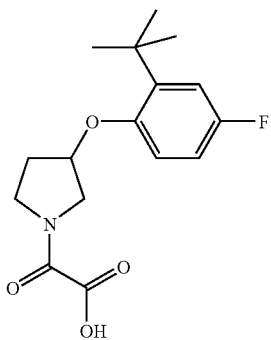 [SMILES: CC(C)(C)c1cc(F)ccc1OC1CCN(C(=O)C(=O)O)C1]

According to a method similar to that in Example 5, the title compound (372 mg, quant.) was obtained as a white solid from methyl [3-(2-tert-butyl-4-fluorophenoxy)pyrrolidin-1-yl](oxo)acetate (385 mg, 1.19 mmol) obtained in Example 231.

¹H NMR (300 MHz, CDCl₃) δ 7.03 (dd, J=10.8, 3.2 Hz, 1H), 6.89-6.80 (m, 1H), 6.69 (dd, J=8.9, 4.7 Hz, 1H), 5.14-4.96 (m, 1H), 4.49-4.35 (m, 1H), 4.22-4.05 (m, 1H), 4.05-3.87 (m, 1H), 3.87-3.71 (m, 1H), 2.52-2.26 (m, 1H), 2.24-2.11 (m, 1H), 1.29 (s, 9H).

Example 233 ethyl 3-[3-(2-tert-butyl-4-fluorophenoxy)pyrrolidin-1-yl]-3-oxopropanoate

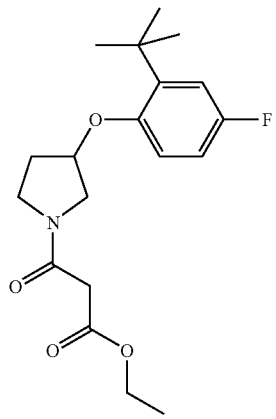 [SMILES: CCOC(=O)CC(=O)N1CCC(Oc2ccc(F)cc2C(C)(C)C)C1]

According to a method similar to that in Example 9, the title compound (502 mg, 89%) was obtained as a colorless oil from 3-(2-tert-butyl-4-fluorophenoxy)pyrrolidine (380 mg, 1.60 mmol) obtained in Reference Example 55 and 3-ethoxy-3-oxopropanoic acid (275 mg, 2.08 mmol).

¹H NMR (300 MHz, CDCl₃) δ 7.07-6.97 (m, 1H), 6.88-6.77 (m, 1H), 6.67 (dd, J=8.9, 4.7 Hz, 1H), 5.08-4.93 (m, 1H), 4.27-4.11 (m, 2H), 3.95-3.57 (m, 4H), 3.49-3.34 (m, 2H), 2.44-2.12 (m, 2H), 1.36-1.20 (m, 12H).

Example 234

3-[3-(2-tert-butyl-4-fluorophenoxy)pyrrolidin-1-yl]-3-oxopropanoic acid

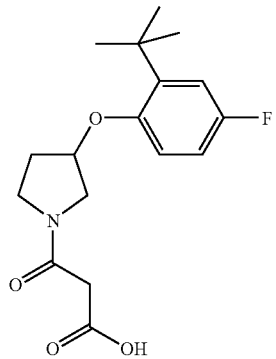 [SMILES: CC(C)(C)c1cc(F)ccc1OC1CCN(C(=O)CC(=O)O)C1]

According to a method similar to that in Example 5, the title compound (386 mg, quant.) was obtained as a white solid from ethyl 3-[3-(2-tert-butyl-4-fluorophenoxy)pyrrolidin-1-yl]-3-oxopropanoate (394 mg, 1.12 mmol) obtained in Example 233.

¹H NMR (300 MHz, CDCl₃) δ 7.10-6.97 (m, 1H), 6.90-6.79 (m, 1H), 6.75-6.56 (m, 1H), 5.14-4.99 (m, 1H), 4.05-3.81 (m, 1H), 3.81-3.59 (m, 3H), 3.46-3.25 (m, 2H), 2.54-2.15 (m, 2H), 1.31 (s, 9H).

Example 235 methyl 4-[3-(2-tert-butyl-4-fluorophenoxy)pyrrolidin-1-yl]-4-oxobutanoate

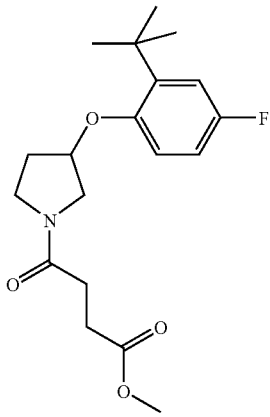 [SMILES: COC(=O)CCC(=O)N1CCC(Oc2ccc(F)cc2C(C)(C)C)C1]

According to a method similar to that in Example 124, the title compound (565 mg, 77%) was obtained as a colorless oil from 3-(2-tert-butyl-4-fluorophenoxy)pyrrolidine (500 mg, 2.10 mmol) obtained in Reference Example 55 and methyl 4-chloro-4-oxobutanoate (413 mg, 2.74 mmol).

¹H NMR (300 MHz, CDCl₃) δ 7.02 (ddd, J=10.8, 7.5, 3.1 Hz, 1H), 6.89-6.78 (m, 1H), 6.74-6.62 (m, 1H), 5.09-4.91 (m, 1H), 3.95-3.56 (m, 7H), 2.77-2.47 (m, 4H), 2.45-2.10 (m, 2H), 1.31 (s, 9H).

Example 236

4-[3-(2-tert-butyl-4-fluorophenoxy)pyrrolidin-1-yl]-4-oxobutanoic acid

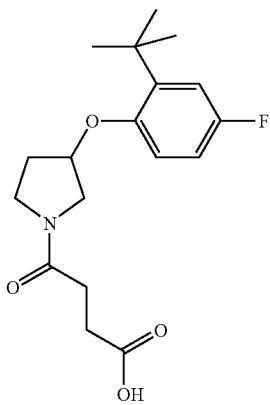 [SMILES: CC(C)(C)c1cc(F)ccc1OC1CCN(C(=O)CCC(=O)O)C1]

According to a method similar to that in Example 5, the title compound (502 mg, 99%) was obtained as a white solid from methyl 4-[3-(2-tert-butyl-4-fluorophenoxy)pyrrolidin-1-yl]-4-oxobutanoate (527 mg, 1.5 mmol) obtained in Example 235.

¹H NMR (300 MHz, CDCl₃) δ 7.08-6.96 (m, 1H), 6.89-6.78 (m, 1H), 6.68 (dd, J=9.0, 4.7 Hz, 1H), 5.12-4.93 (m, 1H), 3.97-3.57 (m, 4H), 2.83-2.50 (m, 4H), 2.49-2.09 (m, 2H), 1.29 (s, 9H).

Example 237

3-[4-(2-tert-butyl-4-fluorophenoxy)piperidin-1-yl]-3-oxopropanenitrile

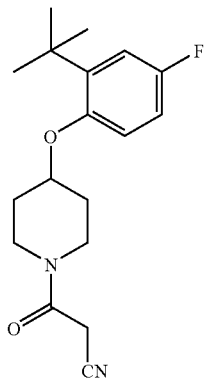 [SMILES: CC(C)(C)c1cc(F)ccc1OC1CCN(C(=O)CC#N)CC1]

According to a method similar to that in Example 9, the title compound (1.96 g, 890) was obtained as a white solid from 4-(2-tert-butyl-4-fluorophenoxy)piperidine hydrochloride (2.0 g, 7.0 mmol) obtained in Reference Example 75 and cyanoacetic acid (768 mg, 9.0 mmol).

¹H NMR (300 MHz, CDCl₃) δ 7.03 (dd, J=11.0, 3.0 Hz, 1H), 6.88-6.77 (m, 1H), 6.72 (dd, J=9.1, 4.9 Hz, 1H), 4.71-4.57 (m, 1H), 3.91-3.63 (m, 3H), 3.60-3.42 (m, 3H), 2.20-1.81 (m, 4H), 1.39 (s, 9H).

Example 238

2-[4-(2-tert-butylphenoxy)piperidin-1-yl]-2-oxo-N-1H-1,2,4-triazol-3-ylacetamide

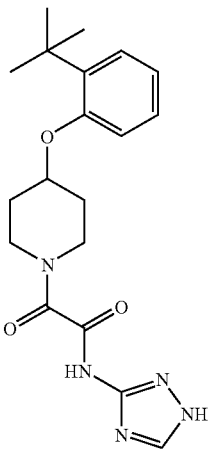 [SMILES: CC(C)(C)c1ccccc1OC1CCN(C(=O)C(=O)Nc2nc[nH]n2)CC1]

According to a method similar to that in Example 9, the title compound (60 mg, 10%) was obtained as a white solid from [4-(2-tert-butylphenoxy)piperidin-1-yl](oxo)acetic acid (500 mg, 1.64 mmol) obtained in Example 52 and 1H-1,2,4-triazol-3-amine (179 mg, 2.13 mmol).

¹H NMR (300 MHz, CDCl₃) δ 8.04 (s, 1H), 7.98 (s, 1H), 7.42-7.29 (m, 1H), 7.24-7.10 (m, 1H), 6.96-6.72 (m, 2H), 4.91-4.61 (m, 1H), 4.31-4.04 (m, 1H), 4.04-3.64 (m, 3H), 2.27-1.90 (m, 4H), 1.53-1.30 (m, 9H).

Example 239

2-({2-[4-(2-tert-butyl-4-fluorophenoxy)piperidin-1-yl]-2-oxoethyl}sulfanyl)phenol

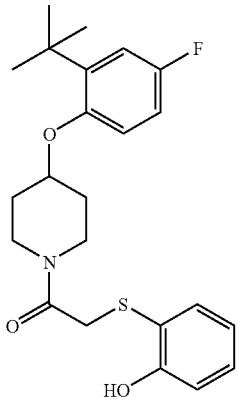 [SMILES: CC(C)(C)c1cc(F)ccc1OC1CCN(C(=O)CSc2ccccc2O)CC1]

1-{2-[4-(2-tert-Butyl-4-fluorophenoxy)piperidin-1-yl]-2-oxoethoxy}-1H-benzotriazole (1.32 g, 3.10 mmol) obtained in Reference Example 76, 2-sulfanylphenol (597 mg, 4.02 mmol) and potassium carbonate (1.28 g, 9.29 mmol) were stirred in DMF (30 mL) at room temperature for 16 hr. The reaction mixture was partitioned between ethyl acetate and saturated aqueous ammonium chloride. The ethyl acetate layer was washed with saturated aqueous sodium hydrogen carbonate solution and saturated brine, dried over anhydrous magnesium sulfate and filtered. The filtrate was concentrated under reduced pressure, and the obtained residue was purified by silica gel column chromatography (hexane:ethyl acetate 95:5-50:50) to give the title compound (377 mg, 30%) as a colorless amorphous form.

$^1$H NMR (300 MHz, CDCl$_3$) δ 9.18 (br s, 1H), 7.51 (dd, J=7.8, 1.7 Hz, 1H), 7.33-7.21 (m, 1H), 7.07-6.95 (m, 2H), 6.89-6.76 (m, 2H), 6.75-6.62 (m, 1H), 4.62-4.49 (m, 1H), 3.85-3.72 (m, 2H), 3.66 (s, 2H), 3.64-3.53 (m, 1H), 3.48-3.33 (m, 1H), 2.04-1.73 (m, 4H), 1.36 (s, 9H).

Example 240

2-({2-[4-(2-tert-butyl-4-fluorophenoxy)piperidin-1-yl]-2-oxoethyl}sulfinyl)phenol

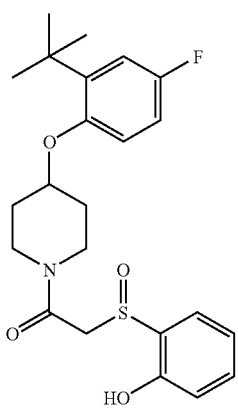 [SMILES: CC(C)(C)c1cc(F)ccc1OC1CCN(C(=O)CS(=O)c2ccccc2O)CC1]

Example 241

2-({2-[4-(2-tert-butyl-4-fluorophenoxy)piperidin-1-yl]-2-oxoethyl}sulfonyl)phenol

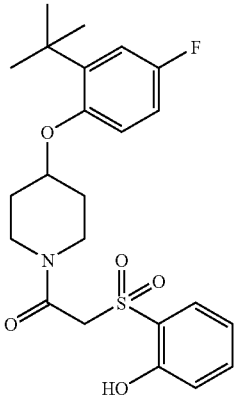 [SMILES: CC(C)(C)c1cc(F)ccc1OC1CCN(C(=O)CS(=O)(=O)c2ccccc2O)CC1]

A solution of 2-({2-[4-(2-tert-butyl-4-fluorophenoxy)piperidin-1-yl]-2-oxoethyl}sulfanyl)phenol (292 mg, 0.70 mmol) obtained in Example 239 and m-chloroperbenzoic acid (275 mg, 1.12 mmol) in ethyl acetate (14 mL) was stirred at 0° C. for 3 hr. Saturated aqueous sodium bisulfite solution (5 mL) was added to the reaction mixture, and the mixture was stirred at room temperature for 30 min. The reaction mixture was partitioned between ethyl acetate and water. The ethyl acetate layer was washed with saturated aqueous sodium hydrogen carbonate solution and saturated brine, dried over anhydrous magnesium sulfate and filtered. The filtrate was concentrated under reduced pressure, and the obtained residue was purified by silica gel column chromatography (hexane:ethyl acetate 90:10-20:80) to give 2-({2-[4-(2-tert-butyl-4-fluorophenoxy)piperidin-1-yl]-2-oxoethyl}sulfinyl)phenol (163 mg, 54%) as a white solid.

$^1$H NMR (300 MHz, CDCl$_3$) δ 10.15 (br s, 1H), 7.45-7.35 (m, 1H), 7.35-7.27 (m, 1H), 7.09-6.88 (m, 3H), 6.87-6.76 (m, 1H), 6.74-6.62 (m, 1H), 4.62-4.47 (m, 1H), 4.45-4.32 (m, 1H), 4.23-4.09 (m, 1H), 3.75-3.57 (m, 3H), 3.57-3.31 (m, 1H), 2.08-1.66 (m, 4H), 1.40-1.33 (m, 9H).

In addition, 2-({2-[4-(2-tert-butyl-4-fluorophenoxy)piperidin-1-yl]-2-oxoethyl}sulfonyl)phenol (126 mg, 40%) was obtained as a white solid.

$^1$H NMR (300 MHz, CDCl$_3$) δ 8.89 (br s, 1H), 7.69 (dd, J=8.3, 1.9 Hz, 1H), 7.60-7.48 (m, 1H), 7.11-6.94 (m, 3H), 6.88-6.76 (m, 1H), 6.71 (dd, J=9.1, 4.9 Hz, 1H), 4.71-4.51 (m, 1H), 4.44-4.23 (m, 2H), 3.88-3.52 (m, 4H), 2.16-1.80 (m, 4H), 1.40 (s, 9H).

Example 242

4-(2-tert-butyl-4-fluorophenoxy)-1-(1H-tetrazol-5-ylacetyl)piperidine

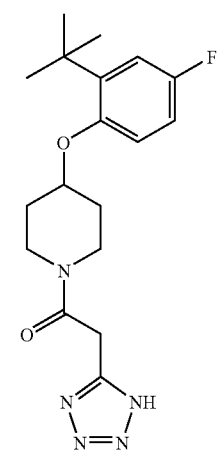 [SMILES: CC(C)(C)c1cc(F)ccc1OC1CCN(C(=O)Cc2nnn[nH]2)CC1]

3-[4-(2-tert-Butyl-4-fluorophenoxy)piperidin-1-yl]-3-oxopropanenitrile (400 mg, 1.26 mmol) obtained in Example 237, ammonium chloride (101 mg, 1.89 mmol) and sodium azide (123 mg, 1.89 mmol) were stirred in DMF (15 mL) at 120° C. for 16 hr. The reaction mixture was cooled to room temperature, and partitioned between ethyl acetate and water. The ethyl acetate layer was washed with saturated brine, dried over anhydrous magnesium sulfate and filtered. The filtrate was concentrated under reduced pressure, and the obtained residue was purified by silica gel column chromatography (hexane:ethyl acetate 40:60-0:100) and by preparative HPLC (device: Gilson Inc., High Throughput Purification system; column: YMC Combiprep ODS-A, S-5 μm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), 5.60 min (SOLUTION A/SOLUTION B=90/10); flow rate: 25 mL/min; detection method: UV 220 nm) to give the title compound (69 mg, 15%).

$^1$H NMR (300 MHz, CDCl$_3$) δ 7.04 (dd, J=10.8, 3.2 Hz, 1H), 6.89-6.79 (m, 1H), 6.72 (dd, J=9.1, 4.5 Hz, 1H), 4.72-4.58 (m, 1H), 4.37-4.16 (m, 2H), 4.01-3.61 (m, 4H), 2.15-1.79 (m, 4H), 1.38 (s, 9H).

Example 243

3-[(2-{3-[(2-tert-butylphenoxy)methyl]azetidin-1-yl}-2-oxoethyl)sulfanyl]-1H-1,2,4-triazole

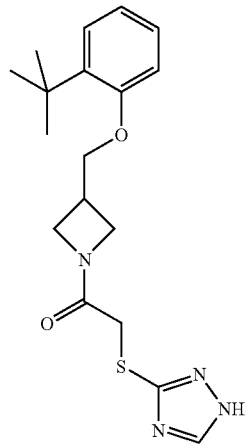 [SMILES: CC(C)(C)c1ccccc1OCC1CN(C(=O)CSc2nc[nH]n2)C1]

According to a method similar to that in Example 239, the title compound (143 mg, 52%) was obtained as a colorless amorphous form from 1-(2-{3-[(2-tert-butylphenoxy)methyl]azetidin-1-yl}-2-oxoethoxy)-1H-benzotriazole (300 mg, 0.76 mmol) obtained in Reference Example 77 and 1H-1,2,4-triazole-3-thiol (100 mg, 0.99 mmol).

$^1$H NMR (300 MHz, CDCl$_3$) δ 8.05-7.92 (m, 1H), 7.31 (dd, J=8.0, 1.5 Hz, 1H), 7.19 (td, J=7.8, 1.5 Hz, 1H), 6.94 (td, J=7.5, 1.3 Hz, 1H), 6.85 (dd, J=8.1, 0.9 Hz, 1H), 4.49 (t, J=8.5 Hz, 1H), 4.35-4.21 (m, 2H), 4.21-4.12 (m, 2H), 4.05 (dd, J=10.2, 5.7 Hz, 1H), 3.60 (s, 2H), 3.32-3.12 (m, 1H), 1.35 (s, 9H).

Example 244

3-[(2-[(3-[(2-tert-butylphenoxy)methyl]azetidin-1-yl]-2-oxoethyl)sulfinyl]-1H-1,2,4-triazole

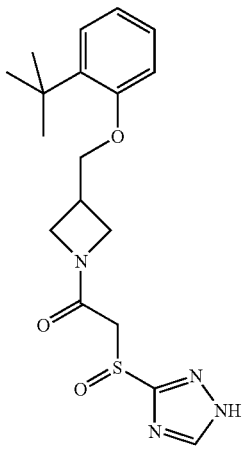 [SMILES: CC(C)(C)c1ccccc1OCC1CN(C(=O)CS(=O)c2nc[nH]n2)C1]

Example 245

3-[(2-{3-[(2-tert-butylphenoxy)methyl]azetidin-1-yl]-2-oxoethyl)sulfonyl}-1H-1,2,4-triazole

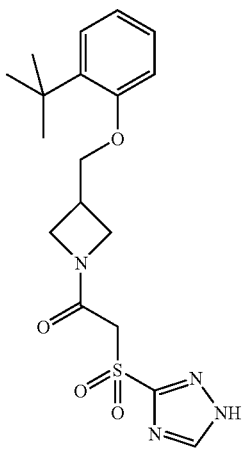 [SMILES: CC(C)(C)c1ccccc1OCC1CN(C(=O)CS(=O)(=O)c2nc[nH]n2)C1]

A solution of 3-[(2-{3-[(2-tert-butylphenoxy)methyl]azetidin-1-yl]-2-oxoethyl)sulfanyl}-1H-1,2,4-triazole (112 mg, 0.31 mmol) obtained in Example 243 and m-chloroperbenzoic acid (122 mg, 0.50 mmol) in ethyl acetate (6.2 mL) was stirred at 0° C. for 3 hr. Saturated aqueous sodium bisulfite solution (5 mL) was added to the reaction mixture, and the mixture was stirred at room temperature for 30 min. The reaction mixture was partitioned between ethyl acetate and water. The ethyl acetate layer was washed with saturated aqueous sodium hydrogen carbonate solution and saturated brine, dried over anhydrous magnesium sulfate and filtered.

The filtrate was concentrated under reduced pressure, and the obtained residue was purified by preparative HPLC (device: Gilson Inc., High Throughput Purification system; column: YMC Combiprep ODS-A, S-5 μm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), 5.60 min (SOLUTION A/SOLUTION B=90/10); flow rate: 25 mL/min; detection method: UV 220 nm) to give 3-[(2-{3-[(2-tert-butylphenoxy)methyl]azetidin-1-yl}-2-oxoethyl)sulfinyl]-1H-1,2,4-triazole (61 mg, 53%) as a white solid.

$^1$H NMR (300 MHz, CDCl$_3$) δ 8.47 (br s, 1H), 7.30-7.22 (m, 1H), 7.15 (t, J=7.8 Hz, 1H), 6.89 (t, J=7.6 Hz, 1H), 6.80 (d, J=8.0 Hz, 1H), 6.61 (s, 1H), 4.47-4.33 (m, 1H), 4.24-3.98 (m, 6H), 3.96-3.84 (m, 1H), 3.17-2.99 (m, 1H), 1.31 (s, 9H).

In addition, 3-[(2-{3-[(2-tert-butylphenoxy)methyl]azetidin-1-yl}-2-oxoethyl)sulfonyl]-1H-1,2,4-triazole (16 mg, 13%) was obtained as a white solid.

$^1$H NMR (300 MHz, CDCl$_3$) δ 8.37 (br s, 1H), 7.33-7.26 (m, 2H), 7.23-7.08 (m, 1H), 6.98-6.88 (m, 1H), 6.88-6.76 (m, 1H), 4.81-4.47 (m, 1H), 4.47-4.18 (m, 4H), 4.18-4.04 (m, 2H), 4.04-3.78 (m, 1H), 3.29-3.04 (m, 1H), 1.36 (s, 9H).

Example 246

2-[4-(2-tert-butyl-4-fluorophenoxy)piperidin-1-yl]-2-oxoethanesulfonic acid

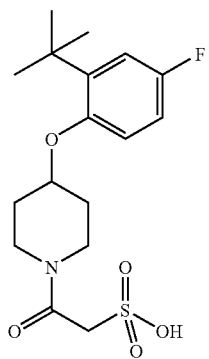 [SMILES: CC(C)(C)c1cc(F)ccc1OC1CCN(C(=O)CS(=O)(=O)O)CC1]

1-{2-[4-(2-tert-Butyl-4-fluorophenoxy)piperidin-1-yl]-2-oxoethoxy}-1H-benzotriazole (950 mg, 2.23 mmol) obtained in Reference Example 76 and sodium sulfite (900 mg, 7.14 mmol) were stirred in water (25 ml) and ethanol (10 mL) at 100° C. for 24 hr. The reaction mixture was cooled to room temperature, acidified with 1N hydrochloric acid, and partitioned between ethyl acetate and water. The ethyl acetate layer was washed with saturated brine, dried over anhydrous magnesium sulfate and filtered. The filtrate was concentrated under reduced pressure, and the obtained residue was purified by silica gel column chromatography (hexane:ethyl acetate 80:20-0:100, ethyl acetate:methanol 99:1-70:30). The obtained white solid was washed with ethyl acetate to give the title compound (31 mg, 4%) as a white solid.

$^1$H NMR (300 MHz, DMSO-d$_6$) δ 7.06-6.91 (m, 3H), 4.76-4.53 (m, 1H), 3.99-3.77 (m, 2H), 3.63 (s, 2H), 3.55-3.37 (m, 1H), 3.28-3.10 (m, 1H), 2.09-1.84 (m, 2H), 1.79-1.62 (m, 1H), 1.61-1.42 (m, 1H), 1.34 (s, 9H).

Reference Example 247 methyl {4-[(2,6-di-tert-butyl-4-fluorophenoxy)methyl]piperidin-1-yl}(oxo)acetate

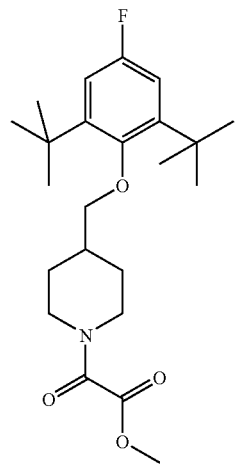 [SMILES: COC(=O)C(=O)N1CCC(COc2c(C(C)(C)C)cc(F)cc2C(C)(C)C)CC1]

According to a method similar to that in Example 124, the title compound (310 mg, 54%) was obtained from 4-[(2,6-di-tert-butyl-4-fluorophenoxy)methyl]piperidine (500 mg, 1.4 mmol) obtained in Reference Example 80 and methyl chloro(oxo)acetate (223 mg, 1.82 mmol).

$^1$H NMR (300 MHz, CDCl$_3$) δ 7.01-6.82 (m, 2H), 4.68-4.55 (m, 1H), 3.88 (s, 3H), 3.81-3.69 (m, 1H), 3.62 (m, J=7.2 Hz, 2H), 3.17 (td, J=13.1, 2.7 Hz, 1H), 2.75 (td, J=13.0, 2.8 Hz, 1H), 2.36-2.17 (m, 1H), 1.87-2.07 (m, 2H), 1.46-1.21 (m, 20H).

Example 248

{4-[(2,6-di-tert-butyl-4-fluorophenoxy)methyl]piperidin-1-yl}(oxo)acetic acid

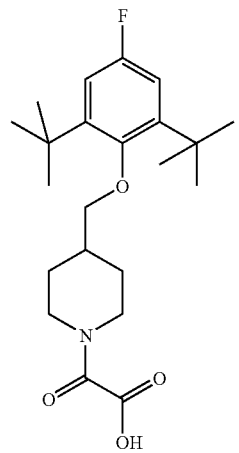 [SMILES: CC(C)(C)c1cc(F)cc(C(C)(C)C)c1OCC1CCN(C(=O)C(=O)O)CC1]

According to a method similar to that in Example 5, the title compound (223 mg, quant.) was obtained as a white solid from methyl {4-[(2,6-di-tert-butyl-4-fluorophenoxy)methyl]piperidin-1-yl}(oxo)acetate (228 mg, 0.56 mmol) obtained in Example 247.

¹H NMR (300 MHz, CDCl₃) δ 6.94 (d, J=10.2 Hz, 2H), 5.21-5.08 (m, 1H), 4.71-4.58 (m, 1H), 3.63 (d, J=7.2 Hz, 2H), 3.21 (td, J=13.1, 2.7 Hz, 1H), 2.86 (td, J=12.9, 2.7 Hz, 1H), 2.39-2.14 (m, 1H), 2.14-1.76 (m, 2H), 1.49-1.22 (m, 20H).

Example 249 ethyl 3-{4-[(2,6-di-tert-butyl-4-fluorophenoxy)methyl]piperidin-1-yl}-3-oxopropanoate

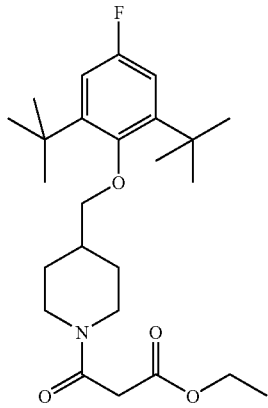 [SMILES: CCOC(=O)CC(=O)N1CCC(COc2c(C(C)(C)C)cc(F)cc2C(C)(C)C)CC1]

According to a method similar to that in Example 9, the title compound (395 mg, 650) was obtained as a white solid from 4-[(2,6-di-tert-butyl-4-fluorophenoxy)methyl]piperidine (500 mg, 1.4 mmol) obtained in Reference Example 80 and 3-ethoxy-3-oxopropanoic acid (240 mg, 1.82 mmol).

¹H NMR (300 MHz, CDCl₃) δ6.93 (m, J=10.6 Hz, 2H), 4.82-4.62 (m, 1H), 4.21 (q, J=7.2 Hz, 2H), 3.91-3.77 (m, 1H), 3.60 (d, J=6.8 Hz, 2H), 3.48 (s, 2H), 3.14 (td, J=13.2, 2.5 Hz, 1H), 2.65 (td, J=13.0, 2.8 Hz, 1H), 2.28-2.15 (m, 1H), 1.95 (t, J=13.4 Hz, 2H), 1.49-1.13 (m, 23H).

Example 250

3-{4-[(2,6-di-tert-butyl-4-fluorophenoxy)methyl]piperidin-1-yl}-3-oxopropanoic acid

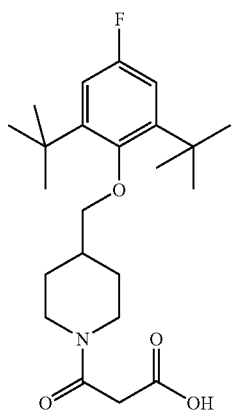 [SMILES: CC(C)(C)c1cc(F)cc(C(C)(C)C)c1OCC1CCN(C(=O)CC(=O)O)CC1]

According to a method similar to that in Example 5, the title compound (328 mg, quant.) was obtained as a white solid from ethyl 3-{4-[(2,6-di-tert-butyl-4-fluorophenoxy)methyl]piperidin-1-yl}-3-oxopropanoate (341 mg, 0.78 mmol) obtained in Example 249.

¹H NMR (300 MHz, CDCl₃) δ 14.34 (br s, 1H), 6.93 (d, J=10.2 Hz, 2H), 4.84-4.65 (m, 1H), 3.95-3.80 (m, 1H), 3.62 (d, J=7.2 Hz, 2H), 3.38 (s, 2H), 3.17 (td, J=13.3, 2.5 Hz, 1H), 2.76 (td, J=12.9, 2.3 Hz, 1H), 2.38-2.17 (m, 1H), 2.16-1.89 (m, 2H), 1.46-1.14 (m, 20H).

Example 251 methyl 4-{4-[(2,6-di-tert-butyl-4-fluorophenoxy)methyl]piperidin-1-yl}-4-oxobutanoate

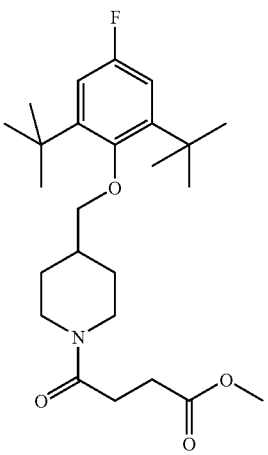 [SMILES: COC(=O)CCC(=O)N1CCC(COc2c(C(C)(C)C)cc(F)cc2C(C)(C)C)CC1]

According to a method similar to that in Example 124, the title compound (384 mg, 63%) was obtained as a white solid from 4-[(2,6-di-tert-butyl-4-fluorophenoxy)methyl]piperidine (500 mg, 1.4 mmol) obtained in Reference Example 80 and methyl 4-chloro-4-oxobutanoate (274 mg, 1.82 mmol).

¹H NMR (300 MHz, CDCl₃) δ 6.92 (m, J=10.6 Hz, 2H), 4.77-4.64 (m, 1H), 4.03-3.90 (m, 1H), 3.71 (s, 3H), 3.60 (d, J=7.2 Hz, 2H), 3.09 (td, J=13.1, 2.7 Hz, 1H), 2.71-2.53 (m, 5H), 2.30-2.11 (m, 1H), 2.04-1.84 (m, 2H), 1.45-1.13 (m, 20H).

Example 252

4-{4-[(2,6-di-tert-butyl-4-fluorophenoxy)methyl]piperidin-1-yl}-4-oxobutanoic acid

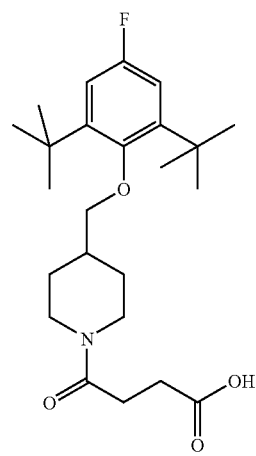 [SMILES: CC(C)(C)c1cc(F)cc(C(C)(C)C)c1OCC1CCN(C(=O)CCC(=O)O)CC1]

According to a method similar to that in Example 5, the title compound (209 mg, 69%) was obtained as a white solid from methyl 4-{4-[(2,6-di-tert-butyl-4-fluorophenoxy)methyl]piperidin-1-yl}-4-oxobutanoate (313 mg, 0.72 mmol) obtained in Example 251.

¹H NMR (300 MHz, CDCl₃) δ 6.93 (m, J=10.2 Hz, 2H), 4.78-4.64 (m, 1H), 3.94 (d, J=13.3 Hz, 1H), 3.61 (d, J=6.8 Hz, 2H), 3.13 (td, J=13.1, 2.3 Hz, 1H), 2.77-2.58 (m, 5H), 2.28-2.21 (m, 1H), 2.09-1.84 (m, 2H), 1.42-1.15 (m, 20H).

Example 253 methyl 4-{4-[(2-tert-butyl-4-fluorophenoxy)methyl]piperidin-1-yl}-4-oxobutanoate

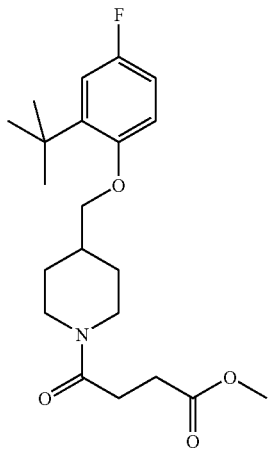 [SMILES: COC(=O)CCC(=O)N1CCC(COc2ccc(F)cc2C(C)(C)C)CC1]

According to a method similar to that in Example 124, the title compound (432 mg, 69%) was obtained as a pale yellow oil from 4-[(2-tert-butyl-4-fluorophenoxy)methyl]piperidine hydrochloride (500 mg, 1.66 mmol) obtained in Reference Example 18 and methyl 4-chloro-4-oxobutanoate (289 mg, 1.92 mmol).

¹H NMR (300 MHz, CDCl₃) δ 7.00 (dd, J=10.9, 3.0 Hz, 1H), 6.81 (dd, J=7.3, 3.0 Hz, 1H), 6.74 (dd, J=9.0, 4.9 Hz, 1H), 4.76-4.60 (m, 1H), 4.04-3.88 (m, 1H), 3.87-3.73 (m, 2H), 3.70 (s, 3H), 3.11 (td, J=13.0, 2.4 Hz, 1H), 2.67 (s, 4H), 2.75-2.55 (m, 1H), 2.23-2.04 (m, 1H), 2.04-1.82 (m, 2H), 1.36 (s, 9H), 1.33-1.26 (m, 2H).

Example 254 methyl [3-(2-tert-butylphenoxy)piperidin-1-yl](oxo)acetate

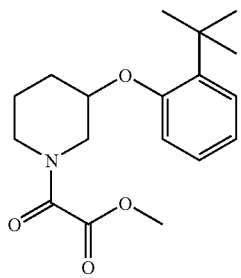 [SMILES: COC(=O)C(=O)N1CCCC(Oc2ccccc2C(C)(C)C)C1]

According to a method similar to that in Example 4, the title compound (0.16 g, 23%) was obtained as a colorless oil from 3-(2-tert-butylphenoxy)piperidine (0.50 g, 2.14 mmol) obtained in Reference Example 69 and methyl chloro(oxo)acetate (0.21 g, 2.35 mmol).

LC/MS ESI(+) m/z: 320 (M+H)⁺.

Example 255

[3-(2-tert-butylphenoxy)piperidin-1-yl](oxo)acetic acid

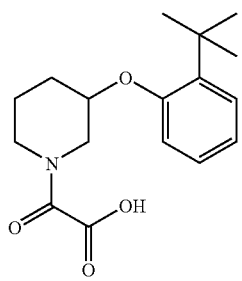 [SMILES: CC(C)(C)c1ccccc1OC1CCCN(C(=O)C(=O)O)C1]

According to a method similar to that in Example 5, the title compound (0.11 g, 82%) was obtained as a white solid from methyl [3-(2-tert-butylphenoxy)piperidin-1-yl](oxo)acetate (0.14 g, 0.44 mmol) obtained in Example 254.

¹H NMR (300 MHz, DMSO-d₆) δ 14.12 (br s, 1H), 7.26-7.19 (m, 1H), 7.19-7.07 (m, 1H), 7.03-6.91 (m, 1H), 6.91-6.78 (m, 1H), 4.70-4.42 (m, 1H), 3.91-3.52 (m, 2H), 3.54-3.21 (m, 2H), 2.17-1.69 (m, 3H), 1.68-1.47 (m, 1H), 1.32 (s, 9H).

Example 256 ethyl 3-[3-(2-tert-butylphenoxy)piperidin-1-yl]-3-oxopropanoate

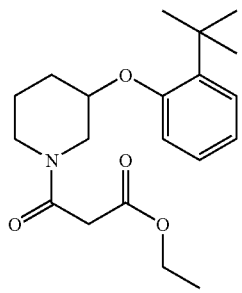 [SMILES: CCOC(=O)CC(=O)N1CCCC(Oc2ccccc2C(C)(C)C)C1]

According to a method similar to that in Example 9, the title compound (0.37 g, 24%) was obtained as a colorless oil from 3-(2-tert-butylphenoxy)piperidine (1.04 g, 4.46 mmol) obtained in Reference Example 69 and 3-ethoxy-3-oxopropanoic acid (0.88 g, 6.69 mmol).

¹H NMR (300 MHz, CDCl₃) δ 7.36-7.28 (m, 1H), 7.21-7.10 (m, 1H), 6.99-6.75 (m, 2H), 4.62-4.33 (m, 1H), 4.30-4.03 (m, 2H), 3.77-3.52 (m, 3H), 3.52-3.18 (m, 3H), 2.29-

2.05 (m, 1H), 2.02-1.76 (m, 2H), 1.75-1.51 (m, 1H), 1.41-1.34 (m, 9H), 1.33-1.20 (m, 3H)

Example 257

3-[3-(2-tert-butylphenoxy)piperidin-1-yl]-3-oxopropanoic acid

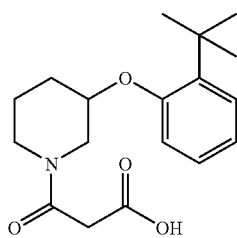 [SMILES: CC(C)(C)c1ccccc1OC1CCCN(C(=O)CC(=O)O)C1]

According to a method similar to that in Example 5, the title compound (0.28 g, 98%) was obtained as a colorless gum-like substance from ethyl 3-[3-(2-tert-butylphenoxy)piperidin-1-yl]-3-oxopropanoate (0.31 g, 0.89 mmol) obtained in Example 256.

$^1$H NMR (300 MHz, DMSO-$d_6$) δ 12.60 (br s, 1H), 7.31-7.08 (m, 2H), 7.06-6.91 (m, 1H), 6.90-6.75 (m, 1H), 4.73-4.38 (m, 1H), 3.93-3.22 (m, 6H), 2.13-1.94 (m, 1H), 1.93-1.70 (m, 2H), 1.68-1.42 (m, 1H), 1.35-1.26 (m, 9H).

Example 258 ethyl 4-[3-(2-tert-butylphenoxy)piperidin-1-yl]-4-oxobutanoate

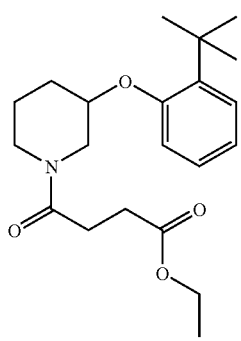 [SMILES: CCOC(=O)CCC(=O)N1CCCC(Oc2ccccc2C(C)(C)C)C1]

According to a method similar to that in Example 4, the title compound (0.68 g, 63%) was obtained as a colorless oil from 3-(2-tert-butylphenoxy)piperidine (0.70 g, 3.0 mmol) obtained in Reference Example 69 and ethyl 4-chloro-4-oxobutanoate (0.54 g, 3.3 mmol).

$^1$H NMR (300 MHz, CDCl$_3$) δ 7.36-7.25 (m, 1H), 7.23-7.06 (m, 1H), 7.01-6.76 (m, 2H), 4.61-4.25 (m, 1H), 4.24-4.01 (m, 2H), 3.85-3.20 (m, 3H), 2.77-2.31 (m, 3H), 2.30-2.00 (m, 2H), 2.01-1.77 (m, 2H), 1.72-1.51 (m, 2H), 1.40-1.32 (m, 9H), 1.32-1.18 (m, 3H).

Example 259

4-[3-(2-tert-butylphenoxy)piperidin-1-yl]-4-oxobutanoic acid

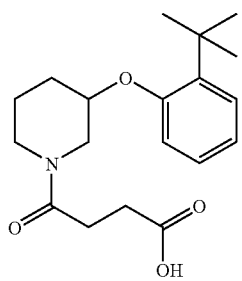 [SMILES: CC(C)(C)c1ccccc1OC1CCCN(C(=O)CCC(=O)O)C1]

According to a method similar to that in Example 5, the title compound (0.48 g, 88%) was obtained as a colorless gum-like substance from ethyl 4-[3-(2-tert-butylphenoxy)piperidin-1-yl]-4-oxobutanoate (0.59 g, 1.63 mmol) obtained in Example 258.

$^1$H NMR (300 MHz, DMSO-$d_6$) δ 11.97 (br s, 1H), 7.29-7.07 (m, 2H), 7.07-6.91 (m, 1H), 6.92-6.73 (m, 1H), 4.70-4.36 (m, 1H), 3.89-3.69 (m, 1H), 3.67-3.38 (m, 2H), 3.40-3.09 (m, 1H), 2.66-2.54 (m, 1H), 2.46-2.14 (m, 2H), 2.10-1.44 (m, 5H), 1.31 (s, 9H).

Example 260 methyl {2-[(2-tert-butylphenoxy)methyl]pyrrolidin-1-yl}(oxo)acetate

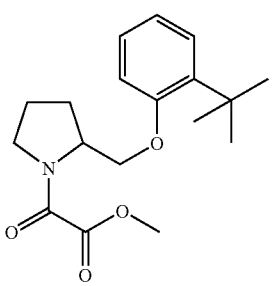 [SMILES: COC(=O)C(=O)N1CCCC1COc1ccccc1C(C)(C)C]

According to a method similar to that in Example 4, the title compound (0.65 g, 53%) was obtained from 2-[(2-tert-butylphenoxy)methyl]pyrrolidine (0.89 g, 3.81 mmol) obtained in Reference Example 82 and methyl chloro(oxo)acetate (0.51 g, 4.20 mmol).

$^1$H NMR (300 MHz, CDCl$_3$) δ 7.34-7.26 (m, 1H), 7.22-7.11 (m, 1H), 7.02-6.79 (m, 2H), 4.60-4.46 (m, 1H), 4.36-

4.25 (m, 1H), 4.18-4.02 (m, 1H), 3.90-3.84 (m, 3H), 3.78-3.67 (m, 2H), 2.32-1.88 (m, 4H), 1.41-1.33 (m, 9H).

Example 261

{2-[(2-tert-butylphenoxy)methyl]pyrrolidin-1-yl}(oxo)acetic acid

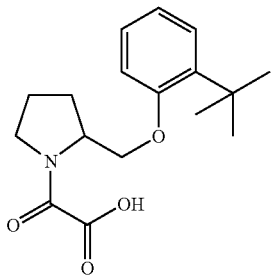 [SMILES: CC(C)(C)c1ccccc1OCC1CCCN1C(=O)C(=O)O]

According to a method similar to that in Example 5, the title compound (0.41 g, 81%) was obtained as a white solid from methyl {2-[(2-tert-butylphenoxy)methyl]pyrrolidin-1-yl}(oxo)acetate (0.53 g, 1.66 mmol) obtained in Example 260.

$^1$H NMR (300 MHz, DMSO-d$_6$) δ 14.10 (br s, 1H), 7.31-7.07 (m, 2H), 7.05-6.72 (m, 2H), 4.55-4.22 (m, 1H), 4.22-3.87 (m, 2H), 3.74-3.28 (m, 2H), 2.30-1.74 (m, 4H), 1.38-1.25 (m, 9H).

Example 262 ethyl 3-{2-[(2-tert-butylphenoxy)methyl]pyrrolidin-1-yl}-3-oxopropanoate

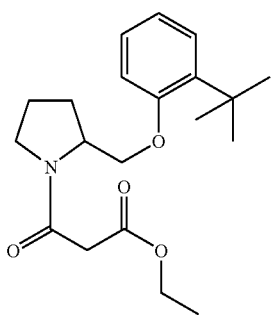 [SMILES: CCOC(=O)CC(=O)N1CCCC1COc1ccccc1C(C)(C)C]

According to a method similar to that in Example 9, the title compound (2.17 g, 67%) was obtained as a pale brown oil from 2-[(2-tert-butylphenoxy)methyl]pyrrolidine (2.17 g, 9.30 mmol) obtained in Reference Example 82 and 3-ethoxy-3-oxopropanoic acid (1.83 g, 13.9 mmol).

$^1$H NMR (300 MHz, CDCl$_3$) δ 7.34-7.23 (m, 1H), 7.21-7.09 (m, 1H), 7.00-6.94 (m, 1H), 6.93-6.79 (m, 1H), 4.62-4.43 (m, 1H), 4.31 (dd, J=9.2, 3.2 Hz, 1H), 4.21 (q, J=6.9 Hz, 2H), 3.99 (dd, J=9.2, 7.7 Hz, 1H), 3.66-3.47 (m, 2H), 3.41 (d, J=4.1 Hz, 2H), 2.30-1.89 (m, 4H), 1.38 (s, 9H), 1.28 (t, J=6.9 Hz, 3H).

Example 263

3-{2-[(2-tert-butylphenoxy)methyl]pyrrolidin-1-yl}-3-oxopropanoic acid

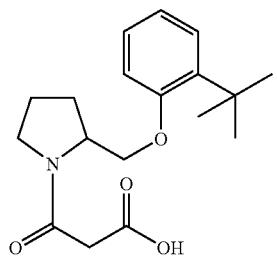 [SMILES: CC(C)(C)c1ccccc1OCC1CCCN1C(=O)CC(=O)O]

According to a method similar to that in Example 5, the title compound (1.66 g, 920) was obtained as a white solid from ethyl 3-{2-[(2-tert-butylphenoxy)methyl]pyrrolidin-1-yl}-3-oxopropanoate (1.96 g, 5.64 mmol) obtained in Example 262.

$^1$H NMR (300 MHz, DMSO-d$_6$) δ 12.60 (br s, 1H), 7.29-7.10 (m, 2H), 7.05-6.95 (m, 1H), 6.93-6.77 (m, 1H), 4.40-4.23 (m, 1H), 4.14 (dd, J=9.5, 3.0 Hz, 1H), 4.00-3.85 (m, 1H), 3.61-3.42 (m, 2H), 3.37 (d like, 2H), 2.14-1.81 (m, 4H), 1.34 (s, 9H).

Example 264 ethyl 4-{2-[(2-tert-butylphenoxy)methyl]pyrrolidin-1-yl}-4-oxobutanoate

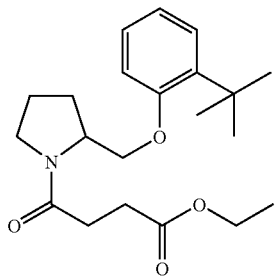 [SMILES: CCOC(=O)CCC(=O)N1CCCC1COc1ccccc1C(C)(C)C]

According to a method similar to that in Example 4, the title compound (0.83 g, 60%) was obtained as a pale brown oil from 2-[(2-tert-butylphenoxy)methyl]pyrrolidine (0.89 g, 3.81 mmol) obtained in Reference Example 82 and ethyl 4-chloro-4-oxobutanoate (0.69 g, 4.20 mmol).

$^1$H NMR (300 MHz, CDCl$_3$) δ 7.33-7.23 (m, 1H), 7.20-7.09 (m, 1H), 6.99-6.79 (m, 2H), 4.55-4.21 (m, 1H), 4.20-

4.08 (m, 2H), 4.02-3.92 (m, 1H), 3.65-3.47 (m, 2H), 2.86-2.48 (m, 5H), 2.32-1.91 (m, 4H), 1.44-1.34 (m, 9H), 1.30-1.21 (m, 3H).

Example 265

4-{2-[(2-tert-butylphenoxy)methyl]pyrrolidin-1-yl}-4-oxobutanoic acid

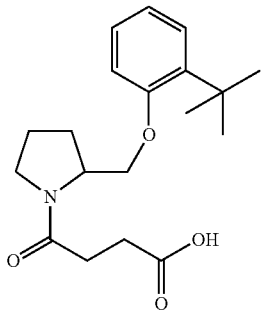 [SMILES: CC(C)(C)c1ccccc1OCC1CCCN1C(=O)CCC(=O)O]

According to a method similar to that in Example 5, the title compound (0.50, 85%) was obtained as a white solid from ethyl 4-{2-[(2-tert-butylphenoxy)methyl]pyrrolidin-1-yl}-4-oxobutanoate (0.64 g, 1.77 mmol) obtained in Example 264.

$^1$H NMR (300 MHz, DMSO-d$_6$) δ 12.05 (s, 1H), 7.29-7.08 (m, 2H), 7.04-6.96 (m, 1H), 6.92-6.78 (m, 1H), 4.36-4.22 (m, 1H), 4.11 (dd, J=9.5, 3.0 Hz, 1H), 3.98-3.82 (m, 1H), 3.57-3.44 (m, 2H), 2.67-2.52 (m, 1H), 2.35-2.48 (m, 3H), 2.18-1.82 (m, 4H), 1.38-1.32 (m, 9H).

Example 266

4-(2-tert-butylphenoxy)piperidine-1-carboxamide

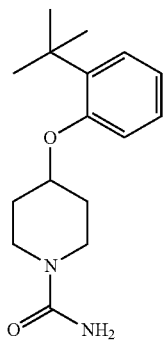

A suspension of 4-(2-tert-butylphenoxy)piperidine hydrochloride (300 mg, 1.12 mmol) obtained in Reference Example 15, isocyanato(trimethyl)silane (154 mg, 1.34 mmol) and triethylamine (232 μL, 1.67 mmol) in THF (10 mL) was stirred at room temperature for 16 hr, 1N hydrochloric acid (3 mL) was added, and the mixture was further stirred for 1 hr. The reaction mixture was partitioned between ethyl acetate-water, and the ethyl acetate layer was washed with saturated brine, dried over anhydrous magnesium sulfate and filtered. The filtrate was concentrated under reduced pressure to give the title compound (303 mg, 99%) as a white solid.

$^1$H NMR (300 MHz, CDCl$_3$) δ 7.31 (dd, J=7.8, 1.7 Hz, 1H), 7.21-7.07 (m, 1H), 6.89 (td, J=7.6, 1.1 Hz, 1H), 6.83 (d, J=8.0 Hz, 1H), 4.72-4.58 (m, 1H), 4.48 (br. s., 2H), 3.65 (ddd, J=13.1, 8.5, 3.8 Hz, 2H), 3.56-3.26 (m, 2H), 2.14-1.80 (m, 4H), 1.38 (s, 9H).

Example 267

4-(2-tert-butyl-4-fluorophenoxy)-1-(1H-pyrazol-3-ylcarbonyl)piperidine

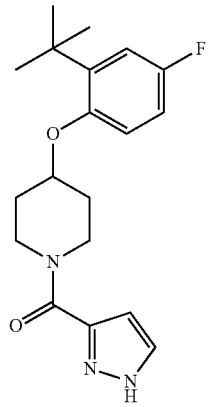 [SMILES: CC(C)(C)c1cc(F)ccc1OC1CCN(C(=O)c2cc[nH]n2)CC1]

According to a method similar to that in Example 9, the title compound (132 mg, 38%) was obtained as a white solid from 4-(2-tert-butyl-4-fluorophenoxy)piperidine hydrochloride (287 mg, 1.0 mmol) obtained in Reference Example 75 and 1H-pyrazole-3-carboxylic acid (146 mg, 9.0 mmol).

$^1$H NMR (300 MHz, CDCl$_3$) δ 7.61 (d, J=2.3 Hz, 1H), 7.03 (dd, J=11.0, 3.0 Hz, 1H), 6.88-6.79 (m, 1H), 6.75 (dd, J=9.1, 4.9 Hz, 1H), 6.69 (d, J=2.3 Hz, 1H), 4.73-4.56 (m, 1H), 4.28-3.76 (m, 4H), 2.20-1.85 (m, 4H), 1.39 (s, 9H).

Example 268

4-(2-tert-butyl-4-fluorophenoxy)-1-(1H-imidazol-4-ylcarbonyl)piperidine

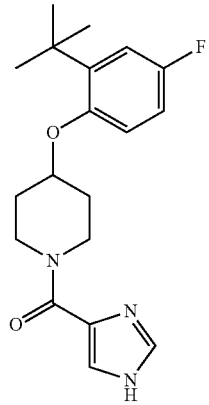 [SMILES: CC(C)(C)c1cc(F)ccc1OC1CCN(C(=O)c2c[nH]cn2)CC1]

According to a method similar to that in Example 9, the title compound (132 mg, 38%) was obtained as a white solid from 4-(2-tert-butyl-4-fluorophenoxy)piperidine hydrochloride (287 mg, 1.0 mmol) obtained in Reference Example 75 and 1H-imidazole-4-carboxylic acid (146 mg, 9.0 mmol).

$^1$H NMR (300 MHz, CDCl$_3$) δ 7.67 (br. s., 1H), 7.50 (br. s., 1H), 7.03 (dd, J=11.0, 3.0 Hz, 1H), 6.90-6.79 (m, 1H), 6.75 (dd, J=9.1, 4.9 Hz, 1H), 4.74-4.56 (m, 1H), 4.36-3.55 (m, 4H), 2.19-2.03 (m, 2H), 2.03-1.87 (m, 2H), 1.38 (s, 9H).

Example 269

2-[4-(2-tert-butylphenoxy)piperidin-1-yl]-2-oxo-N-1H-tetrazol-5-ylacetamide

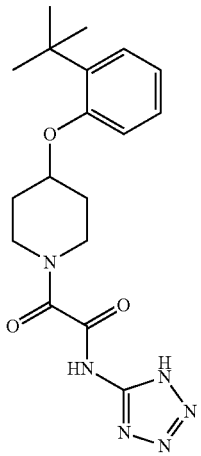 [SMILES: CC(C)(C)c1ccccc1OC1CCN(C(=O)C(=O)Nc2nnn[nH]2)CC1]

A solution of [4-(2-tert-butylphenoxy)piperidin-1-yl](oxo)acetic acid (300 mg, 0.98 mmol) obtained in Example 52 and oxalyl chloride (126 μL, 1.47 mmol) in toluene (5 ml) was stirred at room temperature for 3 hr. The reaction mixture was concentrated, and DMF (1 mL) was added to the residue. The mixture was added to a solution of 1H-tetrazole-5-amine (255 mg, 3.0 mmol) and triethylamine (205 μL, 1.47 mmol) in toluene (10 ml) under ice-cooling, and the mixture was stirred at room temperature for 16 hr. The reaction mixture was partitioned between ethyl acetate-1N hydrochloric acid, and the ethyl acetate layer was washed with saturated brine, dried over anhydrous magnesium sulfate and filtered. The filtrate was concentrated under reduced pressure to give the title compound (317 mg, 87%) as a white solid.

$^1$H NMR (300 MHz, CDCl$_3$) δ 10.62 (br. s., 1H), 7.34 (dd, J=7.8, 1.7 Hz, 1H), 7.22-7.13 (m, 1H), 6.96-6.87 (m, 1H), 6.83 (d, J=8.0 Hz, 1H), 4.83-4.70 (m, 1H), 4.52-4.37 (m, 1H), 4.32-4.16 (m, 1H), 4.06-3.92 (m, 1H), 3.88-3.76 (m, 1H), 2.19-2.00 (m, 4H), 1.41 (s, 9H).

Example 270

2-[4-(2-tert-butylphenoxy)piperidin-1-yl]-2-oxoacetamide

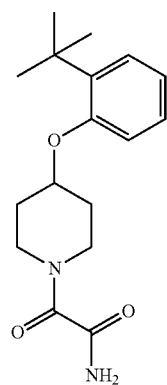

According to a method similar to that in Example 9, the title compound (383 mg, 97%) was obtained as a white solid from [4-(2-tert-butylphenoxy)piperidin-1-yl](oxo)acetic acid (400 mg, 1.30 mmol) and ammonium chloride (73.6 mg, 1.38 mmol) obtained in Example 52.

$^1$H NMR (300 MHz, CDCl$_3$) δ 7.32 (dd, J=7.8, 1.7 Hz, 1H), 7.20-7.12 (m, 1H), 6.97 (br. s., 1H), 6.92-6.85 (m, 1H), 6.83 (d, J=8.0 Hz, 1H), 5.51 (br. s., 1H), 4.81-4.60 (m, 1H), 4.30-4.01 (m, 2H), 3.92-3.67 (m, 2H), 2.21-1.89 (m, 4H), 1.38 (s, 9H).

Example 271 tert-butyl 2-{[4-(2-tert-butylphenoxy)piperidin-1-yl](oxo)acetyl}hydrazinecarboxylate

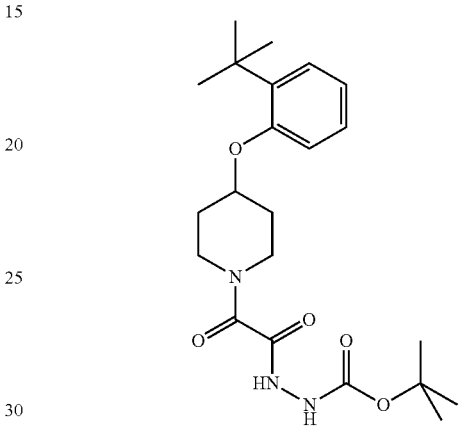

According to a method similar to that in Example 9, the title compound (744 mg, quant.) was obtained as a pale yellow amorphous form from [4-(2-tert-butylphenoxy)piperidin-1-yl](oxo)acetic acid (500 mg, 1.64 mmol) and tert-butyl hydrazinecarboxylate (282 mg, 2.13 mmol) obtained in Example 52.

$^1$H NMR (300 MHz, CDCl$_3$) δ 8.70 (br. s., 1H), 7.32 (dd, J=7.8, 1.7 Hz, 1H), 7.21-7.12 (m, 1H), 6.89 (td, J=7.6, 1.1 Hz, 1H), 6.82 (d, J=8.0 Hz, 1H), 6.55 (br. s., 1H), 4.85-4.59 (m, 1H), 4.20-3.99 (m, 2H), 3.93-3.65 (m, 2H), 2.16-1.90 (m, 4H), 1.49 (s, 9H), 1.42 (s, 9H).

Example 272

2-[4-(2-tert-butylphenoxy)piperidin-1-yl]-2-oxoacetohydrazidetrifluoroacetate

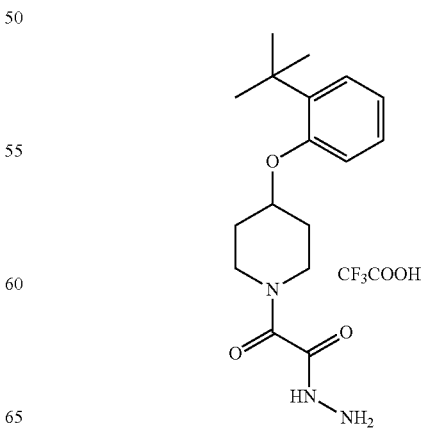

A solution of tert-butyl 2-{[4-(2-tert-butylphenoxy)piperidin-1-yl](oxo)acetyl}hydrazinecarboxylate (714 mg, 1.70 mmol) obtained in Example 271 in trifluoroacetic acid (3 mL) was stirred at room temperature for 16 hr. Water was added to the reaction mixture, and the resulting precipitate was collected by filtration to give the title compound (538 mg, 73%) as a white solid.

$^1$H NMR (300 MHz, DMSO-d$_6$) δ 7.28-7.20 (m, 1H), 7.20-7.10 (m, 1H), 7.02 (d, J=7.6 Hz, 1H), 6.84 (t, J=7.0 Hz, 1H), 4.85-4.69 (m, 1H), 3.94-3.72 (m, 1H), 3.72-3.58 (m, 1H), 3.53-3.30 (m, 2H), 2.13-1.89 (m, 2H), 1.83-1.54 (m, 2H), 1.35 (s, 9H).

Example 273

1-acryloyl-4-(2-tert-butyl-4-fluorophenoxy)piperidine

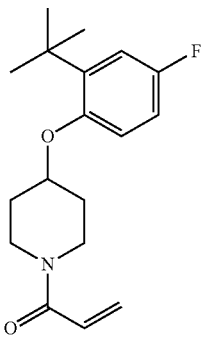 [SMILES: C=CC(=O)N1CCC(Oc2ccc(F)cc2C(C)(C)C)CC1]

According to a method similar to that in Example 269, the title compound (3.16 g, 60%) was obtained as a white solid from 4-(2-tert-butyl-4-fluorophenoxy)piperidine hydrochloride (5.00 g, 17.4 mmol) obtained in Reference Example 75 and 3-bromopropanoic acid (3.72 g, 24.3 mmol).

$^1$H NMR (300 MHz, CDCl$_3$) δ 7.02 (dd, J=11.0, 3.0 Hz, 1H), 6.89-6.78 (m, 1H), 6.78-6.68 (m, 1H), 6.61 (dd, J=16.8, 10.4 Hz, 1H), 6.30 (dd, J=16.8, 2.1 Hz, 1H), 5.70 (dd, J=10.6, 1.9 Hz, 1H), 4.71-4.64 (m, 1H), 3.77 (br. s., 3H), 3.58 (br. s., 1H), 2.10-1.96 (m, 2H), 1.96-1.78 (m, 2H), 1.36 (s, 9H).

Example 274

4-(2-tert-butyl-4-fluorophenoxy)-1-(1H-1,2,4-triazol-3-ylcarbonyl)piperidine

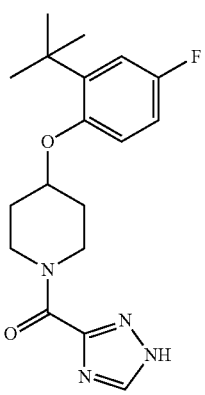 [SMILES: CC(C)(C)c1cc(F)ccc1OC1CCN(C(=O)c2nc[nH]n2)CC1]

According to a method similar to that in Example 9, the title compound (2.83 g, 94%) was obtained as a white solid from 4-(2-tert-butyl-4-fluorophenoxy)piperidine hydrochloride (2.50 g, 8.70 mmol) obtained in Reference Example 75 and 1H-1,2,4-triazole-3-carboxylic acid (1.13 g, 10.0 mmol).

$^1$H NMR (300 MHz, CDCl$_3$) δ 8.18 (s, 1H), 7.04 (dd, J=10.9, 3.0 Hz, 1H), 6.89-6.80 (m, 1H), 6.75 (dd, J=9.0, 4.9 Hz, 1H), 4.75-4.62 (m, 1H), 4.62-4.44 (m, 2H), 4.09-3.85 (m, 2H), 2.23-1.98 (m, 4H), 1.36 (s, 9H).

Example 275

5-{[4-(2-tert-butylphenoxy)piperidin-1-yl]carbonyl}-1,3,4-oxadiazol-2(3H)-one

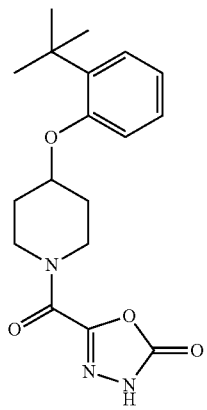 [SMILES: CC(C)(C)c1ccccc1OC1CCN(C(=O)c2n[nH]c(=O)o2)CC1]

A solution of 2-[4-(2-tert-butylphenoxy)piperidin-1-yl]-2-oxoacetohydrazidetrifluoroacetate (235 mg, 0.54 mmol) obtained in Example 272, 1,1'-carbonylbis(1H-imidazole) (108 mg, 0.59 mmol) and 1,8-diazabicyclo[5,4,0]undec-7-en (191 mg, 1.13 mmol) in THF (15 mL) was stirred at room temperature for 16 hr. The reaction mixture was partitioned between ethyl acetate-1N hydrochloric acid, and the ethyl acetate layer was washed with saturated brine, dried over anhydrous magnesium sulfate and filtered. The filtrate was concentrated under reduced pressure to give the title compound (317 mg, 87%) as a white solid.

$^1$H NMR (300 MHz, CDCl$_3$) δ 9.29 (br. s., 1H), 7.33 (dd, J=7.8, 1.7 Hz, 1H), 7.22-7.11 (m, 1H), 6.90 (td, J=7.6, 1.1 Hz, 1H), 6.83 (d, J=8.0 Hz, 1H), 4.86-4.64 (m, 1H), 4.07-3.91 (m, 3H), 3.87-3.71 (m, 1H), 2.18-1.95 (m, 4H), 1.41 (s, 9H).

Example 276

4-(2-tert-butyl-4-fluorophenoxy)-1-{[1-(methylsulfonyl)-1H-1,2,4-triazol-3-yl]carbonyl}piperidine

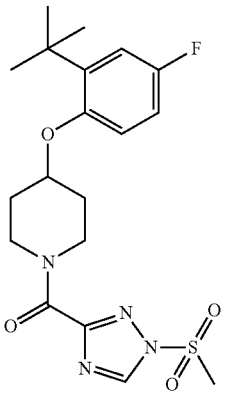 [SMILES: CC(C)(C)c1cc(F)ccc1OC1CCN(C(=O)c2ncn(S(C)(=O)=O)n2)CC1]

To a solution of 4-(2-tert-butyl-4-fluorophenoxy)-1-(1H-1,2,4-triazol-3-ylcarbonyl)piperidine (200 mg, 0.58 mmol)

obtained in Example 274 in pyridine (3 mL) was added methanesulfonyl chloride (99 mg, 0.87 mmol), and the mixture was stirred at room temperature for 16 hr. The reaction mixture was concentrated, and the residue was partitioned between ethyl acetate-water. The ethyl acetate layer was washed with saturated brine, dried over anhydrous magnesium sulfate and filtered. The filtrate was concentrated under reduced pressure to give the title compound (245 mg, 99%) as a white solid.

$^1$H NMR (300 MHz, CDCl$_3$) δ 8.72 (s, 1H), 7.03 (dd, J=10.9, 3.0 Hz, 1H), 6.88-6.79 (m, 1H), 6.73 (dd, J=9.0, 4.9 Hz, 1H), 4.74-4.57 (m, 1H), 4.05-3.78 (m, 3H), 3.77-3.61 (m, 1H), 3.57-3.45 (m, 3H), 2.22-1.88 (m, 4H), 1.38 (s, 9H).

Example 277

5-{2-[4-(2-tert-butyl-4-fluorophenoxy)piperidin-1-yl]-2-oxoethyl}imidazolidine-2,4-dione

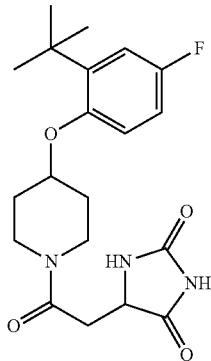 [SMILES: CC(C)(C)c1cc(F)ccc1OC1CCN(C(=O)CC2NC(=O)NC2=O)CC1]

According to a method similar to that in Example 9, the title compound (427 mg, quant.) was obtained as a white solid from 4-(2-tert-butyl-4-fluorophenoxy)piperidine hydrochloride (300 mg, 1.05 mmol) obtained in Reference Example 75 and (2,5-dioxoimidazolidin-4-yl)acetic acid (259 mg, 1.35 mmol).

$^1$H NMR (300 MHz, CDCl$_3$) δ 7.75 (br. s., 1H), 7.03 (dd, J=10.9, 3.0 Hz, 1H), 6.88-6.78 (m, 1H), 6.72 (dd, J=8.7, 4.9 Hz, 1H), 6.11 (s, 1H), 4.69-4.55 (m, 1H), 4.48 (d, J=11.3 Hz, 1H), 3.87-3.53 (m, 3H), 3.53-3.34 (m, 1H), 3.14 (dd, J=16.6, 2.6 Hz, 1H), 2.58 (dd, J=16.8, 11.1 Hz, 1H), 2.09-1.82 (m, 4H), 1.38 (s, 9H).

Example 278

4-{[4-(2-tert-butyl-4-fluorophenoxy)piperidin-1-yl]carbonyl}piperidine-2,6-dione

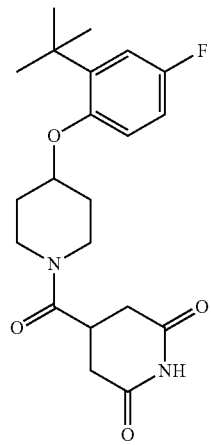 [SMILES: CC(C)(C)c1cc(F)ccc1OC1CCN(C(=O)C2CC(=O)NC(=O)C2)CC1]

According to a method similar to that in Example 9, the title compound (375 mg, 92%) was obtained as a gray solid from 4-(2-tert-butyl-4-fluorophenoxy)piperidine hydrochloride (300 mg, 1.05 mmol) obtained in Reference Example 75 and 2,6-dioxopiperidine-4-carboxylic acid (189 mg, 1.20 mmol).

$^1$H NMR (300 MHz, CDCl$_3$) δ 7.83 (br. s., 1H), 7.03 (dd, J=10.9, 3.0 Hz, 1H), 6.88-6.79 (m, 1H), 6.72 (dd, J=9.0, 4.5 Hz, 1H), 4.69-4.54 (m, 1H), 3.83-3.66 (m, 3H), 3.60-3.47 (m, 1H), 3.47-3.34 (m, 1H), 2.86 (dd, J=16.8, 8.5 Hz, 2H), 2.70 (dd, J=17.3, 4.9 Hz, 2H), 2.09-1.83 (m, 4H), 1.35 (s, 9H).

Example 279

4-{2-[4-(2-tert-butyl-4-fluorophenoxy)piperidin-1-yl]-2-oxoethyl}piperidine-2,6-dione

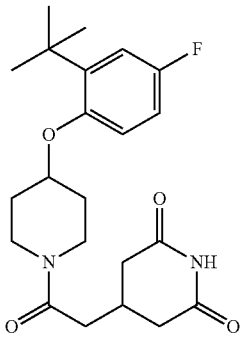 [SMILES: CC(C)(C)c1cc(F)ccc1OC1CCN(C(=O)CC2CC(=O)NC(=O)C2)CC1]

According to a method similar to that in Example 9, the title compound (407 mg, 97%) was obtained as a gray solid from 4-(2-tert-butyl-4-fluorophenoxy)piperidine hydrochloride (300 mg, 1.05 mmol) obtained in Reference Example 75 and (2,6-dioxopiperidin-4-yl)acetic acid (205 mg, 1.20 mmol).

$^1$H NMR (300 MHz, CDCl$_3$) δ 7.88 (s, 1H), 7.03 (dd, J=10.9, 3.0 Hz, 1H), 6.89-6.77 (m, 1H), 6.72 (dd, J=9.0, 4.9 Hz, 1H), 4.67-4.50 (m, 1H), 3.87-3.60 (m, 3H), 3.50-3.35 (m, 1H), 2.91-2.69 (m, 3H), 2.53-2.32 (m, 4H), 2.07-1.79 (m, 4H), 1.35 (s, 9H).

Example 280

3-{2-[4-(2-tert-butyl-4-fluorophenoxy)piperidin-1-yl]-2-oxoethyl}pyrimidine-2,4(1H,3H)-dione

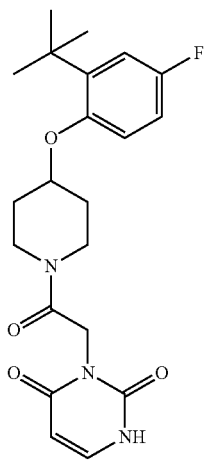 [SMILES: CC(C)(C)c1cc(F)ccc1OC1CCN(C(=O)Cn2c(=O)cc[nH]c2=O)CC1]

According to a method similar to that in Example 9, the title compound (395 mg, 94%) was obtained as a white solid from 4-(2-tert-butyl-4-fluorophenoxy)piperidine hydrochloride (300 mg, 1.05 mmol) obtained in Reference Example 75 and (2,6-dioxo-3,6-dihydropyrimidin-1(2H)-yl)acetic acid (204 mg, 1.20 mmol).

$^1$H NMR (300 MHz, CDCl$_3$) δ 8.26 (br. s., 1H), 7.16 (d, J=8.0 Hz, 1H), 7.03 (dd, J=11.0, 3.0 Hz, 1H), 6.89-6.78 (m, 1H), 6.72 (dd, J=9.1, 4.9 Hz, 1H), 5.75 (dd, J=7.8, 2.1 Hz, 1H), 4.77-4.57 (m, 2H), 4.55-4.40 (m, 1H), 3.90-3.64 (m, 3H), 3.64-3.36 (m, 1H), 2.19-1.84 (m, 4H), 1.39 (s, 9H).

Example 281

5-{[4-(2-tert-butyl-4-fluorophenoxy)piperidin-1-yl]carbonyl}-2,4-dihydro-3H-1,2,4-triazol-3-one

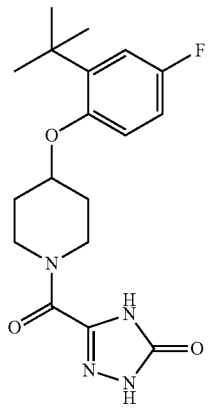 [SMILES: CC(C)(C)c1cc(F)ccc1OC1CCN(C(=O)c2n[nH]c(=O)[nH]2)CC1]

According to a method similar to that in Example 9, the title compound (110 mg, 29%) was obtained as a white solid from 4-(2-tert-butyl-4-fluorophenoxy)piperidine hydrochloride (300 mg, 1.05 mmol) obtained in Reference Example 75 and 5-oxo-4,5-dihydro-1H-1,2,4-triazole-3-carboxylic acid (144 mg, 1.20 mmol).

$^1$H NMR (300 MHz, CDCl$_3$) δ 7.02 (dd, J=10.8, 2.8 Hz, 1H), 6.88-6.77 (m, 1H), 6.71 (dd, J=8.9, 4.7 Hz, 1H), 4.62 (br. s., 1H). 4.47-4.20 (m, 2H), 3.97-3.71 (m, 2H), 2.14-1.81 (m, 4H), 1.36 (s, 9H).

Example 282 methyl [3-(2-tert-butyl-4-methylphenoxy)azetidin-1-yl](oxo)acetate

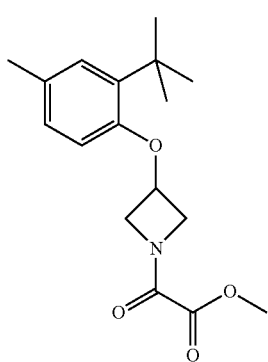

According to a method similar to that in Example 124, the title compound (0.28 g, 67%) was obtained as a white solid from 3-(2-tert-butyl-4-methylphenoxy)azetidine (0.30 g, 1.37 mmol) obtained in Reference Example 84 and methyl chloro(oxo)acetate (0.18 g, 1.50 mmol).

$^1$H NMR (300 MHz, CDCl$_3$) δ 7.12 (d, J=2.3 Hz, 1H), 6.98-6.89 (m, 1H), 6.35 (d, J=8.3 Hz, 1H), 5.05-4.81 (m, 2H), 4.66-4.48 (m, 2H), 4.29-4.16 (m, 1H), 3.87 (s, 3H), 2.29 (s, 3H), 1.38 (s, 9H).

Example 283 ethyl 3-[3-(2-tert-butyl-4-methylphenoxy)azetidin-1-yl]-3-oxopropanoate

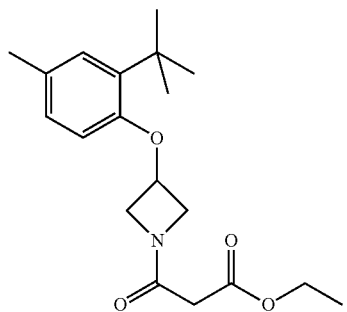 [SMILES: CCOC(=O)CC(=O)N1CC(Oc2ccc(C)cc2C(C)(C)C)C1]

According to a method similar to that in Example 9, the title compound (0.77 g, 97%) was obtained as a colorless oil from 3-(2-tert-butyl-4-methylphenoxy)azetidine (0.52 g, 2.37 mmol) obtained in Reference Example 84 and 3-ethoxy-3-oxopropanoic acid (0.47 g, 3.56 mmol).

$^1$H NMR (300 MHz, CDCl$_3$) δ 7.12 (d, 1H), 6.94 (dd, J=8.3, 2.3 Hz, 1H), 6.35 (d, J=8.3 Hz, 1H), 5.02-4.90 (m, 1H), 4.63-4.54 (m, 1H), 4.51-4.39 (m, 1H), 4.30-4.12 (m, 4H), 3.24 (s, 2H), 2.28 (s, 3H), 1.38 (s, 9H), 1.32-1.25 (m, 3H).

Example 284 ethyl 4-[3-(2-tert-butyl-4-methylphenoxy)azetidin-1-yl]-4-oxobutanoate

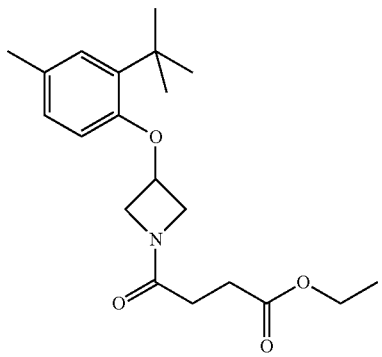 [SMILES: CCOC(=O)CCC(=O)N1CC(Oc2ccc(C)cc2C(C)(C)C)C1]

According to a method similar to that in Example 124, the title compound (0.43 g, 90%) was obtained as a colorless oil from 3-(2-tert-butyl-4-methylphenoxy)azetidine (0.30 g, 1.37 mmol) obtained in Reference Example 84 and ethyl 4-chloro-4-oxobutanoate (0.25 g, 1.50 mmol).

$^1$H NMR (300 MHz, CDCl$_3$) δ 7.12 (d, J=1.9 Hz, 1H), 6.96-6.91 (m, 1H), 6.36 (d, J=8.3 Hz, 1H), 5.01-4.91 (m, 1H), 4.63-4.52 (m, 1H), 4.47-4.36 (m, 1H), 4.28-4.19 (m, 1H), 4.19-4.05 (m, 2H), 2.75-2.59 (m, 3H), 2.46-2.36 (m, 2H), 2.28 (s, 3H), 1.38 (s, 9H), 1.26 (t, J=7.2 Hz, 3H).

Example 285

[3-(2-tert-butyl-4-methylphenoxy) azetidin-1-yl](oxo)acetic acid

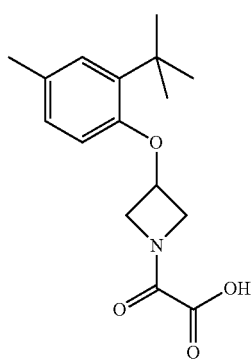 [SMILES: Cc1ccc(OC2CN(C(=O)C(=O)O)C2)c(C(C)(C)C)c1]

According to a method similar to that in Example 5, the title compound (0.18 g, 75%) was obtained as a white solid from methyl [3-(2-tert-butyl-4-methylphenoxy)azetidin-1-yl](oxo)acetate (0.25 g, 0.82 mmol) obtained in Example 282.

$^1$H NMR (300 MHz, DMSO-d$_6$) δ 13.94 (br. s., 1H), 7.06 (d, J=2.3 Hz, 1H), 7.00-6.88 (m, 1H), 6.55 (d, J=8.3 Hz, 1H), 5.12-4.96 (m, 1H), 4.90-4.77 (m, 1H), 4.45 (dd, J=9.8, 6.4 Hz, 1H), 4.29 (dd, J=10.9, 2.6 Hz, 1H), 3.99-3.78 (m, 1H), 2.23 (s, 3H), 1.34 (s, 9H).

Example 286

4-[3-(2-tert-butyl-4-methylphenoxy)azetidin-1-yl]-4-oxobutanoic acid

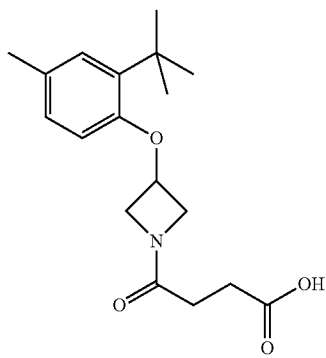 [SMILES: Cc1ccc(OC2CN(C(=O)CCC(=O)O)C2)c(C(C)(C)C)c1]

According to a method similar to that in Example 5, the title compound (0.21 g, 69%) was obtained as a white solid from ethyl 4-[3-(2-tert-butyl-4-methylphenoxy)azetidin-1-yl]-4-oxobutanoate (0.33 g, 0.95 mmol) obtained in Example 284.

$^1$H NMR (300 MHz, DMSO-d$_6$) δ 12.07 (br. s., 1H), 7.05 (d, J=1.9 Hz, 1H), 6.97-6.92 (m, 1H), 6.55 (d, J=8.3 Hz, 1H), 5.12-4.95 (m, 1H), 4.64-4.53 (m, 1H), 4.38-4.21 (m, 1H), 4.10 (dd, J=9.4, 4.1 Hz, 1H), 3.76 (dd, J=10.4, 3.6 Hz, 1H), 2.46-2.38 (m, 2H), 2.36-2.27 (m, 2H), 2.22 (s, 3H), 1.34 (s, 9H).

Example 287

3-[3-(2-tert-butyl-4-methylphenoxy)azetidin-1-yl]-3-oxopropanoic acid

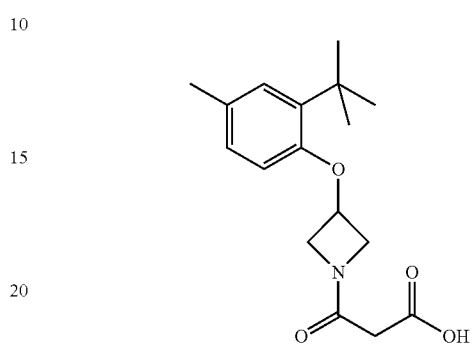

According to a method similar to that in Example 5, the title compound (0.50 g, 83%) was obtained as a white solid from ethyl 3-[3-(2-tert-butyl-4-methylphenoxy)azetidin-1-yl]-3-oxopropanoate (0.66 g, 1.98 mmol) obtained in Example 283.

$^1$H NMR (300 MHz, DMSO-d$_6$) δ 12.59 (br. s., 1H), 7.05 (d, J=1.9 Hz, 1H), 6.95 (dd, J=7.9, 1.9 Hz, 1H), 6.55 (d, J=8.3 Hz, 1H), 5.13-4.96 (m, 1H), 4.63-4.54 (m, 1H), 4.39-4.28 (m, 1H), 4.15-4.07 (m, 1H), 3.80 (dd, J=10.7, 3.6 Hz, 1H), 3.20 (s, 2H), 2.22 (s, 3H), 1.34 (s, 9H).

Example 288

2-[4-(2-tert-butylphenoxy)piperidin-1-yl]-N,N-bis(2-hydroxyethyl)-2-oxoacetamide

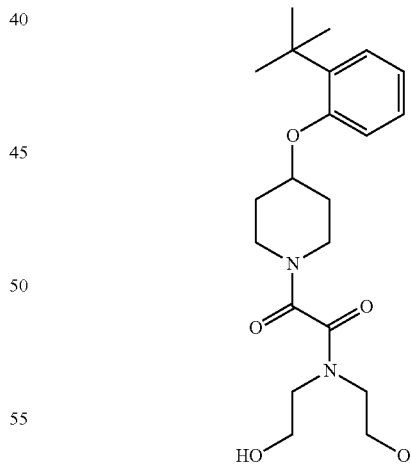

According to a method similar to that in Example 9, the title compound (203 mg, 53%) was obtained as a white solid from [4-(2-tert-butylphenoxy)piperidin-1-yl](oxo)acetic acid (300 mg, 0.98 mmol) and diethanolamine (114 mg, 1.08 mmol) obtained in Example 52.

$^1$H NMR (300 MHz, CDCl$_3$) δ 7.32 (dd, J=7.7, 1.7 Hz, 1H), 7.17 (td, J=7.7, 1.5 Hz, 1H), 6.94-6.85 (m, 1H), 6.82 (d, J=7.9 Hz, 1H), 4.73 (quin, J=4.4 Hz, 1H), 4.12 (br. s., 1H), 4.00-3.85 (m, 3H), 3.85-3.77 (m, 2H), 3.77-3.38 (m, 7H), 3.09 (br. s., 1H), 2.20-1.92 (m, 4H), 1.40 (s, 9H).

Example 289

2-[4-(2-tert-butylphenoxy)piperidin-1-yl]-N-[2-hydroxy-1-(hydroxymethyl)ethyl]-2-oxoacetamide

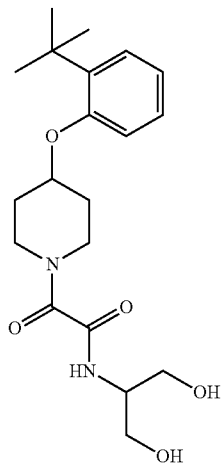 [SMILES: CC(C)(C)c1ccccc1OC1CCN(C(=O)C(=O)NC(CO)CO)CC1]

According to a method similar to that in Example 9, the title compound (273 mg, 730) was obtained as a white solid from [4-(2-tert-butylphenoxy)piperidin-1-yl](oxo)acetic acid (300 mg, 0.98 mmol) and 2-aminopropane-1,3-diol (98 mg, 1.08 mmol) obtained in Example 52.

$^1$H NMR (300 MHz, CDCl$_3$) δ 7.79 (d, J=7.9 Hz, 1H), 7.32 (dd, J=7.7, 1.7 Hz, 1H), 7.22-7.10 (m, 1H), 6.89 (td, J=7.5, 1.1 Hz, 1H), 6.82 (d, J=7.9 Hz, 1H), 4.77-4.64 (m, 1H), 4.19-3.64 (m, 9H), 3.14 (br. s., 2H), 2.20-1.93 (m, 4H), 1.38 (s, 9H).

Example 290

2-[4-(2-tert-butylphenoxy)piperidin-1-yl]-N-(2,3-dihydroxypropyl)-2-oxoacetamide

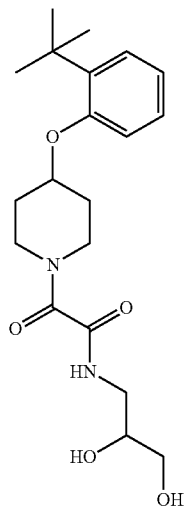 [SMILES: CC(C)(C)c1ccccc1OC1CCN(C(=O)C(=O)NCC(O)CO)CC1]

According to a method similar to that in Example 9, the title compound (320 mg, 86%) was obtained as a colorless oil from [4-(2-tert-butylphenoxy)piperidin-1-yl](oxo)acetic acid (300 mg, 0.98 mmol) and 3-aminopropane-1,2-diol (98 mg, 1.08 mmol) obtained in Example 52.

$^1$H NMR (300 MHz, CDCl$_3$) δ 7.77-7.56 (m, 1H), 7.32 (dd, J=7.7, 1.7 Hz, 1H), 7.21-7.10 (m, 1H), 6.89 (td, J=7.5, 1.1 Hz, 1H), 6.82 (d, J=7.9 Hz, 1H), 4.78-4.64 (m, 1H), 4.26-4.01 (m, 2H), 3.94-3.70 (m, 3H), 3.70-3.47 (m, 3H), 3.47-3.33 (m, 1H), 3.16 (br. s., 1H), 2.88 (br. s., 1H), 2.20-1.91 (m, 4H), 1.40 (s, 9H).

Experimental Example 1

The action of the compound of the present invention to inhibit binding of RBP4 and retinol and TTR was evaluated using the Retinol-RBP4-TTR ELISA (human-type ELISA) system shown below.

1A: Cloning of Human RBP4 Gene and Human TTR Gene

Human RBP4 gene was cloned by PCR using human Universal cDNA (Clontech, QUICK-Clone cDNA) as a template and the following primer set.

```
RBPU:
                                        (SEQ ID NO: 1)
5'-ATATGGATCCACCATGAAGTGGGTGTGGGCGCTC-3'

RBPL:
                                        (SEQ ID NO: 2)
5'-ATATGCGGCCGCCTACAAAAGGTTTCTTTCTGATCTGC-3'
```

PCR reaction was performed according to the protocol attached to Pyrobest polymerase (TAKARA SHUZO CO., LTD.). The obtained PCR product was subjected to agarose gel (1%) electrophoresis, an about 0.6 kb DNA fragment containing RBP4 gene was recovered from the gel, and digested with restriction enzymes BamHI and NotI. The DNA treated with the restriction enzymes was subjected to agarose gel (1%) electrophoresis, an about 0.6 kb DNA fragment was recovered and ligated to plasmid pcDNA3.1(+) (Invitrogen) digested with restriction enzymes BamHI and NotI to give an expression plasmid pcDNA3.1(+)/hRBP4. The DNA sequence of the inserted fragment was confirmed to have matched with the object sequence.

Human TTR gene was cloned by a PCR reaction using human small intestine cDNA (Clontech, QUICK-Clone cDNA) as a template and the following primer set.

```
TTRU:
                                        (SEQ ID NO: 3)
5'-ATATGGATCCACCATGGCTTCTCATCGTCTGCTCC-3'

TTRL:
                                        (SEQ ID NO: 4)
5'-ATATGCGGCCGCTCATTCCTTGGGATTGGTGACGA-3'
```

The PCR reaction was performed according to the protocol attached to Pyrobest polymerase (TAKARA SHUZO CO., LTD.). The obtained PCR product was subjected to agarose gel (1%) electrophoresis, a 0.5 kb DNA fragment containing TTR gene was recovered from the gel, and digested with restriction enzymes BamHI and NotI. The DNA treated with the restriction enzymes was subjected to agarose gel (1%) electrophoresis, an about 0.5 kb DNA fragment was recovered and ligated to plasmid pcDNA3.1(+) (Invitrogen) digested with restriction enzymes BamHI and NotI to give an expression plasmid pcDNA3.1(+)/hTTR. The DNA sequence of the inserted fragment was confirmed to have matched with the object sequence.

1B: Construction of Human RBP4-His Expression Plasmid

EcoRI site was introduced into the 3' end of hRBP4 gene by PCR using the expression plasmid pcDNA3.1(+)/hRBP4 prepared in the above-mentioned 1A as a template and the following primer set.

```
CMVP:
                                                    (SEQ ID NO: 5)
5'-TGGGAGGTCTATATAAGCAGAGCTCG-3'

RBPECO:
                                                    (SEQ ID NO: 6)
5'-ATATGAATTCTTCCTTGGGATTGGTGAC-3'
```

The PCR was performed according to the protocol attached to Z-Taq polymerase (TAKARA SHUZO CO., LTD.). The obtained PCR product was purified using QIAquick PCR purification Kit (QIAGEN), and digested with restriction enzymes BamHI and EcoRI. The DNA treated with the restriction enzymes was subjected to agarose gel (1%) electrophoresis, the obtained about 0.6 kb DNA was recovered and ligated to plasmid pcDNA3.1(+) (Invitrogen) digested with restriction enzymes BamHI and EcoRI to give pcDNA3.1(+)/hRBP4-Eco having EcoRI site at the 3' end of hRBP4 gene.

EcoRI site was introduced into the hTTR gene 3' end by PCR using expression plasmid pcDNA3.1(+)/hTTR prepared in the above-mentioned 1A as a template and CMVP and TTRECO primer set.

```
TTRECO:
                                                    (SEQ ID NO: 7)
5'-ATATGAATTCCAAAAGGTTTCTTTCTGATC-3'
```

PCR reaction was performed according to the protocol attached to Z-Taq polymerase (TAKARA SHUZO CO., LTD.). The obtained PCR product was purified using QIAquick PCR purification Kit (QIAGEN), and digested with restriction enzymes BamHI and EcoRI. The DNA treated with the restriction enzymes was subjected to agarose gel (1%) electrophoresis, the obtained about 0.6 kb DNA was recovered and ligated to plasmid pcDNA3.1(+) (Invitrogen) digested with restriction enzymes BamHI and EcoRI to give pcDNA3.1(+)/hTTR-Eco having EcoRI site at the 3' end of hTTR gene.

TTR-His expression plasmid pcDNA3.1(+)/hTTR-His having His tag added to the C-terminal of human TTR was prepared by inserting a synthetic gene fragment containing His tag sequence prepared by annealing the following oligo DNA to the EcoRI and NotI sites of pcDNA3.1(+)/hTTR-Eco prepared above.

```
HISENU:
                                                    (SEQ ID NO: 8)
5'-AATTCCATCATCATCATCATCACTAGGC-3'

HISENL:
                                                    (SEQ ID NO: 9)
5'-GGCCGCCTAGTGATGATGATGATGATGG-3'
```

HISENU and HISENL were each dissolved at a concentration of 25 pmole/uL, heated at 94° C. for 5 min and cooled to room temperature to give a synthetic gene fragment containing His tag sequence. pcDNA3.1(+)/hTTR-Eco was digested with EcoRI and NotI, the DNA treated with the restriction enzyme was subjected to agarose gel (1%) electrophoresis, the obtained about 5.9 kb DNA was recovered, the synthetic gene fragment containing the His tag sequence was ligated thereto to give TTR-His expression plasmid pcDNA3.1(+)/hTTR-His having His tag added to the C-terminal of human TTR.

RBP4-His expression plasmid pcDNA3.1(+)/hRBP4-His having His tag added to the C-terminal of human RBP4 was prepared as follows. pcDNA3.1(+)/hRBP4-Eco was digested with restriction enzymes EcoRI and DraIII, subjected to agarose gel (1%) electrophoresis and the obtained about 6.0 kb DNA was recovered. pcDNA3.1(+)/hTTR-His was digested with restriction enzymes EcoRI and DraIII and subjected to agarose gel (1%) electrophoresis, and the obtained about 0.6 kb DNA was recovered. Both fragments were ligated to give RBP4-His expression plasmid pcDNA3.1(+)/hRBP4-His having His tag added to the C-terminal of human RBP4.

1C: Preparation of Human RBP4-His

Human RBP4-His was expressed using FreeStyle293 expression system (Invitrogen) and expression plasmid pcDNA3.1(+)/hRBP4-His prepared in the above-mentioned 1B. According to the protocol attached to the FreeStyle293 expression system, 600 mL of culture medium was used for the expression. After transfection and culture for 3 days, the culture supernatant containing secreted hRBP4-His was recovered. The culture supernatant was repeatedly concentrated using VIVACELL250 (molecular weight cut off 10K, VIVASCIENCE) and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human RBP4-His fraction was obtained by elution with 0-0.35M NaCl gradient. The fractions were concentrated to about 5 mL using Vivaspin 20 (molecular weight cut off 10K, VIVASCIENCE). The concentrated solution was passed through HiLoad 26/60 Superdex 200 pg column (2.6 cm ID×60 cm, GE Healthcare) equilibrated with TBS (pH 7.4) and eluted with TBS (pH 7.4). The fractions containing human RBP4-His were is collected and concentrated to about 8 mL using Vivaspin 20 (molecular weight cut off 10K, VIVASCIENCE). About 8 mg of human RBP4-His was obtained from 600 mL of the culture medium.

1D: Preparation of Human TTR

Human TTR was expressed using FreeStyle293 expression system (Invitrogen) and expression plasmid pcDNA3.1(+)/hTTR prepared in the above-mentioned 1A. According to the protocol attached to the FreeStyle293 expression system, 600 mL of culture medium was used for the expression. After transfection and culture for 3 days, the culture supernatant containing secreted human TTR was recovered. The culture supernatant was repeatedly concentrated using VIVACELL250 (molecular weight cut off 10K, VIVASCIENCE) and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human TTR fraction was obtained by elution with 0-0.55M NaCl gradient. This fraction was repeatedly concentrated using Vivaspin 20 (molecular weight cut off 10K, VIVASCIENCE) and diluted with 20 mM Tris (pH 8), whereby the buffer was substituted. The liquid was passed through HiLoad Q Sepharose HP column (1.6 cm ID×10 cm, GE Healthcare) equilibrated with 20 mM Tris buffer (pH 8) at a flow rate of 1.0 mL/min to allow adsorption and human TTR fraction was obtained by elution with 0-0.4M NaCl gradient. The fractions were concentrated to about 5 mL using Vivaspin 20 (molecular weight cut off 10K, VIVASCIENCE). The concentrated solution was passed through HiLoad 26/60 Superdex 75 pg column (2.6 cm ID×60 cm, GE Healthcare) equilibrated with PBS (pH 7.4) and eluted with PBS (pH 7.4). The fractions containing human TTR were collected and concentrated to about 5 mL using Vivaspin 20 (molecular weight cut off 10K, VIVASCIENCE). About 6 mg of human TTR was obtained from 600 mL of the culture medium.

1E: Preparation of Human TTR-Biotin

Human TTR prepared in the above-mentioned 1D was labeled with biotin using Biotinylation Kit (Sulfo-Osu) (DOJINDO LABORATORIES) according to the attached protocol, whereby human TTR-biotin was prepared. Human TTR 5.0 mg was repeatedly concentrated using Vivaspin 6 (molecular weight cut off 10K, VIVASCIENCE) and diluted with 50 mM $NaHCO_3$, whereby the buffer was substituted. The solution was diluted with 50 mM $NaHCO_3$ to human TTR concentration of 2.0 mg/mL, then aqueous Biotin-(AC5)2 Sulfo-OSu solution (10 mg/mL) (9.9 uL) was added and reacted at 25° C. for 2 hr. The solution after the reaction was passed through NAP-25 column (GE Healthcare) equilibrated with PBS (pH 7.4), eluted with PBS (pH 7.4) and an eluate (3.5 mL) containing human TTR-biotin was collected.

Binding Assay by Retinol-RBP4-TTR ELISA

This ELISA system detects a complex of retinol, RBP4 and TTR by Streptoavidin-Biotin reaction.

His-tagged human RBP4 used was prepared in the above-mentioned 1C.

Biotinylate human TTR used was prepared in the above-mentioned 1E.

Streptavidin (20 µl) (10 µg/ml Streptavidin type II (Wako Pure Chemical Industries, Ltd.), 10 mM Tris-HCl (pH 7.5), 10 mM NaCl) was added to a 384 well black maxisorp plate (Nunc), and the plate was subjected to centrifugation (1000 rpm, 1 min) and coated overnight at 4° C. The plate was washed twice with PBST (PBS, 0.05% Tween 20, 100 µl/well) and blocked with 25% Block Ace (Snow Brand Milk Products Co., Ltd., PBS, 100 µl/well). The plate was subjected to centrifugation (1000 rpm, 1 min) and incubated at room temperature for 4 hr or overnight at 4° C. The plate was washed twice with PEST (PBS, 0.05% Tween 20, 100 µl/well), and biotinylated human TTR (stock solution concentration 1.3 mg/ml) diluted 1000-fold with PBST was added at 20 µl/well. The plate was subjected to centrifugation (1000 rpm, 1 min) and stood still at room temperature for 1.5 hr or overnight at 4° C. The plate was washed 3 times with PBST (100 µl/well), and His-tagged human RBP4 (stock solution concentration 0.96 mg/ml) diluted 4000-fold with a reaction buffer (50 mM Tris-HCl, 150 mM NaCl, 0.005% Tween 20, 1 mM DTT, 0.1% BSA) was added at 10 µl/well. The dilution series (8 doses from 10 mM, 200-fold concentration) of the compound was prepared with DMSO, and 1 µl of each was added to a reaction buffer (200 µl) containing retinol (0.5 µM) (Sigma-Aldrich Co.). A reaction buffer (200 µl) containing retinol and added with DMSO was used as a positive control, and reaction buffer (200 µl) free of retinol and added with DMSO was used as a negative control. Mixed solutions of retinol and the compound were added to the plate at 15 µl/well. The mixture was stirred in a platemixer subjected to centrifugation (1000 rpm, 1 min) and reacted at room temperature for 2 hr. A 35% Block Ace solution diluted with the reaction buffer was added at 10 µl/well, centrifuged (1000 rpm, 1 min) and reacted at room temperature for 30 min. The plate was washed 3 times with PBST (100 µl/well) and SuperSignal ELISA Femto Maximum Sensitivity Substrate reagent (PIERCE) was added at 30 µl/well, and the luminescence was measured by a platereader (Wallac).

The binding inhibitory rate of the compound was determined by 100×(test compound value−negative control value)/(positive control value−negative control value). The binding activity ($IC_{50}$) was calculated from the binding inhibitory rate at each compound concentration using a graph drawing software, Prism (GraphPad Software Inc.). The results are shown below.

TABLE 1

| Example No. | human RBP4 binding inhibitory activity ($IC_{50}$ nM) |
|---|---|
| 6 | 20 |
| 10 | 36 |
| 12 | 210 |
| 14 | 24 |
| 17 | 10 |
| 20 | 290 |
| 50 | 5.0 |
| 80 | 20 |
| 121 | 790 |
| 143 | 23 |
| 164 | 15 |
| 189 | 71 |
| 197 | 40 |
| 207 | 12 |
| 215 | 34 |

From the above results, it is clear that the compound of the present invention inhibits binding of RBP4 with retinol and TTR.

Experimental Example 2

A blood RBP4 lowering action of the compound of the present invention was evaluated using C57BL/6J mouse.

Male 7- to 15-week-old C57BL/6J mice (Charles River Laboratories Japan Inc.) were individually bred for acclimation for 4-6 days under conditions with free access to CE-2 solid food (CLEA Japan, Inc.), and grouped based on the body weight (5 per group). The next day of grouping, blood samples were collected from the orbital venous plexus, and plasma was separated (0 hr value). Thereafter, the test compounds (Examples 12, 143, 164, 189, 197, 207 and 215) were orally administered at a dose of 50 mg/kg (solvent: 0.5% methylcellulose solution (10 mL/kg)). At 4, 7 and 24 hr after administration of the compounds, blood samples were collected from the orbital venous plexus, and plasma was separated. A 0.5% methylcellulose solution (10 mL/kg) was orally administered to the control group.

The RBP4 level of the collected plasma was measured by ELISA. RBP4 was quantified by the following steps using a rabbit anti-mouse RBP4 polyclonal antibody (Hokudo Co., Ltd). A 96 well ELISA plate was coated with 50 µg/mL of the antibody (100 µL) and stood at 4° C. overnight. After blocking with BlockAce (DAINIPPON PHARMACEUTICAL CO., LTD.), mouse RBP4 or a sample (100 µL) was added and the plate was stood at room temperature for 2 hr. After washing with PBS-0.5% Tween 20, HRP-labeled anti-RBP4 antibody (prepared by labeling RBP4 polyclonal antibody (Hokudo Co., Ltd) with HRP (DOJINDO LABORATORIES)) was added by 100 µL, and the plate was stood at room temperature for 1 hr. After washing, TMB (Dako Cytomations) was added, and the mixture was stood at room temperature for 20 min to allow color development, and the reaction was quenched with 2N sulfuric acid. Thereafter, the absorbance at A450 nm was measured on a platereader. The amount of change from the initial value of each animal was determined as a relative value from the control group (% of initial/Control) at each time point. The results are shown in the following in mean±standard deviation (n=5).

TABLE 2

| | RBP4 (% of initial/Control) | | |
|---|---|---|---|
| Example No. | 4 hr later | 7 hr later | 24 hr later |
| 12 | 57.7 ± 3.6 | 44.3 ± 2.0 | 50.0 ± 3.4 |
| 143 | 46.7 ± 6.6 | 36.2 ± 4.2 | 45.2 ± 9.1 |
| 164 | 55.6 ± 6.3 | 46.4 ± 7.2 | 74.5 ± 8.9 |
| 189 | 51.5 ± 1.7 | 42.1 ± 1.3 | 69.7 ± 9.6 |
| 197 | 39.2 ± 1.4 | 29.2 ± 1.0 | 40.4 ± 3.0 |
| 207 | 55.6 ± 1.0 | 49.0 ± 1.3 | 69.5 ± 6.6 |
| 215 | 64.3 ± 1.2 | 60.6 ± 0.6 | 64.7 ± 4.3 |

All of the above-mentioned compounds showed lower levels than the control group at 4 hr and the lowest level at 7 hr after administration by single oral administration. These results show that the compound of the present invention has a blood RBP4-lowering action.

Experimental Example 3

An anti-diabetes action and a blood triglyceride (hereinafter TG)-lowering action of the compound of the present invention were evaluated using Zucker fa/fa rats.

Experimental Example 3A

Anti-Diabetes Action Using Zucker fa/fa Rat
(Takeda Pharmaceutical Company Limited)

Male 7-week-old Zucker fa/fa rats (Takeda Pharmaceutical Company Limited) were bred in group on CE-2 solid food (CLEA Japan, Inc.) until 7-week-old, thereafter bred on high-fat diet D06110702 (LSG Corporation) for acclimation under conditions with free access to food. At 11-week-old, the rats were grouped based on the body weight, blood glucose level, glycated hemoglobin level, blood RBP4 level and blood insulin level value (6 per group). Thereafter, the test compound (Example 143) was orally administered at a dose of 30 mg/kg (solvent: 0.5% methylcellulose solution (5 mL/kg)) for 2 weeks. The next day of the final administration of the compound, blood samples were collected from the tail vein, and plasma was separated. Using the collected plasma, (1) RBP4 concentration and (2) glycated hemoglobin level were measured. (1) was quantified according to the protocol described in Experimental Example 2. (2) was measured using Tosoh Corporation automatic glycohemoglobin analyzer (HLC-723 GHbV A1c2.2 or HLC-723G7 GHbV A1c2.2).

A 0.5% methylcellulose solution (5 mL/kg) was orally administered to the control group. As a result, the blood RBP4 concentration and glycated hemoglobin showed significant decrease by the oral administration (30 mg/kg) of the compound (Example 143) for 2 weeks. The results are shown in the is following in mean±standard deviation (n=6). In the following Table, glycated hemoglobin change is obtained by subtracting the value before administration from that after administration.

TABLE 3A

| | RBP4 (μg/mL) | glycated hemoglobin change(%) |
|---|---|---|
| control | 35.2 ± 16.3 | 1.4 ± 0.3 |
| Example 143 | 7.3 ± 1.2 | 0.6 ± 0.4 |

The compound of the present invention significantly decreased the glycated hemoglobin level in correlation with decreased blood RBP4 concentration.

Experimental Example 3B

TG-Lowering Action Using Zucker fa/fa Rat
(Charles River Laboratories Japan Inc.)

Male 10-week-old Zucker fa/fa rats (Charles River Laboratories Japan Inc.) were bred in group on CE-2 solid food (CLEA Japan, Inc.) until 12-week-old for acclimation under conditions with free access to food. At 12-week-old, the rats were grouped based on the body weight, blood glucose level, glycated hemoglobin level, blood RBP4 level and blood triglyceride blood (hereinafter TG) (5 per group). Thereafter, the test compound (Example 12) was orally administered at a dose of 30 mg/kg (solvent: 0.5% methylcellulose solution (3 mL/kg)) for 2 weeks. The next day of the final administration of the compound, blood samples were collected from the tail vein, and plasma was separated. Using the collected plasma, (1) RBP4 concentration and (2) TG level were measured. (1) was quantified according to the protocol described in Experimental Example 2. (2) was measured using Hitachi fully automatic analyzer (Model 7070).

A 0.5% methylcellulose solution (5 mL/kg) was orally administered to the control group. As a result, the blood RBP4 concentration and TG showed significant decrease by the oral administration (30 mg/kg) of the compound (Example 12) for 2 weeks. The results are shown in the following in mean±standard deviation (n=5).

TABLE 3B

| | RBP4 (μg/mL) | TG (mg/dL) |
|---|---|---|
| control | 26.4 ± 2.6 | 922.3 ± 230.7 |
| Example 12 | 8.2 ± 1.1 | 650.8 ± 130.6 |

The compound of the present invention showed significant decrease in TG in correlation with decreased blood RBP4 concentration.

| Formulation Example 1 (production of capsules) | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved.

The sieved powder is mixed with 4) (14 g) and 5) (1 g), and punched by a tableting machine, whereby 1000 tablets containing 30 mg of the compound of Example 1 per tablet are obtained.

This application is based on a U.S. patent application No. 60/960,897, the contents of which are incorporated in full herein.

INDUSTRIAL APPLICABILITY

The compound of the present invention has a superior RBP4-lowering action, diabetes, obesity and the like, and is useful as a medicament for the prophylaxis or treatment of disease and condition mediated by increased RBP4.

[Sequence Listing Free Text]
SEQ ID NO: 1: PCR primer (RBPU)
SEQ ID NO: 2: PCR primer (RBPL)
SEQ ID NO: 3: PCR primer (TTRU)
SEQ ID NO: 4: PCR primer (TTRL)
SEQ ID NO: 5: PCR primer (CMVP)
SEQ ID NO: 6: PCR primer (RBPECO)
SEQ ID NO: 7: PCR primer (TTRECO)
SEQ ID NO: 8: oligonucleotide (HISENU) for forming synthetic gene fragment containing His tag sequence
SEQ ID NO: 9: oligonucleotide (HISENL) for forming synthetic gene fragment containing His tag sequence

The invention claimed is:

1. A compound represented by the formula

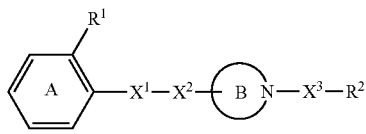

(I)

wherein ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine;
$X^3$ is CO or $SO_2$;
$R^2$ is an optionally substituted hydrocarbon group, an optionally substituted heterocyclic group, an optionally substituted hydroxy group, an optionally substituted mercapto group, a cyano group, a nitro group, an acyl group, or a halogen atom, provided that when $X^3$ is CO, then $R^2$ is not a tert-butoxy group,
or a salt thereof.

2. The compound according to claim 1, wherein ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine;
$X^3$ is CO; and
$R^2$ is an acyl group or an optionally substituted hydrocarbon group.

3. The compound according to claim 1, wherein ring A is benzene optionally further substituted by 1 to 3 substituents selected from the group consisting of (1) a halogen atom, (2) an optionally halogenated $C_{1-6}$ alkyl group and (3) an optionally halogenated $C_{1-6}$ alkoxy group.

4. The compound according to claim 1, wherein $R^1$ is an isopropyl group or a tert-butyl group.

5. The compound according to claim 1, wherein $X^1$ is O.

6. The compound according to claim 1, wherein $X^2$ is a bond or methylene.

7. The compound according to claim 1, wherein ring B is

8. The compound according to claim 1, wherein $X^3$ is CO.

9. The compound according to claim 1, wherein $R^2$ is an acyl group or an optionally substituted hydrocarbon group.

10. The compound according to claim 1, wherein ring A is benzene optionally further substituted by 1 to 3 substituents selected from the group consisting of (1) a halogen atom, (2) an optionally halogenated $C_{1-6}$ alkyl group and (3) an optionally halogenated $C_{1-6}$ alkoxy group;
$R^1$ is an isopropyl group or a tert-butyl group;
$X^1$ is O;
$X^2$ is a bond or methylene;
ring B is

$X^3$ is CO; and
$R^2$ is an acyl group or an optionally substituted hydrocarbon group.

11. 4-(3-(2-tert-Butylphenoxy)azetidin-1-yl)-4-oxobutanoic acid or a salt thereof.

12. 3-{3-[(2-tert-Butyl-4-fluorophenoxy)methyl]azetidin-1-yl}-3-oxopropanoic acid or a salt thereof.

13. 2-{[3-(2-tert-Butyl-4-chlorophenoxy)azetidin-1-yl]carbonyl}pyridine or a salt thereof.

14. 4-[3-(2-tert-Butyl-4-chlorophenoxy)azetidin-1-yl]-4-oxobutanoic acid or a salt thereof.

15. {3-[(2-tert-Butyl-4-chlorophenoxy)methyl]azetidin-1-yl}(oxo)acetic acid or a salt thereof.

16. A pharmaceutical composition comprising the compound according to claim 1 and a pharmacologically acceptable carrier.

17. The pharmaceutical composition according to claim 16 which is a therapeutic agent for type 2 diabetes.

18. A retinol-binding protein 4-lowering agent comprising a compound represented by the formula

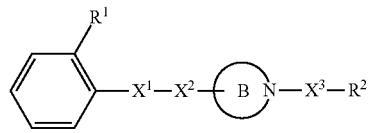

wherein
ring A is benzene optionally further substituted;
$R^1$ is an optionally substituted branched $C_{3-6}$ alkyl group;
$X^1$ is O, S, SO, $SO_2$ or NH;
$X^2$ is a bond or a $C_{1-3}$ alkylene group;
ring B is azetidine;
$X^3$ is CO or $SO_2$; and
$R^2$ is an optionally substituted hydrocarbon group, an optionally substituted heterocyclic group, an optionally substituted hydroxy group, an optionally substituted mercapto group, a cyano group, a nitro group, an acyl group, or a halogen atom,
or a salt thereof,
wherein the agent is a therapeutic agent for type 2 diabetes.

19. {3-[(2-tert-butylphenoxy)methyl]azetidin-1-yl}(oxo)acetic acid or a salt thereof.

20. {3-[(2-tert-butyl-4-chlorophenoxy)methyl]azetidin-1-yl}(oxo)acetic acid or a salt thereof.

21. 3-{3-[(2-tert-butylphenoxy)methyl]azetidin-1-yl}-3-oxopropanoic acid or a salt thereof.

* * * * *

UNITED STATES PATENT AND TRADEMARK OFFICE
CERTIFICATE OF CORRECTION

PATENT NO. : 8,586,571 B2
APPLICATION NO. : 12/738486
DATED : November 19, 2013
INVENTOR(S) : Shizuo Kasai It is certified that error appears in the above-identified patent and that said Letters Patent is hereby corrected as shown below:

In the Claims

Claim 18, in column 254, lines 5-10:

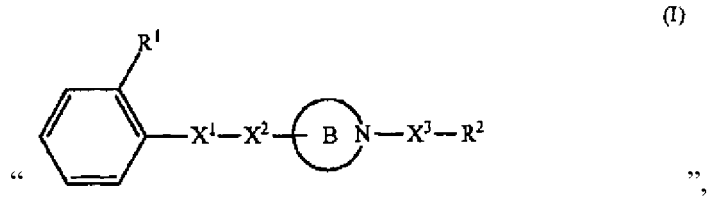

should be changed to

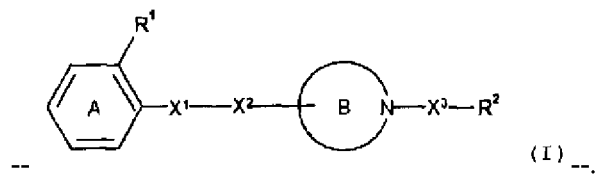

Signed and Sealed this
Thirtieth Day of September, 2014

Michelle K. Lee
*Deputy Director of the United States Patent and Trademark Office*

```
SEQUENCE LISTING

<160> NUMBER OF SEQ ID NOS: 9

<210> SEQ ID NO 1
<211> LENGTH: 34
<212> TYPE: DNA
<213> ORGANISM: Artificial sequence
<220> FEATURE:
<223> OTHER INFORMATION: Synthetic construct; PCR primer (RBPU)

<400> SEQUENCE: 1
atatggatcc accatgaagt gggtgtgggc gctc                              34

<210> SEQ ID NO 2
<211> LENGTH: 38
<212> TYPE: DNA
<213> ORGANISM: Artificial sequence
<220> FEATURE:
<223> OTHER INFORMATION: Synthetic construct; PCR primer (RBPL)

<400> SEQUENCE: 2
atatgcggcc gcctacaaaa ggtttctttc tgatctgc                          38

<210> SEQ ID NO 3
<211> LENGTH: 35
<212> TYPE: DNA
<213> ORGANISM: Artificial sequence
<220> FEATURE:
<223> OTHER INFORMATION: Synthetic construct; PCR primer (TTRU)

<400> SEQUENCE: 3
atatggatcc accatggctt ctcatcgtct gctcc                             35

<210> SEQ ID NO 4
<211> LENGTH: 35
<212> TYPE: DNA
<213> ORGANISM: Artificial sequence
<220> FEATURE:
<223> OTHER INFORMATION: Synthetic construct; PCR primer (TTRL)

<400> SEQUENCE: 4
atatgcggcc gctcattcct tgggattggt gacga                             35

<210> SEQ ID NO 5
<211> LENGTH: 26
<212> TYPE: DNA
<213> ORGANISM: Artificial sequence
<220> FEATURE:
<223> OTHER INFORMATION: Synthetic construct; PCR primer (CMVP)

<400> SEQUENCE: 5
```

-continued

```
tgggaggtct atataagcag agctcg                                    26

<210> SEQ ID NO 6
<211> LENGTH: 28
<212> TYPE: DNA
<213> ORGANISM: Artificial sequence
<220> FEATURE:
<223> OTHER INFORMATION: Synthetic construct; PCR primer (RBPECO)

<400> SEQUENCE: 6
atatgaattc ttccttggga ttggtgac                                  28

<210> SEQ ID NO 7
<211> LENGTH: 30
<212> TYPE: DNA
<213> ORGANISM: Artificial sequence
<220> FEATURE:
<223> OTHER INFORMATION: Synthetic construct; PCR primer (TTRECO)

<400> SEQUENCE: 7
atatgaattc caaaaggttt ctttctgatc                                30

<210> SEQ ID NO 8
<211> LENGTH: 28
<212> TYPE: DNA
<213> ORGANISM: Artificial sequence
<220> FEATURE:
<223> OTHER INFORMATION: Synthetic construct; oligonucleotide for
      preparation of synthetic gene fragment containing His tag sequence
      (HISENU)

<400> SEQUENCE: 8
aattccatca tcatcatcat cactaggc                                  28

<210> SEQ ID NO 9
<211> LENGTH: 28
<212> TYPE: DNA
<213> ORGANISM: Artificial sequence
<220> FEATURE:
<223> OTHER INFORMATION: Synthetic construct; oligonucleotide for
      preparation of synthetic gene fragment containing His tag sequence
      (HISENL)

<400> SEQUENCE: 9
ggccgcctag tgatgatgat gatgatgg                                  28
```